US012466893B2

(12) United States Patent
Algate et al.

(10) Patent No.: US 12,466,893 B2
(45) **Date of Patent: *Nov. 11, 2025**

(54) ANTIGEN BINDING PROTEINS

(71) Applicant: Glaxo Group Limited, Stevenage (GB)

(72) Inventors: Paul Algate, Issaquah, WA (US); Stephanie Jane Clegg, Stevenage (GB); Jennifer L. Craigen, Stevenage (GB); Paul Andrew Hamblin, Stevenage (GB); Alan Peter Lewis, Stevenage (GB); Patrick Mayes, Devon, PA (US); Radha Shah Parmar, Stevenage (GB); Trevor Anthony Kenneth Wattam, Stevenage (GB)

(73) Assignee: Glaxo Group Limited, Stevenage (GB)

(*) Notice: Subject to any disclaimer, the term of this patent is extended or adjusted under 35 U.S.C. 154(b) by 500 days.

This patent is subject to a terminal disclaimer.

(21) Appl. No.: 17/863,174

(22) Filed: Jul. 12, 2022

(65) Prior Publication Data

US 2023/0137032 A1 May 4, 2023

Related U.S. Application Data

(60) Division of application No. 16/815,677, filed on Mar. 11, 2020, now Pat. No. 11,419,945, which is a continuation of application No. 15/828,770, filed on Dec. 1, 2017, now abandoned, which is a continuation of application No. 14/974,675, filed on Dec. 18, 2015, now abandoned, which is a continuation of application No. 13/795,314, filed on Mar. 12, 2013, now Pat. No. 9,273,141, which is a continuation of application No. PCT/EP2012/059762, filed on May 24, 2012.

(60) Provisional application No. 61/490,732, filed on May 27, 2011.

(51) Int. Cl.

| | |
|---|---|
| ***A61K 39/00*** | (2006.01) |
| ***A61K 38/05*** | (2006.01) |
| ***A61K 47/68*** | (2017.01) |
| ***C07K 16/28*** | (2006.01) |
| ***C07K 16/30*** | (2006.01) |

(52) U.S. Cl.

CPC .......... *C07K 16/3061* (2013.01); *A61K 38/05* (2013.01); *A61K 47/68031* (2023.08); *A61K 47/6849* (2017.08); *C07K 16/2803* (2013.01); *C07K 16/2878* (2013.01); *A61K 2039/505* (2013.01); *C07K 2317/24* (2013.01); *C07K 2317/33* (2013.01); *C07K 2317/41* (2013.01); *C07K 2317/56* (2013.01); *C07K 2317/73* (2013.01); *C07K 2317/732* (2013.01); *C07K 2317/76* (2013.01); *C07K 2317/77* (2013.01); *C07K 2317/92* (2013.01)

(58) Field of Classification Search

CPC .......... A61K 47/68031; A61K 47/6849; A61K 2039/505; C07K 16/2803; C07K 16/2878; C07K 2317/24

See application file for complete search history.

(56) References Cited

U.S. PATENT DOCUMENTS

| | | | |
|---|---|---|---|
| 5,635,483 | A | 6/1997 | Pettit et al. |
| 5,968,753 | A | 10/1999 | Tseng-Law et al. |
| 6,214,345 | B1 | 4/2001 | Firestone et al. |
| 6,884,869 | B2 | 4/2005 | Senter et al. |
| 6,962,702 | B2 | 11/2005 | Hansen et al. |
| 7,083,785 | B2 | 8/2006 | Browning et al. |
| 7,091,186 | B2 | 8/2006 | Senter et al. |
| 7,498,298 | B2 | 3/2009 | Doronina et al. |
| 7,553,816 | B2 | 6/2009 | Senter et al. |
| 7,659,241 | B2 | 2/2010 | Senter et al. |
| 7,745,394 | B2 | 6/2010 | Doronina et al. |
| 7,750,116 | B1 | 7/2010 | Doronina et al. |
| 7,829,531 | B2 | 11/2010 | Senter et al. |
| 7,837,980 | B2 | 11/2010 | Alley et al. |
| 7,851,437 | B2 | 12/2010 | Senter et al. |
| 7,964,566 | B2 | 6/2011 | Doronina et al. |
| 7,964,567 | B2 | 6/2011 | Doronina et al. |
| 7,994,135 | B2 | 8/2011 | Doronina et al. |
| 8,039,273 | B2 | 10/2011 | Jeffrey |
| 8,163,551 | B2 | 4/2012 | Alley et al. |
| 8,288,352 | B2 | 10/2012 | Doronina et al. |
| 8,343,928 | B2 | 1/2013 | Doronina et al. |
| 8,455,622 | B2 | 6/2013 | McDonagh et al. |
| 8,512,707 | B2 | 8/2013 | Doronina et al. |
| 8,557,780 | B2 | 10/2013 | Doronina et al. |
| 8,568,728 | B2 | 10/2013 | Jeffrey |

(Continued)

FOREIGN PATENT DOCUMENTS

| | | |
|---|---|---|
| WO | 0040716 A2 | 7/2000 |
| WO | 0112812 A2 | 2/2001 |

(Continued)

OTHER PUBLICATIONS

Dogan et al (Blood cancer Journal 10:73 2020 (Year: 2020).*

(Continued)

*Primary Examiner* — Lei Yao

(74) *Attorney, Agent, or Firm* — Carly Shanahan

(57) ABSTRACT

The present invention concerns antigen binding proteins and fragments thereof which specifically bind B Cell Maturation Antigen (BCMA), particularly human BCMA (hBCMA) and which inhibit the binding of BAFF and APRIL to the BCMA receptor. Further disclosed are pharmaceutical compositions, screening and medical treatment methods.

31 Claims, 25 Drawing Sheets

Specification includes a Sequence Listing.

(56) References Cited

U.S. PATENT DOCUMENTS

| | | | |
|---|---|---|---|
| 8,574,907 | B2 | 11/2013 | Alley et al. |
| 9,273,141 | B2 | 3/2016 | Algate et al. |
| 2002/0028178 | A1 | 3/2002 | Hanna et al. |
| 2003/0054497 | A1 | 3/2003 | Co et al. |
| 2003/0105000 | A1 | 6/2003 | Pero et al. |
| 2009/0220502 | A1 | 9/2009 | Brandt et al. |
| 2009/0226434 | A1 | 9/2009 | Auer et al. |
| 2010/0021474 | A1 | 1/2010 | Kirchhofer et al. |
| 2010/0267932 | A1 | 10/2010 | Eon-Duval et al. |
| 2013/0280280 | A1 | 10/2013 | Algate et al. |
| 2014/0105915 | A1 | 4/2014 | Algate et al. |
| 2016/0193358 | A1 | 7/2016 | Algate et al. |
| 2022/0411512 | A1 | 12/2022 | Hoos et al. |

FOREIGN PATENT DOCUMENTS

| | | | |
|---|---|---|---|
| WO | 0124811 | A1 | 4/2001 |
| WO | 0160397 | A1 | 8/2001 |
| WO | 2002066516 | A2 | 8/2002 |
| WO | 03072713 | A2 | 9/2003 |
| WO | 2005075511 | A1 | 8/2005 |
| WO | 2006067210 | A1 | 6/2006 |
| WO | 2010104949 | A2 | 9/2010 |
| WO | 2011042548 | A1 | 4/2011 |
| WO | 2011108008 | A2 | 9/2011 |
| WO | 2012066058 | A1 | 5/2012 |
| WO | 2012163805 | A1 | 12/2012 |

OTHER PUBLICATIONS

Abcam, "KD value: A quantitative measurement of antibody affinity", 8 pages (2017).

Burgess et al., "Possible dissociation of the heparin-binding and mitogenic activities of heparin-binding (acidic fibroblast) growth factor-1 from its receptor-binding activities by site-directed mutagenesis of a single lysine residue", Journal of Cell Biology, vol. 111 Issue 5, pp. 2129-2138 (1990).

Cai et al., "DNA minor groove binders: Back in the groove", Cancer Treatment Reviews, vol. 35, pp. 437-450 (2009).

Carter et al., "Antibody-Drug Conjugates for Cancer Therapy", Cancer Journal, vol. 14, No. 3, pp. 154-169 (2008).

Casset et al., "A peptide mimetic of an anti-CD4 monoclonal antibody by rational design", Biochemical and Biophysical Research Communications, vol. 307, pp. 198-205 (2003).

Claudio et al., "A molecular compendium of genes expressed in multiple myeloma," Blood, vol. 100, No. 6, pp. 2175-2186, (2002).

Colman P.M., "Effects of amino acid sequence changes on antibody-antigen interactions Original", Research in Immunology, vol. 145, Issue 1, pp. 33-36 (1994).

Doronina et al., "Enhanced Activity of Monomethylauristatin F through Monoclonal Antibody Delivery: Effects of Linker Technology on Efficacy and Toxicity", Bioconjugate Chemistry, vol. 17, Issue 1, pp. 114-124 (2006).

Güssow et al., "Humanization of monoclonal antibodies", Methods in Enzymology, vol. 203, pp. 99-121 (1991).

Hudson et al., "Engineered antibodies", Nature Medicine, vol. 9, pp. 129-134 (2003).

Ibragimova, et al., "Stability of the β-Sheet of the WW Domain: A Molecular Dynamics Simulation Study", Biophysical Journal, vol. 77, Issue 4, pp. 2191-2198 (1999).

Jefferis et al., "Interaction sites on human IgG-Fc for FcγR: current models", Immunology Letters, vol. 82, Issues 1-2, pp. 57-65 (2002).

Lazar et al., "Engineered antibody Fc variants with enhanced effector function", PNAS, vol. 103, No. 11, pp. 4005-4010 (2006).

MacCallum et al., "Antibody-antigen Interactions: Contact Analysis and Binding Site Topography", Journal of Molecular Biology, vol. 262, Issue 5, pp. 732-745 (1996).

Mori et al., "Non-fucosylated therapeutic antibodies: the next generation of therapeutic antibodies", Cytotechnology, vol. 55, Issue 2, pp. 109-114 (2007).

PB64476T OA U.S. Appl. No. 13/795,314 Final Rejection dated Apr. 14, 2015.

Peters et al., "Antibody-drug conjugates as novel anti-cancer chemotherapeutics," Bioscience Reports, vol. 35, e00225, doi:10.1042/BSR20150089 (2015).

Polson et al., "Antibody-Drug Conjugates for the Treatment of Non-Hodgkin's Lymphoma: Target and Linker-Drug Selection", Cancer Res., vol. 69, No. 6, pp. 2358-2364, DOI: 10.1158/0008-5472.CAN-08-2250 (2009), Correction, DOI: 10.1158/0008-5472.CAN-09-4551, 1275 (Jan. 26, 2010).

Rudikoff et al., "Single amino acid substitution altering antigen-binding specificity", Proceedings of the National Academy of Sciences, vol. 79, No. 6, pp. 1979-1983 (1982).

Ryan et al., "Antibody targeting of B-cell maturation antigen on malignant plasma cells", Mol. Cancer Ther., vol. 6, No. 11, pp. 3009-3018 (2007).

Shadidi et al., "An Anti-leukemic Single Chain Fv Antibody Selected from a Synthetic Human Phage Antibody Library", BBRC, vol. 280, pp. 548-552 (2001).

Shu et al., "B cell maturation protein is a receptor for the tumor necrosis factor family member TALL-1", Proceedings of the National Academy of Sciences, vol. 97, No. 16, pp. 9156-9161 (2000).

Yamane-Ohnuki et al., "Establishment of FUT8 Knockout Chinese Hamster Ovary Cells: An Ideal Host Cell Line for Producing Completely Defucosylated Antibodies with Enhanced Antibody-Dependent Cellular Cytotoxicity", Biotechnology and Bioengineering, vol. 87, No. 5, pp. 614-622 (2004).

Yang et al., "CDR Walking Mutagenesis for the Affinity Maturation of a Potent Human Anti-HIV-1 Antibody into the Picomolar Range", J. Mol. Biol., vol. 254, pp. 392-403 (1995).

International Search Report and Written Opinion for International Application No. PCT/EP2012/059762, mailed Aug. 31, 2012, 13 Pages.

Janeway C.A., et al., The Interaction of the Antibody Molecules with Sepcific Antigen, Immuno Biology 5, 2001, pp. 100-101 (4 Pages).

"NCI-H929 [H929] ATCC CRL-9068," *Homo sapiens* Bone Marrow PI, 1 Page, [Retrieed on May 14, 2015] Retrieved from URL: http://www.atcc.org/products/all/CRL-9O68.aspx&p=1&rel=characteristics#characteristics.

* cited by examiner

ANTIGEN BINDING PROTEINS

CROSS REFERENCE TO RELATED APPLICATIONS

This application is a divisional of U.S. application Ser. No. 16/815,677 filed Mar. 11, 2020 (issued as U.S. Pat. No. 11,419,945), which is a continuation of U.S. application Ser. No. 15/828,770 filed Dec. 1, 2017 (abandoned), which is a continuation of U.S. application Ser. No. 14/974,675 filed Dec. 18, 2015 (abandoned), which is a continuation of U.S. application Ser. No. 13/795,314 filed Mar. 12, 2013 (issued as U.S. Pat. No. 9,273,141), which is a continuation of International Application No. PCT/EP2012/059762, filed May 24, 2012, which claims priority to and benefit of U.S. Provisional Application No. 61/490,732 filed on May 27, 2011, each of which is incorporated by reference herein in its entirety.

STATEMENT REGARDING SEQUENCE LISTING

The Sequence Listing associated with this application is provided in XML format in lieu of a paper copy, and is hereby incorporated by reference into the specification. The name of the XLM file containing the Sequence Listing is 054624-09-5021-US05_ST_26_Sequence_Listing.xml. The text file is about 288,579 bytes, was created on or about Jul. 20, 2022, and is being submitted electronically via EFS-Web.

FIELD OF THE INVENTION

The present invention relates to antigen binding proteins and fragments thereof that specifically bind B cell maturation antigen (BCMA) and in particular human BCMA (hBCMA).

The present invention also concerns methods of treating diseases or disorders with said antigen binding fragments, pharmaceutical compositions comprising said antigen binding fragments and methods of manufacture. Other embodiments of the present invention will be apparent from the description below.

BACKGROUND OF THE INVENTION

BCMA (CD269 or TNFRSF17) is a member of the TNF receptor superfamily. It is a non-glycosylated integral membrane receptor for the ligands BAFF and APRIL. BCMA's ligands can also bind additional receptors: TACI (Transmembrane Activator and Calcium modulator and cyclophilin ligand Interactor), which binds APRIL and BAFF; as well as BAFF-R (BAFF Receptor or BR3), which shows restricted but high affinity for BAFF. Together, these receptors and their corresponding ligands regulate different aspects of humoral immunity, B-cell development and homeostasis.

BCMA's expression is typically restricted to the B-cell lineage and is reported to increase in terminal B-cell differentiation. BCMA is expressed by human plasma blasts, plasma cells from tonsils, spleen and bone marrow, but also by tonsillar memory B cells and by germinal centre B cells, which have a TACI-BAFFR low phenotype (Darce et al, 2007). BCMA is virtually absent on naïve and memory B-cells (Novak et al., 2004a and b). The BCMA antigen is expressed on the cell surface so is accessible to the antibody, but is also expressed in the golgi. As suggested by its expression profile, BCMA signalling, typically linked with B-cell survival and proliferation, is important in the late stages of B-cell differentiation, as well as the survival of long lived bone marrow plasma cells (O'Connor et al., 2004) and plasmablasts (Avery et al., 2003). Furthermore, as BCMA binds APRIL with high affinity, the BCMA-APRIL signalling axis is suggested to predominate at the later stages of B-cell differentiation, perhaps being the most physiologically relevant interaction.

Multiple Myeloma (MM) is a clonal B-cell malignancy that occurs in multiple sites within the bone marrow before spreading to the circulation; either de novo, or as a progression from monoclonal gammopathy of undetermined significance (MGUS). It is commonly characterised by increases in paraprotein and osteoclast activity, as well as hypercalcaemia, cytopenia, renal dysfunction, hyperviscosity and peripheral neuropathy. Decreases in both normal antibody levels and numbers of neutrophils are also common, leading to a life threatening susceptibility to infection. BCMA has been implicated in the growth and survival of myeloma cell lines in vitro (Novak et al., 2004a and b; Moreaux et al., 2004).

BCMA expression (both transcript and protein) is reported to correlate with disease progression in MM. Using Affymetrix microarrays, it was demonstrated that the TACI and BCMA genes were over-expressed in Multiple Myeloma Cells (MMC) compared with their normal counterparts (Moreaux et al, 2004). Gene expression analysis has been used to compare human myeloma cells with purified plasma cells from patients with MGUS and from normal bone marrow as well as with primary tumour cells from B-cell lineage leukaemias (Bellucci et al, 2005). The BCMA gene was highly expressed in all myeloma samples. Although purified plasma cells from patients with MGUS had lower expression of BCMA, there was no significant difference when compared with the expression found in normal plasma cells or myeloma cells. In contrast, BCMA expression was significantly lower in B-cell Chronic Lymphocytic Leukaemia (CLL), pre-B Acute Lymphocytic Leukaemia (ALL) and T-cell ALL (T-ALL).

Mouse models that transgenically over-express BAFF or APRIL have a significant increase in B-cell lymphomas (Batten et al., 2004—BAFF; Planelles et al., 2004—APRIL). In humans, excess BAFF and APRIL have been detected in the sera and micro-environments of patients with a number of B-cell malignancies, as well as other B-cell disorders.

All patent and literature references disclosed within the present specification are expressly and entirely incorporated herein by reference.

Multiple myeloma cell line H929 or ARH77-hBCMA 10B5 BCMA expressing transfectant cells were stained with either murine anti BCMA antibodies (solid histogram) or murine IgG2a isotype control (open histograms). Cells were analysed by FACS to detect antibody bound to the cells.

Figure 5:
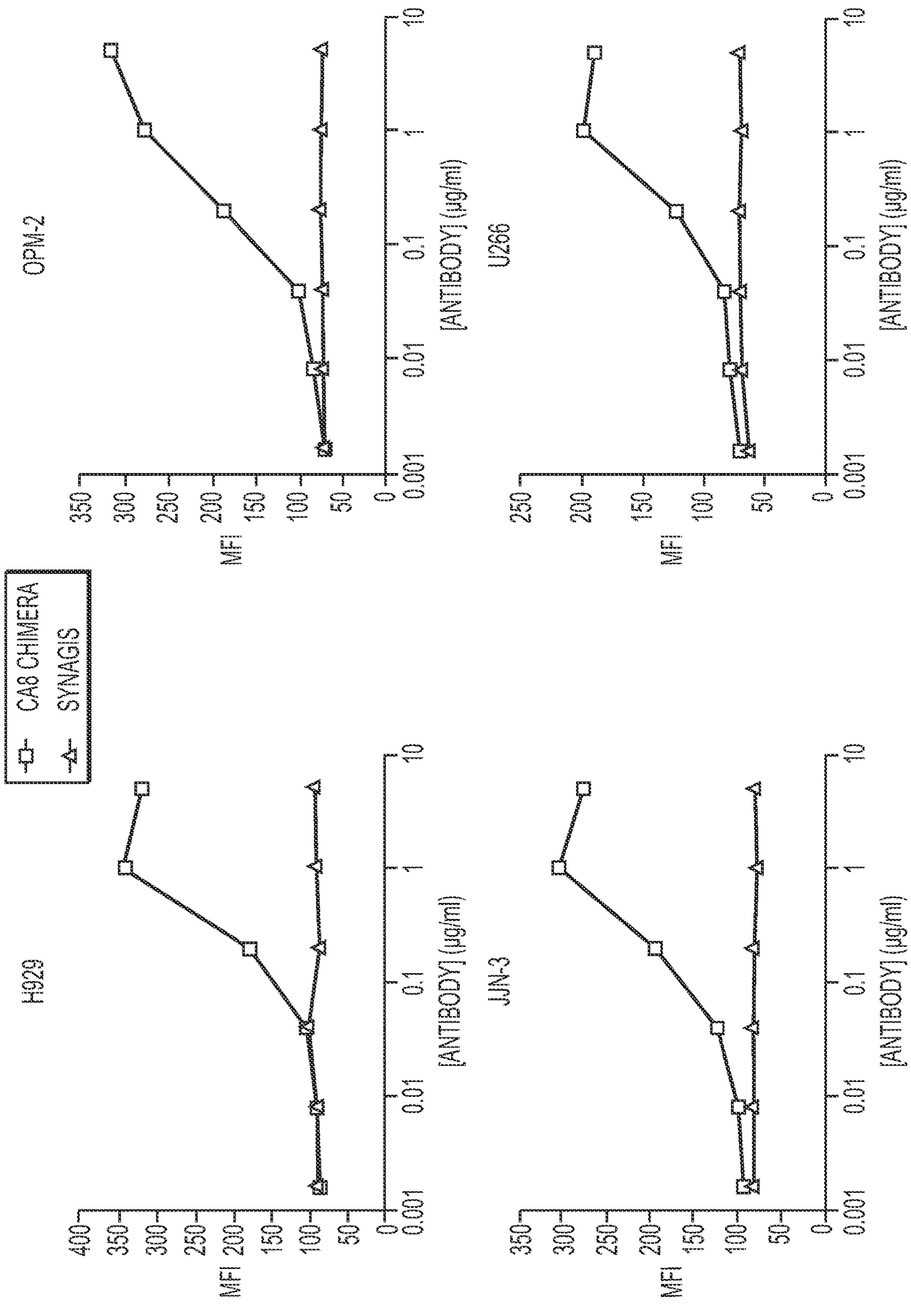

FIG. 5: Cell binding assay—Figure showing binding of chimeric CA8 to a panel of multiple myeloma cell lines as determined by FACS. Binding to H929, OPM-2, JJN-3 and U266 was tested by flow cytometry and mean fluorescence intensity (MFI) values measured to determine binding. Synagis was used as an irrelevant isotype control.

Figure 6A:
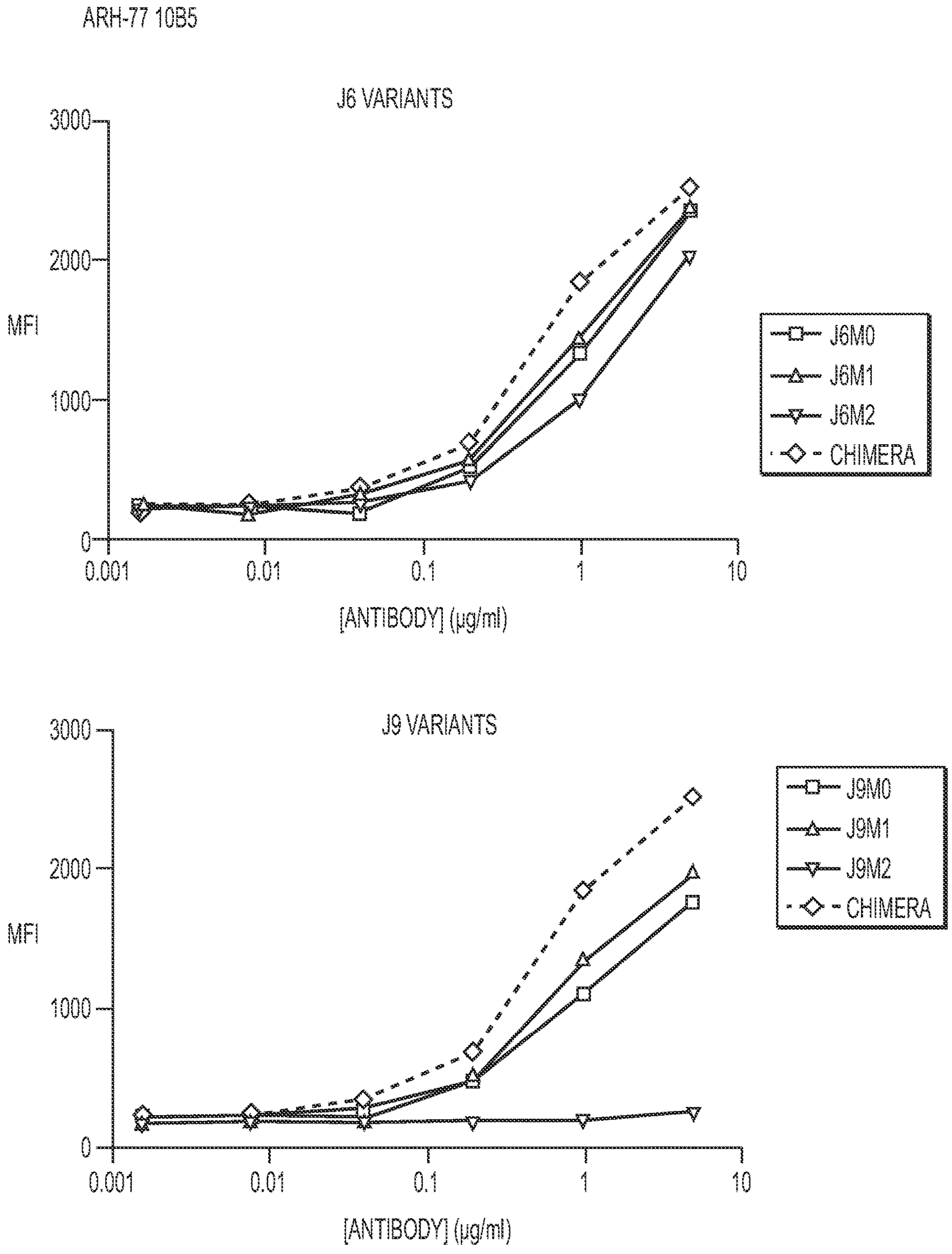
Figure 6B:
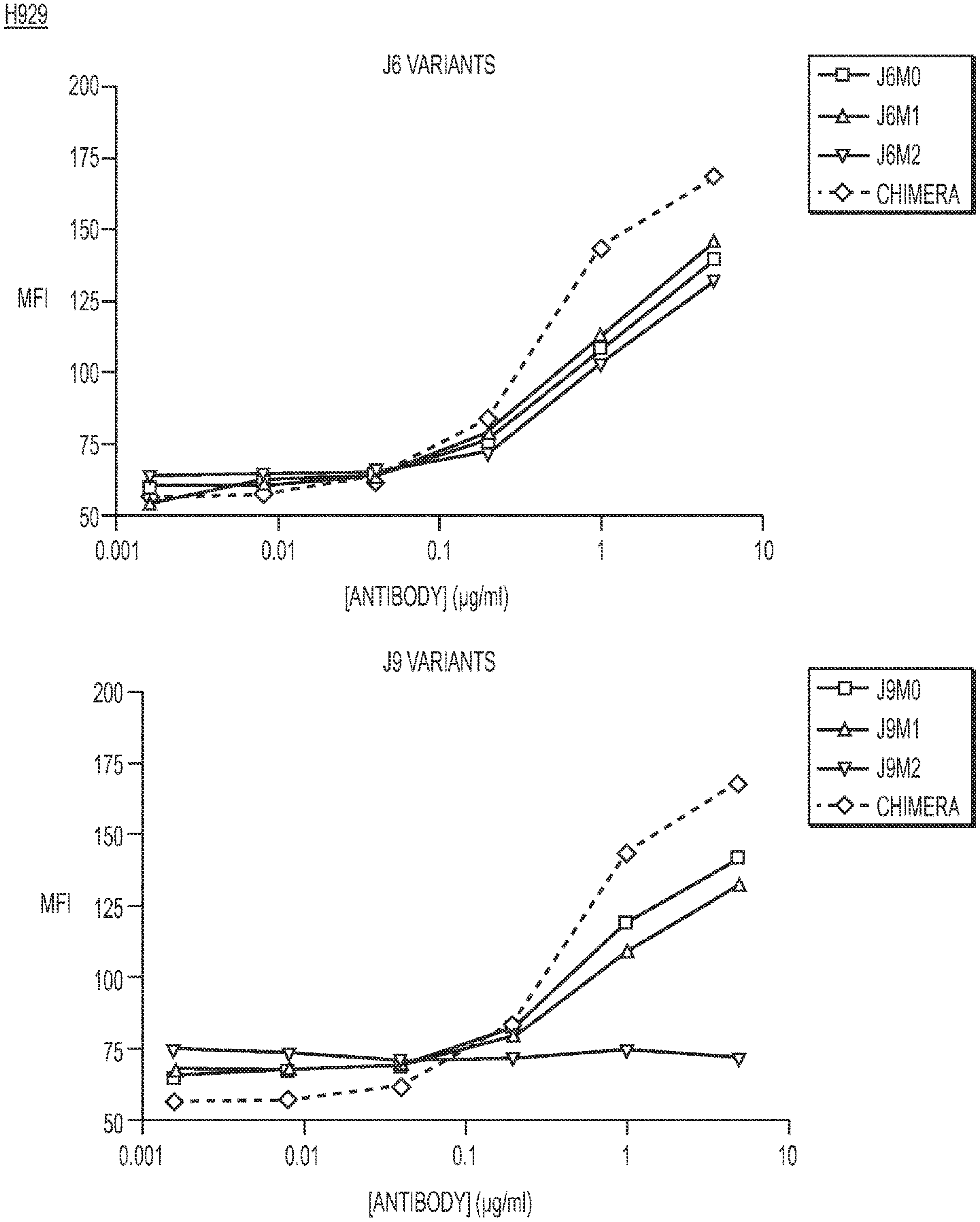

FIG. 6A and FIG. 6B: Cell binding assay—FIG. 6A showing binding curves of humanised CA8 variants to BCMA transfected ARH77 cells; and FIG. 6B showing multiple myeloma H929 cells as determined by FACS. Humanised variants J6M0, J6M1, J6M2, J9M0, J9M1 and J9M2 were tested by flow cytometry and mean fluorescence intensity (MFI) values measured to determine binding compared to the CA8 chimera.

Figure 7A:
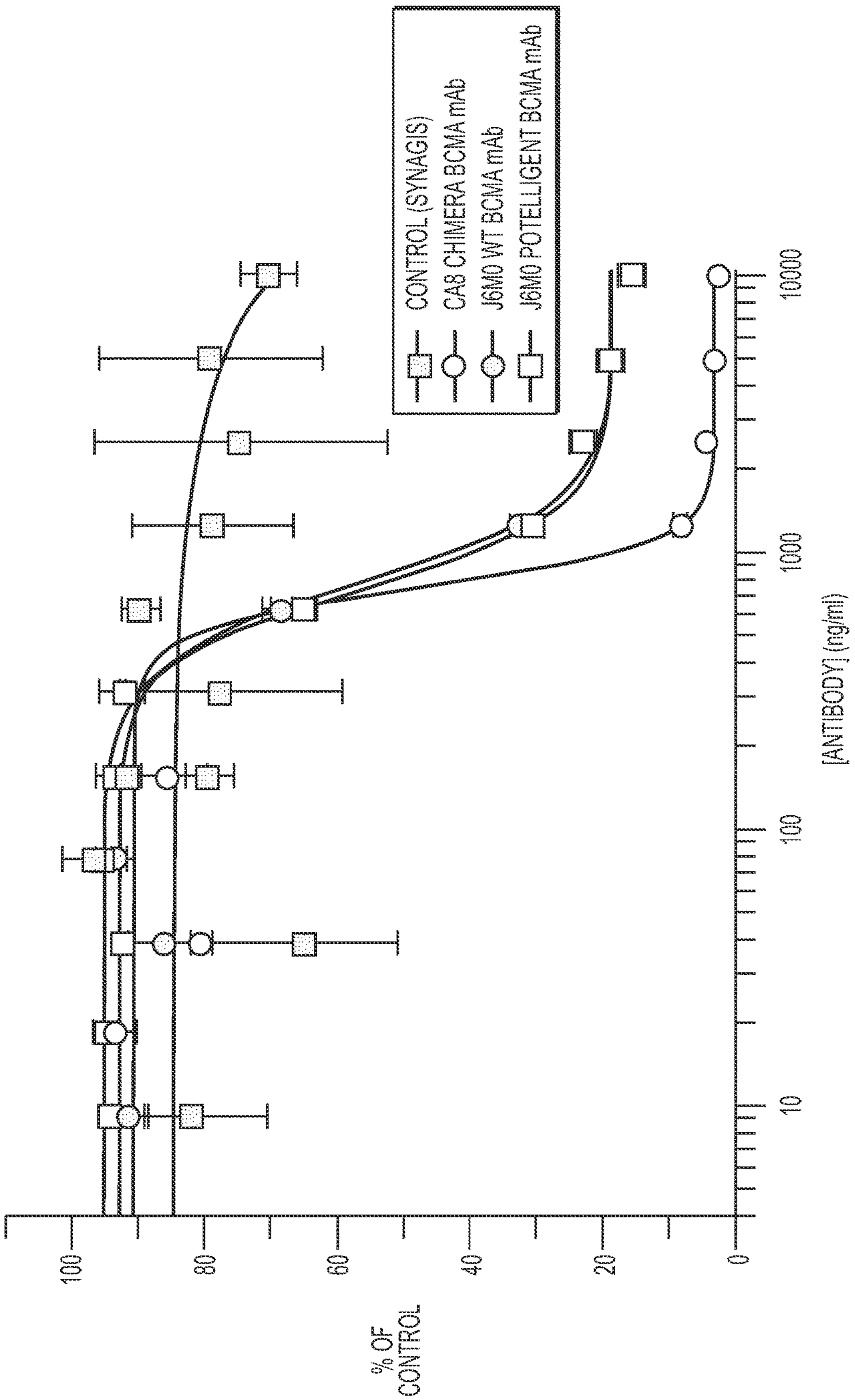
Figure 7B:
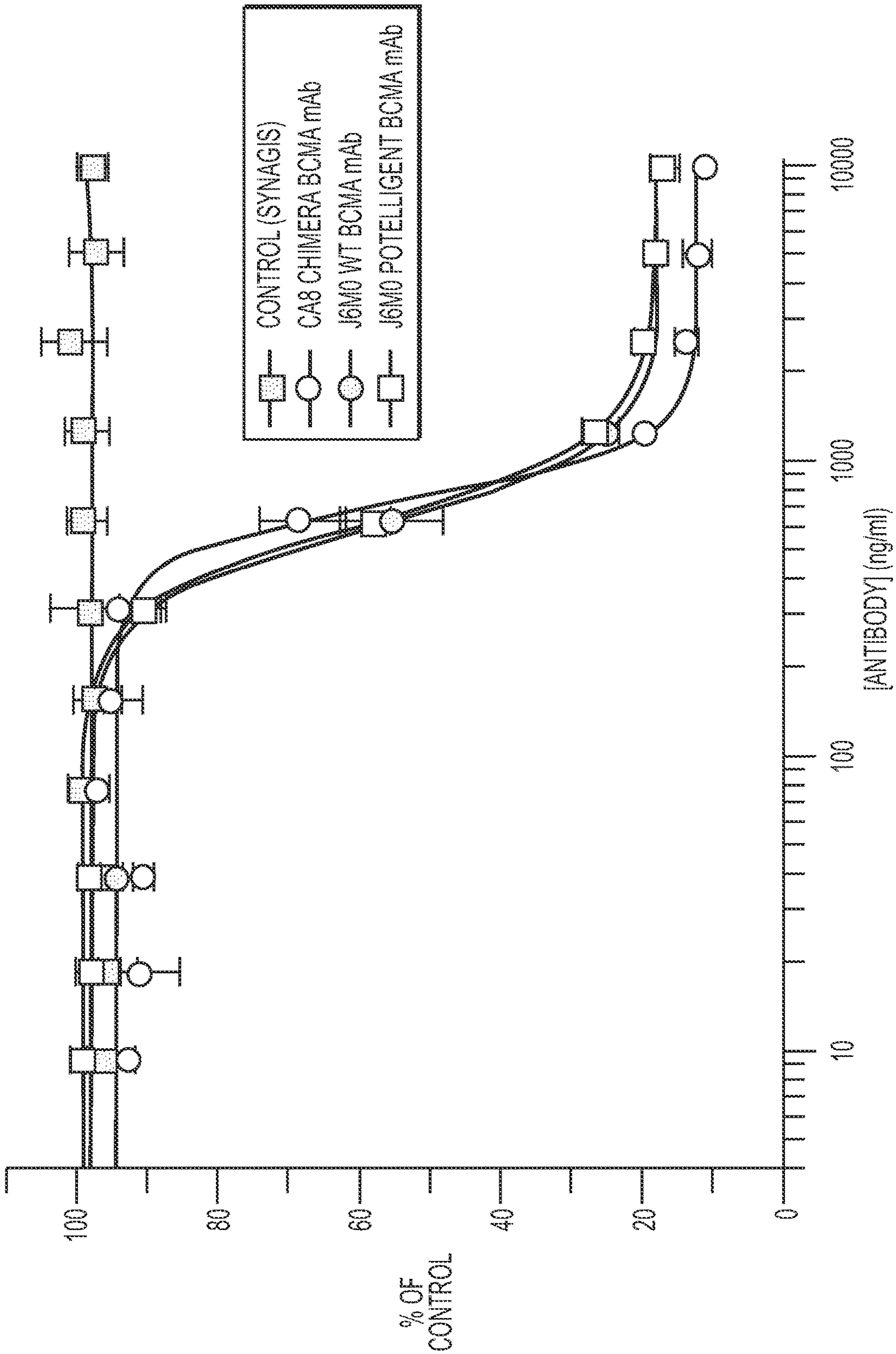
Figure 7C:
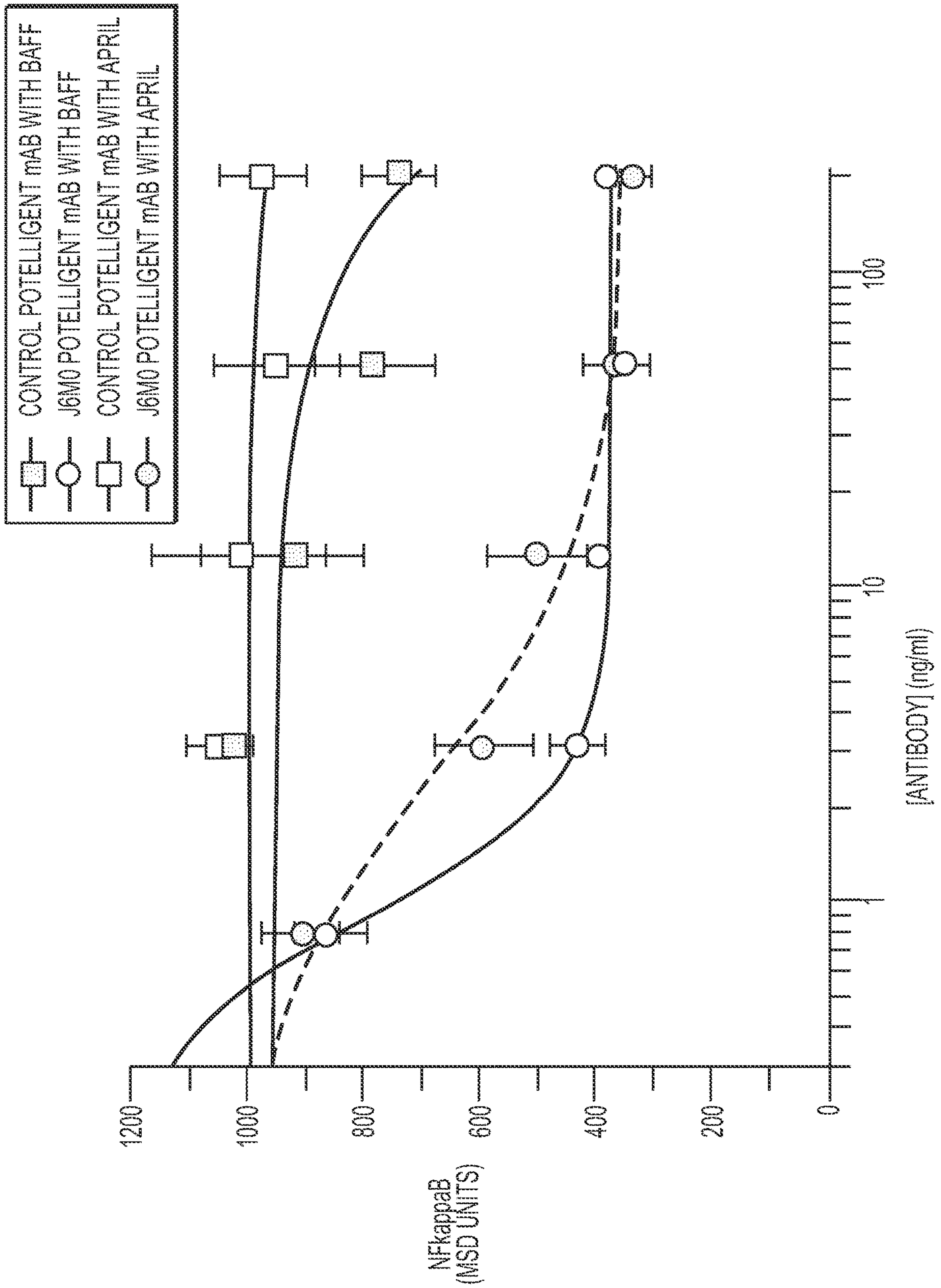

FIG. 7A, FIG. 7B, and FIG. 7C: Ligand neutralisation assays—FIG. 7A and FIG. 7B showing the ability of CA8 and J6M0 to neutralise binding of recombinant BAFF (FIG. 7A) or APRIL (FIG. 7B) to recombinant BCMA coated on an ELISA plate. OD values were used to calculate the antibody mediated inhibition of the maximal signal achieved by the relevant ligand alone binding to recombinant BCMA. Data is reported as percentage inhibition of the maximal signal. Antibodies tested were chimeric CA8 and humanised CA8 version J6M0 in both wild type and afucosylated (Potelligent) form.

FIG. 7C showing the ability of J6M0 BCMA antibody in inhibition of BAFF or APRIL induced phosphorylation of NFKappaB in H929 cells. H-929 cells were washed 3 times to remove any sBCMA and resuspended in serum free medium. J6M0 potelligent antibody was added to a 96 well plate to give a final well concentrations up to 100 ug/ml along with BAFF or APRIL ligand to give a final well concentration of 0.6 or 0.2 ug/ml respectively. H-929 cells were then plated at 7.5×104cells/well in serum free medium. 30 minutes later the cells were lysed and phosphorylated NFkappaB levels measured using a MSD pNFkappaB assay. MSD reader 502819.This data was from one independently generated experiments. Each data point is the mean/sd of two replicates.

Figure 8A:
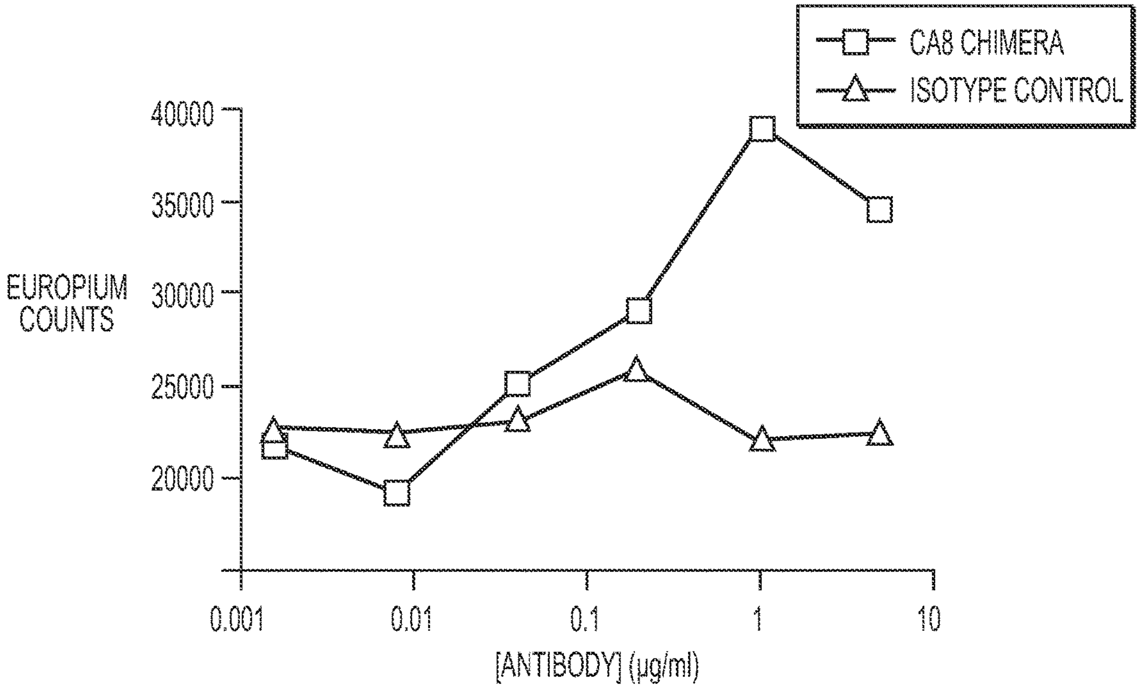
Figure 8B:
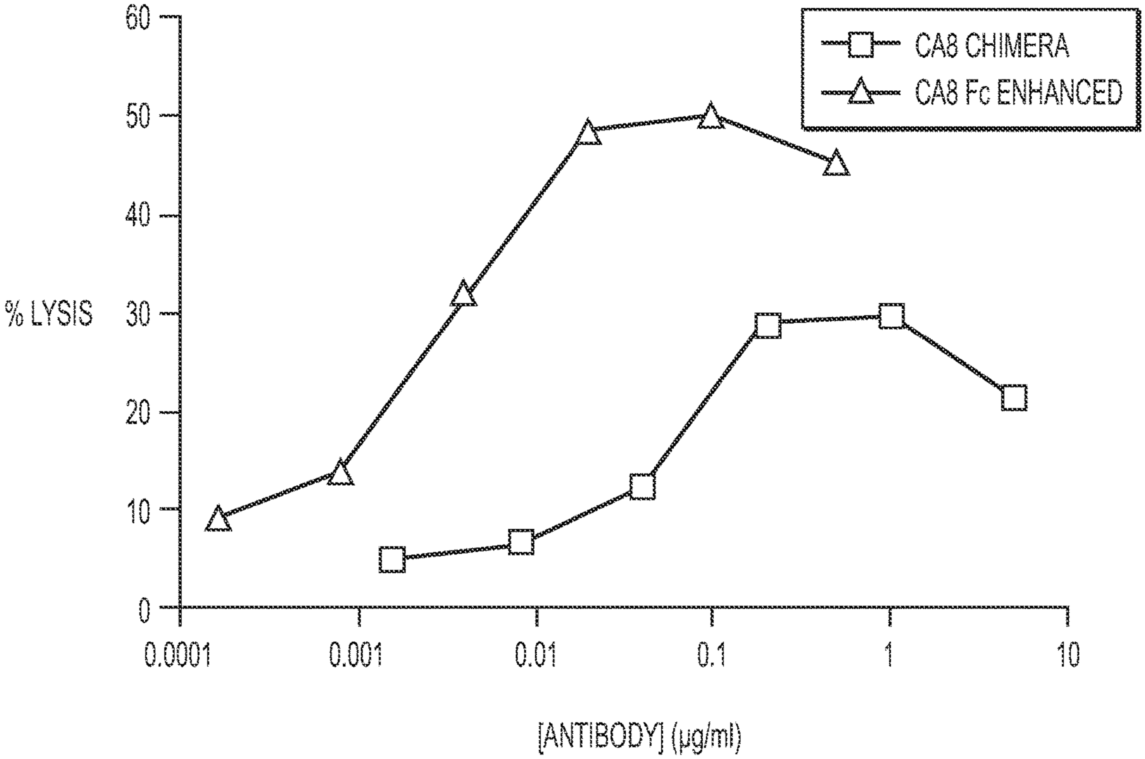

FIG. 8A and FIG. 8B: ADCC assay—Figures showing ADCC activity of chimeric CA8 and defucosylated (Fc enhanced) CA8 with target cells expressing BCMA.

Human NK cells were incubated with europium labelled ARH77 10B5 BCMA transfected target cells in the presence of varying concentrations of antibody. Europium release from the target cells was measured and specific lysis calculated. FIG. 8A: ADCC dose response curves of chimeric CA8 compared to isotype control. FIG. 8B: ADCC dose response curves for chimeric CA8 and defucosylated chimeric CA8 (Fc enhanced), against the BCMA expressing cell line ARH77 10B5.

Figure 9:
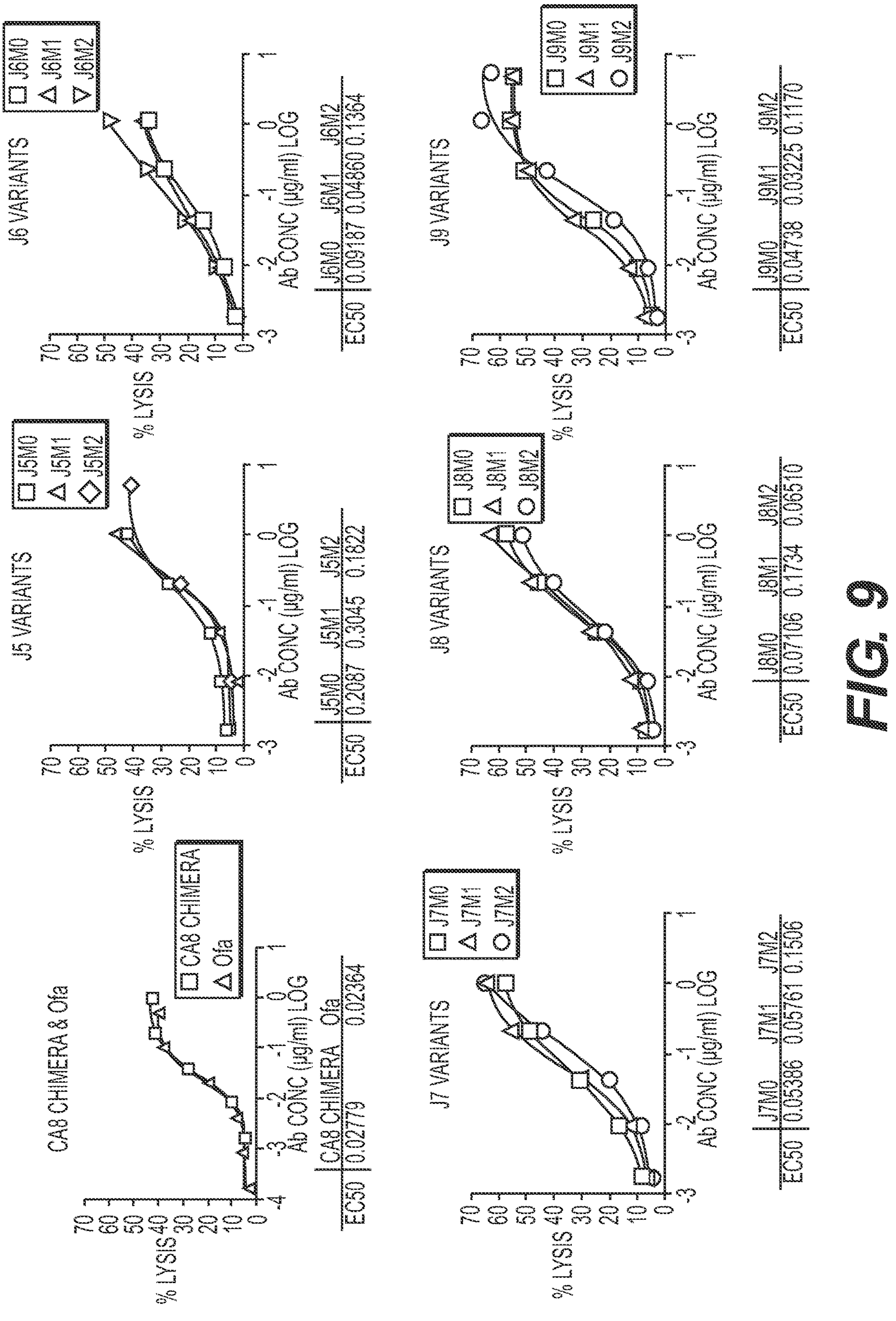

FIG. 9: ADCC assay—Figure showing ADCC assay on CA8 humanised antibodies using ARH77 BCMA expressing target cells.

Human PBMC were incubated with europium labelled ARH77 BCMA transfected target cells in the presence of a range of concentrations of the J5, J6, J7, J8 or J9 series of humanised CA8 antibodies. Europium release from the target cells was measured and specific lysis calculated. EC50 values are shown in ug/ml.

Figure 10:
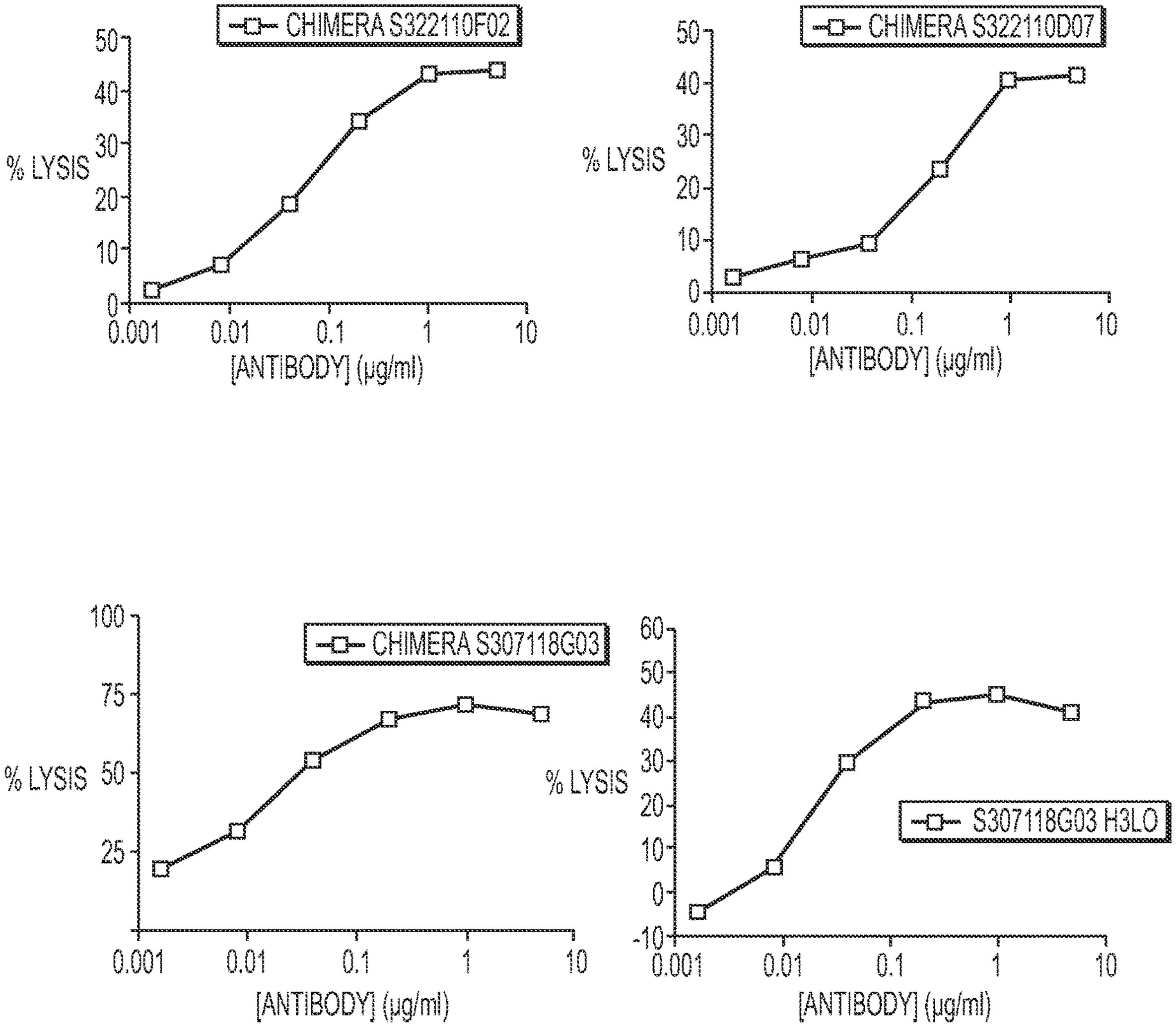

FIG. 10: ADCC assay—Figure showing ADCC activity of chimeric S322110F02 chimeric S322110D07, chimeric S307118G03 and humanised S307118G03 H3L0 against ARH7710B5 target cells with purified NK cells as effector cells. Human NK target cells were incubated with europium labelled ARH77 10B5 BCMA transfected target cells in the presence of varying concentrations of antibody. Europium release from the target cells was measured and specific lysis calculated.

Figure 11:
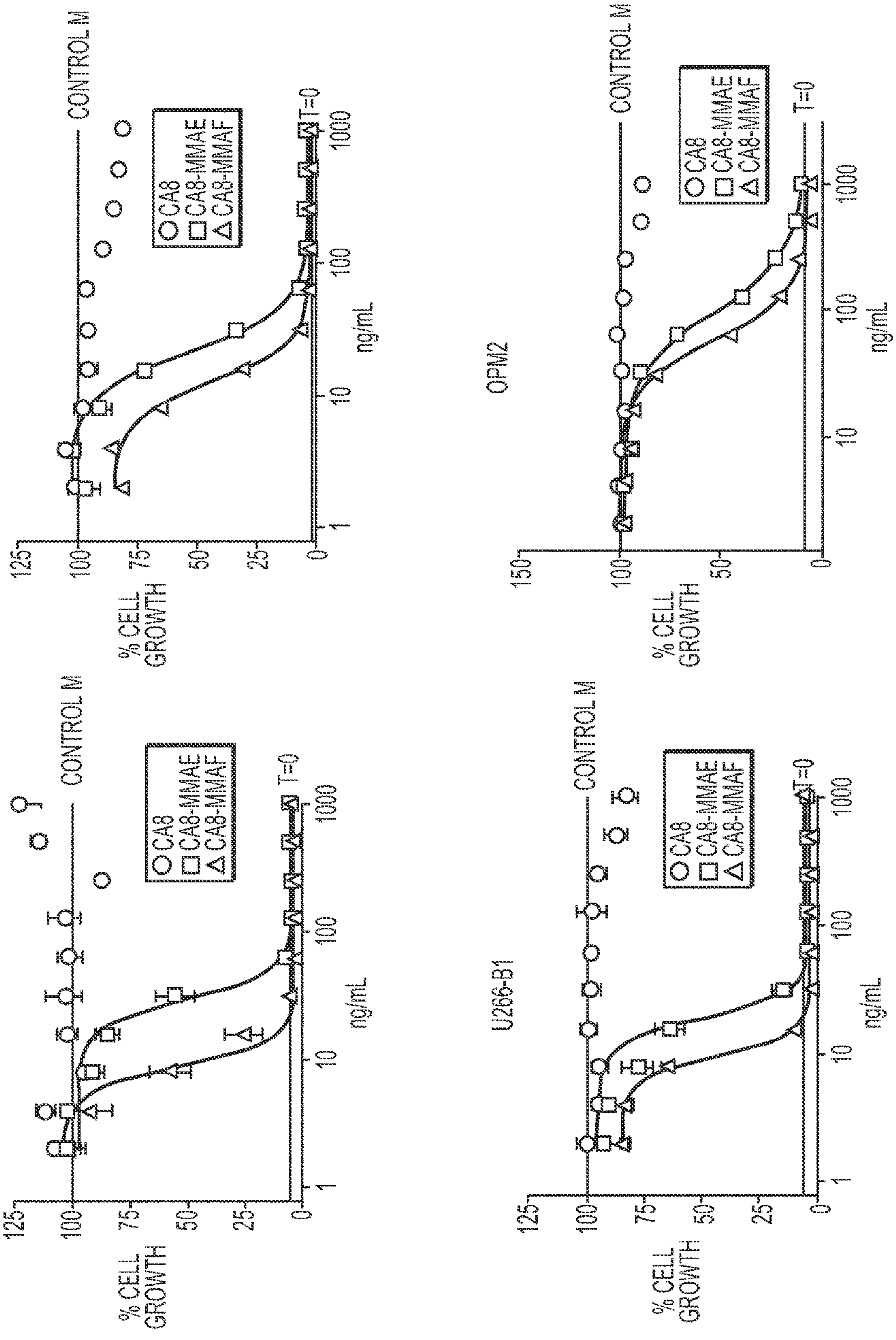

FIG. 11: Viability assay dose response curves—Figure showing dose response curves in a cell viability assay for chimeric CA8 antibody, chimeric CA8-vcMMAE and chimeric CA8-mcMMAF antibody-drug conjugates in human multiple myeloma cell lines NCI-H929, U266-B1, JJN3 and OPM2. Antibody was added to the cells and the number of viable cells after 96 hours measured using CelltiterGlo.Data points represent the mean of triplicate CellTiterGlo measurements. Error bars represent standard error.

Figure 12A:
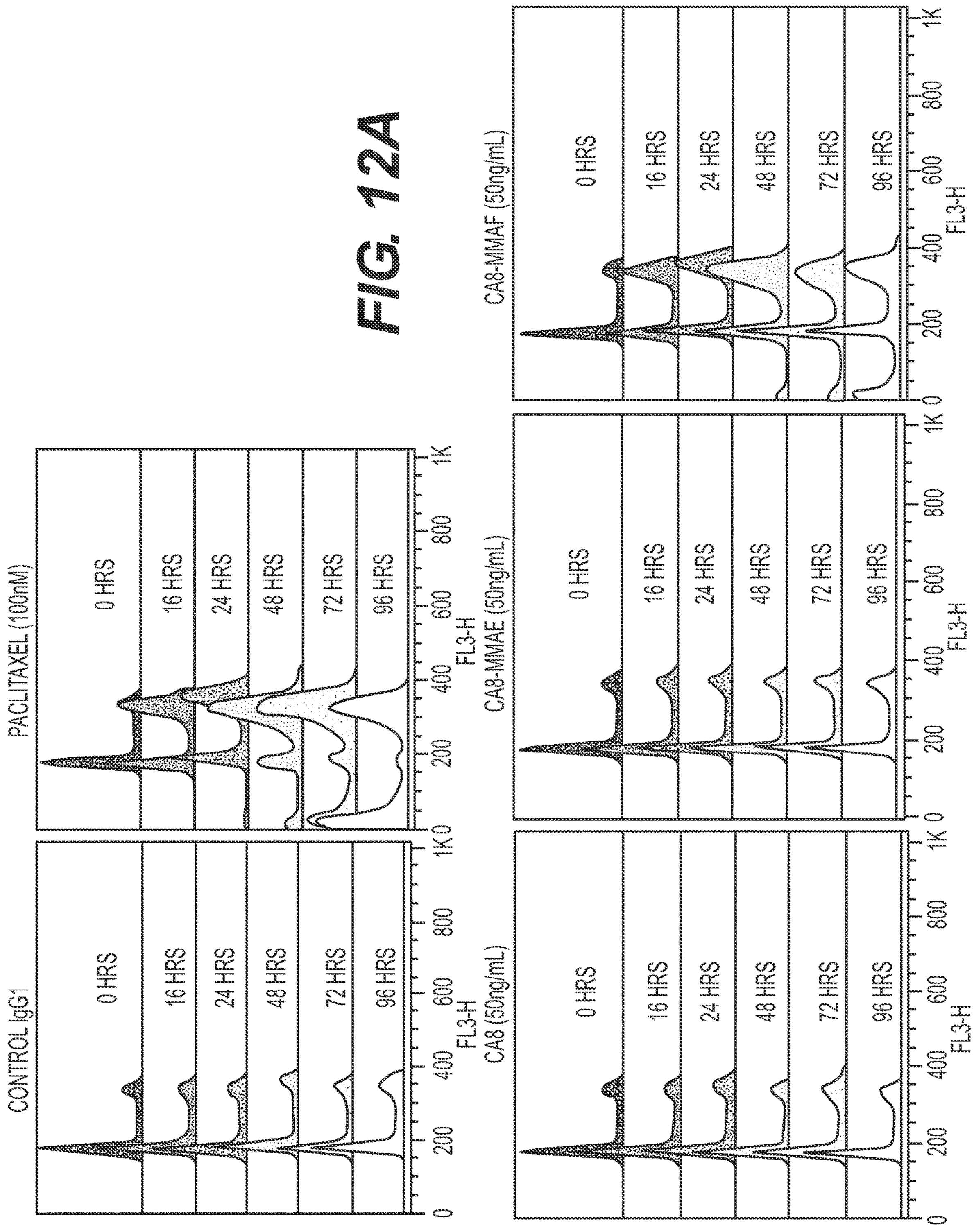
Figure 12B:
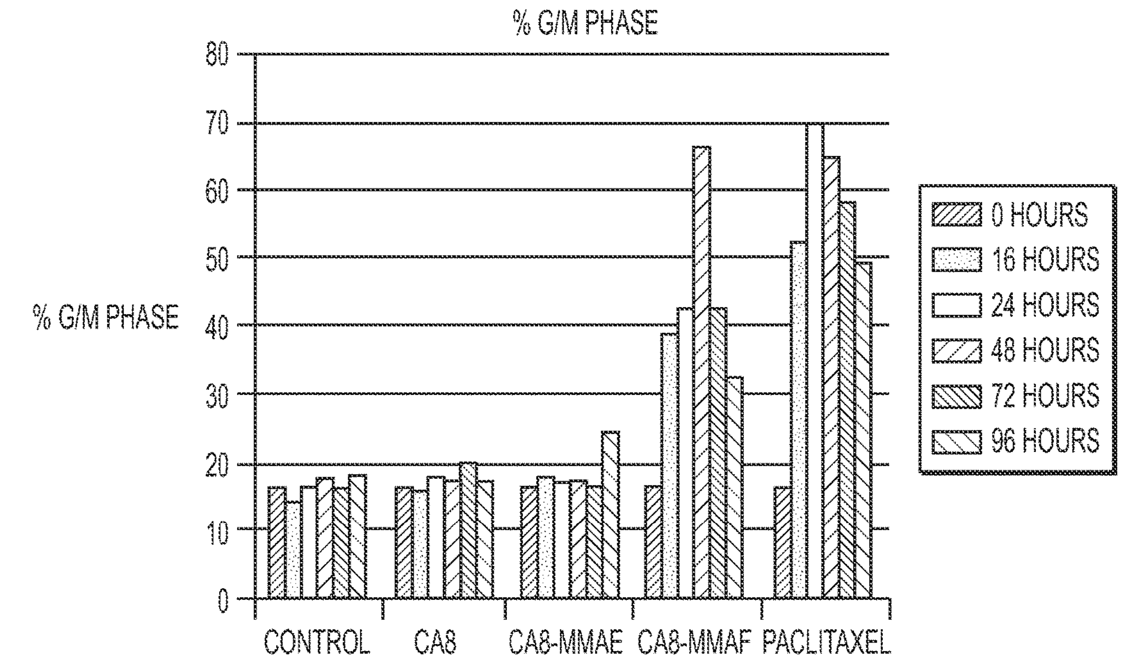
Figure 12C:
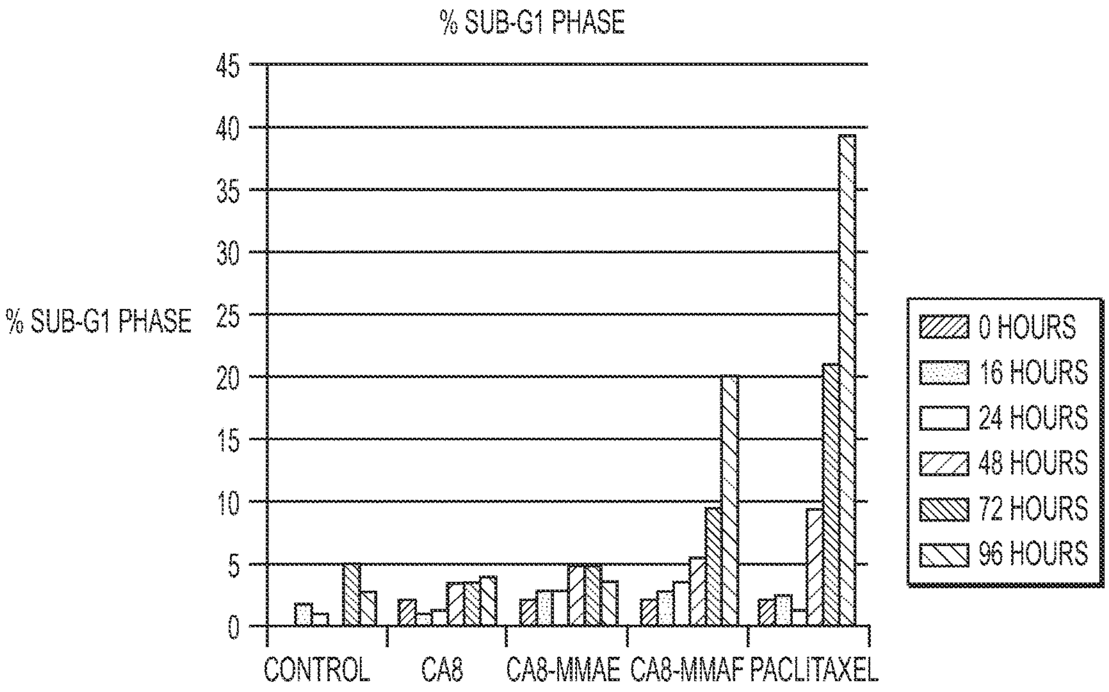

FIG. 12A, FIG. 12B and FIG. 12C: Impact of CA8 chimeric antibody on cell cycle. FIG. 12A: Cell cycle histograms of NCI-H929 cells treated with unconjugated chimeric CA8, chimeric CA8-vcMMAE ADC or chimeric CA8-mcMMAF ADC at 50 ng/mL for the timepoints indicated. Pactitaxel (100 nM) was used as a positive control for G2/M cell cycle arrest and cell death. Control human IgG1 was used as a negative control. Cell cycle analysis was carried out at the times shown on the graphs. FIG. 12B: Quantification of the 4N DNA cell population indicative of G2/M arrest and FIG. 12C: sub-2N DNA cell population indicative of cell death for each of the treatments indicated. Cells were seeded in 12-well plates ($2\times10^5$ cells per well in 1 mL of RPMI+10% FBS). Antibody or ADC was added 6 hours after cell seeding.

Figure 13A:
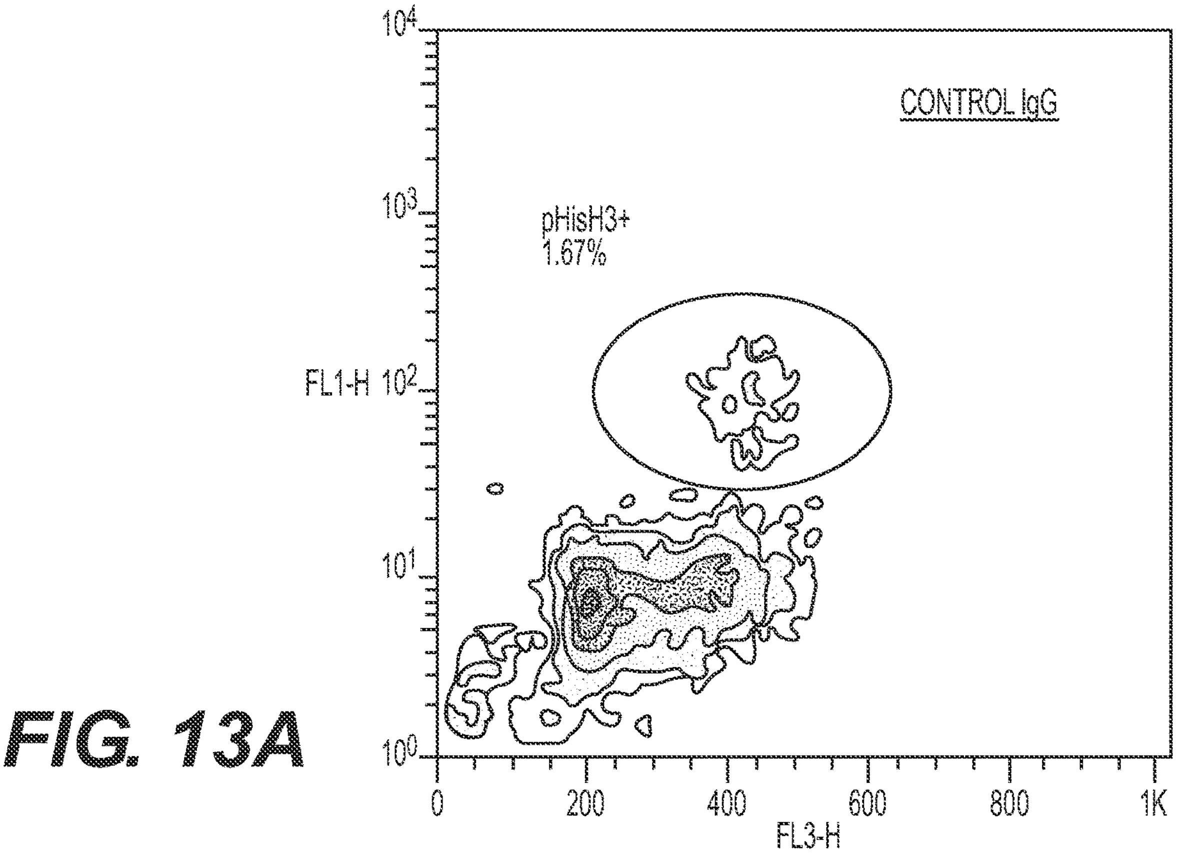
Figure 13B:
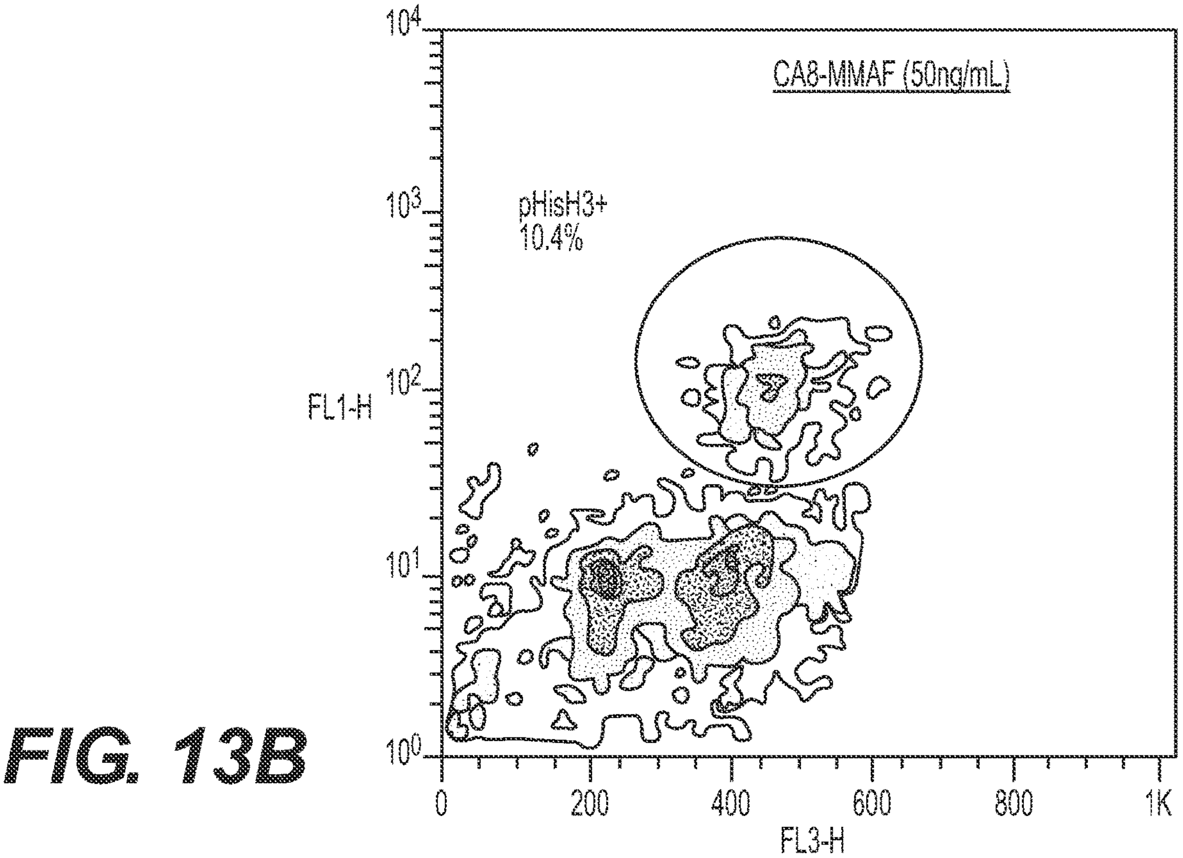

FIG. 13A, and FIG. 13B: Impact of chimeric CA8 on phospho-histone H3. Chimeric CA8 ADC treatment results in increased phospho-Histone H3 staining of NCI-H929 cells.

FIG. 13A and FIG. 13B: Dot plots of cells stained with propidium iodide to measure DNA content (FL3-H) x-axis and anti-phospho-Histone H3 (Thr11) antibody (FL1-H) y-axis after treatment with either Control IgG FIG. 13A or chimeric CA8-mcMMAF FIG. 13B. Results show quantification of phospho-Histone H3 positive NCI-H929 cells after a 48 hour treatment with the indicated concentrations of chimeric CA8 ADCs. Pactitaxel (100 nM) was used as a positive control for mitotic arrest and control chimera IgG1 was used as a negative control. Cells were seeded in 12-well plates ($2\times10^5$ cells per well in 1 mL of RPMI+10% FBS). Antibody or ADC was added 6 hours after cell seeding.

Figure 14A:
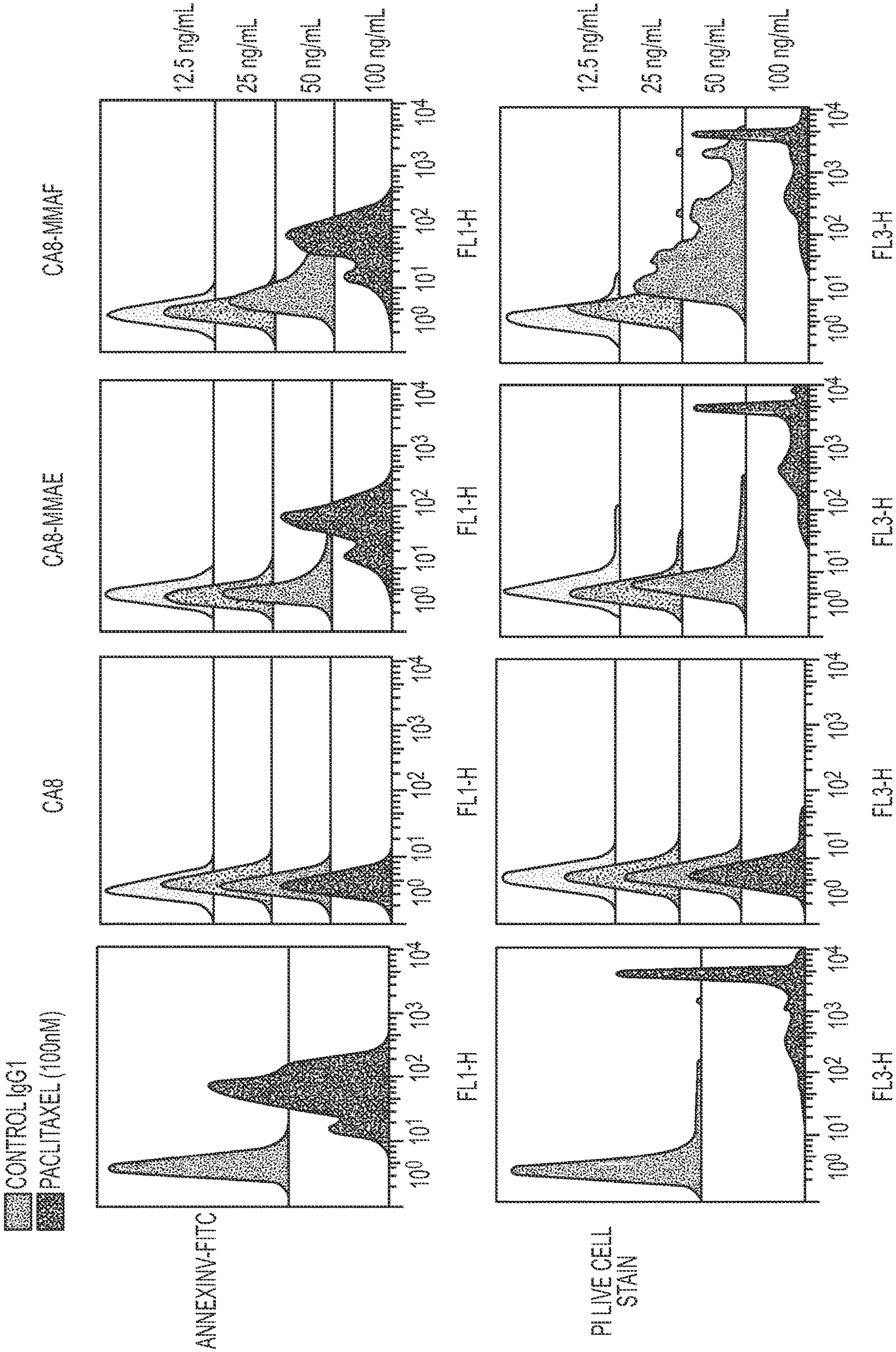
Figure 14B:
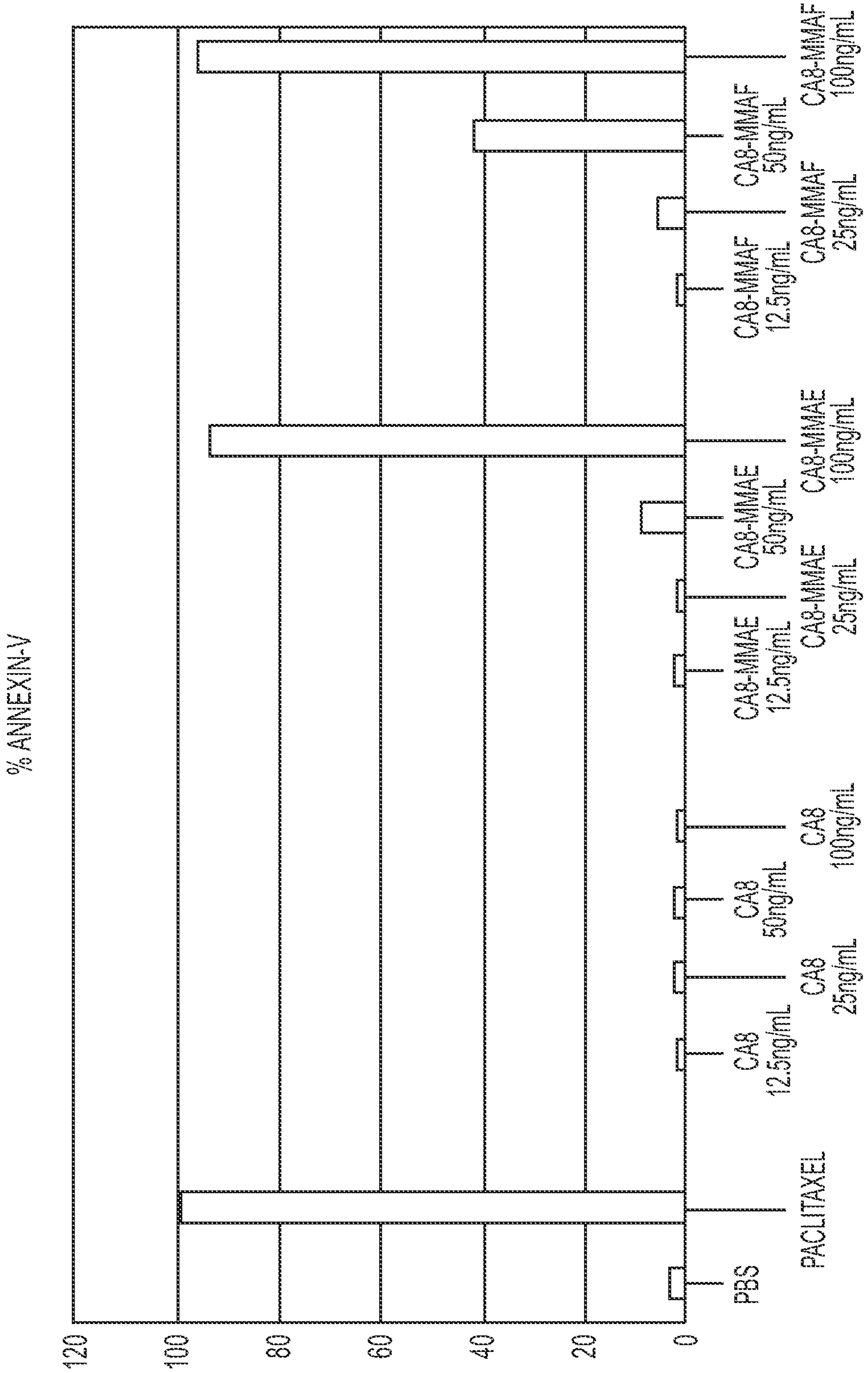

FIG. 14A, and FIG. 14B: Impact of chimeric CA8 on Annexin-V.

Chimeric CA8 ADC treatment results in increased Annexin-V staining of NCI-H929 cells. FIG. 14A showing histograms of Annexin-V-FITC (FL1-H; top panels) and Live cell propidium iodide staining (FL3-H; bottom panels) after treatment with increasing concentrations of chimeric CA8 ADCs. FIG. 14B of Annexin-V positive NCI-H929 cells after a 96 hour treatment with the indicated showing quantification concentrations of chimeric CA8 ADCs. Pactitaxel (100 nM) was used as a positive control for apoptosis and control chimera IgG1 was used as a negative control. Cells were seeded in 12-well plates ($2\times10^5$ cells per well in 1 mL of RPMI+10% FBS). Antibody or ADC was added 6 hours after cell seeding.

Figure 15:
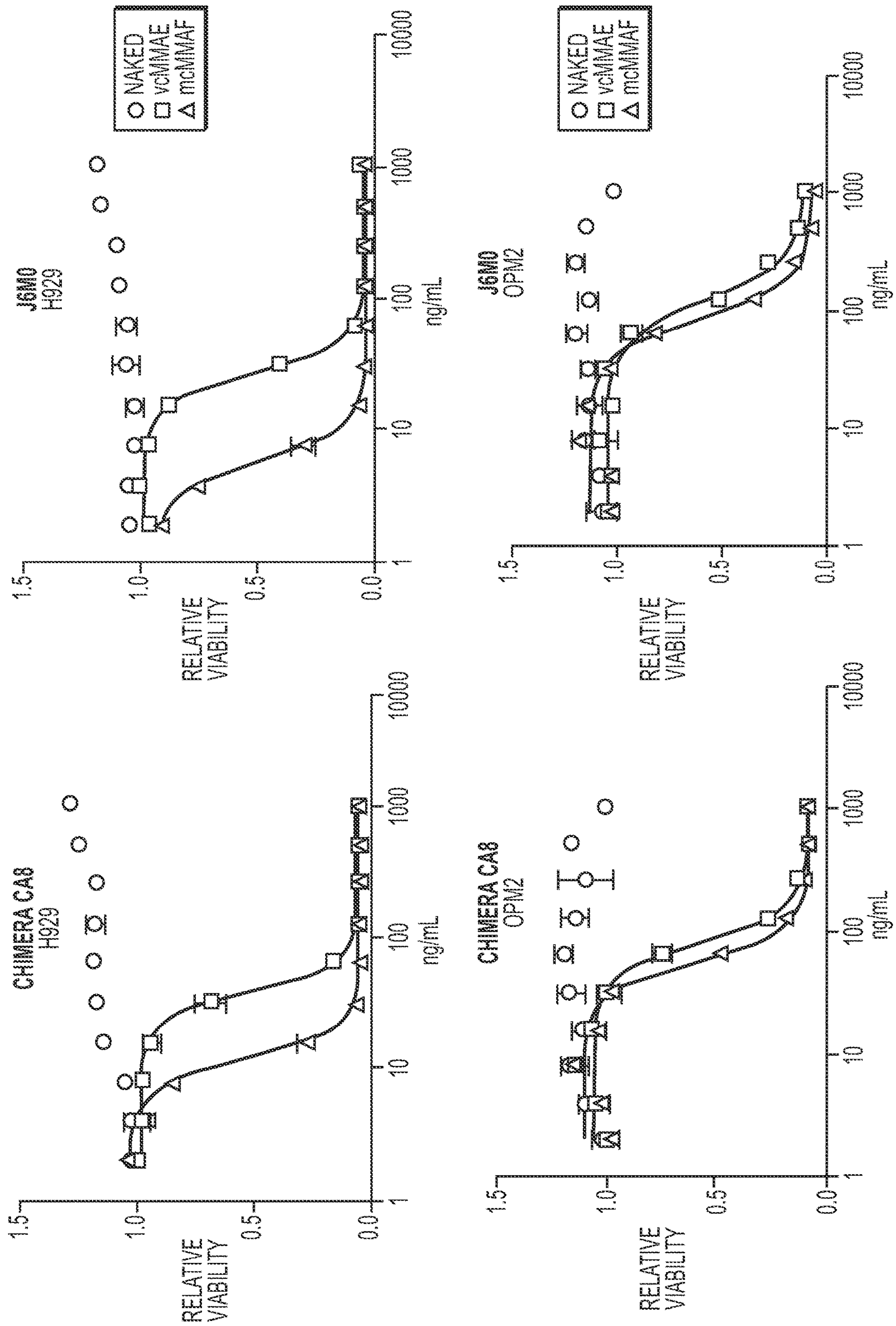

FIG. 15: Viability assay dose response curves—Figure showing dose response curves for the unconjugated (Naked) and vcMMAE and mcMMAF antibody-drug conjugates of chimeric CA8 or humanized J6M0 antibodies. Antibody drug conjugates were tested against human multiple myeloma cell lines NCI-H929 and OPM2.

Figure 16:
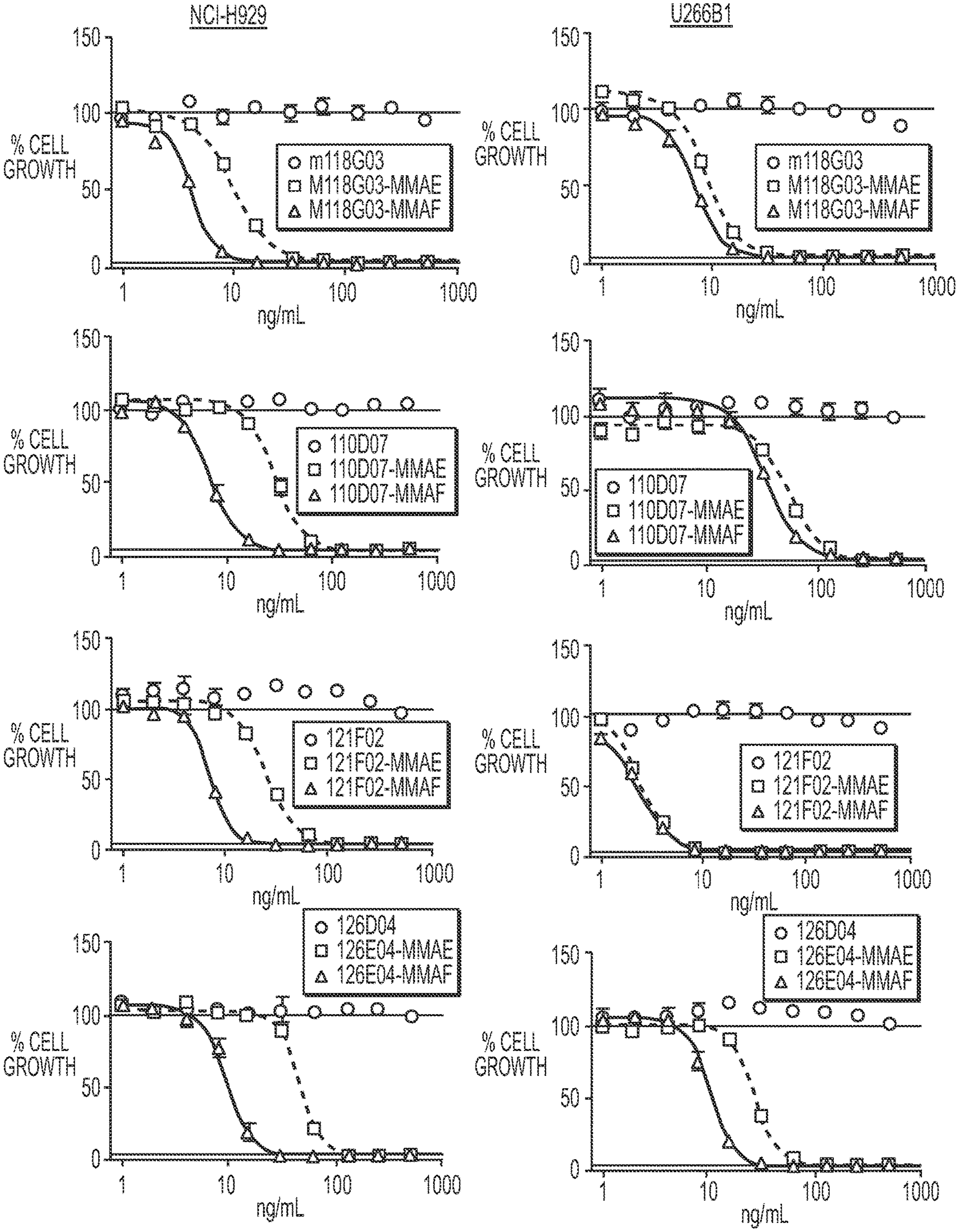

FIG. 16: Viability assay dose response curves—Figure showing dose response curves for the unconjugated antibodies, vcMMAE and mcMMAF antibody-drug conjugates of murine anti-BCMA antibodies S332121F02, S322110D07, S332126E04 and S307118G03 in human multiple myeloma cell lines NCI-H929 and U266-B1.

Figure 17:
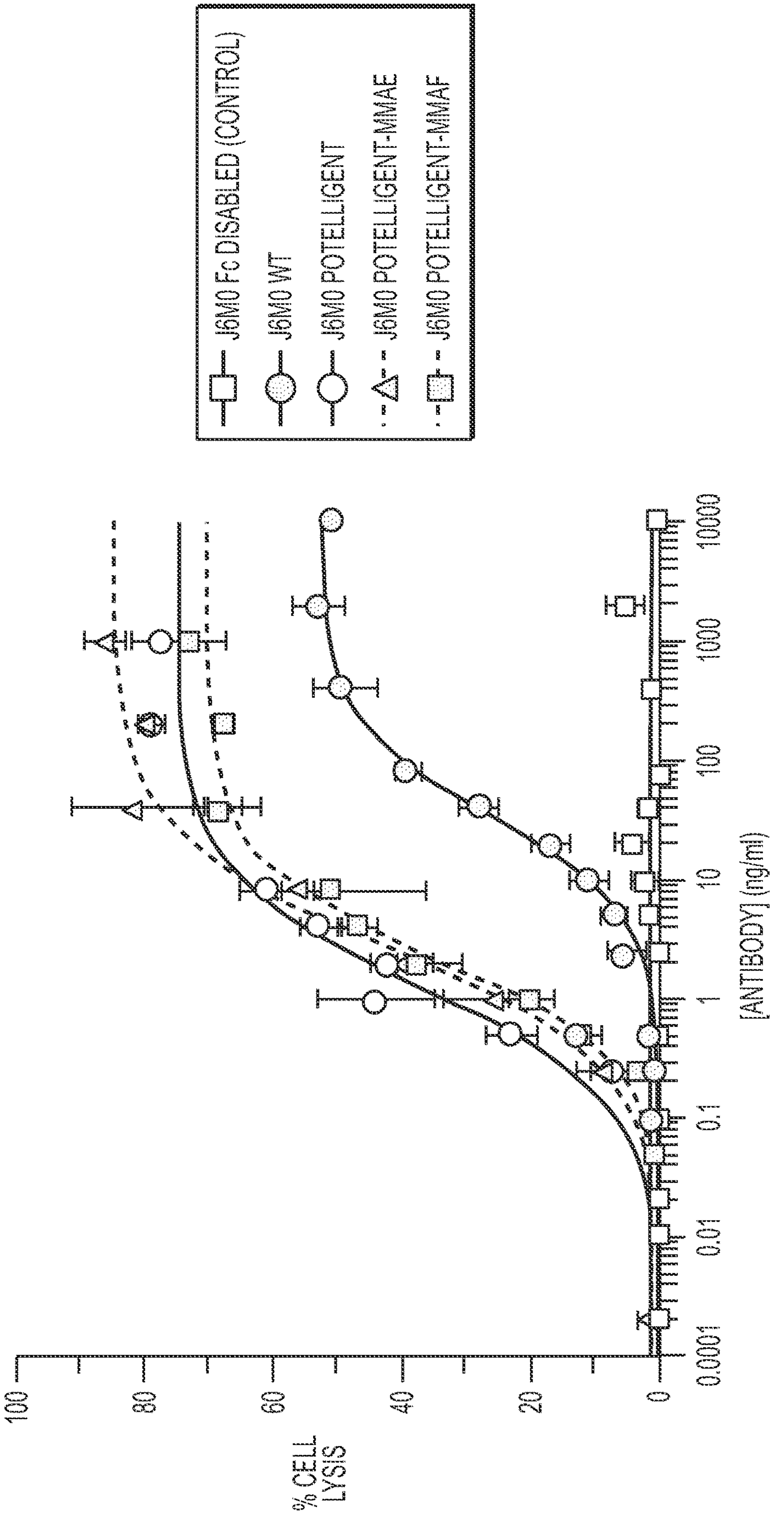

FIG. 17: ADCC activity of ADC J6M0 molecules—Figure showing ADCC assay on J6M0 antibodies using ARH77 BCMA expressing target cells. Human PBMC were incubated with europium labelled ARH77 BCMA transfected target cells in the presence of a range of concentrations of J6M0 WT and potelligent BCMA antibodies conjugated to MMAE, MMAF, or unconjugated Europium release was monitored on the Victor 2 1420 multilabel reader.

Figure 18:
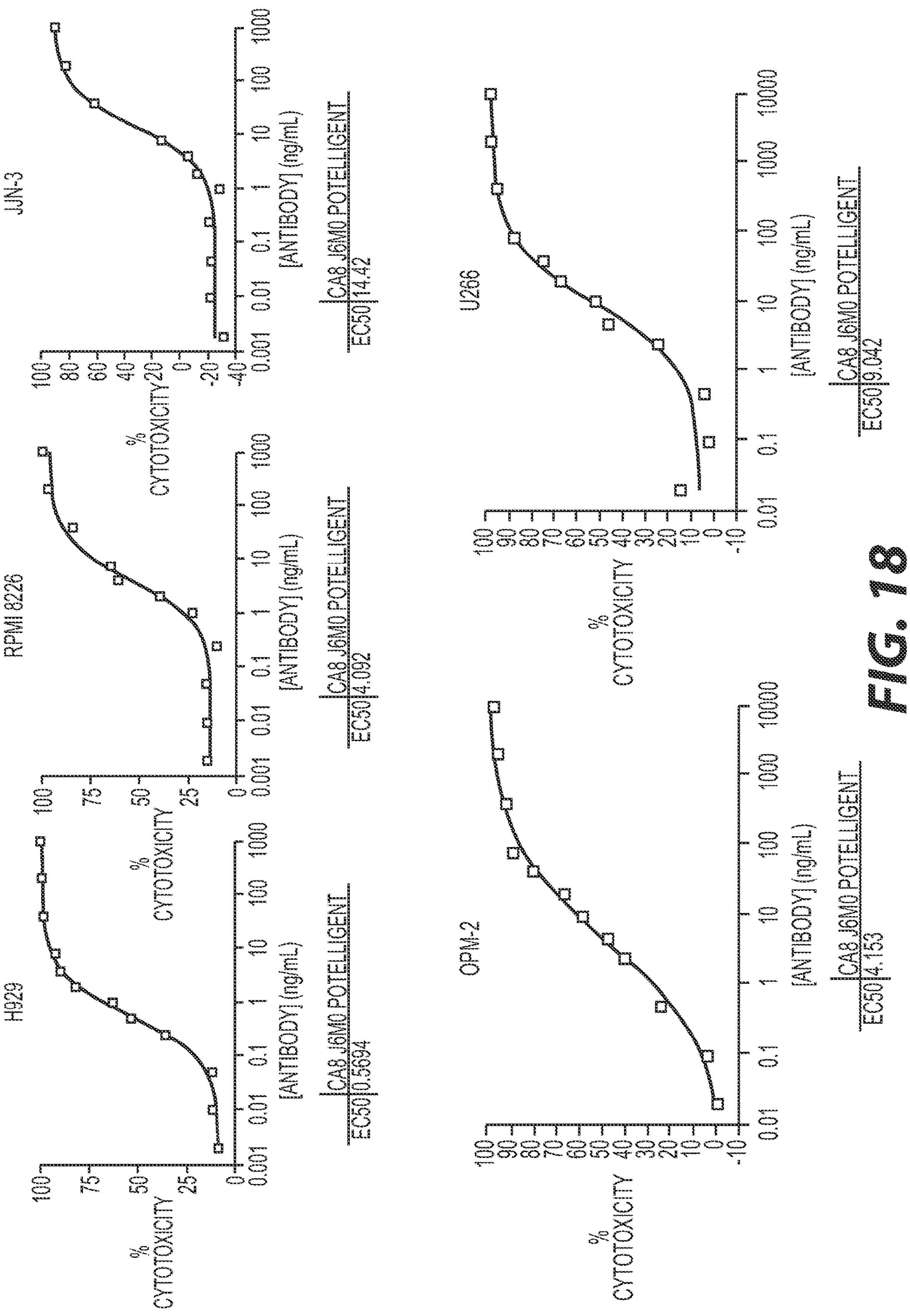

FIG. 18: ADCC dose response curves of CA8 J6M0 Potelligent against a panel of 5 multiple myeloma lines—Human PBMC were incubated with multiple myeloma target cells in the presence of varying concentrations of CA8 J6M0 potelligent antibody at an E:T ratio of 50:1 for 18 hours. The percentage of target cells remaining in the effecter plus target mixture was then measured by FACS using a fluorescently labelled anti-CD138 antibody to detect the target cells and the percent cytotoxicity calculated. Example dose response curves for CA8 J6M0 potelligent against the five multiple myeloma cell lines tested—H292, RPMI8226, JJN-3, OPM-2, and U266. Each data point is from a singlicate value.

Figure 19:
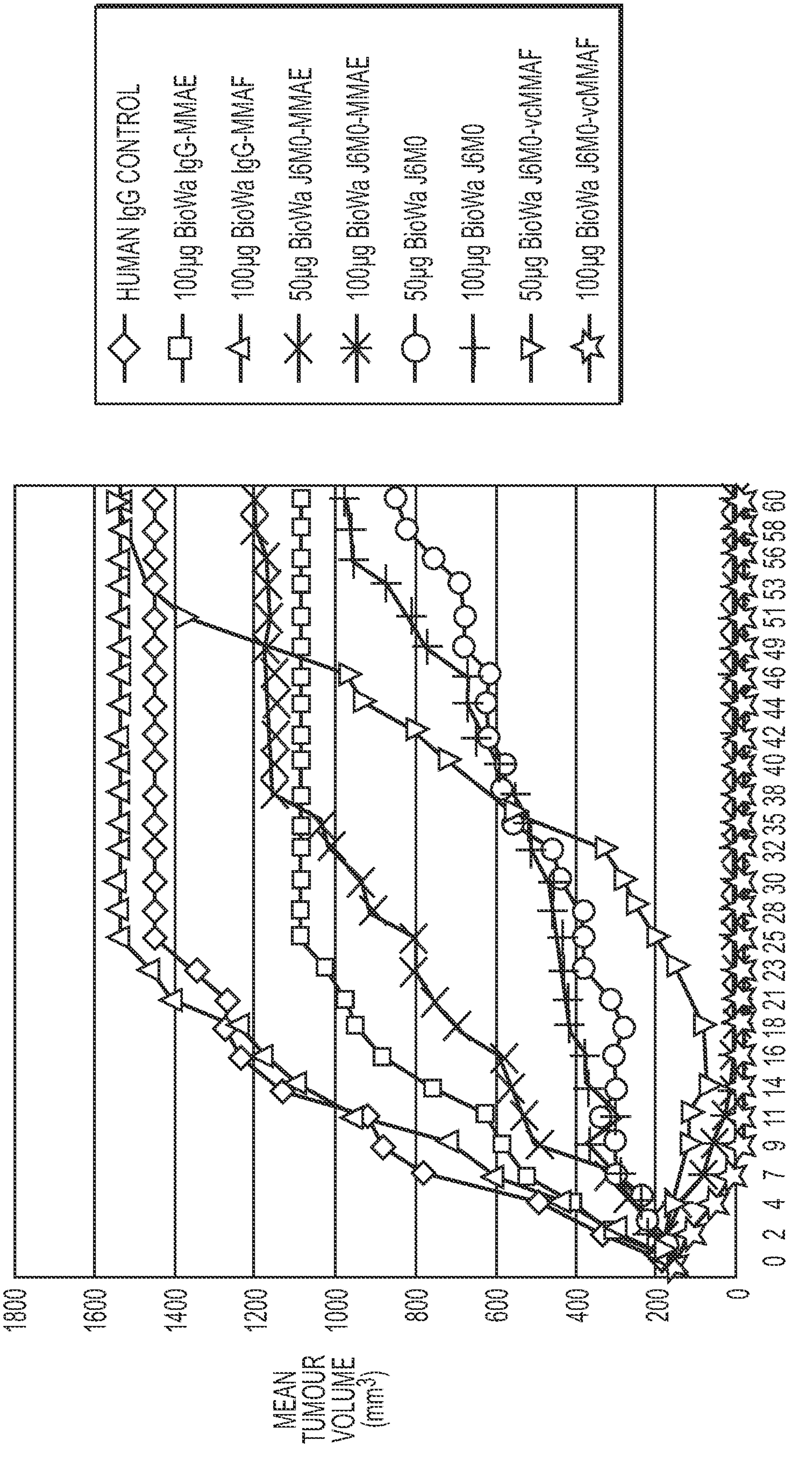
Figure 20:
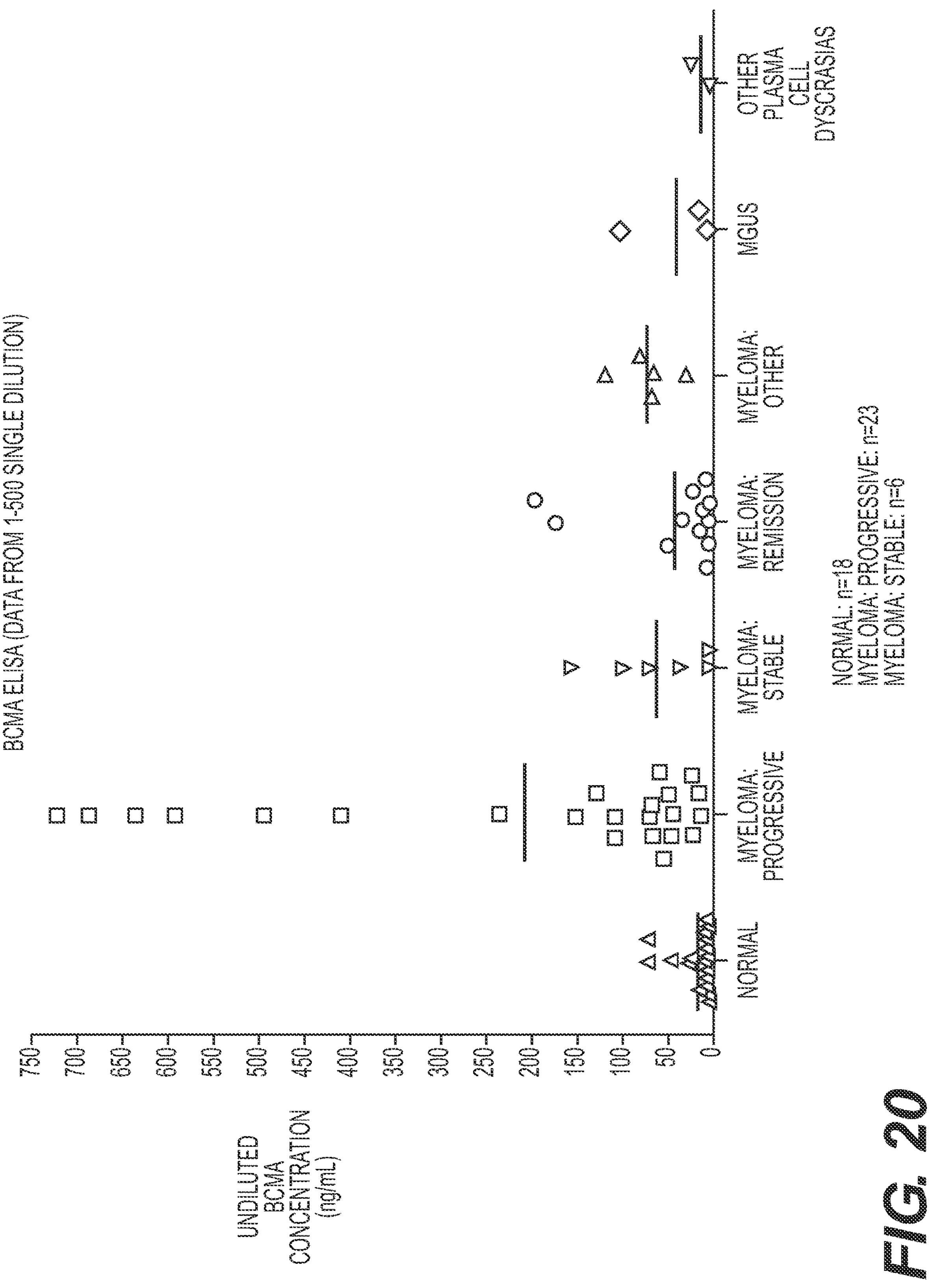

FIG. 19: Effect of dose escalation of J6M0 and drug conjugated J6M0 on the growth and establishment of NCI-H929 cells in CB.17 SCID mice. Calculated tumour volumes of NCI-H929 tumours in CB17 SCID mice following twice weekly intraperitoneal dosing of either 50 or 100 ug J6M0 anti-BCMA or IgG1 isotype control unconjugated, or conjugated to MMAE or MMAF for 2 weeks. Data points represent mean tumour volume of n=5 per group FIG. 20: Determination of soluble BCMA levels in serum from healthy volunteers and myeloma patients. Serum samples were collected from MM patient samples were from a variety of stages (progressive disease, remission, relapsed, newly diagnosed, and others). The samples shown in the figure are those from serum diluted 1/500 prior to the assay.

A Human BCMA/TNFRSF17 sandwich ELISA kit from R& D Systems which measures soluble human BCMA levels was used to detect BCMA following the standard protocol provided with the kit.

SUMMARY OF THE INVENTION

The present invention provides antigen binding proteins which bind to membrane bound targets and wherein the antigen binding protein is capable of internalisation. In a further embodiment there is provided an immunoconjugate comprising the antigen binding protein of the present invention and a cytotoxic agent. In a further embodiment the antigen binding protein has ADCC effector function for example the antigen binding protein has enhanced ADCC effector function.

The present invention provides antigen binding proteins which specifically bind to BCMA, for example antibodies which specifically bind to BCMA and which inhibit the binding of BAFF and/or APRIL to the BCMA receptor. The present invention also provides antigen binding proteins which specifically bind to BCMA and which inhibits the binding of BAFF and/or APRIL to BCMA wherein the antigen binding protein is capable of binding to FcγRIIIA or is capable of FcγRIIIA mediated effector function.

The antigen binding proteins of the present invention specifically bind to BCMA and inhibit the binding of BAFF and/or APRIL to BCMA wherein the antigen binding protein has enhanced binding to FcγRIIIA or has enhanced FcγRIIIA mediated effector function. In one embodiment the antigen binding protein is capable of internalisation.

In one aspect of the invention there is provided an antigen binding protein according to the invention as herein described which binds to non-membrane bound BCMA, for example to serum BCMA.

In one embodiment of the present invention there is provided an immunoconjugate comprising the antigen binding protein of the present invention and a cytotoxic agent.

In a further embodiment the antigen binding proteins are conjugated to a toxin such as an auristatin. In yet a further embodiment the drug conjugate is vcMMAE or mcMMAF.

The antigen binding proteins of the present invention are related to, or derived from a murine monoclonal antibody CA8. The CA8 murine heavy chain variable region amino acid sequence is provided as SEQ ID NO. 7 and the CA8 murine light chain variable region amino acid sequence is provided as SEQ ID NO. 9.

The antigen binding proteins of the present invention are related to, or derived from a murine monoclonal antibody S336105A07. The S336105A07 murine heavy chain variable region amino acid sequence is provided as SEQ ID NO. 140 and the S336105A07 murine light chain variable region amino acid sequence is provided as SEQ ID NO. 144.

Other murine monoclonal antibodies from which antigen binding proteins of the present invention may also be derived are included in Table C.

The heavy chain variable regions (VH) of the present invention may comprise the following CDRs or variants of these CDR's (as defined by Kabat (Kabat et al; Sequences of proteins of Immunological Interest NIH, 1987)):

CDRH1 is provided as SEQ ID NO. 1 or SEQ ID NO. 182
CDRH2 is provided as SEQ ID NO. 2 or SEQ ID NO. 183
CDRH3 is provided as SEQ ID NO. 3 or SEQ ID NO. 184

The light chain variable regions (VL) of the present invention may comprise the following CDRs or variants of these CDR's (as defined by Kabat (Kabat et al; Sequences of proteins of Immunological Interest NIH, 1987)):

CDRL1 is provided as SEQ ID NO. 4 or SEQ ID NO. 185
CDRL2 is provided as SEQ ID NO. 5 or SEQ ID NO. 186
CDRL3 is provided as SEQ ID NO. 6 or SEQ ID NO. 187

The invention also provides a polynucleotide sequence encoding a heavy chain variable region of any of the antigen-binding proteins described herein, and a polynucleotide encoding a light chain variable region of any of the antigen-binding proteins described herein.

The invention also provides a polynucleotide sequence encoding a heavy chain of any of the antigen-binding proteins described herein, and a polynucleotide encoding a light chain of any of the antigen-binding proteins described herein.

Such polynucleotides represent the coding sequence which corresponds to the equivalent polypeptide sequences, however it will be understood that such polynucleotide sequences could be cloned into an expression vector along with a start codon, an appropriate signal sequence and a stop codon.

The invention also provides a recombinant transformed or transfected host cell comprising one or more polynucleotides encoding a heavy chain and/or a light chain of any of the antigen-binding proteins described herein.

The invention further provides a method for the production of any of the antigen-binding proteins described herein which method comprises the step of culturing a host cell comprising a first and second vector, said first vector comprising a polynucleotide encoding a heavy chain of any of the antigen-binding proteins described herein and said second vector comprising a polynucleotide encoding a light chain of any of the antigen-binding proteins described herein, in a suitable culture media, for example serum-free culture media.

The invention further provides a pharmaceutical composition comprising an antigen-binding protein as described herein and a pharmaceutically acceptable carrier.

In a further aspect, the present invention provides a method of treatment or prophylaxis of a disease or disorder responsive to inhibiting or blocking BCMA such as the modulation of the interaction between BCMA and its ligands, BAFF or APRIL which method comprises the step of administering to said patient a therapeutically effective amount of the antigen binding protein thereof as described herein.

It is therefore an object of the present invention to provide a therapeutic approach to the treatment of B cell related disorders or diseases such as antibody mediated or plasma cell mediated diseases or plasma cell malignancies such as for example Multiple Myeloma (MM). In particular it is an object of the present invention to provide antigen binding proteins, especially antibodies that specifically bind BCMA (e.g. hBCMA) and modulate (i.e. inhibit or block) the interaction between BCMA and its ligands such as BAFF and/or APRIL in the treatment of diseases and disorders responsive to modulation of that interaction.

In another aspect of the present invention there is provided a method of treating a human patient afflicted with a B cell related disorders or diseases such as antibody mediated or plasma cell mediated diseases or plasma cell malignancies such as for example Multiple Myeloma (MM) which method comprises the step of administering to said patient a therapeutically effective amount of the antigen binding protein as described herein.

In another aspect of the present invention there is provided a method of treating a human patient afflicted with Rheumatoid Arthritis, Psoriasis, Type 1 Diabetes Mellitus or Multiple Sclerosis which method comprises the step of administering to said patient a therapeutically effective amount of the antigen binding protein as described herein.

DETAILED DESCRIPTION OF THE INVENTION

The present invention provides antigen binding proteins which bind to membrane bound targets and wherein the antigen binding protein is capable of internalisation. In a further embodiment there is provided an immunoconjugate comprising the antigen binding protein of the present invention and a cytotoxic agent. In a further embodiment the antigen binding protein has ADCC effector function for example the antigen binding protein has enhanced ADCC effector function.

In one such embodiment there is provided antigen binding proteins or fragments thereof which specifically bind to BCMA, for example which specifically binds human BCMA (hBCMA) and which inhibit the binding of BAFF and/or APRIL to the BCMA receptor.

In a further embodiment the antigen binding proteins or fragments of the present invention specifically bind to BCMA and inhibit the binding of BAFF and/or APRIL to BCMA wherein the antigen binding proteins or fragments thereof have the ability to bind to FcγRIIIA and mediate FcgRIIIA mediated effector functions, or have enhanced FcγRIIIA mediated effector function. In one embodiment of the invention as herein provided the antigen binding proteins are capable of internalisation.

In one aspect of the invention there is provided an antigen binding protein according to the invention as herein described which binds to non-membrane bound BCMA, for example to serum BCMA.

In one aspect of the invention there is provided an antigen binding protein as herein described wherein the antigen binding protein comprises CDRH3 of SEQ ID NO.3 or a variant of SEQ ID NO. 3.

In a further aspect of the invention there is provided an antigen binding protein as herein described wherein the antigen binding protein further comprises one or more of: CDR H1 of SEQ. ID. NO: 1, CDRH2: SEQ. ID. NO: 2: CDRL1: SEQ. ID. NO: 4, CDRL2: SEQ. ID. NO: 5 and/or CDRL3: SEQ. ID. NO: 6 and or variants thereof.

In one aspect of the invention there is provided an antigen binding protein as herein described wherein the antigen binding protein comprises CDRH3 of SEQ ID NO.184 or a variant of SEQ ID NO. 184.

In a further aspect of the invention there is provided an antigen binding protein as herein described wherein the antigen binding protein further comprises one or more of: CDR H1 of SEQ. ID. NO: 182, CDRH2: SEQ. ID. NO: 183: CDRL1: SEQ. ID. NO: 185, CDRL2: SEQ. ID. NO: 186 and/or CDRL3: SEQ. ID. NO: 187 and or variants thereof.

In yet a further aspect the antigen binding protein comprises CDR H3 of SEQ. ID. NO: 3: CDRH2: SEQ. ID. NO: 2: CDR H1 of SEQ. ID. NO: 1: CDRL1: SEQ. ID. NO: 4: CDRL2: SEQ. ID. NO: 5 and CDRL3: SEQ. ID. NO: 6.

In yet a further aspect the antigen binding protein comprises CDR H3 of SEQ. ID. NO: 184: CDRH2: SEQ. ID. NO: 183: CDR H1 of SEQ. ID. NO: 182: CDRL1: SEQ. ID. NO: 185: CDRL2: SEQ. ID. NO: 186 and CDRL3: SEQ. ID. NO: 187.

The antigen binding proteins of the present invention may comprise heavy chain variable regions and light chain variable regions of the invention which may be formatted into the structure of a natural antibody or functional fragment or equivalent thereof. An antigen binding protein of the invention may therefore comprise the VH regions of the invention formatted into a full length antibody, a (Fab')2 fragment, a Fab fragment, or equivalent thereof (such as scFV, bi- tri- or tetra-bodies, Tandabs etc.), when paired with an appropriate light chain. The antibody may be an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. Furthermore, the antigen binding protein may comprise modifications of all classes e.g. IgG dimers, Fc mutants that no longer bind Fc receptors or mediate C1q binding. The antigen binding protein may also be a chimeric antibody of the type described in WO86/01533 which comprises an antigen binding region and a non-immunoglobulin region.

The constant region is selected according to any functionality required e.g. an IgG1 may demonstrate lytic ability through binding to complement and/or will mediate ADCC (antibody dependent cell cytotoxicity).

The antigen binding proteins of the present invention are derived from the murine antibody having the variable regions as described in SEQ ID NO:7 and SEQ ID NO:9 or non-murine equivalents thereof, such as rat, human, chimeric or humanised variants thereof, for example they are derived from the antibody having the variable heavy chain sequences as described in SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 and SEQ ID NO:29 and/or the variable light chain sequences as described in SEQ ID NO:31, SEQ ID NO:33 and/or SEQ ID NO:35.

In another embodiment the antigen binding proteins of the present invention are derived from an antibody having the variable heavy chain sequences as described in SEQ ID NO:116 or SEQ ID NO:118 and/or the variable light chain sequences as described in SEQ ID NO:120, or SEQ ID NO: 122.

In another embodiment the antigen binding proteins of the present invention are derived from an antibody having the variable heavy chain sequences as described in SEQ ID NO:140 and/or the variable light chain sequences as described in SEQ ID NO:144.

In one aspect of the invention there is provided an antigen binding protein comprising an isolated heavy chain variable domain selected from any one of the following: SEQ ID NO: 11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:116 or SEQ ID NO:118.

In another aspect of the invention there is provided an antigen binding protein comprising an isolated light chain variable domain selected from any one of the following: SEQ ID NO:31, SEQ ID NO:33 or SEQ ID NO:35, SEQ ID NO:120 or SEQ ID NO:122.

In a further aspect of the invention there is provided an antigen binding protein comprising an isolated heavy chain variable domain selected from any one of the following: SEQ ID NO: 11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 and SEQ ID NO:29 and an isolated light chain variable domain selected from any one of the following: SEQ ID NO:31, SEQ ID NO:33 and/or SEQ ID NO:35.

In one aspect the antigen binding protein of the present invention comprises a heavy chain variable region encoded by SEQ. ID. NO:23 and a light chain variable region encoded by SEQ. ID. NO:31

In one aspect the antigen binding protein of the present invention comprises a heavy chain variable region encoded by SEQ. ID. NO:27 and a light chain variable region encoded by SEQ. ID. NO:31.

In one aspect the antigen binding protein of the present invention comprises a heavy chain variable region encoded by SEQ. ID. NO:29 and a light chain variable region encoded by SEQ. ID. NO:31.

In one aspect the antigen binding protein of the present invention comprises a heavy chain variable region encoded by SEQ. ID. NO:116 and a light chain variable region encoded by SEQ. ID. NO:120

In one aspect the antigen binding protein of the present invention comprises a heavy chain variable region encoded by SEQ. ID. NO:118 and a light chain variable region encoded by SEQ. ID. NO:122

In one aspect there is provided a polynucleotide encoding an isolated variable heavy chain said polynucleotide comprising SEQ. ID. NO. 12, or SEQ. ID. NO. 14, or SEQ. ID. NO. 16, or SEQ. ID. NO. 18, or SEQ. ID. NO. 20, or SEQ. ID. NO. 22, or SEQ. ID. NO. 24, or SEQ. ID. NO. 26, or SEQ. ID. NO. 28, or SEQ. ID. NO. 30 or SEQ. ID. NO. 117 or SEQ. ID. NO. 119 or SEQ. ID. NO. 141.

In one aspect there is provided a polynucleotide encoding an isolated variable light chain said polynucleotide comprising SEQ. ID. NO. 32, or SEQ. ID. NO. 34, or SEQ. ID. NO. 36 or SEQ. ID. NO. 121 or SEQ. ID. NO.123 or SEQ. ID. NO. 145.

In a further aspect there is provided a polynucleotide encoding an isolated variable heavy chain said polynucleotide comprising SEQ. ID. NO. 24, or SEQ. ID. NO. 28 or SEQ. ID. NO. 30 and a polynucleotide encoding an isolated variable light chain said polynucleotide comprising SEQ. ID. NO. 32, or SEQ. ID. NO. 34.

In yet a further aspect there is provided a polynucleotide encoding an isolated variable heavy chain said polynucleotide comprising SEQ. ID. NO. 24 and a polynucleotide encoding an isolated variable light chain said polynucleotide comprising SEQ. ID. NO.32.

In yet a further aspect there is provided a polynucleotide encoding an isolated variable heavy chain said polynucleotide comprising SEQ. ID. NO. 117 and a polynucleotide encoding an isolated variable light chain said polynucleotide comprising SEQ. ID. NO.121.

In yet a further aspect there is provided a polynucleotide encoding an isolated variable heavy chain said polynucleotide comprising SEQ. ID. NO. 119 and a polynucleotide encoding an isolated variable light chain said polynucleotide comprising SEQ. ID. NO.123.

In yet a further aspect there is provided a polynucleotide encoding an isolated variable heavy chain said polynucleotide comprising SEQ. ID. NO. 141 and a polynucleotide encoding an isolated variable light chain said polynucleotide comprising SEQ. ID. NO.145.

In a further aspect the antigen binding protein may comprise any one of the variable heavy chains as described herein in combination with any one of the light chains as described herein.

In one aspect the antigen binding protein is an antibody or antigen binding fragment thereof comprising one or more CDR's according to the invention described herein, or one or both of the heavy or light chain variable domains according to the invention described herein. In one embodiment the antigen binding protein binds primate BCMA. In one such embodiment the antigen binding protein additionally binds non-human primate BCMA, for example cynomolgus macaque monkey BCMA.

In another aspect the antigen binding protein is selected from the group consisting of a dAb, Fab, Fab', $F(ab')_2$, Fv, diabody, triabody, tetrabody, miniantibody, and a minibody.

In one aspect of the present invention the antigen binding protein is a humanised or chimaeric antibody, in a further aspect the antibody is humanised.

In one aspect the antibody is a monoclonal antibody.

In one aspect of the present invention there is provided an antibody with the heavy chain sequence as set forth in SEQ ID NO: 55 or SEQ ID NO: 59 or SEQ ID NO: 61.

In one aspect of the present invention there is provided an antibody with the light chain sequence as set forth in SEQ ID NO: 63 or SEQ ID NO: 65.

In a further aspect of the invention there is provided an antibody with the heavy chain sequence of SEQ ID NO: 55 and a light chain sequence as set forth in SEQ ID NO: 63.

In one embodiment there is provided an antigen binding protein which competes with an antigen binding protein of the invention as herein described. In one such embodiment there is therefore provided an antigen binding protein which competes with an antigen binding protein which comprises the heavy chain variable sequence of SEQ ID NO 23 and the light chain variable region of SEQ ID NO 31.

In a further embodiment there is therefore provided an antigen binding protein which competes with an antigen binding protein which comprises a heavy chain variable sequence selected from one of SEQ ID NO 27, SEQ ID NO 29, SEQ ID NO 116, SEQ ID NO 118 and SEQ ID NO 140 and a light chain variable region selected from one of SEQ ID NO 31, SEQ ID NO 120, SEQ ID NO 122 and SEQ ID NO 144.

In another aspect the antigen binding protein binds to human BCMA with high affinity for example when measured by Biacore the antigen binding protein binds to human BCMA with an affinity of 20 nM or less or an affinity of 15 nM or less or an affinity of 5 nM or less or an affinity of 1000 pM or less or an affinity of 500 pM or less or an affinity of 400 pM or less, or 300 pM or less or for example about 120 pM. In a further embodiment the antigen binding protein binds to human BCMA when measured by Biacore of between about 100 pM and about 500 pM or between about 100 pM and about 400 pM, or between about 100 pM and about 300 pM. In one embodiment of the present invention the antigen binding protein binds BCMA with an affinity of less than 150 pm.

In one such embodiment, this is measured by Biacore, for example as set out in Example 4.

In another aspect the antigen binding protein binds to human BCMA and neutralises the binding of the ligands BAFF and/or APRIL to the BCMA receptor in a cell neutralisation assay wherein the antigen binding protein has an IC50 of between about 1 nM and about 500 nM, or between about 1 nM and about 100 nM, or between about 1 nM and about 50 nM, or between about 1 nM and about 25 nM, or between about 5 nM and about 15 nM. In a further embodiment of the present invention the antigen binding protein binds BCMA and neutralises BCMA in a cell neutralisation assay wherein the antigen binding protein has an IC50 of about 10 nM.

In one such embodiment, this is measured by a cell neutralisation assay, for example as set out in Example 4.6.

The antigen binding proteins, for example antibodies of the present invention may be produced by transfection of a host cell with an expression vector comprising the coding sequence for the antigen binding protein of the invention. An expression vector or recombinant plasmid is produced by placing these coding sequences for the antigen binding protein in operative association with conventional regulatory control sequences capable of controlling the replication and expression in, and/or secretion from, a host cell. Regulatory sequences include promoter sequences, e.g., CMV promoter, and signal sequences which can be derived from other known antibodies. Similarly, a second expression vector can be produced having a DNA sequence which encodes a complementary antigen binding protein light or heavy chain. In certain embodiments this second expression vector is identical to the first except insofar as the coding sequences and selectable markers are concerned, so to ensure as far as possible that each polypeptide chain is functionally expressed. Alternatively, the heavy and light chain coding sequences for the antigen binding protein may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antigen binding protein of the invention. The antigen binding protein which includes the association of both the recombinant heavy chain and/or light chain is screened from culture by appropriate assay, such as ELISA or RIA. Similar conventional techniques may be employed to construct other antigen binding proteins.

Suitable vectors for the cloning and subcloning steps employed in the methods and construction of the compositions of this invention may be selected by one of skill in the art. For example, the conventional pUC series of cloning vectors may be used. One vector, pUC19, is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention. The expression vectors may also be characterized by genes suitable for amplifying expression of the heterologous DNA sequences, e.g., the mammalian dihydrofolate reductase gene (DHFR). Other vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antigen binding proteins of the present invention. Host cells useful for the cloning and other manipulations of these cloning vectors are also conventional. However, cells from various strains of *E. Coli* may be used for replication of the cloning vectors and other steps in the construction of antigen binding proteins of this invention.

Suitable host cells or cell lines for the expression of the antigen binding proteins of the invention include mammalian cells such as NS0, Sp2/0, CHO (e.g. DG44), COS, HEK, a fibroblast cell (e.g., 3T3), and myeloma cells, for example it may be expressed in a CHO or a myeloma cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant Fabs or other embodiments of the present invention (see, e.g., Plückthun, A., Immunol. Rev., 130:151-188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host, or in alternative embodiments the molecule may express in the bacterial host and then be subsequently re-folded. For example, various strains of *E. Coli* used for expression are well-known as host cells in the field of biotechnology. Various strains of *B. Subtilis, Streptomyces*, other bacilli and the like may also be employed in this method.

Where desired, strains of yeast cells known to those skilled in the art are also available as host cells, as well as insect cells, e.g. *Drosophila* and *Lepidoptera* and viral expression systems. See, e.g. Miller et al., Genetic Engineering, 8:277-298, Plenum Press (1986) and references cited therein.

The general methods by which the vectors may be constructed, the transfection methods required to produce the host cells of the invention, and culture methods necessary to produce the antigen binding protein of the invention from such host cell may all be conventional techniques. Typically, the culture method of the present invention is a serum-free culture method, usually by culturing cells serum-free in suspension. Likewise, once produced, the antigen binding proteins of the invention may be purified from the cell culture contents according to standard procedures of the art, including ammonium 21eroxidi precipitation, affinity columns, column chromatography, gel electrophoresis and the like. Such techniques are within the skill of the art and do not limit this invention. For example, preparations of altered antibodies are described in WO 99/58679 and WO 96/16990.

Yet another method of expression of the antigen binding proteins may utilize expression in a transgenic animal, such as described in U.S. Pat. No. 4,873,316. This relates to an expression system using the animals casein promoter which when transgenically incorporated into a mammal permits the female to produce the desired recombinant protein in its milk.

In a further embodiment of the invention there is provided a method of producing an antibody of the invention which method comprises the step of culturing a host cell transformed or transfected with a vector encoding the light and/or heavy chain of the antibody of the invention and recovering the antibody thereby produced.

In accordance with the present invention there is provided a method of producing an anti-BCMA antibody of the present invention which binds to and neutralises the activity of human BCMA which method comprises the steps of;

- providing a first vector encoding a heavy chain of the antibody;
- providing a second vector encoding a light chain of the antibody;
- transforming a mammalian host cell (e.g. CHO) with said first and second vectors;
- culturing the host cell of step (c) under conditions conducive to the secretion of the antibody from said host cell into said culture media;
- recovering the secreted antibody of step (d).

Once expressed by the desired method, the antibody is then examined for in vitro activity by use of an appropriate assay. Presently conventional ELISA assay formats are employed to assess qualitative and quantitative binding of the antibody to BCMA. Additionally, other in vitro assays may also be used to verify neutralizing efficacy prior to subsequent human clinical studies performed to evaluate the persistence of the antibody in the body despite the usual clearance mechanisms.

The dose and duration of treatment relates to the relative duration of the molecules of the present invention in the human circulation, and can be adjusted by one of skill in the art depending upon the condition being treated and the general health of the patient. It is envisaged that repeated dosing (e.g. once a week or once every two weeks or once every 3 weeks) over an extended time period (e.g. four to six months) maybe required to achieve maximal therapeutic efficacy.

In one embodiment of the present invention there is provided a recombinant transformed, transfected or transduced host cell comprising at least one expression cassette, for example where the expression cassette comprises a polynucleotide encoding a heavy chain of an antigen binding protein according to the invention described herein and further comprises a polynucleotide encoding a light chain of an antigen binding protein according to the invention described herein or where there are two expression cassettes and the $1^{st}$ encodes the light chain and the second encodes the heavy chain. For example in one embodiment the first expression cassette comprises a polynucleotide encoding a heavy chain of an antigen binding protein comprising a constant region or antigen binding fragment thereof which is linked to a constant region according to the invention described herein and further comprises a second cassette comprising a polynucleotide encoding a light chain of an antigen binding protein comprising a constant region or antigen binding fragment thereof which is linked to a constant region according to the invention described herein for example the first expression cassette comprises a polynucleotide encoding a heavy chain selected from SEQ. ID. NO:56, or SEQ. ID. NO: 60 or SEQ. ID. NO: 62 and a second expression cassette comprising a polynucleotide encoding a light chain selected from SEQ. ID. NO: 64 or SEQ. ID. NO: 66.

In another embodiment of the invention there is provided a stably transformed host cell comprising a vector comprising one or more expression cassettes encoding a heavy chain and/or a light chain of the antibody comprising a constant region or antigen binding fragment thereof which is linked to a constant region as described herein. For example such host cells may comprise a first vector encoding the light chain and a second vector encoding the heavy chain, for example the first vector encodes a heavy chain selected from SEQ. ID. NO: 55, or SEQ. ID. NO: 59 or SEQ. ID. NO: 61 and a second vector encoding a light chain for example the light chain of SEQ ID NO: 63 or SEQ. ID. NO: 65. In one such example the first vector encodes a heavy chain selected from SEQ. ID. NO: 55 and a second vector encoding a light chain for example the light chain of SEQ ID NO: 63.

In another embodiment of the present invention there is provided a host cell according to the invention described herein wherein the cell is eukaryotic, for example where the cell is mammalian. Examples of such cell lines include CHO or NS0.

In another embodiment of the present invention there is provided a method for the production of an antibody comprising a constant region or antigen binding fragment thereof which is linked to a constant region according to the invention described herein which method comprises the step of culturing a host cell in a culture media, for example serum-free culture media.

In another embodiment of the present invention there is provided a method according to the invention described herein wherein said antibody is further purified to at least 95% or greater (e.g. 98% or greater) with respect to said antibody containing serum-free culture media.

In yet another embodiment there is provided a pharmaceutical composition comprising an antigen binding protein and a pharmaceutically acceptable carrier.

In another embodiment of the present invention there is provided a kit-of-parts comprising the composition according to the invention described herein described together with instructions for use.

The mode of administration of the therapeutic agent of the invention may be any suitable route which delivers the agent to the host. The antigen binding proteins, and pharmaceutical compositions of the invention are particularly useful for parenteral administration, i.e., subcutaneously (s.c.), intrathecally, intraperitoneally, intramuscularly (i.m.) or intravenously (i.v.). In one such embodiment the antigen binding proteins of the present invention are administered intravenously or subcutaneously.

Therapeutic agents of the invention may be prepared as pharmaceutical compositions containing an effective amount of the antigen binding protein of the invention as an active ingredient in a pharmaceutically acceptable carrier. In one embodiment the prophylactic agent of the invention is an aqueous suspension or solution containing the antigen binding protein in a form ready for injection. In one embodiment the suspension or solution is buffered at physiological pH. In one embodiment the compositions for parenteral administration will comprise a solution of the antigen binding protein of the invention or a cocktail thereof dissolved in a pharmaceutically acceptable carrier. In one embodiment the carrier is an aqueous carrier. A variety of aqueous carriers may be employed, e.g., 0.9% saline, 0.3% glycine, and the like. These solutions may be made sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antigen binding protein of the invention in such pharmaceutical formulation can vary widely, i.e., from less than about 0.5%, usually at or at least about 1% to as much as about 15 or 20% by weight and will be selected primarily based on fluid volumes, viscosities, etc., according to the particular mode of administration selected.

Thus, a pharmaceutical composition of the invention for intravenous infusion could be made up to contain about 250 ml of sterile Ringer's solution, and about 1 to about 30 or 5 mg to about 25 mg of an antigen binding protein of the invention per ml of Ringer's solution. Actual methods for preparing parenterally administrable compositions are well known or will be apparent to those skilled in the art and are described in more detail in, for example, Remington's Pharmaceutical Science, $15^{th}$ ed., Mack Publishing Company, Easton, Pennsylvania. For the preparation of intravenously administrable antigen binding protein formulations of the invention see Lasmar U and Parkins D "The formulation of Biopharmaceutical products", Pharma. Sci. Tech.today, page 129-137, Vol.3 (3 Apr. 2000); Wang, W "Instability, stabilisation and formulation of liquid protein pharmaceuticals", Int. J. Pharm 185 (1999) 129-188; Stability of Protein Pharmaceuticals Part A and B ed Ahem T. J., Manning M. C., New York, NY: Plenum Press (1992); Akers, M. J. "Excipient-Drug interactions in Parenteral Formulations", J.Pharm Sci 91 (2002) 2283-2300; Imamura, K et al "Effects of types of sugar on stabilization of Protein in the dried state", J Pharm Sci 92 (2003) 266-274; Izutsu, Kkojima, S. "Excipient crystalinity and its protein-structure-stabilizing effect during freeze-drying", J Pharm. Pharmacol, 54 (2002) 1033-1039; Johnson, R, "Mannitol-sucrose mixtures-versatile formulations for protein peroxidise24g24n", J. Pharm. Sci, 91 (2002) 914-922; and Ha,E Wang W, Wang Y. j. "Peroxide formation in polysorbate 80 and protein stability", J. Pharm Sci, 91, 2252-2264, (2002) the entire contents of which are incorporated herein by reference and to which the reader is specifically referred.

In one embodiment the therapeutic agent of the invention, when in a pharmaceutical preparation, is present in unit dose forms. The appropriate therapeutically effective dose will be determined readily by those of skill in the art. Suitable doses may be calculated for patients according to their weight, for example suitable doses may be in the range of about 0.1 to about 20 mg/kg, for example about 1 to about 20 mg/kg, for example about 10 to about 20 mg/kg or for example about 1 to about 15 mg/kg, for example about 10 to about 15 mg/kg or for example 1-5 mg/kg. In one embodiment the antibody is given 1-5 mg/kg every 3 weeks. To effectively treat conditions such as Multiple myeloma, SLE or IPT in a human, suitable doses may be within the range of about 0.1 to about 1000 mg, for example about 0.1 to about 500 mg, for example about 500 mg, for example about 0.1 to about 100 mg, or about 0.1 to about 80 mg, or about 0.1 to about 60 mg, or about 0.1 to about 40 mg, or for example about 1 to about 100 mg, or about 1 to about 50 mg, of an antigen binding protein of this invention, which may be administered parenterally, for example subcutaneously, intravenously or intramuscularly. Such dose may, if necessary, be repeated at appropriate time intervals selected as appropriate by a physician.

The antigen binding proteins described herein can be lyophilized for storage and reconstituted in a suitable carrier prior to use. This technique has been shown to be effective with conventional immunoglobulins and art-known peroxidise and reconstitution techniques can be employed.

In another aspect of the invention there is provided an antigen binding protein as herein described for use in a medicament.

In one aspect of the present invention there is provided an antigen binding protein according to the invention as herein described for use in the treatment of rheumatoid arthritis, Type 1 Diabetes Mellitus, multiple sclerosis or psoriasis wherein said method comprises the step of administering to said patient a therapeutically effective amount of the antigen binding protein as described herein.

In one embodiment of the present invention, methods are provided for treating cancer in a human comprising administering to said human an antigen binding protein that specifically binds to BCMA. In some instances the antigen binding protein is part of an immunoconjugate.

In another aspect of the present invention there is provided an antigen binding protein according to the invention as herein described for use in the treatment of a B-cell mediated or plasma cell mediated disease or antibody mediated disease or disorder selected from Multiple Myeloma (MM), chronic lymphocytic leukemia (CLL), Non-secretory multiple myeloma, Smoldering multiple myeloma, Monoclonal gammopathy of undetermined significance (MGUS), Solitary plasmacytoma (Bone, Extramedullary), Lymphoplasmacytic lymphoma (LPL), Waldenstrom's Macroglobulinemia, Plasma cell leukemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpasture's syndrome, Idiopathic thrombocytopenic purpura (ITP), Acute glomerulonephritis, Pemphigus and Pemphigoid disorders, and Epidermolysis bullosa acquisita; or any Non-Hodgkin's Lymphoma B-cell leukemia or Hodgkin's lymphoma (HL) with BCMA expression or any diseases in which patients develop neutralising antibodies to recombinant protein replacement therapy wherein said method comprises the step of administering to said patient a therapeutically effective amount of the antigen binding protein as described herein.

B-cell disorders can be divided into defects of B-cell development/immunoglobulin production (immunodeficiencies) and excessive/uncontrolled proliferation (lymphomas, leukemias). As used herein, B-cell disorder refers to both types of diseases, and methods are provided for treating B-cell disorders with an antigen binding protein.

In a particular aspect, the disease or disorder is selected from the group consisting of Multiple Myeloma (MM), Chronic Lymphocytic Leukaemia (CLL), Solitary Plasmacytoma (Bone, Extramedullary), Waldenstrom's Macroglobulinemia.

In one aspect of the present invention the disease is Multiple Myeloma, Smoldering Multiple Myeloma (SMM) or Solitary Plasmacytoma (Bone, Extramedullary).

In one aspect of the present invention the disease is Multiple Myeloma.

In one aspect of the present invention the disease is Systemic lupus erythematosus (SLE)

In one aspect of the present invention the disease is Idiopathic thrombocytopenic purpura (ITP)

Use of the antigen binding protein as described herein in the manufacture of a medicament for the treatment of diseases and disorders as described herein is also provided.

For example in one aspect of the invention there is provided the use of the antigen binding protein as described herein for use in the treatment or prophylaxis of diseases and disorders responsive to modulation (such as inhibiting or blocking) of the interaction between BCMA and the ligands BAFF and APRIL.

In another aspect of the invention there is provided the use of the antigen binding protein as described herein for use in the treatment or prophylaxis of an antibody mediated or plasma cell mediated disease or disorder selected from rheumatoid arthritis, Type 1 Diabeted Mellitus, multiple sclerosis or psoriasis.

In another aspect of the invention there is provided the use of the antigen binding protein as described herein for use in the treatment or prophylaxis of an antibody mediated or plasma cell mediated disease or disorder selected from Multiple Myeloma (MM), chronic lymphocytic leukemia (CLL), Monoclonal gammopathy of undetermined significance (MGUS), Smoldering multiple myeloma (SMM), Solitary Plasmacytoma (Bone, Extramedullary), Waldenstrom's Macroglobulinemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpastures syndrome, Idiopathic thrombocytopenic purpura (ITP), Acute glomerulonephritis, Pemphigus and Pemphigoid disorders and Epidermolysis bullosa acquisita, any Non-Hodgkin Lymphoma and Leukemia with BCMA expression or any diseases in which patients develop neutralising antibodies to recombinant protein replacement therapy wherein said method comprises the step of administering to said patient a therapeutically effective amount of the antigen binding protein as described herein.

In one aspect, the invention provides a pharmaceutical composition comprising an antigen binding protein of the present invention or a functional fragment thereof and a pharmaceutically acceptable carrier for treatment or prophylaxis of rheumatoid arthritis, Type 1 Diabetes Mellitus, multiple sclerosis or psoriasis or an antibody mediated or plasma cell mediated disease or disorder selected from selected from Multiple Myeloma (MM), chronic lymphocytic leukemia (CLL), Monoclonal gammopathy of undetermined significance (MGUS), Smoldering multiple myeloma (SMM), Solitary Plasmacytoma (Bone, Extramedullary), Waldenström's Macroglobulinemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpastures syndrome, Idiopathic thrombocytopenic purpura (ITP), Acute glomerulonephritis, Pemphigus and Pemphigoid disorders and Epidermolysis bullosa acquisita, any Non-Hodgkin Lymphoma and Leukemia with BCMA expression or any diseases in which patients develop neutralising antibodies to recombinant protein replacement therapy wherein said method comprises the step of administering to said patient a therapeutically effective amount of the antigen binding protein as described herein.

In another embodiment of the present invention there is provided a method of treating a human patient afflicted with rheumatoid arthritis, Type 1 Diabetes Mellitus, multiple sclerosis or psoriasis or an antibody mediated or plasma cell mediated disorder or disease which method comprises the step of administering a therapeutically effective amount of the antigen binding protein according to the invention as described herein, for example there is provided a method of treating a human patient afflicted with an antibody mediated or plasma cell mediated disease or disorder selected from In another aspect of the present invention there is provided an antigen binding protein according to the invention as herein described for use in the treatment of an antibody mediated or plasma cell mediated disease or disorder selected from Multiple Myeloma (MM), Chronic Lymphocytic Leukaemia (CLL)Monoclonal gammopathy of undetermined significance (MGUS), Smoldering multiple myeloma (SMM), Solitary Plasmacytoma (Bone, Extramedullary), Waldenström's Macroglobulinemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpastures syndrome, Idiopathic thrombocytopenic purpura (ITP), Acute glomerulonephritis, Pemphigus and Pemphigoid disorders and Epidermolysis bullosa acquisita, any Non-Hodgkin Lymphoma and Leukemia with BCMA expression or any diseases in which patients develop neutralising antibodies to recombinant protein replacement therapy wherein said method comprises the step of administering a pharmaceutical composition comprising an antigen binding protein according to the invention herein in combination with a pharmaceutically acceptable carrier.

In a further embodiment there is provided a method of treating a human patient afflicted with Multiple Myeloma (MM).

Definitions

As used herein, the terms "cancer," "neoplasm," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent Bcell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s(T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma,and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenström's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

The term "antigen binding protein" as used herein refers to antibodies, antibody fragments and other protein constructs which are capable of binding to and neutralising human BCMA.

The terms Fv, Fc, Fd, Fab, or F(ab)2 are used with their standard meanings (see, e.g., Harlow et al., Antibodies A Laboratory Manual, Cold Spring Harbor Laboratory, (1988)).

The term "antibody" is used herein in the broadest sense and specifically covers monoclonal antibodies (including full length monoclonal antibodies), polyclonal antibodies, multispecific antibodies (e.g. bispecific antibodies)

The term "monoclonal antibody" as used herein refers to an antibody obtained from a population of substantially homogenous antibodies i.e. the individual antibodies comprising the population are identical except for possible naturally occurring mutations that may be present in minor amounts. Monoclonal antibodies are highly specific being directed against a single antigenic binding site. Furthermore, in contrast to polyclonal antibody preparations which typically include different antibodies directed against different determinants (epitopes), each monoclonal antibody is directed against a single determinant on the antigen.

A "chimeric antibody" refers to a type of engineered antibody in which a portion of the heavy and/or light chain is identical with or homologous to corresponding sequences in antibodies derived from a particular donor antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (USPatent No. 4, 816,567 and Morrison et al. *Proc. Natl. Acad. Sci. USA* 81:6851-6855) (1984)).

A "humanised antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl Acad Sci USA, 86:10029-10032 (1989), Hodgson et al., Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies—see for example EP-A-0239400 and EP-A-054951.

For nucleic acids, the term "substantial identity" indicates that two nucleic acids, or designated sequences thereof, when optimally aligned and compared, are identical, with appropriate nucleotide insertions or deletions, in at least about 80% of the nucleotides, at least about 90% to about 95%, or at least about 98% to about 99.5% of the nucleotides. Alternatively, substantial identity exists when the segments will hybridize under selective hybridization conditions, to the complement of the strand.

"Identity," means, for polynucleotides and polypeptides, as the case may be, the comparison calculated using an algorithm provided in (1) and (2) below:

(1) Identity for polynucleotides is calculated by multiplying the total number of nucleotides in a given sequence by the integer defining the percent identity divided by 100 and then subtracting that product from said total number of nucleotides in said sequence, or:

$$nn \leq xn-(xn \cdot y),$$

wherein nn is the number of nucleotide alterations, xn is the total number of nucleotides in a given sequence, y is 0.95 for 95%, 0.97 for 97% or 1.00 for 100%, and · is the symbol for the multiplication operator, and wherein any non-integer product of xn and y is rounded down to the nearest integer prior to subtracting it from xn. Alterations of a polynucleotide sequence encoding a polypeptide may create nonsense, missense or frameshift mutations in this coding sequence and thereby alter the polypeptide encoded by the polynucleotide following such alterations.

(2) Identity for polypeptides is calculated by multiplying the total number of amino acids by the integer defining the percent identity divided by 100 and then subtracting that product from said total number of amino acids, or.

$$na \leq xa-(xa \cdot y),$$

wherein na is the number of amino acid alterations, xa is the total number of amino acids in the sequence, y is 0.95 for 95%, 0.97 for 97% or 1.00 for 100%, and · is the symbol for the multiplication operator, and wherein any non-integer product of xa and y is rounded down to the nearest integer prior to subtracting it from xa For nucleotide and amino acid sequences, the term "identical" indicates the degree of identity between two nucleic acid or amino acid sequences when optimally aligned and compared with appropriate insertions or deletions.

"Isolated" means altered "by the hand of man" from its natural state, has been changed or removed from its original environment, or both. For example, a polynucleotide or a polypeptide naturally present in a living organism is not "isolated," but the same polynucleotide or polypeptide separated from the coexisting materials of its natural state is "isolated", including but not limited to when such polynucleotide or polypeptide is introduced back into a cell, even if the cell is of the same species or type as that from which the polynucleotide or polypeptide was separated.

Throughout the present specification and the accompanying claims the term "comprising" and "comprises" incorporates "consisting of" and "consists of". That is, these words are intended to convey the possible inclusion of other elements or integers not specifically recited, where the context allows.

The term "specifically binds" as used throughout the present specification in relation to antigen binding proteins of the invention means that the antigen binding protein binds human BCMA (hBCMA) with no or insignificant binding to other human proteins. The term however does not exclude the fact that antigen binding proteins of the invention may also be cross-reactive with other forms of BCMA, for example primate BCMA. For example in one embodiment the antigen binding protein does not bind to TACI or BAFF-R.

The term "inhibits" as used throughout the present specification in relation to antigen binding proteins of the invention means that the biological activity of BCMA is reduced in the presence of the antigen binding proteins of the present invention in comparison to the activity of BCMA in the absence of such antigen binding proteins. Inhibition may be due but not limited to one or more of blocking ligand binding, preventing the ligand activating the receptor, and/or down regulating the BCMA. Inhibits can also refer to an antigen binding protein binding to BCMA and causing cell apoptosis or ADCC.The antibodies of the invention may neutralise the activity of the BCMA ligands BAFF and/or APRIL binding to BCMA. Levels of neutralisation can be measured in several ways, for example by use of the assays as set out in the examples below, for example in 4.4 in an H929 cell NFkB signalling assay. The BCMA ligands BAFF and APRIL are able to induce NFkB signalling and downstream events following binding to BCMA. The neutralisation of BCMA in this assay is measured by assessing the ability of anti-BCMA monoclonal antibodies to inhibit BAFF or APRIL driven NFkB induction.

If an antibody or antigen binding fragment thereof is capable of neutralisation then this is indicative of inhibition of the interaction between human BAFF or APRIL and BCMA. Antibodies which are considered to have neutralising activity against human BCMA would have an IC50 of less than 30 micrograms/ml, or less than 20 micrograms/ml, or less than 10 micrograms/ml, or less than 5 micrograms/ml or less than 1 micrograms/ml or less than 0.1 micrograms/ml in the H929 stimulation assay as set out in Example 4.4

"CDRs" are defined as the complementarity determining region amino acid sequences of an antibody which are the hypervariable domains of immunoglobulin heavy and light chains. There are three heavy chain and three light chain CDRs (or CDR regions) in the variable portion of an immunoglobulin. Thus, "CDRs" as used herein may refer to all three heavy chain CDRs, or all three light chain CDRs (or both all heavy and all light chain CDRs, if appropriate).

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

The CDR sequences of antibodies can be determined by the Kabat numbering system (Kabat et al; (Sequences of proteins of Immunological Interest NIH, 1987), alternatively they can be determined using the Chothia numbering system (Al-Lazikani et al., (1997) JMB 273,927-948), the contact definition method (MacCallum R. M., and Martin A. C. R. and Thornton J. M, (1996), Journal of Molecular Biology, 262 (5), 732-745) or any other established method for numbering the residues in an antibody and determining CDRs known to the skilled man in the art Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Table A below represents one definition using each numbering convention for each CDR or binding unit. The Kabat numbering scheme is used in Table X to number the variable domain amino acid sequence. It should be noted that some of the CDR definitions may vary depending on the individual publication used.

TABLE A

| | Kabat CDR | Chothia CDR | AbM CDR | Contact CDR | Minimum binding unit |
|---|---|---|---|---|---|
| H1 | 31-35/35A/35B | 26-32/33/34 | 26-35/35A/35B | 30-35/35A/35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

Throughout this specification, amino acid residues in antibody sequences are numbered according to the Kabat scheme. Similarly, the terms "CDR", "CDRL1", "CDRL2", "CDRL3", "CDRH1", "CDRH2", "CDRH3" follow the Kabat numbering system as set forth in Kabat et al; Sequences of proteins of Immunological Interest NIH, 1987.

The terms "Variant" refers to at least one, two or three amino acid changes in the sequence. These amino acid changes may be deletion, substitution or addition but are preferably substitution. In one such embodiment the substitutions are conservative substitutions.

In an alternative embodiment the variant sequence contains at least one substitution whilst retaining the canonical of the antigen binding protein.

The complementarity determining regions (CDRs) L1, L2, L3, H1 and H2 tend to structurally exhibit one of a finite number of main chain conformations. The particular canonical structure class of a CDR is defined by both the length of the CDR and by the loop packing, determined by residues located at key positions in both the CDRs and the framework regions (structurally determining residues or SDRs). Martin and Thornton (1996; J Mol Biol 263:800-815) have generated an automatic method to define the "key residue" canonical templates. Cluster analysis is used to define the canonical classes for sets of CDRs, and canonical templates are then identified by analysing buried hydrophobics, hydrogen-bonding residues, and e.g. conserved glycines. The CDRs of antibody sequences can be assigned to canonical classes by comparing the sequences to the key residue templates and scoring each template using identity or similarity matrices.

The terms "VH" and "VL" are used herein to refer to the heavy chain variable domain and light chain variable domain respectively of an antibody.

As used herein the term "domain" refers to a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. An "antibody single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain (VH, VHH, VL) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid VHH dAbs. Camelid VHH are immunoglobulin single variable domain polypeptides that are derived from species including camel, llama, alpaca, dromedary, and guanaco, which produce heavy chain antibodies naturally devoid of light chains. Such VHH domains may be humanised according to standard techniques available in the art, and such domains are still considered to be "domain antibodies" according to the invention. As used herein "VH includes camelid VHH domains. NARV are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol. 44, 656-665 (2006) and US20050043519A.

The term "Epitope-binding domain" refers to a domain that specifically binds an antigen or epitope independently of a different V region or domain, this may be a domain antibody (dAb), for example a human, camelid or shark immunoglobulin single variable domain or it may be a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEl and GroES; 38eroxidise38g (trans-body); ankyrin repeat protein (DARPin); peptide aptamer; C-type lectin domain (Tetranectin); human γ-crystallin and human ubiquitin (affilins); PDZ domains; scorpion toxinkunitz type domains of human protease inhibitors; and fibronectin (adnectin); which has been subjected to protein engineering in order to obtain binding to a ligand other than the natural ligand.

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies. For further details see Journal of Immunological Methods 248 (1-2), 31-45 (2001)

Lipocalins are a family of extracellular proteins which transport small hydrophobic molecules such as steroids, bilins, retinoids and lipids. They have a rigid β-sheet secondary structure with a numer of loops at the open end of the conical structure which can be engineered to bind to different target antigens. Anticalins are between 160-180 amino acids in size, and are derived from lipocalins. For further details see Biochim Biophys Acta 1482: 337-350 (2000), US7250297B1 and US20070224633

An affibody is a scaffold derived from Protein A of *Staphylococcus aureus* which can be engineered to bind to antigen. The domain consists of a three-helical bundle of approximately 58 amino acids. Libraries have been generated by randomisation of surface residues. For further details see Protein Eng. Des. Sel. 17, 455-462 (2004) and EP1641818A1 Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007)

A Transferrin is a monomeric serum transport glycoprotein. Transferrins can be engineered to bind different target antigens by insertion of peptide sequences in a permissive surface loop. Examples of engineered transferrins scaffolds include the Trans-body. For further details see J. Biol. Chem 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomising residues in the first α-helix and a β-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

Fibronectin is a scaffold which can be engineered to bind to antigen. Adnectins consists of a backbone of the natural amino acid sequence of the $10^{th}$ domain of the 15 repeating units of human fibronectin type III (FN3). Three loops at one end of the β-sandwich can be engineered to enable an Adnectin to specifically recognize a therapeutic target of interest. For further details see Protein Eng. Des. Sel. 18, 435-444 (2005), US20080139791, WO2005056764 and US6818418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005).

Microbodies are derived from naturally occurring microproteins of 25-50 amino acids in length which contain 3-4 cysteine bridges—examples of microproteins include KalataB1 and conotoxin and knottins. The microproteins have a loop which can be engineered to include upto 25 amino acids without affecting the overall fold of the microprotein. For further details of engineered knottin domains, see WO2008098796.

Other epitope binding domains include proteins which have been used as a scaffold to engineer different target antigen binding properties include human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins) are reviewed in Chapter 7—Non-Antibody Scaffolds from Handbook of Therapeutic Antibodies (2007, edited by Stefan Dubel) and Protein Science 15:14-27 (2006). Epitope binding domains of the present invention could be derived from any of these alternative protein domains.

As used herein, the term "antigen-binding site" refers to a site on a protein which is capable of specifically binding to antigen, this may be a single domain, for example an epitope-binding domain, or it may be paired VH/VL domains as can be found on a standard antibody. In some embodiments of the invention single-chain Fv (ScFv) domains can provide antigen-binding sites.

The terms "mAbdAb" and dAbmAb" are used herein to refer to antigen-binding proteins of the present invention. The two terms can be used interchangeably, and are intended to have the same meaning as used herein.

The term "antigen binding protein" as used herein refers to antibodies, antibody fragments for example a domain antibody (dAb), ScFv, Fab, Fab2, and other protein constructs. Antigen binding molecules may comprise at least one Ig variable domain, for example antibodies, domain antibodies (dAbs), Fab, Fab', F(ab')2, Fv, ScFv, diabodies, mAbdAbs, affibodies, heteroconjugate antibodies or bispecific antibodies. In one embodiment the antigen binding molecule is an antibody. In another embodiment the antigen binding molecule is a dAb, i.e. an immunoglobulin single variable domain such as a VH, VHH or VL that specifically binds an antigen or epitope independently of a different V region or domain. Antigen binding molecules may be capable of binding to two targets, i.e. they may be dual targeting proteins. Antigen binding molecules may be a combination of antibodies and antigen binding fragments such as for example, one or more domain antibodies and/or one or more ScFvs linked to a monoclonal antibody. Antigen binding molecules may also comprise a non-Ig domain for example a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEl and GroES; 41eroxidise41g (trans-body); ankyrin repeat protein (DARPin); peptide aptamer; C-type lectin domain (Tetranectin); human γ-crystallin and human ubiquitin (affilins); PDZ domains; scorpion toxinkunitz type domains of human protease inhibitors; and fibronectin (adnectin); which has been subjected to protein engineering in order to obtain binding to OSM. As used herein "antigen binding protein" will be capable of antagonising and/or neutralising human OSM. In addition, an antigen binding protein may inhibit and or block OSM activity by binding to OSM and preventing a natural ligand from binding and/or activating the gp130 receptor.

The term "Effector Function" as used herein is meant to refer to one or more of Antibody dependant cell mediated cytotoxic activity (ADCC), Complement-dependant cytotoxic activity (CDC) mediated responses, Fc-mediated phagocytosis and antibody recycling via the FcRn receptor. For IgG antibodies, effector functionalities including ADCC and ADCP are mediated by the interaction of the heavy chain constant region with a family of Fcγ receptors present on the surface of immune cells. In humans these include FcγRI (CD64), FcγRII (CD32) and FcγRIII (CD16). Interaction between the antigen binding protein bound to antigen and the formation of the Fc/Fcγ complex induces a range of effects including cytotoxicity, immune cell activation, phagocytosis and release of inflammatory cytokines. The interaction between the constant region of an antigen binding protein and various Fc receptors (FcR) is believed to mediate the effector functions of the antigen binding protein. Significant biological effects can be a consequence of effector functionality, in particular, antibody-dependent cellular cytotoxicity (ADCC), fixation of complement (complement dependent cytotoxicity or CDC), and half-life/clearance of the antigen binding protein. Usually, the ability to mediate effector function requires binding of the antigen binding protein to an antigen and not all antigen binding proteins will mediate every effector function. Effector function can be measured in a number of ways including for example via binding of the FcγRIII to Natural Killer cells or via FcγRI to monocytes/macrophages to measure for ADCC effector function. For example an antigen binding protein of the present invention can be assessed for ADCC effector function in a Natural Killer cell assay. Examples of such assays can be found in Shields et al, 2001 The Journal of Biological Chemistry, Vol. 276, p6591-6604; Chappel et al, 1993 The Journal of Biological Chemistry, Vol 268, p25124-25131; Lazar et al, 2006 PNAS, 103; 4005-4010.

Examples of assays to determine CDC function include that described in 1995 J Imm Meth 184:29-38.

Some isotypes of human constant regions, in particular IgG4 and IgG2 isotypes, essentially lack the functions of a) activation of complement by the classical pathway; and b) antibody-dependent cellular cytotoxicity. Various modifications to the heavy chain constant region of antigen binding proteins may be carried out depending on the desired effector property. IgG1 constant regions containing specific mutations have separately been described to reduce binding to Fc receptors and therefore reduce ADCC and CDC (Duncan et al. Nature 1988, 332; 563-564; Lund et al. J. Immunol. 1991, 147; 2657-2662; Chappel et al. PNAS 1991, 88; 9036-9040; Burton and Woof, Adv. Immunol. 1992, 51; 1-84; Morgan et al., Immunology 1995, 86; 319-324; Hezareh et al., J. Virol. 2001, 75 (24); 12161-12168).

In one embodiment of the present invention there is provided an antigen binding protein comprising a constant region such that the antigen binding protein has reduced ADCC and/or complement activation or effector functionality. In one such embodiment the heavy chain constant region may comprise a naturally disabled constant region of IgG2 or IgG4 isotype or a mutated IgG1 constant region. Examples of suitable modifications are described in EP0307434. One example comprises the substitutions of alanine residues at positions 235 and 237 (EU index numbering).

Human IgG1 constant regions containing specific mutations or altered glycosylation on residue Asn297 have also been described to enhance binding to Fc receptors. In some cases these mutations have also been shown to enhance ADCC and CDC (Lazar et al. PNAS 2006, 103; 4005-4010; Shields et al. J Biol Chem 2001, 276; 6591-6604; Nechansky et al. Mol Immunol, 2007, 44; 1815-1817).

In one embodiment of the present invention, such mutations are in one or more of positions selected from 239, 332 and 330 (IgG1), or the equivalent positions in other IgG isotypes. Examples of suitable mutations are S239D and 1332E and A330L. In one embodiment the antigen binding protein of the invention herein described is mutated at positions 239 and 332, for example S239D and 1332E or in a further embodiment it is mutated at three or more positions selected from 239 and 332 and 330, for example S239D and 1332E and A330L. (EU index numbering).

In an alternative embodiment of the present invention, there is provided an antigen binding protein comprising a heavy chain constant region with an altered glycosylation profile such that the antigen binding protein has enhanced effector function. For example, wherein the antigen binding protein has enhanced ADCC or enhanced CDC or wherein it has both enhanced ADCC and CDC effector function. Examples of suitable methodologies to produce antigen binding proteins with an altered glycosylation profile are described in WO2003011878, WO2006014679 and EP1229125, all of which can be applied to the antigen binding proteins of the present invention.

The present invention also provides a method for the production of an antigen binding protein according to the invention comprising the steps of.

a) culturing a recombinant host cell comprising an expression vector comprising the isolated nucleic acid as described herein, wherein the FUT8 gene encoding alpha-1,6-fucosyltransferase has been inactivated in the recombinant host cell; and b) recovering the antigen binding protein.

Such methods for the production of antigen binding proteins can be performed, for example, using the POTELLIGENT™ technology system available from BioWa, Inc. (Princeton, NJ) in which CHOK1SV cells lacking a functional copy of the FUT8 gene produce monoclonal antibodies having enhanced antibody dependent cell mediated cytotoxicity (ADCC) activity that is increased relative to an identical monoclonal antibody produced in a cell with a functional FUT8 gene. Aspects of the POTELLIGENT™ technology system are described in U.S. Pat. Nos. 7,214,775, 6,946,292, WO0061739 and WO0231240 all of which are incorporated herein by reference. Those of ordinary skill in the art will also recognize other appropriate systems.

In one embodiment of the present invention there is provided an antigen binding protein comprising a chimaeric heavy chain constant region for example an antigen binding protein comprising a chimaeric heavy chain constant region with at least one CH2 domain from IgG3 such that the antigen binding protein has enhanced effector function, for example wherein it has enhanced ADCC or enhanced CDC, or enhanced ADCC and CDC functions. In one such embodiment, the antigen binding protein may comprise one CH2 domain from IgG3 or both CH2 domains may be from IgG3.

Also provided is a method of producing an antigen binding protein according to the invention comprising the steps of:

a) culturing a recombinant host cell comprising an expression vector comprising an isolated nucleic acid as described herein wherein the expression vector comprises a nucleic acid sequence encoding an Fc domain having both IgG1 and IgG3 Fc domain amino acid residues; and b) recovering the antigen binding protein.

Such methods for the production of antigen binding proteins can be performed, for example, using the COMPLEGENT™ technology system available from BioWa, Inc. (Princeton, NJ) and Kyowa Hakko Kogyo (now, Kyowa Hakko Kirin Co., Ltd.) Co., Ltd. In which a recombinant host cell comprising an expression vector in which a nucleic acid sequence encoding a chimeric Fc domain having both IgG1 and IgG3 Fc domain amino acid residues is expressed to produce an antigen binding protein having enhanced complement dependent cytotoxicity (CDC) activity that is increased relative to an otherwise identical antigen binding protein lacking such a chimeric Fc domain. Aspects of the COMPLEGENT™ technology system are described in WO2007011041 and US20070148165 each of which are incorporated herein by reference. In an alternative embodiment CDC activity may be increased by introducing sequence specific mutations into the Fc region of an IgG chain. Those of ordinary skill in the art will also recognize other appropriate systems.

It will be apparent to those skilled in the art that such modifications may not only be used alone but may be used in combination with each other in order to further enhance effector function.

In one such embodiment of the present invention there is provided an antigen binding protein comprising a heavy chain constant region which comprises a mutated and chimaeric heavy chain constant region for example wherein an antigen binding protein comprising at least one CH2 domain from IgG3 and one CH2 domain from IgG1, wherein the IgG1 CH2 domain has one or more mutations at positions selected from 239 and 332 and 330 (for example the mutations may be selected from S239D and I332E and A330L) such that the antigen binding protein has enhanced effector function, for example wherein it has one or more of the following functions, enhanced ADCC or enhanced CDC, for example wherein it has enhanced ADCC and enhanced CDC. In one embodiment the IgG1 CH2 domain has the mutations S239D and I332E.

In an alternative embodiment of the present invention there is provided an antigen binding protein comprising a chimaeric heavy chain constant region and which has an altered glycosylation profile. In one such embodiment the heavy chain constant region comprises at least one CH2 domain from IgG3 and one CH2 domain from IgG1 and has an altered glycosylation profile such that the ratio of fucose to mannose is 0.8:3 or less, for example wherein the antigen binding protein is defucosylated so that said antigen binding protein has an enhanced effector function in comparison with an equivalent antigen binding protein with an immunoglobulin heavy chain constant region lacking said mutations and altered glycosylation profile, for example wherein it has one or more of the following functions, enhanced ADCC or enhanced CDC, for example wherein it has enhanced ADCC and enhanced CDC.

In an alternative embodiment the antigen binding protein has at least one IgG3 CH2 domain and at least one heavy chain constant domain from IgG1 wherein both IgG CH2 domains are mutated in accordance with the limitations described herein.

In one aspect of the invention there is provided a method of producing an antigen binding protein according to the invention described herein comprising the steps of:

a) culturing a recombinant host cell containing an expression vector containing an isolated nucleic acid as described herein, said expression vector further comprising a Fc nucleic acid sequence encoding a chimeric Fc domain having both IgG1 and IgG3 Fc domain amino acid residues, and wherein the FUT8 gene encoding alpha-1,6-fucosyltransferase has been inactivated in the recombinant host cell; and b) recovering the antigen binding protein.

Such methods for the production of antigen binding proteins can be performed, for example, using the ACCRETAMAB™ technology system available from BioWa, Inc. (Princeton, NJ) which combines the POTELLIGENT™ and COMPLEGENT™ technology systems to produce an antigen binding protein having both ADCC and CDC enhanced activity that is increased relative to an otherwise identical monoclonal antibody lacking a chimeric Fc domain and which has fucose on the oligosaccharide.

In yet another embodiment of the present invention there is provided an antigen binding protein comprising a mutated and chimeric heavy chain constant region wherein said antigen binding protein has an altered glycosylation profile such that the antigen binding protein has enhanced effector function, for example wherein it has one or more of the following functions, enhanced ADCC or enhanced CDC. In one embodiment the mutations are selected from positions 239 and 332 and 330, for example the mutations are selected from S239D and 1332E and A330L. In a further embodiment the heavy chain constant region comprises at least one CH2 domain from IgG3 and one Ch2 domain from IgG1. In one embodiment the heavy chain constant region has an altered glycosylation profile such that the ratio of fucose to mannose is 0.8:3 or less for example the antigen binding protein is defucosylated, so that said antigen binding protein has an enhanced effector function in comparison with an equivalent non-chimaeric antigen binding protein or with an immunoglobulin heavy chain constant region lacking said mutations and altered glycosylation profile.

Immunoconjugates

Also provided is an immunoconjugate (interchangeably referred to as "antibody-drug conjugates," or "ADCs")comprising an antigen binding protein according to the invention as herein described including, but not limited to, an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

Immunoconjugates have been used for the local delivery of cytotoxic agents, i.e., drugs that kill or inhibit the growth or proliferation of cells, in the treatment of cancer (Lambert, J. (2005) Curr. Opinion in Pharmacology 5:543-549; Wu et al. (2005) Nature Biotechnology 23(9):1137-1146; Payne, G. (2003) i 3:207-212; Syrigos and Epenetos (1999) Anticancer Research 19:605-614; Niculescu-Duvaz and Springer (1997) Adv. Drug Deliv. Rev. 26:151-172; U.S. Pat. No. 4,975,278). Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Baldwin et al., Lancet (Mar. 15, 1986) pp. 603-05; Thorpe (1985) "Antibody Carriers Of Cytotoxic Agents In Cancer Therapy: A Review," in Monoclonal Antibodies '84: Biological And Clinical Applications (A. Pinchera et al., eds) pp. 475-506. Both polyclonal antibodies and monoclonal antibodies have been reported as useful in these strategies (Rowland et al., (1986) Cancer Immunol. Immunother. 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342).

In one embodiment, the present invention includes immunoconjugates having the following general structure:

ABP-((Linker)$_n$-Ctx)$_m$

Wherein ABP is an antigen binding protein

Linker is either absent or any a cleavable or non-cleavable linker described herein Ctx is any cytotoxic agent described herein n is 0, 1, 2, or 3 and m is 1, 2, 3, 4, 5, 6, 7, 8, 9 or 10.

Examples of antibodies linked by an MC linker with auristatins such as MMAE and MMAF are depicted in the following structures:

L-MC-MMAE

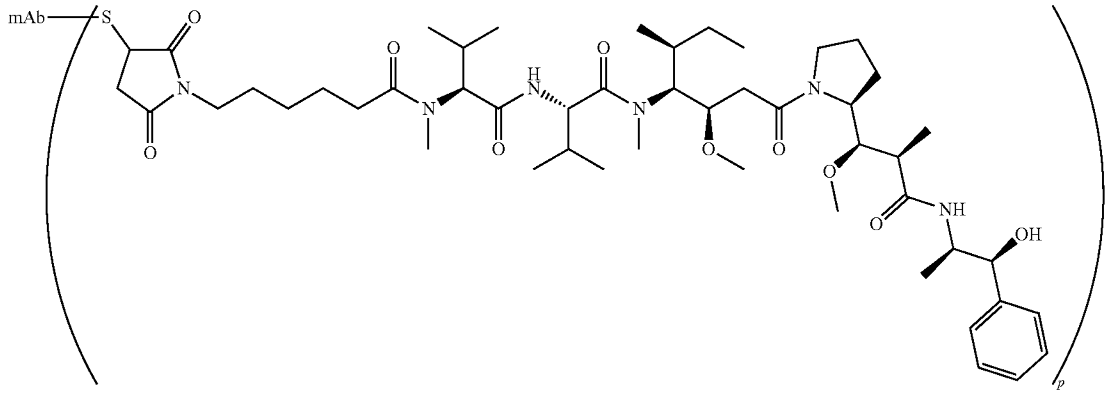

or

L-MC-MMAF

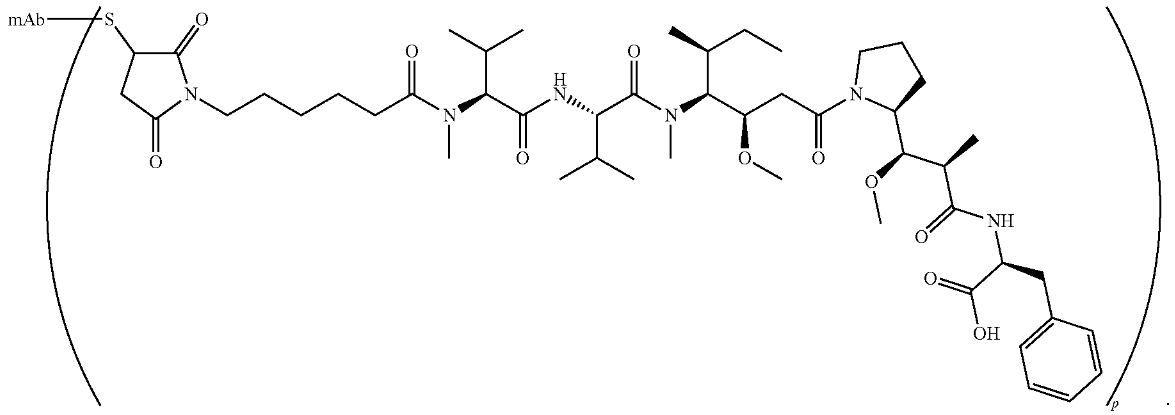

In certain embodiments, an immunoconjugate comprises an antigen binding protein, including but not limited to, an antibody and a chemotherapeutic agent or other toxin. Chemotherapeutic agents useful in the generation of immunoconjugates are described herein. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{211}At$, $^{212}Bi$, $^{131}I$, $^{131}In$, $^{90}Y$, and $^{186}Re$.

Antigen binding proteins of the present invention may also be conjugated to one or more toxins, including, but not limited to, a calicheamicin, maytansinoids, dolastatins, auristatins, a trichothecene, and CC1065, and the derivatives of these toxins that have toxin activity. Suitable cytotoxic agents include, but are not limited to, an auristatin including dovaline-valine-dolaisoleunine-dolaproine-phenylalanine (MMAF) and monomethyl auristatin E (MMAE) as well as ester forms of MMAE, a DNA minor groove binding agent, a DNA minor groove alkylating agent, an enediyne, a lexitropsin, a duocarmycin, a taxane, including paclitaxel and docetaxel, a puromycin, a dolastatin, a maytansinoid, and a vinca alkaloid. Specific cytotoxic agents include topotecan, morpholino-doxorubicin, rhizoxin, cyanomorpholino-doxorubicin, dolastatin-10, echinomycin, combretatstatin, chalicheamicin, maytansine, DM-1, DM-4, netropsin. Other suitable cytotoxic agents include anti-tubulin agents, such as an auristatin, a vinca alkaloid, a podophyllotoxin, a taxane, a baccatin derivative, a cryptophycin, a maytansinoid, a combretastatin, or a dolastatin. Antitubulin agent include dimethylvaline-valine-dolaisoleuine-dolaproine-phenylalanine-p-phenylened-iamine (AFP), MMAF, MMAE, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, DM-4 or eleutherobin.

Antibody drug conjugates were produced by conjugating the small molecule anti-tubulin agent monomethylauristatin E (MMAE) or monomethylauristatin F (MMAF) to the antibodies. In the case of MMAE the linker consists of a thiol-reactive maleimide, a caproyl spacer, the dipeptide valine-citrulline, and p-aminobenzyloxycarbonyl, a self-immolative fragmenting group. In the case of MMAF a protease-resistant maleimidocaproyl linker is used. The conjugation process leads to heterogeneity in drug-antibody attachment, varying in both the number of drugs bound to each antibody molecule (mole ratio [MR]), and the site of attachment. The most prevalent species is the material with an MR=4; less prevalent are materials with MR of 0, 2, 6, and 8. The overall average drug-to-antibody MR is approximately 4.

Production of Immunoconjugates

The points of attachment are cysteines produced by mild reduction of the interchain disulfides of the antibody which is carried out whilst antibodies are immobilised on Protein G affinity resin (thus enabling the use of large reagent excesses without intermediate purifications). While immobilized, a large excess of TCEP will fully reduce the interchain disulfides but has no impact upon the binding of the antibody to the resin.

The number of thiols per antibody generated by this procedure depends upon the source and isotype of the antibodies. For example, human (and mouse-human chimeric) IgG1s have 4 reducible disulfides, and thus generate 8 thiols upon full reduction, whereas murine IgG1s have 5 reducible disulfides and produce 10 thiols. If ADCs with the maximal drug loading (e.g., 10 drugs per antibody for the murine IgG1s) are desired, then the maleimido-drug-linker can simply be added to the immobilized antibodies in sufficient excess to ensure complete conjugation. However, ADCs with fewer drugs per antibody can also be prepared from fully reduced antibodies by including a biologically inert capping agent such as N-ethyl maleimide (NEM) which occupies some of the available thiols on the antibody. When the maleimido-drug-linker and the capping agent are added simultaneously to the fully reduced antibody and in large excess (at least 3-fold), the two maleimide electrophiles compete for the limiting number of available thiols. In this fashion, the drug loading is determined by the relative thiol reaction rates of the drug-linker and capping agent, and thus can be considered to be under kinetic control. The relative reaction rates of maleimido-drug-linkers do vary significantly, and thus the molar ratio of drug-linker to NEM present in a reaction mix must be determined empirically to arrive at a panel of ADCs with a desired level of drug loading. The mole fraction of the drug linkers SGD-1006 (vcMMAE) and SGD-1269 (mcMMAF) in NEM mixtures which yield ADCs with approximately 4 drugs per antibody are summarized in Table 2 for common human and murine IgG isotypes.

Auristatins and Dolastatins

In some embodiments, the immunoconjugate comprises an antigen binding protein or antibody conjugated to dolastatins or dolastatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al. (2001) Antimicrob. Agents and Chemother. 45(12):3580-3584) and have anticancer (U.S. Pat. No. 5,663,149) and antifungal activity (Pettit et al. (1998) Antimicrob. Agents Chemother. 42:2961-2965). The dolastatin or auristatin (which are pentapeptide derivatives of dolastatins) drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," U.S. Pat. No. 7,498,298, the disclosure of which is expressly incorporated by reference in its entirety. As used herein, the abbreviation "MMAE" refers to monomethyl auristatin E. As used herein the abbreviation "MMAF" refers to dovaline-valine-dolaisoleuine-dolaproine-phenylalanine.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides," volume 1, pp 76-136, 1965, Academic Press) that is well known in the field of peptide chemistry. The auristatin/dolastatin drug moieties may be prepared according to the methods of U.S. Pat. Nos. 5,635,483; 5,780,588; Pettit et al. (1989) J. Am. Chem. Soc. 111:5463-5465; Pettit et al. (1998) Anti-Cancer Drug Design 13:243-277; Pettit, G. R., et al. Synthesis, 1996, 719-725; and Pettit et al. (1996) J. Chem. Soc. Perkin Trans. 15:859-863. See also Doronina (2003) Nat Biotechnol 21(7):778-784; "Monomethylvaline Compounds Capable of Conjugation to Ligands," U.S. Pat. No. 7,498,298, filed Nov. 5, 2004, hereby incorporated by reference in its entirety (disclosing, e.g., linkers and methods of preparing monomethylvaline compounds such as MMAE and MMAF conjugated to linkers). Biologically active organic compounds which act as cytotoxic agents, specifically pentapeptides, are disclosed in U.S. Pat. Nos. 6,884,869; 7,498,298; 7,098,308; 7,256,257; and 7,423,116. Monoclonal antibodies linked with MMAE adn MMAF as well as various derivatives of auristatins and methods of making them are described in U.S. Pat. No. 7,964,566.

Examples of auristatins include MMAE and MMAF the structures of which are shown below:

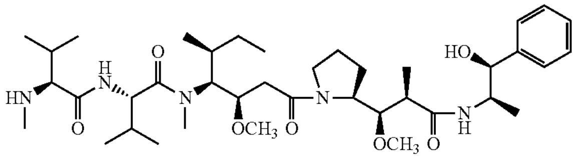

MMAE

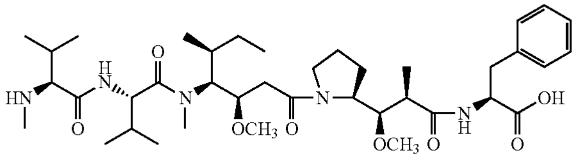

MMAF

Maytansine and Maytansinoids

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Highly cytotoxic maytansinoid drugs drugs can be prepared from ansamitocin precursors produced by fermentation of microorganisms such as *Actinosynnema*. Methods for isolating ansamitocins are described in U.S. Pat. No. 6,573,074. Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Maytansinoids are maytansinol and maytansinol analogues modified in the aromatic ring or at other positions of the maytansinol molecule, such as various maytansinol esters. Methods for preparing matansinoids for linkage with antibodies are disclosed in U.S. Pat. Nos. 6,570,024 and 6,884,874.

Calicheamicin

The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, gamma.1I, .alpha.2I, .alpha.3I, N-acetyl-.gamma.1I, PSAG and .theta.I1 (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include At211, I131, I125, Y90, Re186, Re188, Sm153, Bi212, P32, Pb212 and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as tc99m or I123, Re186, Re188 and In111 can be attached via a cysteine residue in the peptide. Yttrium-90 can be attached via a lysine residue. The IODOGEN method (Fraker et al. (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Preparation of ADCs

In antibody drug conjugates, the antibody can be conjugated directly to the cytotoxic agent or via a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker. Other suitable linkers include linkers hydrolyzable at a pH of less than 5.5, such as a hydrazone linker. Additional suitable cleavable linkers include disulfide linkers.

Bristol-Myers Squibb has described particular lysosomal enzyme-cleavable antitumor drug conjugates. See, for example, U.S. Pat. No. 6,214,345. Seattle Genetics has published applications U.S. Pat. Appl. 2003/0096743 and U.S. Pat. Appl. 2003/0130189, which describe p-aminobenzylethers in drug delivery agents. The linkers described in these applications are limited to aminobenzyl ether compositions.

Conjugates of the antigen binding protein and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

Additionally the linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-1 carboxylate ("SMCC"), and N-Succinimidyl (4-iodo-acetyl)aminobenzoate ("SIAB"). Additional linker components are known in the art and some are described herein. See also "Monomethylvaline Compounds Capable of Conjugation to Ligands," U.S. Pat. No. 7,498,298, filed Nov. 5, 2004, the contents of which are hereby incorporated by reference in its entirety.

Linkers may also comprises amino acids and/or amino acid analogs. Amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzyme, for example, a tumor-associated protease, cathepsin B, C and D, or a plasmin protease.

Antigen binding proteins and antibodies may be made reactive for conjugation with linker reagents. Nucleophilic groups on antibodies include, but are not limited to: (i) N-terminal amine groups, (ii) side chain amine groups, e.g., lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antigen binding proteins and antibodies may also be modified to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehydes can be reacted with a drug moiety or linker nucleophile.

Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Peptidyl linkers may be cleavable by enzymes that are present cells. For example, a peptidyl linker that is cleavable by the thiol-dependent protease cathepsin-B, which is highly expressed in cancerous tissue, can be used (e.g., a Phe-Leu or a Gly-Phe-Leu-Gly (SEQ ID NO:50) linker). Other such linkers are described, e.g., in U.S. Pat. No. 6,214,345. In specific embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of ADC or ADC derivative, are cleaved when the ADC or ADC derivative present in an extracellular environment (e.g., in plasma). Whether a linker is not substantially sensitive to the extracellular environment can be determined, for example, by incubating independently with plasma both (a) the ADC or ADC derivative (the "ADC sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the ADC sample with that present in control sample, as measured, for example, by high performance liquid chromatography.

In other, non-mutually exclusive embodiments, the linker promotes cellular internalization. In certain embodiments, the linker promotes cellular internalization when conjugated to the therapeutic agent (i.e., in the milieu of the linker-therapeutic agent moiety of the ADC or ADC derivate as described herein). In yet other embodiments, the linker promotes cellular internalization when conjugated to both the therapeutic agent and the antigen binding protein or antibody or derivative thereof (i.e., in the milieu of the ADC or ADC derivative as described herein).

A variety of linkers that can be used with the present compositions and methods are described in WO 2004010957 entitled "Drug Conjugates and Their Use for Treating Cancer, An Autoimmune Disease or an Infectious Disease" filed Jul. 31, 2003, and U.S. Provisional Application No. 60/400,403, entitled "Drug Conjugates and their use for treating cancer, an autoimmune disease or an infectious disease", filed Jul. 31, 2002 (the disclosure of which is incorporated by reference herein).

Alternatively, a fusion protein comprising the antigen binding protein and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

The term "Non Human antibody or antibody fragment thereof" as used herein is meant to refer to antibodies or fragments thereof which originate from any species other than human wherein human includes chimeric antibodies.

The term "donor antibody" refers to an antibody (monoclonal, and/or recombinant) which contributes the amino acid sequences of its variable domains, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but preferably all) of the amino acid sequences encoding its heavy and/or light chain framework regions and/or its heavy and/or light chain constant regions to the first immunoglobulin partner. The human antibody is the acceptor antibody.

The term "Human acceptor sequence" as used herein is meant to refer to a framework of an antibody or antibody fragment thereof comprising the amino acid sequence of a VH or VL framework derived from a human antibody or antibody fragment thereof or a human consensus sequence framework into which CDR's from a non-human species may be incorporated.

The term "incorporation" of CDR's or hypervariable regions as used herein encompasses any means by which the non-human CDR's are situated with the human acceptor framework. It will be appreciated that this can be achieved in various ways, for example, nucleic acids encoding the desired amino acid sequence can be generated by mutating nucleic acids encoding the non-human variable domain sequence so that the framework residues thereof are changed to human acceptor framework residues, or by mutating nucleic acid encoding the human variable domain sequence so that the CDR's are changed to non-human residues, or by synthesizing nucleic acids encoding the desired sequence. In one embodiment the final sequence is generated in silico.

The present invention is now described by way of example only. The appended claims may include a generalisation of one of more of the following examples.

EXAMPLES

Example 1 Monoclonal Antibody Generation and Selection 1.1 Immunisation Strategies The anti human BCMA mAb murine parental CA8 was identified from hybridomas derived from mice immunized with full length human BCMA. A BALB/c mouse was immunized i.p. with 25 μg of recombinant (rBCMA) protein combined with CFA. The mouse was boosted three times at one-month intervals with 25 μg of full length rBCMA protein+10 μg monophosphoryl lipid A-stable emulsion (MPL-SE) (Corixa Corporation, Seattle, WA) and given a pre-fusion boost of 30 μg rBCMA protein i.v. 3 days prior to fusion. Hybridomas were either generated and cloned using the ClonaCell-HY hybridoma cloning kit (StemCell Technologies, Vancouver, BC) or using a conventional method. In the conventional method, B cells from the spleens of the immunized animals were fused with Sp2/0 myeloma cells in the presence of PEG (Sigma-Aldrich, St. Louis, MO). After overnight recovery, fused cells were plated at limiting dilution in 96-well plates and subjected to hypoxanthine-aminopterin-thymidine selection. Hybridoma culture supernatants were examined for the presence of anti-BCMA antibodies by ELISA and flow cytometry The anti human BCMA mAb murine parental S307118G03 was identified from hybridomas derived from SJL mice immunized with recombinant human BCMA/TNFRSF17-Fc chimera (R&D 193-Fc) using the RIMMS method (Rapid immunisation multiple sites). At Day 0, 5 ug protein per mouse was emulsified in AS02a adjuvant at 2 sites on back (over haunches and over shoulders) and subjacent to the major lymph nodes at 4 sites on front. On day 6 and day 11 2.5 ug protein per mouse in RIBI adjuvant was injected subjacent to the major lymph nodes at 4 sites on front. On day 14 the animals were sacrificed. The lymph nodes and spleen were excised, disrupted and a PEG1500 induced somatic cell fusion performed using a 3:1 ratio with mouse myeloma cells X63 AG8 653.GFP.Bcl-2.11 (BioCat 112754; R17209/58). The fusion was plated out into 10×96 well plates and screened directly from these. The anti human BCMA mAb murine parental S336105A07 was identified from hybridomas derived from identical immunisations. The lymph nodes and spleen were excised at day 14, disrupted, and a Cytopulse electrofusion was performed using a 1:1 ratio with mouse myeloma cells X63 AG8 653.GFP.Bcl-2.11 (BioCat 112754; R17209/58). The fusion was plated out into omnitrays containing semi solid medium prior to picking into 10×96 well plates and was screened directly from these 5 days later.

The anti human BCMA murine parental mAbs S332121F02 and S332126E04 were identified from hybridomas derived from SJL mice immunized with recombinant Fc fusion of the extracellular domain of human BCMA (4-53)BCMA using the RIMMS method (Rapid immunisation). At Day 0, 5 ug protein per mouse was emulsified in AS02a adjuvant at 2 sites on back (over haunches and over shoulders) and subjacent to the major lymph nodes at 4 sites on front. On day 6 5 ug recombinant cyno BCMA-Fc protein per mouse in RIBI adjuvant was injected subjacent to the major lymph nodes at 4 sites on front. On day 11 2.5 ug recombinant human BCMA-Fc and 2.5 ug recombinant cyno BCMA-Fc per mouse in RIBI adjuvant was injected subjacent to the major lymph nodes at 4 sites on front. On day 14 the animals were sacrificed and cells treated as for S307118G03.

The anti human BCMA murine parental mAb S322110D07 was identified from hybridomas derived from SJL mice immunised with recombinant Fc fusion of the extracellular domain of human BCMA (4-53) in complex with recombinant human April (R&D 5860-AP/CF) premixed at 1:1 molar ratio. The mice were immunized i.p. with 5 ug April/Cyno BCMA-Fc complex in PBS, suspended in RIBI adjuvant, 100 ul dose per mouse and boosted 3 times at 3-4 week intervals with 2.5 ug April/Cyno BCMA-Fc complex in PBS, suspended in RIBI adjuvant, 100 ul dose per mouse injected via intraperitoneal route and given a pre-fusion boost of the same immunogen 1 day prior to fusion and treated as for S307118G03.

The anti human BCMA mAb murine parental S335115G01 and S335122F05 were identified from hybridomas derived from SJL mice immunized with a mixture of recombinant Fc fusion of the extracellular domain of human BCMA (4-53) and recombinant Fc fusion of the extracellular domain of cyno BCMA (4-52) using the RIMMS method (Rapid immunisation multiple sites). At Day 0, 2, 5 ug of each protein per mouse was emulsified in AS02a adjuvant and injected at 2 sites on the back (over haunches and over shoulders) and subjacent to the major lymph nodes at 4 sites on front. On day 6 and day 11 2.5 ug of each protein per mouse in RIBI adjuvant was injected subjacent to the major lymph nodes at 4 sites on front. On day 14 the animals were sacrificed. The lymph nodes and spleen were excised, disrupted and a Cytopulse electrofusion was performed using a 1:1 ratio with mouse myeloma cells X63 AG8 653.GFP.Bcl-2.11 (BioCat 112754; R17209/58). The fusion was plated out into omnitrays containing semi solid medium prior to picking into 32×96 well plates and was screened directly from these 5 days later.

Example 2 Humanisation 2.1 Cloning of CA8 Hybridoma Variable Regions

Total RNA was extracted from CA8 hybridoma cells, heavy and light variable domain cDNA sequence was then generated by reverse transcription and polymerase chain reaction (RT-PCR). The forward primer for RT-PCR was a mixture of degenerate primers specific for murine immunoglobulin gene leader-sequences and the reverse primer was specific for the antibody constant regions. Reverse primers specific for IgG1, IgG2a and IgG2b were used in this case as the isotype was unknown. To design the primers, DNA multiple sequence alignments of the leader sequences of the mouse $V_H$ and $V_k$ genes were generated.

2.2 Cloning of Chimeric CA8

The DNA expression constructs encoding the chimeric antibody were prepared de novo by build-up of overlapping oligonucleotides including restriction sites for cloning into mammalian expression vectors as well as a human signal sequence. HindIII and SpeI restriction sites were introduced to frame the $V_H$ domain containing the signal sequence for cloning into mammalian expression vectors containing the human γ1 constant region. HindIII and BsiWI restriction sites were introduced to frame the VL domain containing the signal sequence for cloning into mammalian expression vector containing the human kappa constant region.

2.3 Cloning of the Humanised CA8 Variants

The DNA expression constructs encoding the humanised antibody variants were prepared de novo by build-up of overlapping oligonucleotides including restriction sites for cloning into mammalian expression vectors as well as a human signal sequence. HindIII and SpeI restriction sites were introduced to frame the $V_H$ domain containing the signal sequence for cloning into mammalian expression vectors containing the human γ1 constant region. HindIII and BsiWI restriction sites were introduced to frame the VL domain containing the signal sequence for cloning into mammalian expression vector containing the human kappa constant region. 2.4 Expression of the recombinant CA8 antibodies (including antibody quantification) Expression plasmids encoding the heavy and light chains respectively were transiently co-transfected into HEK 293 6E cells and expressed at small scale to produce antibody. Antibodies were quantified by ELISA. ELISA plates were coated with anti human IgG (Sigma 13382) at 1 mg/ml and blocked with blocking solution (4% BSA in Tris buffered saline). Various dilutions of the tissue culture supernatants were added and the plate was incubated for 1 hour at room temperature. Dilutions of a known standard antibody were also added to the plate. The plate was washed in TBST and binding was detected by the addition of a peroxidise labelled anti human kappa light chain antibody (Sigma A7164) at a dilution of 1/1000 in blocking solution. The plate was incubated for 1 hour at room temp before washing in TBST. The plate was developed by addition of OPD substrate (Sigma P9187) and colour development stopped by addition of 2M $H_2SO_4$. Absorbance was measured at 490 nm and a standard curve plotted using data for the known standard dilutions. The standard curve was used to estimate the concentration of antibody in the tissue culture supernatants. Larger scale antibody preparations were purified using protein A and concentrations were measured using a Nanodrop (Thermo Scientific).

TABLE 1

Design of CA8 variable heavy and light humanised variants

| Humanised VH | Template | Backmutations (Kabat#) |
|---|---|---|
| J0 | Straight graft of CA8 VH CDRs onto IGHV1_69 + JH1 minigene | None |
| J1 | J0 | G27Y, S30T |
| J2 | J1 | A93T |
| J3 | J2 | A24G, K73T |
| J4 | J3 | M48I, V67A, I69L |
| J5 | J3 | N99D |
| J6 | J0 | N99D |
| J7 | J1 | N99D |
| J8 | J2 | N99D |
| J9 | J4 | N99D |
| M0 | Straight graft of CA8 VL CDRs onto IGKV1_39 + JK2 minigene | None |
| M1 | M0 | F71Y |
| M2 | M1 | M4L, K45E, L47V |

2.5 Defucosylated Antibody Production

To generate defucosylated antibodies the heavy and light chains respectively were co-transfected into CHO DG44 MS705 BioWa cells and expressed at scale to produce antibody. Briefly, 30 μg DNA was linearised overnight with Not1, the DNA was ethanol precipitated and re-dissolved in TE buffer. From culture, 2.4×107 BioWa DG44 cells were obtained and washed in 14 ml of warmed PBS-sucrose. The cells were spun and the pellet resuspended in 1.6 ml of PBS-sucrose. Half (0.8 ml) of aforementioned cells, suspended in PBS-sucrose, were added to a BioRad cuvette with the 30 μg of linearised DNA (in 50 μl TE buffer). A BioRad GenePulser was programmed to 380V with a capacitance of 25 pF and the cuvette was entered for electroporation. The resulting 850 ul of electroporated cells and DNA were added to (80 ml) warmed SFM512 medium (including phenol red, 2×HT (nucleosides), glutamax and Gibco supplement4). Finally, the resulting 80 ml of cell suspension was transferred (150 μl/well) to each well of one of 4×96-well plates. After 48 hours, the medium was changed to nucleoside free by removing approximately 130 μl of conditioned and replacing with 150 μl of fresh selection medium SFM512 medium (including phenol red and glutamax). Every 3-4 days, 130-150 μl of conditioned medium was removed and replaced with fresh, selection medium. Wells were monitored for colour change and assayed for IgG concentration as discussed previously.

2.6 Additional Antibodies—Cloning of Hybridoma Variable Regions

Total RNA was extracted from S307118G03, S332121F02, S332126E04, S322110D07, S336105A07, S335115G01 and S335122F05 hybridoma cells. Heavy and light variable domain cDNA sequence was then generated by reverse transcription and polymerase chain reaction (RT-PCR). The forward primer for RT-PCR was a mixture of degenerate primers specific for murine immunoglobulin gene leader-sequences and the reverse primer was specific for the antibody constant regions, in this case isotype IgG2a. Primers were designed based on a strategy described by Jones and Bendig (Bio/Technology 9:88, 1991). RT-PCR was carried out for both V-region sequences to enable subsequent verification of the correct V-region sequences. DNA sequence data was obtained for the V-region products generated by the RT-PCR.

2.7 Additional Antibodies—Cloning of the Chimeras

The DNA expression constructs encoding the chimeric antibodies were prepared de novo by infusion advantage PCR cloning (Clonetech) of the V-gene PCR products into mammalian expression vectors. This cloning method enabled fusion the murine variable regions to human IgG1 H chain and kappa L chain constant regions.

2.8 S307118G03—Cloning of the Humanized Variants

Cloning was carried out as for paragraph 2.3.

2.9 S307118G03 Expression of the Recombinant Antibodies

Expression plasmids encoding the relevant heavy and light chains (listed in Table 8 below) were transiently co-transfected into HEK 293 6E cells and expressed at small scale to produce antibody. The antibodies were Protein A purified from the supernatants and quantified using the Nanodrop spectrophotometer.

8 below) were transiently co-transfected into HEK 293 6E cells and expressed at small scale to produce antibody. The antibodies were Protein A purified from the supernatants and quantified using the Nanodrop spectrophotometer.

Example 3 Conjugation of Antibodies to vcMMAE and mcMMAF to Form Antibody Drug Conjugates (ADC)

Table B Chemical structures of drug-linkers

SGD-1006 (vcMMAE)

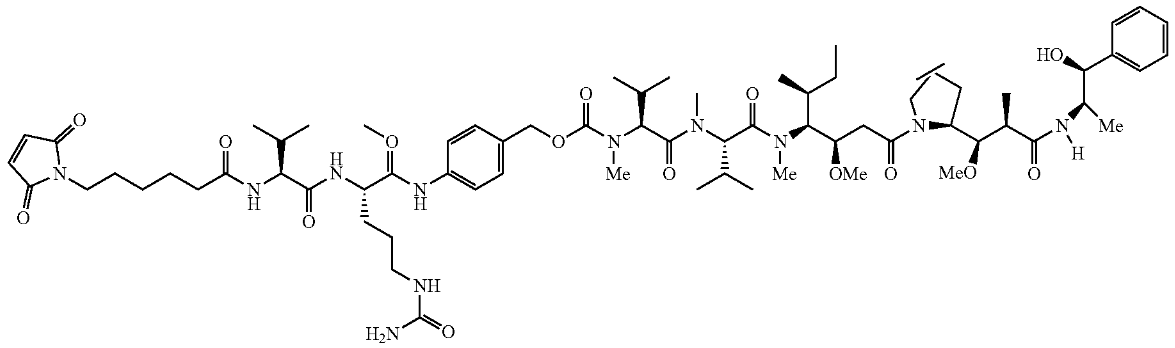

SGD-1269 (mcMMAF)

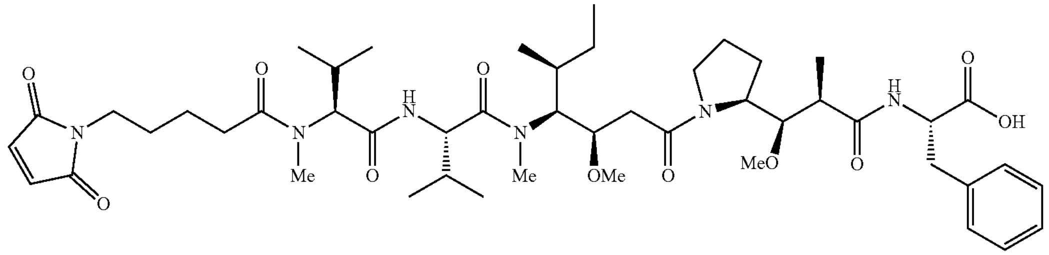

Gammabind Plus Protein G Sepharose (GE Healthcare) resin slurry (75 uL) was added to a each well of a deep well (2 mL capacity) filter plate. The antibodies to be conjugated were grouped by species and isotype and up to 0.5 mg of each antibody transferred to each well of the plate. Each antibody was transferred to two separate wells to facilitate the preparation of two conjugates, with the drug-linkers SGD-1006 and SGD-1269. The filter plate was then shaken at 1200 RPM for 2 hours at 5° C. to bind the antibodies to the resin. The filter plate was then centrifuged at 500×g for 3 minutes to ensure complete pulldown of all fluids and resin to the bottom of the each well.

The bound antibodies were then reduced by adding 500 μL of 10 mM TCEP in 100 mM KPO4, 150 mM NaCl, pH 7, 1 mM EDTA and shaking for 30 minutes at 22° C. Following reduction, the plate was again centrifuged to remove the TCEP solution and subsequently washed with PBS+1 mM EDTA, 1 mL per well. The wash solution was removed by centrifugation and the process repeated 3 times for a total of 4 washes. The bound and reduced antibodies were then conjugated using a mixture of NEM and drug linker prepared in accordance with the mole fractions indicated in Table 2.

TABLE 2

| Antibody (species/isotype) | Reducible Disulfides | SGD-1006 mole fraction | SGD-1269 mole fraction |
|---|---|---|---|
| Human IgG1* | 4 | 0.675 | 0.688 |
| Murine IgG1 | 5 | 0.500 | 0.586 |
| Murine IgG2a | 5 | 0.500 | 0.586 |
| Murine IgG2b | 6 | 0.463 | 0.481 |

*also for murine/human IgG1 chimerics

Separate mixtures of NEM and drug linker were thus prepared for each antibody species/isotype using 10 mM DMSO stock solutions of SGD-1006, SGD-1269 (See Table B) and NEM. When mixed at the appropriate ratio the total maleimide concentration was therefore still 10 mM, and this value was used to calculate the volume of maleimide solution to be added to each well. For example for a murine IgG1 with 5 reducible disulfides (10 available thiols when reduced) 0.5 mg of antibody at 150 kD is 3.33 nmol corresponding to 33.3 nmol of thiol. A 3-fold excess is therefore 100 nmol of total maleimide or 10 μL of the 10 mM drug linker/NEM mix. For the SGD-1269 conjugate this mix would then be prepared with 5.86 μL of SGD-1269 and 4.14 μL of NEM. The maleimide mix would then be diluted into 500 μL of PBS prior to addition to the immobilized reduced antibody. In practice, since multiple antibodies of each isotype were conjugated simultaneously a single SGD-1269/NEM mixed solution for each isotype was prepared by multiplying the number of wells containing that isotype by 10 μL per well then diluting into a volume of PBS equal to 500 μL times the number of wells. In like fashion a total of eight drug-linker/NEM mixes were prepared—four with SGD-1006 and four with SGD-1269—and diluted into PBS. These mixes were then added to the reduced antibodies (500 μL per well) and the plate was shaken for 30 minutes at 22° C. The plate was then centrifuged as above to remove the excess reaction solution, and subsequently washed 4 times with PBS as before.

The bound ADCs were then eluted by adding 200 μL of 50 mM glycine pH 2.5 to each well and shaking the plate for 3 minutes at 1200 RPM. While shaking 20 μL of neutralization buffer (1M potassium phosphate, pH 7.4, 500 mM NaCl, 0.2% Tween-20) was added to each well of a 1 mL collection plate. The ADCs were then eluted into the collection plate by spinning at 1500×g for 6 minutes. The collection plate was then shaken briefly to ensure complete mixing of the neutralization buffer.

The concentration of each ADC was then determined with an absorbance plate reader by transferring the solutions into a UV assay plate (Costar model 3635, Corning) and measuring the optical density at 280 nm. An average IgG extinction coefficient of 1.45 mL mg−1 cm−1 was used to provide an adequate estimation of ADC concentration across the panel. To confirm successful conjugation, a reversed phase protein HPLC method (described below) was used to estimate the drug loading of the isotype controls. For the plate containing the humanization variants of CA8 this method was used to estimate the loading of all ADCs directly.

The reversed phase protein chromatography method for determining drug loading employs the PLRP-S polymeric stationary phase (Agilent Technologies). Since the antibodies were fully reduced during the conjugation process all of the antibody subunits elute from the column as single polypeptide chains allowing the subpopulations of light and heavy chain species with varying levels of drug loading to be evaluated separately. Thus, the analysis of these data allow for the calculation of the average light chain drug loading and the average heavy chain drug loading as independent factors which can then be combined to determine average antibody drug loading with the basic knowledge that each antibody is comprised of two light and two heavy chains. The chromatographic conditions were as follows: A PRLP-S column, 1000 Å, 50×2.1 mm, 8 μm particle size (Agilent Technologies) with water+0.05% TFA as mobile phase A and acetonitrile+0.01% TFA as mobile phase B; elution with a linear gradient of 27% B to 42% B in 12.5 minutes.

Anti-BCMA antibodies were conjugated with SGD-1006 and SGD-1269 in three separate batches over a period of seven months. In the first batch a total of 29 antibodies were conjugated (resulting in 58 ADCs). The drug loading of each isotype control determined by PLRP chromatography and the data are summarized in Table 3.

TABLE 3

| Isotype | SGD-1006 loading | SGD-1269 loading |
|---|---|---|
| cIgG1 (control P) | 4.23 | 4.35 |
| cIgG1 (control M) | 4.42 | 4.41 |
| mIgG1 | 4.26 | 4.04 |
| mIgG2a | 4.51 | 4.57 |
| mIgG2b | 4.39 | 4.18 |

For the second batch an additional 25 antibodies were conjugated (resulting in 50 ADCs). The drug loading of each isotype control was again determined by PLRP chromatography and the data are summarized in Table 4.

TABLE 4

| Isotype | SGD-1006 loading | SGD-1269 loading |
|---|---|---|
| cIgG1 | 3.96 | 3.78 |
| mIgG1 | 3.95 | 3.32 |
| mIgG2a | 4.53 | 3.60 |
| mIgG2b | 4.32 | 3.49 |

In the third batch 30 antibodies were conjugated (resulting in 60 ADCs), including 13 humanized variants of CA8. In this final batch, the drug loading of all ADCs were determined and are summarized in the following two plate maps. (Table 5 & 6)

TABLE 5

| drug loading | 1 | 2 | 3 | 4 | 5 | 6 | 7 | 8 | 9 | 10 |
|---|---|---|---|---|---|---|---|---|---|---|
| A | 3.7 | 4.0 | 3.6 | 3.8 | 3.8 | 3.5 | 3.9 | 2.8 | 3.8 | 3.8 |
| B | 3.7 | 3.6 | 3.5 | 3.7 | 4.0 | 3.4 | 3.7 | 3.3 | 3.8 | 3.9 |
| C | 3.6 | 3.8 | 3.5 | 3.7 | 3.6 | 3.3 | 3.8 | 4.7 | 3.8 | 3.7 |
| D | 3.4 | 3.6 | 3.6 | 3.9 | 3.9 | 3.4 | 3.2 | 4.8 | 3.8 | 3.9 |
| E | 3.9 | | 3.8 | 3.9 | 3.4 | 3.6 | | 3.3 | 3.7 | 3.4 |
| F | 3.7 | | | 4.0 | 3.6 | 3.5 | | | 3.8 | 3.7 |
| G | 3.6 | | | 3.6 | | 3.4 | | | 3.7 | |
| H | | | | 3.6 | | | | | 3.6 | |
| | SGD-1006 (vc-MMAE) ADCs | | | | | SGD-1269 (mc-MMAF) ADCs | | | | |
| | 3.7<br>4.1% | 3.8<br>5.1% | 3.6<br>3.4% | 3.8<br>4.8% | | 3.4<br>2.8% | 3.7<br>8.5% | 3.8<br>24.1% | 3.7<br>3.4% | |

TABLE 6

| | mIgG1 | mIgG2a | mIgG2b | humanized | | mIgG1 | mIgG2a | mIgG2b | humanized | |
|---|---|---|---|---|---|---|---|---|---|---|
| | 1 | 2 | 3 | 4 | 5 | 6 | 7 | 8 | 9 | 10 |
| A | control | control | control | CA8 J6M2 | CA8 J8M2 | control | control | control | CA8 JSM0 | CA8 JSM2 |
| B | S336106D07 | S336105A07 | S336107G08 | CA8 J6M0 | CA8 J9M0 | S336306D07 | S336105A07 | S336107G08 | CA8 J6M1 | CA8 J9M0 |
| C | S335115G03 | S335122F05 | S336104A09 | CA8 J6M1 | CA8 J9M1 | S335115G03 | S335122F05 | S336104A09 | CA8 J6M2 | CA8 J9M1 |
| D | S335115G01 | S335128A12 | S335107H11 | CA8 J7M2 | CA8 J9M2 | S335115G01 | S335128A12 | S335107H11 | CA8 JIM0 | CA7 J9M2 |

TABLE 6-continued

| | mIgG1 | mIgG2a | mIgG2b | humanized | | mIgG1 | mIgG2a | mIgG2b | humanized | |
|---|---|---|---|---|---|---|---|---|---|---|
| | 1 | 2 | 3 | 4 | 5 | 6 | 7 | 8 | 9 | 10 |
| E | S335106E08 | | S335339E11 | CA8 17M1 | CA8 Fc ENH | S335106E08 | | S335119E11 | CA8 J7M1 | CA8 Fe ENH |
| F | S335132E01 | | | CA8 JTM2 | GRITS28785 | S335132E01 | | | CA8 J7M2 | GRITS28785 |
| G | S341106G02 | | | CA8 JSM0 | | S341106G02 | | | CA8 JSM0 | |
| | | | | CA8 J8M1 | | | | | CA8 JSM1 | |
| | SGD-1006 (vc-MMAE) ADCs | | | | | SGD-1269 (mc-MMAF) ADCs | | | | |

Mean drug loading and % CV are indicated for each isotype series at the bottom. An uncharacteristically large variability in drug loading was observed for the SGD-1269 ADCs prepared with mIgG2b antibodies; the reason for this is unclear. Also, the Fc-enhanced CA8 antibodies yielded somewhat lower drug loading levels than the other CA8 human variants; to address this, additional Fc-enhanced CA8 was conjugated in a solution-phase reaction to better match the drug loading achieved for the other antibodies.

Example 4—Binding Data 4.1 FMAT Binding Assay to Show Binding of Chimeric CA8 to Cells Expressing Human or Cyno BCMA.

Cryopreserved transfected human, cyno BCMA and mock transfected HEK293 cells were recovered from LN2 storage. Assay wells were prepared with human chimeric CA8 antibody, at a range of different concentrations, mixed with human BCMA HEK293, cyno BCMA HEK293 and mock transfected cells respectively. Anti-human IgG FMAT Blue secondary conjugate was added for detection of human chimeric CA8. The assay plates were left for a minimum of 90 minutes before the result was read on the ABI8200 (FMAT) plate reader. This showed that the CA8 antibody in chimeric form binds well to both human and cyno BCMA proteins expressed on HEK293 cells.

Figure 1:
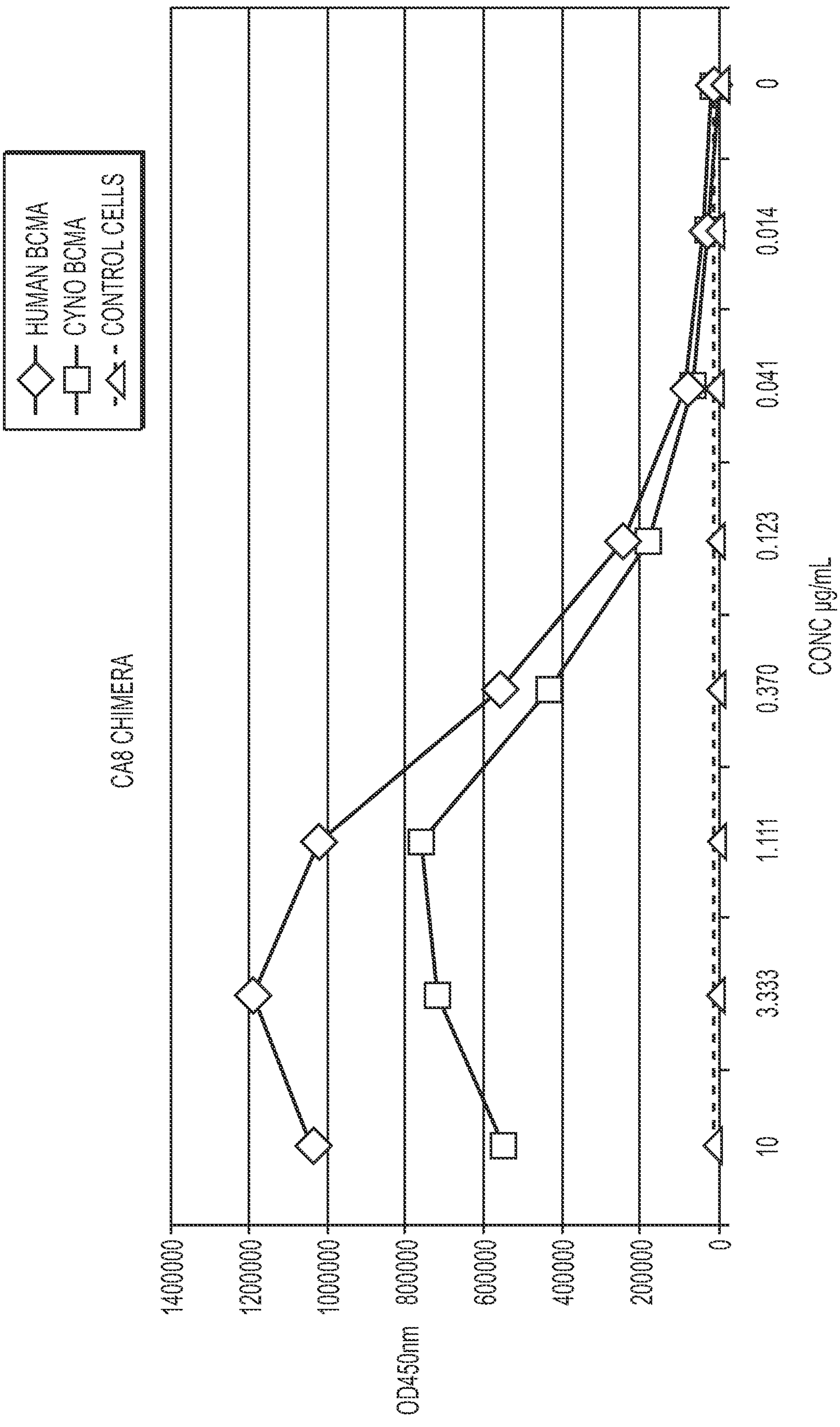
FIG. 1: FMAT Binding Assay—Figure showing the results of the FMAT assay for CA8 antibody binding to human and cyno BCMA expressing HEK293 cells. Human chimeric CA8 binds well to human and cyno BCMA expressing cells.

Results are shown in FIG. 1.

4.2 ELISA Experiment Showing Binding of Chimeric CA8 to Recombinant BCMA Protein Chimeric CA8 antibodies were tested for binding to human BCMA and cyno BCMA expressed as Fc fusions. Human BCMA-Fc and cyno BCMA-Fc were coated to ELISA plates and the plates were blocked using BSA to reduce non specific binding. CA8 chimeric antibodies were added in a concentration range from 5 ug/ml to 0.1 ug/ml to the human and cyno BCMA coated ELISA plates. Any bound human chimeric CA8 antibody was detected using anti-human IgG HRP conjugated secondary antibody as appropriate. HRP substrate (TMB) was added to develop the ELISA. This showed that CA8 antibody binds to recombinant human and cyno BCMA in an ELISA assay.

Figure 2:
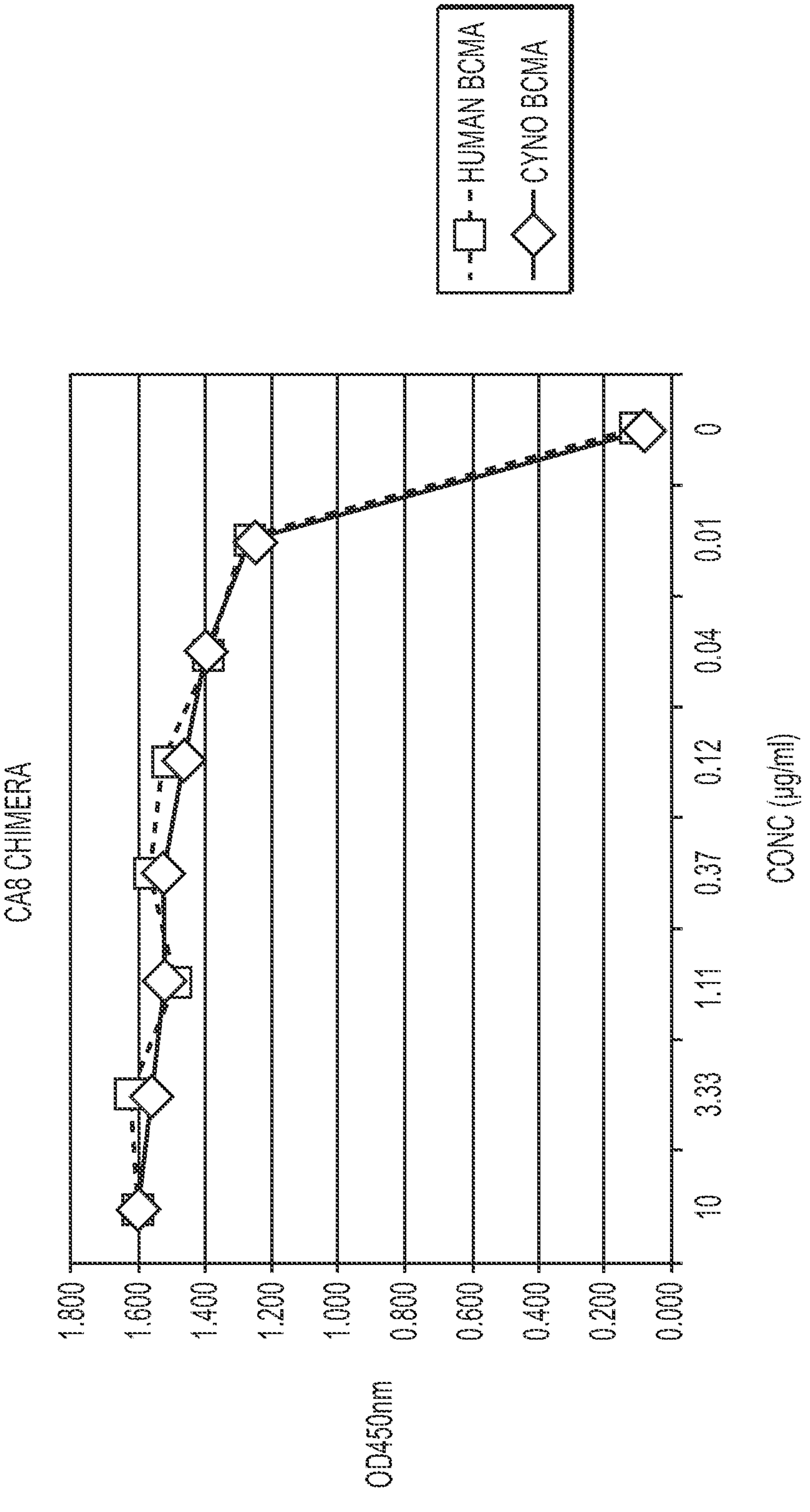
FIG. 2: ELISA Binding Assay—Figure showing the ELISA results for CA8 antibodies binding to human and cyno BCMA recombinant proteins. This clearly shows that human chimeric CA8 antibodies bind to human and cyno BCMA proteins equally.

Results are shown in FIG. 2.

4.3 Biacore Experiment to Show CA8 Antibody Binding to BCMA and TACI Proteins to Determine Cross Reactivity with TACI Protein.

CA8 chimera antibody was injected and captured on protein A. (A protein A derivitised sensorchip was used). Residual protein A binding was blocked with an injection of a high concentration of human IgG solution. BCMA-Fc, TACI-Fc or BAFF-R-Fc solutions were then tested for binding to the antibody. The 3 proteins were injected in sequence and binding events were measured. The surface was regenerated between injection of each protein.

Sensorgrams were analysed in the Biaevaluation program. Double reference subtraction was done to remove instrument noise and any non-specific binding from the sensorgram curves. This showed that CA8 was specific for binding to BCMA binding and not to TACI and BAFFR.

Figure 3:
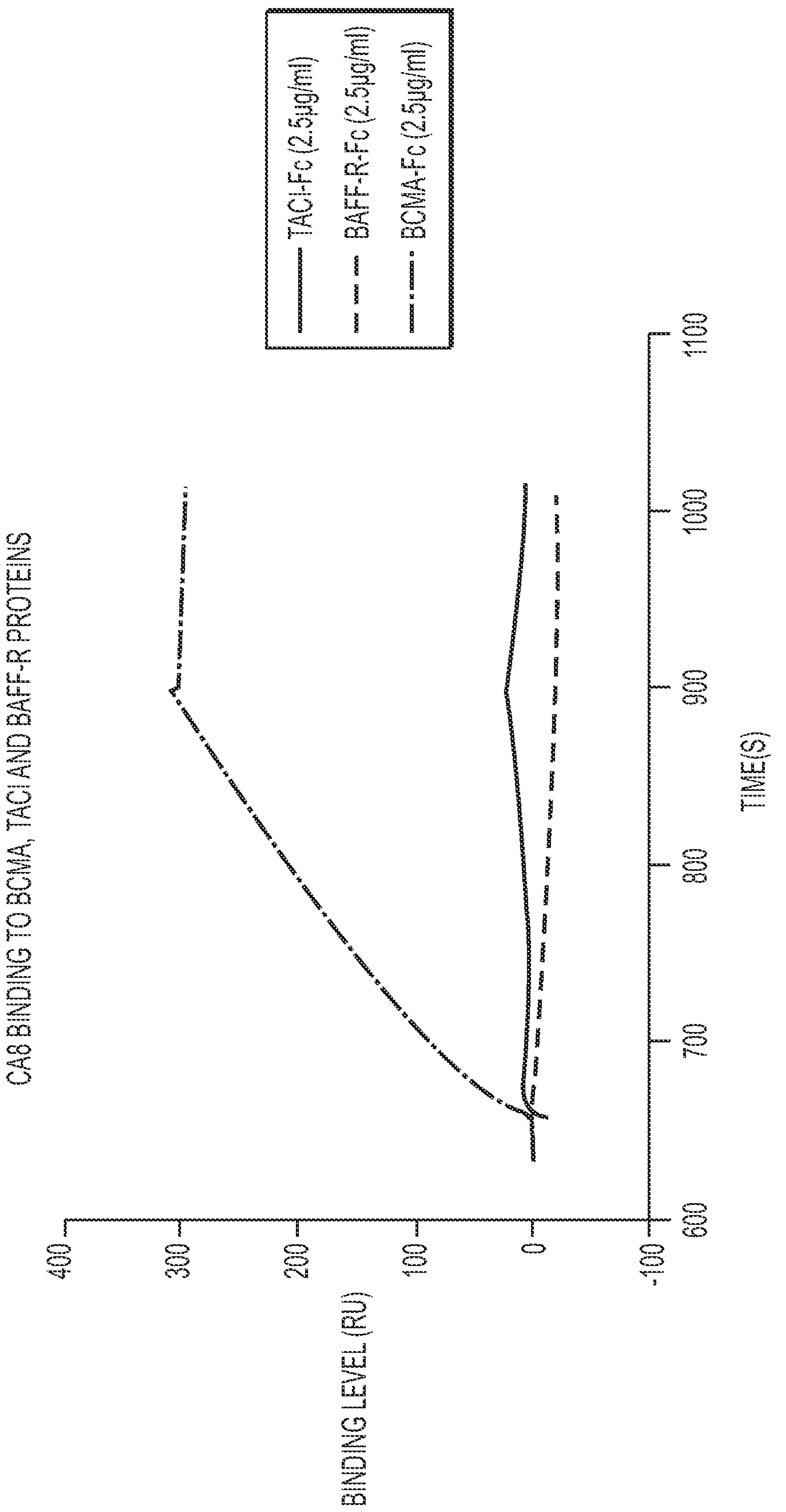
FIG. 3: BiaCore Binding Assay—Figure showing the binding of CA8 to BCMA-Fc, TACI-Fc and BAFF-R-Fc proteins in the Biacore experiment. CA8 chimera antibody does not bind to TACI or BAFF-R proteins.

Binding of the CA8 antibody to BCMA-Fc, TACI-Fc and BAFF-R-Fc was plotted out as shown in FIG. 3.

4.4 Cell Binding and Neutralisation Data 4.4.1 Binding of Murine Anti BCMA Antibodies to Multiple Myeloma Cells and BCMA Expressing Cells Multiple myeloma cell line H929 and ARH77-hBCMA 10B5 BCMA expressing transfectant cells were stained with murine S332211D07, S3332121F02 or S332126E04 or murine isotype control at 5 μg/mL. Multiple myeloma cell line H929 was stained with murine 5307118G03. Cells were incubated for 20 mins at room temperature (RT) and then washed with FACS buffer (PBS+0.5% BSA+0.1% sodium azide) to remove unbound antibody. Cells were incubated with a secondary PE labelled anti-mouse IgG antibody for 15 minutes at RT and then washed with FACS buffer to remove unbound antibody. Cells were analysed by FACS to detect antibody bound to the cells.

Figure 4:
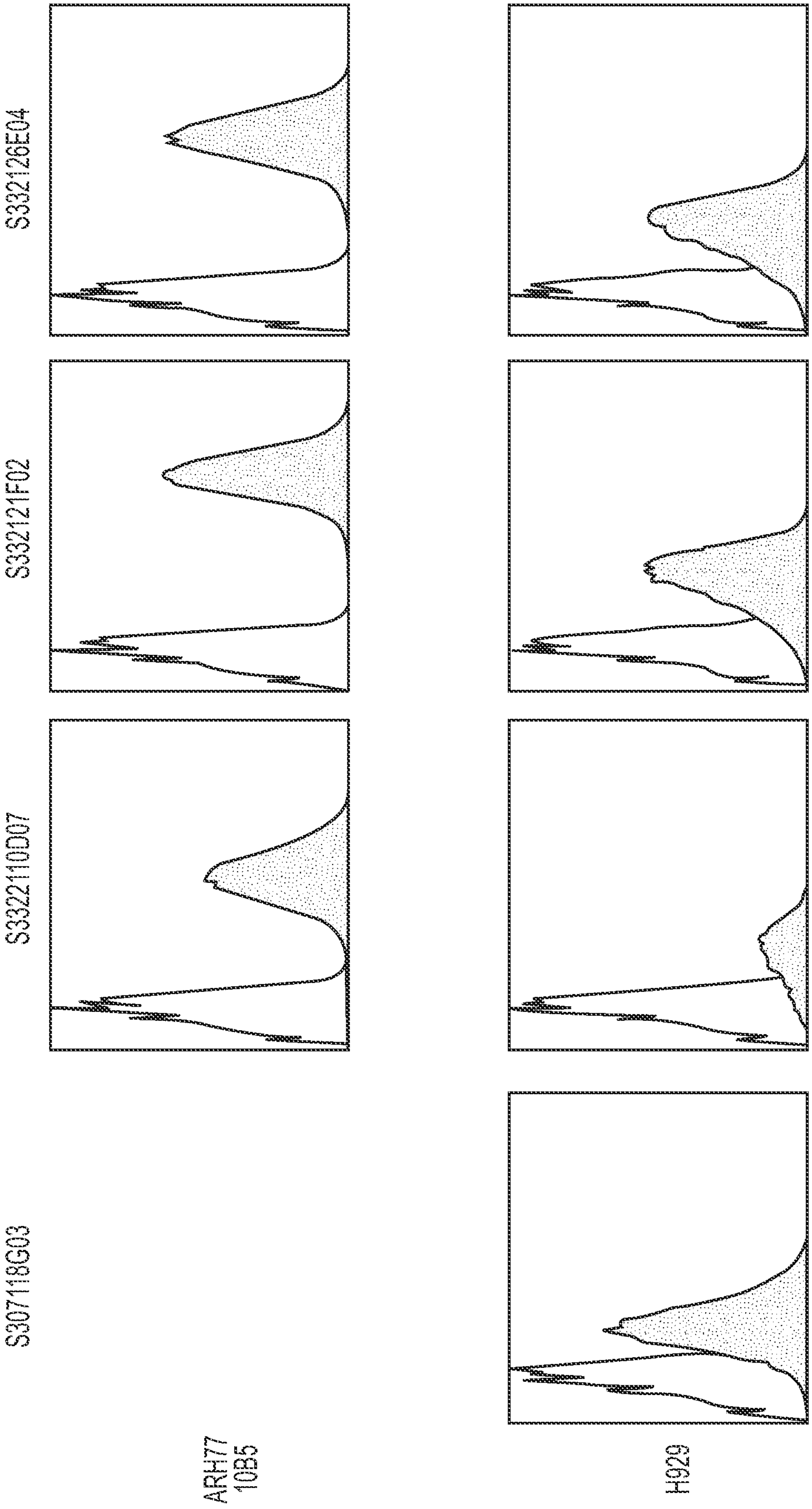
FIG. 4: Cell binding assay—Figure showing binding of murine S307118G03, S3222110D07, S332121F02 and S332126E04 to H929 multiple myeloma cells and S3322110D07, S332121F02 and S332126E04 to the BCMA transfected ARH77 cells as determined by FACS.

The results (FIG. 4) showed that all 4 murine antibodies bound to the H929 multiple myeloma cell line and the three antibodies tested on ARH77 BCMA transfected cells bound to these.

4.4.2 Binding Curve of Chimeric CA8 to Multiple Myeloma Cells as Determined by FACS A panel of multiple myeloma cell lines were used to determine the binding of chimeric CA8. Cell lines H929, OPM-2, JJN-3 and U266 were stained with either chimeric CA8 or irrelevant antibody (Synagis) at varying concentrations for 20 minutes at RT. Cells were then washed with FACS buffer (PBS+0.5% BSA+0.1% sodium azide) to remove unbound antibody. Cells were incubated with a secondary PE labelled anti-human IgG antibody for 15 minutes at RT and then washed with FACS buffer to remove unbound antibody. Cells were analysed by FACS and mean fluorescence intensity (MFI) values measured to determine binding.

Result:s showed that chimeric CA8 bound to multiple myeloma cell lines H929, OPM-2, JJN-3 & U266 in a dose dependent manner (FIG. 5).

4.4.3 Binding of Humanised CA8 to BCMA Transfected Cells as Determined by FACS

ARH77-hBCMA 10B5 BCMA expressing transfectant cells or H929 cells were stained with either chimeric CA8 or humanised variants of CA8 designated J6M0, J6M1, J6M2, J9M0, J9M1, J9M2 at varying concentrations for 20 minutes at RT. Cells were then washed with FACS buffer (PBS+0.5% BSA+0.1% sodium azide) to remove unbound antibody. Cells were incubated with a secondary PE labelled anti-human IgG antibody for 15 minutes at RT and then washed with FACS buffer to remove unbound antibody. Cells were analysed by FACS and mean fluorescence intensity (MFI) values measured to determine binding. Results showed that chimeric CA8 and all antibodies tested apart from J9M2 bound to ARH77-hBCMA 10B5 BCMA expressing transfectant cells and H929 cells in a dose dependent manner (FIG. 6).

4.5 Demonstration of Ability of CA8 and the Humanised Version J6M0 to Neutralise Binding of BAFF or APRIL to Recombinant BCMA.

The aim of this assay was to assess the ability of antibody CA8, and humanised version J6M0 in both wild type and afucosylated (Potelligent) form, at various concentrations, to neutralise the binding ability of either BCMA ligand, BAFF or APRIL.

96 well flat bottomed plates were coated overnight with 1 μg/mL solution of recombinant human BCMA Fc 4-53 in PBS. Following a wash step using 0.05% TWEEN20, plates were blocked with 2% Bovine Serum Albumin solution in PBS for 1 hour at room temperature. Plates were washed as before and 40 μL of each antibody (murine IgG, murine CA8, and chimeric CA8), starting at 10 μg/mL, titrated at 1 in 2 in duplicate was added to the relevant wells and incubated for 1 hour at room temperature. 40 μL of 2% BSA was added to the relevant control wells. 10 μL of either recombinant human BAFF (2149-BF/CF, R&D Systems) or recombinant human APRIL (5860-AP/CF, R&D Systems) was added at 30 ng/mL and 750 ng/mL respectively, giving a final concentration of 6 ng/mL and 150 ng/mL respectively in each well. Equivalent volume of 2% BSA was added to the relevant control wells. Plates were allowed to incubate for 2 hours at room temperature, after which they were washed as before. Biotinylated anti-human ligand (BAFF BAF124 or APRIL BAF884, R&D Systems) was added to the relevant wells at 50 ng/mL and incubated for 1 hour. Following a wash step, 50 μL of a 1:4000 dilution of Streptavidin-HRP (Amersham RPN4401) was added to each well and incubated for 30 minutes at room temperature. The wash process was repeated again followed by the addition of 100 μL of Tetramethylbenzidine substrate solution (T8665, Sigma) into each well. Plates were incubated for 20-25 minutes at room temperature, wrapped in foil. The reaction was stopped with the addition of 100 μL of 1M $H_2SO_4$. Optical density was determined at 450 nm using Spectromax reader. See FIGS. 7A and B.

In a plate based assay for neutralisation of binding of BAFF or APRIL to BCMA, the EC50 values calculated for chimeric CA8 were 0.695 μg/mL and 0.773 μg/mL respectively. The values for the humanised J6M0 were 0.776 ng/ml and 0.630 ng/ml. The vaues for the J6M0 potelligent version were 0.748 and 0.616 ng/ml respectively.

4.6 Effect of Chimerised CA8 and Humanised J6M0 BCMA Antibody on BAFF or APRIL Induced Phosphorylation of NFkB in H929 Cells.

In one set of experiments, H-929 cells were plated at 75,000 cells/well in a 96 well plate in serum free medium. The chimeric CA8 antibody was added 24 hours later to give final well concentrations up to 200 ug/ml. Ten minutes later, BAFF or APRIL ligand were added to the cells to give final well concentrations of 0.6 or 0.3 ug/ml respectively. After 30 minutes the cells were lysed and phosphorylated NfkappaB levels measured using a MSD pNFkappaB assay.

The chimeric BCMA antibody CA8 neutralised both BAFF and APRIL induced NfkappaB cell signalling in H-929 cells. It was particularly potent at neutralising BAFF induced NfkappaB cell signalling in this cell type with a mean IC50 of 10 nM, compared to 257 nM for APRIL induced NfkappaB cell signalling.

Meaned Data for 2 Experiments

IC50s were 10 nM for BAFF induced NfkappaB neutralisation and 257 nM for APRIL induced NfkappaB neutralisation (mean of 2 independent experiments) are shown in Table 7.

TABLE 7

| | BAFF induced IC50 | | APRIL induced IC50 | |
|---|---|---|---|---|
| | ug/ml | nM | ug/ml | nM |
| BCMA antibody CA8 | 1.5 | 10 | 38.5 | 256.7 |

A further set of experiments were carried out to aim to understand why there was such a discrepancy between the potency in neutralisation of APRIL and BAFF in the cell based system. Following the discovery of the soluble form of BCMA the experimental design was changed to include a step where the H929 cells were washed prior to the assay to reduce the interference from the antibody binding to soluble BCMA. H-929 cells were washed 3 times to remove any sBCMA and resuspended in serum free medium. J6M0 potelligent antibody was added to a 96 well plate to give a final well concentrations up to 100ug/ml along with BAFF or APRIL ligand to give a final well concentration of 0.6 or 0.2 ug/ml respectively. H-929 cells were then plated at 7.5×104 cells/well in serum free medium. 30 minutes later the cells were lysed and phosphorylated NFkappaB levels measured using a MSD pNFkappaB assay.This is data from one experiment. Each data point is the mean/sd of two replicates.The data from this experiment is shown in FIG. 7*c*. The IC50s for inhibition of BAFF and APRIL signalling were determined as 0.91ug/ml and 2.43ug/ml respectively.

4.7 ProteOn Analysis of Anti-BCMA CA8 Chimeric and Humanised Constructs

The initial screen of CA8 chimeric and humanised variants was carried out on the ProteOn XPR36 (Biorad). The method was as follows; Protein A was immobilised on a GLC chip (Biorad, Cat No: 176-5011) by primary amine coupling, CA8 variants were then captured on this surface and recombinant human BCMA (in house or commercial US Biological, B0410) materials (run 2 only)) passed over at 256, 64, 16, 4, 1 nM with a 0 nM injection (i.e. buffer alone) used to double reference the binding curves, the buffer used is the HBS-EP buffer. 50 mM NaOH was used to regenerate the capture surface. The data was fitted to the 1:1 model using the analysis software inherent to the ProteOn XPR36. Run 1 corresponds to the first screen of humanised CA8 variants (J0 to J5 series) and run 2 to the second screen of humanised CA8 variants (J5 to J9 series). Both runs were carried out at 25° C.

The data obtained from run are set out in Table 8 and data from run 2 are set in Table 9 Several molecules in the Run 2 (Table 09) failed to give affinity values measurable by ProteOn, this was due to the off-rate being beyond the sensitivity of the machine in this assay, this does however indicate that all these molecules bind tightly to recombinant human BCMA. From Run 1 the data indicates that some constructs did not show any binding to recombinant cyno BCMA.

TABLE 8

Run 1-Kinetics analyses of anti-BCMA molecules against Recombinant Human BCMA

| Sample name | Human in house BCMA ka | kd | KD (nM) | Cyno in house BCMA ka | kd | KD (nM) |
|---|---|---|---|---|---|---|
| CA8 humanised J5M0 | 2.16E+05 | 1.88E−05 | 0.087 | 3.25E+05 | 8.14E−06 | 0.025 |
| CA8 humanised J5M2 | 2.67E+05 | 3.21E−05 | 0.12 | 4.30E+05 | 4.70E−05 | 0.109 |
| CA8 humanised J5M1 | 2.97E+05 | 4.32E−05 | 0.145 | 4.81E+05 | 5.41E−05 | 0.112 |
| CA8 humanised J4M1 | 2.54E+05 | 7.04E−05 | 0.278 | 3.50E+05 | 7.10E−05 | 0.203 |
| CA8 humanised J4M2 | 2.51E+05 | 7.06E−05 | 0.281 | 3.44E+05 | 6.15E−05 | 0.179 |
| CA8 humanised J0M2 | 2.25E+05 | 6.97E−05 | 0.31 | 3.26E+05 | 1.84E−04 | 0.563 |
| CA8 humanised J3M2 | 2.66E+05 | 9.64E−05 | 0.362 | 3.69E+05 | 5.87E−05 | 0.159 |
| CA8 humanised J0M1 | 2.31E+05 | 8.60E−05 | 0.373 | 3.32E+05 | 1.67E−04 | 0.503 |
| CA8 humanised J0MO | 2.45E+05 | 1.06E−04 | 0.435 | 3.58E+05 | 2.32E−04 | 0.648 |
| CA8 humanised J3M1 | 2.85E+05 | 1.25E−04 | 0.438 | 4.04E+05 | 7.93E−05 | 0.196 |
| CA8 humanised J2M2 | 2.05E+05 | 9.87E−05 | 0.482 | 2.98E+05 | 3.17E−05 | 0.106 |
| CA8 Chimera | 2.41E+05 | 1.25E−04 | 0.519 | 3.82E+05 | 1.74E−04 | 0.457 |
| CA8 humanised J2M1 | 2.04E+05 | 1.72E−04 | 0.842 | 2.96E+05 | 6.46E−05 | 0.218 |
| CA8 humanised J4M0 | 2.42E+05 | 2.20E−04 | 0.906 | 3.34E+05 | 2.89E−04 | 0.866 |
| CA8 humanised J1M2 | 2.15E+05 | 2.46E−04 | 1.14 | 3.19E+05 | 9.67E−05 | 0.303 |
| CA8 humanised J3M0 | 2.08E+05 | 2.85E−04 | 1.37 | 2.93E+05 | 1.54E−04 | 0.526 |
| CA8 humanised J1M1 | 2.27E+05 | 3.43E−04 | 1.51 | 3.33E+05 | 1.47E−04 | 0.442 |
| CA8 humanised J2M0 | 1.95E+05 | 3.77E−04 | 1.94 | 2.81E+05 | 1.51E−04 | 0.538 |
| CA8 humanised JIM0 | 1.78E+05 | 5.02E−04 | 2.82 | 2.47E+05 | 2.10E−04 | 0.849 |
| S307118G03 Chimera | 4.75E+05 | 1.95E−03 | 4.11 | No | Analysable | Binding |
| S307118G03 humanised H3L1 | 4.69E+05 | 2.28E−03 | 4.86 | No | Analysable | Binding |
| S307118G03 humanised H3L0 | 2.86E+05 | 1.52E−03 | 5.31 | No | Analysable | Binding |
| S307118G03 humanised H2L0 | 3.78E+05 | 2.41E−03 | 6.36 | No | Analysable | Binding |
| S307118G03 humanised H2L1 | 3.38E+05 | 2.15E−03 | 6.37 | No | Analysable | Binding |
| S307118G03 humanised H4L1 | No | Analysable | Binding | No | Analysable | Binding |

TABLE 9

Run 2-Kinetics analyses of anti-BCMA molecules against Recombinant Human BCMA
For antibodies J8M0, J9M0, J8M1, J9M2, J7M2, J5M0, J7M1, J7M0, J8M2, J9M1, J5M2, J5Ml the off rate was beyond the sensitivity of the assay hence no data shown.

| Sample Name | Human in house BCMA ka | kd | KD (nM) | commercial human BCMA ka | kd | KD (nM) | Cyno in house BCMA ka | kd | KD (nM) |
|---|---|---|---|---|---|---|---|---|---|
| CA8 Chimera | 2.51E+05 | 1.03E−04 | 0.412 | 7.05E+05 | 9.79E−05 | 0.139 | 5.89E+04 | 1.21E−04 | 2.060 |
| CA8 humanised J6M1 | 2.17E+05 | 2.70E−05 | 0.124 | 5.92E+05 | 3.75E−05 | 0.063 | 4.88E+04 | 2.58E−04 | 5.300 |
| CA8 humanised J6M0 | 2.40E+05 | 7.40E−05 | 0.308 | 6.23E+05 | 5.37E−05 | 0.086 | 5.64E+04 | 3.18E−04 | 5.630 |
| CA8 humanised J6M2 | 2.01E+05 | 4.06E−05 | 0.202 | 5.63E+05 | 3.97E−05 | 0.071 | 4.41E+04 | 3.02E−04 | 6.860 |
| S307118G03 H5L0 | No Analysable Binding | | | V weak signal | | | No | Analysable | Binding |
| S307118G03 H5L1 | No Analysable Binding | | | V weak signal | | | No | Analysable | Binding |
| S307118G03 Chimera | 4.79E+05 | 1.65E−03 | 3.44 | 1.55E+06 | 1.48E−03 | 0.956 | No | Analysable | Binding |

4.8 BIAcore Analysis of Anti-BCMA CA8 Chimeric and Humanised Constructs (J7 to J9 Series)

Protein A was immobilised on a CM5 chip (GE Healthcare, Cat No: BR-1005-30) by primary amine coupling and this surface was then used to capture the antibody molecules. Recombinant human BCMA (US Biological, B0410) was used as analyte at 256 nM, 64 nM, 16 nM, 4 nM and 1 nM. Regeneration of the capture surface was carried out using 50 mM NaOH. All binding curves were double referenced with a buffer injection (i.e. 0 nM) and the data was fitted to the using the 1:1 model inherent to T100 evaluation software. The run was carried out at 37° C., using HBS-EP as the running buffer.

The results showed the molecules tested with the exception of J9M2 bind to recombinant human BCMA, with similar affinity as the chimeric molecule. Data generated from this experiment are presented in table 10.

TABLE 10

Kinetics analysis of anti-BCMA humanised molecules against Recombinant Human BCMA

| Sample name | Human commercial BCMA ka | kd | KD (nM) | Cyno in house BCMA ka | kd | KD (nM) |
|---|---|---|---|---|---|---|
| CA8 humanised J9M1 | 1.96E+07 | 3.50E−04 | 0.018 | 6.77E+05 | 2.99E−04 | 0.442 |
| CA8 humanised J9M0 | 4.95E+06 | 1.74E−04 | 0.035 | 7.03E+05 | 3.24E−04 | 0.46 |
| CA8 Chimera | 3.27E+07 | 1.18E−03 | 0.036 | 1.15E+06 | 3.49E−04 | 0.305 |
| CA8 humanised J8M1 | 2.66E+06 | 1.34E−04 | 0.05 | 2.82E+05 | 3.62E−04 | 1.284 |
| CA8 humanised J8M0 | 2.44E+06 | 1.26E−04 | 0.052 | 3.89E+05 | 4.18E−04 | 1.076 |
| CA8 humanised J7M1 | 2.35E+06 | 1.31E−04 | 0.056 | 3.70E+05 | 3.91E−04 | 1.057 |
| CA8 humanised J8M2 | 2.63E+06 | 1.50E−04 | 0.057 | 3.83E+05 | 5.06E−04 | 1.324 |
| CA8 humanised J7M2 | 2.37E+06 | 1.35E−04 | 0.057 | 3.46E+05 | 4.47E−04 | 1.293 |
| CA8 humanised J7M0 | 2.36E+06 | 1.51E−04 | 0.064 | 3.21E+05 | 3.67E−04 | 1.143 |
| CA8 humanised J9M2 | No | Analysable | Binding | 4.88E+05 | 2.52E−04 | 0.515 |

4.9 BIAcore Analysis of Anti-BCMA CA8 Chimeric and Humanised Constructs J6M0 and J9M0

Protein A was immobilised on a CM5 chip (GE Healthcare, Cat No: BR-1005-30) by primary amine coupling and this surface was then used to capture the antibody molecules. Recombinant human BCMA (US Biological, B0410) was used as analyte at 256 nM, 64 nM, 16 nM, 4 nM and 1 nM. Regeneration of the capture surface was carried out using 50 mM NaOH. All binding curves were double referenced with a buffer injection (i.e. 0 nM) the data was fitted to the using the 1:1 model inherent to T100 evaluation software. The run was carried out at 25° C. and 37° C. for experiment 1 and only 37° C. for experiment 2 using HBS-EP as the running buffer.

The both runs identified J9M0 as the best molecule in term of overall affinity to human BCMA. Data generated from this experiment are presented in table 11.

TABLE 11

Kinetics analyses of anti-BCMA humanised molecules against Human BCMA

| Sample | Human commercial BCMA 25° C. Experiment 1 ka | kd | KD (nM) | 37° C. Experiment 1 ka | kd | KD (nM) | 37° C. Experiment 2 ka | kd | KD (nM) |
|---|---|---|---|---|---|---|---|---|---|
| J9M0 | 1.59E+06 | 3.38E−05 | 0.021 | 3.75E+06 | 1.58E−04 | 0.042 | 3.62E+06 | 1.89E−04 | 0.052 |
| J6M0 | 1.01E+06 | 1.22E−04 | 0.121 | 2.12E+06 | 1.48E−03 | 0.698 | 3.78E+06 | 1.88E−03 | 0.498 |
| Chimera CA8 | 1.88E+06 | 2.63E−04 | 0.140 | 1.72E+07 | 8.72E−04 | 0.051 | 1.88E+07 | 1.04E−03 | 0.055 |

4.10. ProteOn Analysis of New Anti-BCMA Chimeric Constructs

The initial screen of the new chimeric variants from the second batch of hybridomas was carried out on the ProteOn XPR36 (Biorad). The method was as follows; Protein A was immobilised on a GLM chip (Biorad, Cat No: 176-5012) by primary amine coupling, anti-BCMA variants were then captured on this surface and recombinant human BCMA (in house material) passed over at 256, 64, 16, 4, 1 nM with a 0 nM injection (i.e. buffer alone) used to double reference the binding curves, the buffer used is the HBS-EP buffer. Regeneration of the capture surface was carried out using 50 mM NaOH. The data was fitted to the 1:1 model using the analysis software inherent to the ProteOn XPR36. The run was carried out at 25° C. Data generated from this experiment are presented in table 12.

TABLE 12

Kinetics analyses of anti-BCMA humanised molecules against Human BCMA

| Sample name | In house human BCMA ka | kd | KD (nM) |
|---|---|---|---|
| S332110D07 | 3.11E+05 | 3.77E−03 | 12.100 |
| S332121F02 | 3.73E+05 | 6.45E−03 | 17.300 |

Example 5 Cell Killing Assays 5.1 ADCC Potencies of Chimeric CA8 and Defucosylated Chimeric CA8 Version in ARH77 Cells Expressing BCMA Human natural killer (NK) cells were incubated with europium labelled ARH77 BCMA transfected target cells (10B5) in the presence of varying concentrations of antibody at an E:T ratio of 5:1 for 2 hours. Europium release from the target cells was measured and specific lysis calculated.

Result: Chimeric CA8 and defucosylated chimeric CA8 killed BCMA expressing target cells via ADCC. The defucosylated chimeric antibody showed more potent ADCC activity, as measured by a higher percent lysis achieved with all the target cells tested and a ten-fold lower $EC_{50}$ on the high BCMA expressing target cell line 10B5, compared to the parent chimeric antibody. See FIGS. 8A and 8B.

5.2 ADCC Activity of CA8 Humanised Antibodies Using ARH77 BCMA Expressing Target Cells and PBMC as Effectors Human PBMC were incubated with europium labelled ARH77 BCMA transfected target cells (10B5) in the presence of varying concentrations of humanised versions of CA8 antibody (5ug/ml to 0.005ug/ml) at an E:T ratio of 5:1 for 2 hours. Europium release from the target cells was measured and specific lysis calculated.

Result:

Result: All the J5, J6, J7 J8 & J9 series of humanised variants of CA8 showed ADCC activity against the ARH77 high BCMA expressing cell line 10B5 in a dose dependent manner. ADCC was at a similar level as that found in the experiments using chimeric CA8 molecule. See FIG. 9.

5.3 ADCC Potencies of Chimeric S322110F02, S322110D07 and S307118G03 and Humanised S307118G03 H3L0 Against ARH77 10B5 Cells Expressing BCMA with Purified NK Cells as Effector Cells Human natural killer (NK) target cells were incubated with europium labelled ARH77 BCMA transfected target cells (10B5) in the presence of varying concentrations of antibody at an E:T ratio of 5:1 for 2 hours. Europium release from the target cells was measured and specific lysis calculated.

Result: all 4 antibodies tested showed ADCC activity against ARH77 10B5 cells. See FIG. 10.

5.4 Antibody-Drug Conjugate (ADC) Activity of Chimeric CA8 ADCs.

Measuring ADC activity of chimeric CA8 antibody, chimeric CA8-mcMMAF antibody drug conjugates and chimeric CA8-vcMMAE antibody drug conjugates against human multiple myeloma cell lines.

Muliple Myeloma cell lines were treated with chimeric CA8 antibody-drug conjugates to determine the ADC concentrations required for growth inhibition and death.

The antibody drug conjugates tested were added to wells containing multiple myeloma cells at concentrations ranging from 1ug/ml to 5 ng/ml. The plates were incubated at 37° C. for 96 hours at which point viable cells were quantitated using Cell titre Glo. The unconjugated chimeric CA8 antibody showed no significant growth inhibitory activity at the antibody concentrations that were tested. The chimeric CA8-mcMMAF antibody-drug conjugate showed greater growth inhibitory activity than the chimeric CA8-vcMMAE antibody-drug conjugate in all 4 of the multiple myeloma cell lines that were tested. See FIG. 11 and Table 13

TABLE 13

$IC_{50}$ values represented in ng/mL for the chimeric CA8-vcMMAE and the chimeric CA8-mcMMAF antibody-drug conjugates in 4 different multiple myeloma cell lines

| Multiple Myeloma cell lines | $IC_{50}$ (ng/mL) CA8 chimera-vcMMAE | CA8 chimera-mcMMAF |
|---|---|---|
| NCI-H929 | 29.5 | 8.8 |
| U266-B1 | 18.9 | 9.7 |
| JJN3 | 21.8 | 12.4 |
| OPM2 | 92.7 | 58.1 |

5.5 Measuring Cell Cycle Arrest Activity of Chimeric CA8 Antibody, Chimeric CA8-mcMMAF Antibody Drug Conjugates and Chimeric CA8-vcMMAE Antibody Drug Conjugates Against Human Multiple Myeloma Cell Line H929.

To determine the mechanism that chimeric CA8 Antibody Drug Conjugates (ADC's) cause growth inhibition in multiple myeloma cells, the cell cycle of NCI-H929 cells was monitored by measuring cellular DNA content through fixed cell propidium iodide staining at multiple timepoints following chimeric CA8 antibody and chimeric CA8 ADC treatment.

At the chimeric CA8 ADC concentration tested (50 ng/mL), the chimeric CA8-mcMMAF ADC caused significant G2/M cell cycle arrest (4N DNA content) which peaked at 48 hours. At the later timepoints 48, 72 and 96 hours, treatment with the chimeric CA8-mcMMAF ADC resulted in accumulation of a cell population with sub-2N DNA content, which is representative of cell death. At the 50 ng/mL concentration tested the chimeric CA8-vcMMAE ADC had no significant effect on G2/M cell cycle arrest or sub-G1 accumulation. See FIG. 12.

5.6 Phospho-Histone-H3 (Thr11) Staining as a Marker for Chimeric CA8-mcMMAF Antibody Drug Conjugate and Chimeric CA8-vcMMAE Antibody Drug Conjugate Induced Mitotic Arrest.

To determine if the accumulation of cells with 4N DNA content is a specific result of mitotic arrest induced by the chimeric CA8 ADCs NCI-H929 cells were stained with an anti-phospho- Histone H3 antibody following treatment with increasing concentrations of unconjugated chimeric CA8, chimeric CA8-vcMMAE or chimeric CA8-mcMMAFfor 48 hours. Treatment with chimeric CA8 ADCs resulted in a dose-dependent accumulation of NCI-H929 cells that stained positive for 85eroxidi-Histone H3 (Thr11), a specific marker of mitotic cells. The chimeric CA8-mcMMAF ADC caused accumulation of 85eroxidi-Histone H3 positive cells at lower concentrations than the chimeric CA8-vcMMAE ADC. See FIG. 13.

5.7 Measuring Apoptosis in NCI-H929 Cells in Response to Chimeric CA8 ADCs by Staining for Annexin V.

To determine if the accumulation of cells with sub-2N DNA content is a specific result of apoptosis induced by the chimeric CA8 ADCs, NCI-H929 cells were stained with an anti-Annexin-V antibody following treatment with increasing concentrations of unconjugated chimeric CA8, chimeric CA8-vcMMAE or chimeric CA8-mcMMAFfor 48 hours. Treatment with chimeric CA8 ADCs resulted in a dose-dependent accumulation of NCI-H929 cells that stained positive for Annexin-V, a specific marker of apoptosis. The chimeric CA8-mcMMAF ADC caused accumulation of Annexin-V positive cells at lower concentrations than the chimeric CA8-vcMMAE ADC. See FIG. 14.

5.8 Antibody-Drug Conjugate (ADC) Activity of Humanised Variants of CA8 Anti-BCMA Antibody-Drug Conjugates.

Cells were plated in 96-well plates (4,000 cells per well in 100 μL of RPMI+10% FBS) Naked antibody or ADC was added 6 hours after cell seeding and plates were incubated for 144 hours. Growth inhibition in the presence of the antibodies or ADCs was measured at 144 hours using Cell Titre glo. Data points represent the mean of triplicate CellTiterGlo measurements. Error bars represent standard error.

Multiple Myeloma cell lines NCI-H929 and OPM2 were treated with humanized CA8 anti-BCMA antibody-drug conjugates to determine the ADC concentrations required for growth inhibition and death. The mcMMAF and vcMMAE antibody-drug conjugate forms of these antibodies showed significant growth inhibitory activity comparable to that found with the CA8 chimera. Variant J6M0 showed higher potency than the chimera and data is shown in FIG. 15 in H929 cells and OPM2 cells. The mcMMAF antibody-drug conjugate showed greater growth inhibitory activity than the vcMMAE antibody-drug conjugate for all antibodies in both cell lines tested. Results for all humanized variants are shown in Table 14.

TABLE 14

$IC_{50}$ values represented in ng/mL for the anti BCMA antibody-drug conjugates in NCI-H929 and U266-B1 cells

| | NCI-H929 | | OPM2 | |
|---|---|---|---|---|
| | mcMMAF Average IC50 (ng/mL) | vcMMAE Average IC50 (ng/mL) | mcMMAF Average IC50 (ng/mL) | vcMMAE Average IC50 (ng/mL) |
| CA8 chimera | 11.64 | 37.96 | 57.04 | 80.01 |
| CA8 J6M0 | 5.97 | 27.67 | 87.22 | 121.2 |

TABLE 14-continued $IC_{50}$ values represented in ng/mL for the anti BCMA antibody-drug conjugates in NCI-H929 and U266-B1 cells

| | NCI-H929 | | OPM2 | |
|---|---|---|---|---|
| | mcMMAF Average IC50 (ng/mL) | vcMMAE Average IC50 (ng/mL) | mcMMAF Average IC50 (ng/mL) | vcMMAE Average IC50 (ng/mL) |
| CA8 J6M1 | 14.6 | 51.89 | 205.6 | 239.9 |
| CA8 J6M2 | 9.5 | 39.71 | 112.9 | 144.7 |
| CA8 J7M0 | 18.97 | 52.25 | 93.27 | 127.1 |
| CA8 J7M1 | 17.87 | 43.97 | 95.35 | 107.5 |
| CA8 J7M2 | 31.63 | 55.13 | 102.6 | 115.9 |
| CA8 J8M0 | 15.67 | 59.94 | 89.95 | 132 |
| CA8 J8M1 | 17.04 | 46.55 | 82.96 | 115.8 |
| CA8 J8M2 | 15.08 | 55.98 | 72.63 | 124.5 |
| CA8 J9M0 | 14.95 | 48.5 | 58.6 | 109.8 |
| CA8 J9M1 | 15.19 | 55.1 | 55.88 | 115 |
| CA8 J9M2 | 20.87 | 55.77 | 80.35 | 111.7 |

5.9 Antibody-Drug Conjugate (ADC) Activity of Other Murine Anti-BCMA Antibody-Drug Conjugates.

Cells were plated in 96-well plates (4,000 cells per well in 100 uL of RPMI+10% FBS) Antibody or ADC was added 6 hours after cell seeding and plates were incubated for 144 hours. Growth inhibition in the presence of the ADCs was measured at 144 hours using Cell Titre glo. The mean of triplicate CellTiterGlo measurements are shown. Table 15a and 15b are from experiments carried out at different times on different series of antibodies. Multiple Myeloma cell lines NCI-H929 and U266-B1 were used for antibodies in Table 15a.

The mcMMAF and vcMMAE antibody-drug conjugate forms of murine antibodies S322110D07, S332121F02 and S332136E04 showed significant growth inhibitory activity. The mcMMAF antibody-drug conjugate showed greater growth inhibitory activity than the vcMMAE antibody-drug conjugate in all of the murine anti-BCMA antibodies tested where activity was seen. IC50 figures are shown in Table 15a. See FIG. 16 for dose response curves for these three antibodies and also S107118G03. Error bars represent standard error. NCI-H929, U266-B1, JJN3 and OPM2 cells for antibodies in Table 15b were treated with a different series of murine anti-BCMA antibody-drug conjugates to determine the ADC concentrations required for growth inhibition and death. IC50 figures are shown in Table 15b. All 5 antibodies shown on the table had significant ADC activity.

TABLE 15a $IC_{50}$ values represented in ng/mL for the anti BCMA antibody-drug conjugates in NCI-H929 and U266-B1 cells
IC50 (ng/mL)

| Antibody | NCI-H929 -vcMMAE | NCI-H929 -mcMMAF | U226-B1 -vcMMAE | U226-B1 -mcMMAF |
|---|---|---|---|---|
| S322110D07 mIgG1 | 28.4 | 6.7 | 53.3 | 33.3 |
| S332121F02 mIgG1 | 24.5 | 7 | 2.3 | 2.5 |
| S332126E04 mIgG1 | 46.8 | 9.7 | 27.1 | 10.6 |

TABLE 15b $IC_{50}$ values represented in ng/ml for the anti BCMA antibody-drug conjugates in NCI-H929, U266-B1, JJN3 and OPM2 cells

| Average IC50 (ng/ml) | NCI-H929 vcMMAE | NCI-H929 mcMMAF | U266B1 vcMMAE | U266B1 mcMMAF | JJN3 vcMMAE | JJN3 mcMMAF | OPM2 vcMMAE | OPM2 mcMMAF |
|---|---|---|---|---|---|---|---|---|
| S335115G01 | 14.9 | 4.2 | 38.8 | 18.5 | 73.9 | 45.8 | 162.4 | 197.2 |
| S336105A07 | 17.8 | 5.1 | 21.4 | 9.3 | 54.2 | 23.2 | 95.5 | 73.7 |
| S335122F05 | 10.9 | 4.2 | 21.1 | 14.1 | 29.5 | 25.5 | 98.4 | 128.7 |
| S335106E08 | 19.2 | 7.9 | 36.8 | 32.6 | 189.8 | 214.1 | 243.9 | 307.5 |
| S335128A12 | 86.3 | 28.3 | 101.8 | 104.1 | >500 | >500 | >500 | >500 |

TABLE 16

$EC_{50}$ values generated on 13 independent assays using 11 donors (designated A-K) across the five multiple myeloma cell lines.

| Donor | $EC_{50}$ (ng/mL) H929 | RPMI | JJN-3 | OPM-2 | U266 |
|---|---|---|---|---|---|
| A | 1.43 | NA | 1.64 | NA | NA |
| B | 0.57 | NA | NA | NA | NA |
| C | 0.73 | NA | 1.01 | NA | NA |
| C | 1.81 | NA | NA | NA | NA |
| A | 2.05 | NA | NA | NA | NA |

5.10 ADCC Potency of Conjugated, Afucosylated J6M0 (Potelligent)

Afucosylated J6M0 conjugated to MMAE or MMAF was tested in ADCC assays using BCMA transfectants to ensure that its ADCC activity was not compromised by the conjugation. Europium labelled ARH77-10B5 cells were incubated with various J6M0 WT and Potelligent BCMA antibodies at concentrations up to 10000 ng/ml for 30 minutes prior to the addition of PBMCs (PBMC: target cell ratio 50:1). Two hours later an aliquot of cell media was sampled and mixed with enhancement solution. After 30 minutes on a plate shaker, europium release was monitored on the Victor 2 1420 multi-label reader. Datapoints represent means of triplicate values. This data is representative of 2 experiments.

There were no significant differences in ADCC potency between the unconjugated and ADC forms of J6M0 Potelligent. In the same experiment a wild type version of J6M0 was included to show how the potency compares to the afucosylated version. As expected, defucosylation resulted in a lower EC50 and higher maximal lysis. No lysis was observed with the Fc disabled form of J6M0. (FIG. 17)

5.11 ADCC Potency of Afucosylated J6M0 on MM Cell Lines

Human PBMC were incubated with multiple myeloma target cells at an E:T ratio of 50:1 in presence of varying concentrations of afucosylated (Potelligent) J6M0 The percentage of target cells remaining in the effector+target cell mixture after 18 hours was measured by FACS using a fluorescently labelled anti-CD138 antibody to detect the target cells and the percent lysis calculated. This is representative of several experiments.

J6M0 Potelligent antibody showed ADCC activity against all five multiple myeloma target cell lines tested. This was important to test since earlier studies were carried out using transfected cells. Results are shown in FIG. 18. Full dataset with multiple donors is shown in Table 16 The potencies were all in a similar range as those found with the transfectants. The ADCC activity was not directly related to BCMA surface expression on these cell lines.

TABLE 16-continued $EC_{50}$ values generated on 13 independent assays using 11 donors (designated A-K) across the five multiple myeloma cell lines.

| Donor | $EC_{50}$ (ng/mL) H929 | RPMI | JJN-3 | OPM-2 | U266 |
|---|---|---|---|---|---|
| D | NA | 4.09 | NA | NA | NA |
| E | NA | NA | 14.4 | NA | NA |
| F | 2.18 | NA | NA | NA | NA |
| G | NA | NA | 26.3 | NA | NA |
| H | 4.79 | NA | 111.3 | NA | NA |
| I | NA | NA | 40.1 | NA | NA |
| J | 2.19 | 20.4 | 4.89 | NA | NA |
| K | ND | ND | 4.52 | 4.15 | 9.04 |

Example 6. Xenograft Data 6.1 Murine xenografts of human MM cell lines were tested to ensure that antibody potency detected in vitro can also be demonstrated in vivo. The cell line selected for xenograft studies was NCI-H929 which is sensitive to ADC and ADCC killing in vitro. Studies were carried out in immunocompromised CB.17 SCID mice which lack T and B cells but maintain NK cells to allow for ADCC activity. However it should be noted that although human IgG1 can engage murine Fc receptors, the Potelligent enhancement does not improve the affinity as it does with human Fc receptors.

6.2 Impact of Unconjugated and MMAE or MMAF Conjugated J6M0 on NCI-H929 Tumour Growth.

In order to independently analyze both the ADCC and ADC activities of J6M0 we tested J6M0 antibody in the presence and absence of MMAF or MMAE conjugation. By testing the unconjugated J6M0, any anti-tumour effects could be attributed to some combination of ADDC and functional inhibitory activity.

Mice with NCI-H929 tumours that had reached a volume of 200 $mm^3$ on average were treated with a human IgG1 control or the J6M0 antibody (unconjugated, MMAE or MMAF) twice weekly at a dose of 50 ug or 100ug, for 2 weeks. Results from this study show that a 100 ug dose of the J6M0-MMAF conjugate resulted in elimination of tumours in those mice which have completed the dosing. The J6M0-MMAF mice were maintained for 40 days after the last dose with no recurrence of tumour occurring. These results from this experiment demonstrate that MMAF conjugation had increased anti-tumour activity over both unconjugated J6M0 antibody and J6M0-MMAE conjugate See FIG. 19.

Example 7 Evaluation of Soluble BCMA Levels from MM Patient Serum 7.1 It is currently unknown whether BCMA is present extracellularly and can be detected in the blood. In this work, we determined the serum level of human BCMA from MM patients. Serum samples from 54 MM and plasma cell dyscrasia patients and 20 normal control samples were analyzed by ELISA. Human Subject Approval was obtained from Western Institutional Review Board.

7.2 Assessment of Serum Human BCMA Levels

Blood, from patients and normal controls in the clinic, were collected in serum collection tubes. MM patient samples were from a variety of stages (progressive disease, remission, relapsed, newly diagnosed, and others). The Blood samples were spun at 10,000 rpm for 10 minutes and serum transferred into sterile micro-centrifuge plastic tubes.

A Human BCMA/TNFRSF17 ELISA kit from R& D Systems (catalog #DY193E) which measures soluble human BCMA levels was used to detect BCMA following the standard protocol supplied with the kit.

Briefly, 96 well micro-plates were coated with 100ul per well capture antibody and incubated overnight at 4° C. The plates were washed three times with wash buffer (0.05% Tween 20 in PBS, pH 7.2) and blocked with 300ul of 1% BSA in PBS at room temperature for 2 hours. The plates were washed three times with washing buffer. 100ul of serum sample or standard was added into each well and incubated for 2 hours at room temperature. The plates were washed three times with washing buffer and then 100ul of the detection antibody was added to each well and incubated 2 hours at room temperature. 100ul of Streptavidin-HRP was added in each well after washing plates three times and incubated in dark room for 20 minutes. The plates were washed three times and added 50ul stop solution and then determined by micro-plate reader with 570 nM wavelength.

A series of assays were carried out in order to determine the serum dilution factor appropriate for the levels of BCMA which were present. A dilution factor of 1:500 was found to be suitable for the majority of samples and is the dilution factor used in the data shown in FIG. 20. The full data set is shown in Table 17.

Patient and normal control serum samples diluted and run in triplicates had BCMA levels determined. The serum levels of BCMA were significantly elevated in the sera from MM patients compared with normal controls in this study-.When the disease subset was divided further there was a trend towards elevated serum levels of BCMA in the sera from progressing MM patients compared with those in remission. This is the first report identifying serum BCMA in any human disease and suggests that these levels may be a novel biomarker for monitoring disease status and therapeutic response of MM patients and for other patients with plasma cell mediated diseases.

TABLE 17

Figures represent serum concentration of soluble BCMA in ng/ml calculated from samples diluted at 1/50, 1/500 and 1/5000. P values were calculated using the one tailed T-Test and 95% significance values are below the table.

| 1-5000 | Normal | Myeloma: Progressive | Myeloma: Stable | Myeloma: Remission | Myeloma: Other | MGUS | Other Plasma Cell Dyscrasias |
|---|---|---|---|---|---|---|---|
| Mean | 14.130 | 500.804 | 154.762 | 151.201 | 94.457 | 84.912 | 22.838 |
| 1-500 Triplicate | Normal | Myeloma: Progressive | Myeloma: Stable | Myeloma: Remission | Myeloma: Other | MGUS | Other Plasma Cell Dyscrasias |
| Mean | 15.901 | 215.877 | 81.135 | 43.294 | 97.584 | 53.894 | 22.838 |
| 1-500 Single | Normal | Myeloma: Progressive | Myeloma: Stable | Myeloma: Remission | Myeloma: Other | MGUS | Other Plasma Cell Dyscrasias |
| Mean | 16.620 | 207.028 | 61.576 | 42.796 | 71.372 | 40.623 | 14.099 |
| 1-50 Trial 1 | Normal | Myeloma: Progressive | Myeloma: Stable | Myeloma: Remission | Myeloma: Other | MGUS | Other Plasma Cell Dyscrasias |
| Mean | 25.568 | 129.544 | 41.983 | 40.507 | 65.120 | 42.067 | 51.650 |

TABLE 17-continued

Figures represent serum concentration of soluble BCMA in ng/ml calculated from samples diluted at 1/50, 1/500 and 1/5000. P values were calculated using the one tailed T-Test and 95% significance values are below the table.

| 1-50 Trial 2 | Normal | Myeloma: Progressive | Myeloma: Stable | Myeloma: Remission | Myeloma: Other | MGUS | Other Plasma Cell Dyscrasias |
|---|---|---|---|---|---|---|---|
| Mean | 17.160 | 119.220 | 34.567 | 34.264 | 54.780 | 26.333 | 51.650 |

P-Values (One Tailed T-Test, 95% Significance)
~1-500 Single
Normal vs Progressive: p = .0010*
Progressive vs Remission: p = .0146*
~1-500 Triplicate
Normal vs Progressive: p = .0004*
Progressive vs Remission: p = .0091*
~1-50 Trial 1
Normal vs Progressive: p = .0171*
Progressive vs Remission: p = .0777
~1-50 Trial 2
Normal vs Progressive: p = .0184*
Progressive vs Remission: p = .0876

*shows significance

Sequence Summary (Table C)

| Description | Amino acid sequence | Polynucleotide sequence |
|---|---|---|
| CA8 CDRH1 | SEQ. I.D. NO: 1 | n/a |
| CA8 CDRH2 | SEQ. I.D. NO: 2 | n/a |
| CA8 CDRH3 | SEQ. I.D. NO: 3 | n/a |
| CA8 CDRL1 | SEQ. I.D. NO: 4 | n/a |
| CA8 CDRL2 | SEQ. I.D. NO: 5 | n/a |
| CA8 CDRL3 | SEQ. I.D. NO: 6 | n/a |
| CA8 $V_H$ domain (murine) | SEQ. I.D. NO: 7 | SEQ. I.D. NO: 8 |
| CA8 $V_L$ domain (murine) | SEQ. I.D. NO: 9 | SEQ. I.D. NO: 10 |
| CA8 Humanised $V_H$ J0 | SEQ. I.D. NO: 11 | SEQ. I.D. NO: 12 |
| CA8 Humanised $V_H$ J1 | SEQ. I.D. NO: 13 | SEQ. I.D. NO: 14 |
| CA8 Humanised $V_H$ J2 | SEQ. I.D. NO: 15 | SEQ. I.D. NO: 16 |
| CA8 Humanised $V_H$ J3 | SEQ. I.D. NO: 17 | SEQ. I.D. NO: 18 |
| CA8 Humanised $V_H$ J4 | SEQ. I.D. NO: 19 | SEQ. I.D. NO: 20 |
| CA8 Humanised $V_H$ J5 | SEQ. I.D. NO: 21 | SEQ. I.D. NO: 22 |
| CA8 Humanised $V_H$ J6 | SEQ. I.D. NO: 23 | SEQ. I.D. NO: 24 |
| CA8 Humanised $V_H$ J7 | SEQ. I.D. NO: 25 | SEQ. I.D. NO: 26 |
| CA8 Humanised $V_H$ J8 | SEQ. I.D. NO: 27 | SEQ. I.D. NO: 28 |
| CA8 Humanised $V_H$ J9 | SEQ. I.D. NO: 29 | SEQ. I.D. NO: 30 |
| CA8 Humanised $V_L$ M0 | SEQ. I.D. NO: 31 | SEQ. I.D. NO: 32 |
| CA8 Humanised $V_L$ M1 | SEQ. I.D. NO: 33 | SEQ. I.D. NO: 34 |
| CA8 Humanised $V_L$ M2 | SEQ. I.D. NO: 35 | SEQ. I.D. NO: 36 |
| Human BCMA CD33-hBCMA ECD (1-53) TEV-Fc | SEQ. I.D. NO: 37 | SEQ. I.D. NO: 38 |
| Human BCMA CD33-hBCMA ECD (4-53) TEV-Fc | SEQ. I.D. NO: 39 | SEQ. I.D. NO: 40 |
| Cyno BCMA CD33 cyno BCMA ECD (4-52) TEV-Fc | SEQ. I.D. NO: 41 | SEQ. I.D. NO: 42 |
| CA8 J0 Humanised heavy chain | SEQ. I.D. NO: 43 | SEQ. I.D. NO: 44 |
| CA8 J1 Humanised heavy chain | SEQ. I.D. NO: 45 | SEQ. I.D. NO: 46 |
| CA8 J2 Humanised heavy chain | SEQ. I.D. NO: 47 | SEQ. I.D. NO: 48 |
| CA8 J3 Humanised heavy chain | SEQ. I.D. NO: 49 | SEQ. I.D. NO: 50 |
| CA8 J4 Humanised heavy chain | SEQ. I.D. NO: 51 | SEQ. I.D. NO: 52 |
| CA8 J5 Humanised heavy chain | SEQ. I.D. NO: 53 | SEQ. I.D. NO: 54 |
| CA8 J6 Humanised heavy chain | SEQ. I.D. NO: 55 | SEQ. I.D. NO: 56 |
| CA8 J7 Humanised heavy chain | SEQ. I.D. NO: 57 | SEQ. I.D. NO: 58 |
| CA8 J8 Humanised heavy chain | SEQ. I.D. NO: 59 | SEQ. I.D. NO: 60 |
| CA8 J9 Humanised heavy chain | SEQ. I.D. NO: 61 | SEQ. I.D. NO: 62 |
| CA8 M0 Humanised light chain | SEQ. I.D. NO: 63 | SEQ. I.D. NO: 64 |
| CA8 M1 Humanised light chain | SEQ. I.D. NO: 65 | SEQ. I.D. NO: 66 |
| CA8 M2 Humanised light chain | SEQ. I.D. NO: 67 | SEQ. I.D. NO: 68 |
| S307118G03 $V_H$ domain (murine) | SEQ. I.D. NO: 69 | SEQ. I.D. NO: 70 |
| S307118G03 $V_L$ domain (murine) | SEQ. I.D. NO: 71 | SEQ. I.D. NO: 72 |
| S307118G03 heavy chain (chimeric) | SEQ. I.D. NO: 73 | SEQ. I.D. NO: 74 |
| S307118G03 light chain (chimeric) | SEQ. I.D. NO: 75 | SEQ. I.D. NO: 76 |
| S307118G03 Humanised $V_H$ H0 | SEQ. I.D. NO: 77 | SEQ. I.D. NO: 78 |
| S307118G03 humanised $V_H$ H1 | SEQ. I.D. NO: 79 | SEQ. I.D. NO: 80 |

-continued

Sequence Summary (Table C)

| Description | Amino acid sequence | Polynucleotide sequence |
|---|---|---|
| S307118G03 humanised $V_H$ H2 | SEQ. I.D. NO: 81 | SEQ. I.D. NO: 82 |
| S307118G03 humanised $V_H$ H3 | SEQ. I.D. NO: 83 | SEQ. I.D. NO: 84 |
| S307118G03 humanised $V_H$ H4 | SEQ. I.D. NO: 85 | SEQ. I.D. NO: 86 |
| S307118G03 humanised $V_H$ H5 | SEQ. I.D. NO: 87 | SEQ. I.D. NO: 88 |
| S307118G03 humanised $V_L$ L0 | SEQ. I.D. NO: 89 | SEQ. I.D. NO: 90 |
| S307118G03 humanised $V_L$ L1 | SEQ. I.D. NO: 91 | SEQ. I.D. NO: 92 |
| S307118G03 CDRH1 | SEQ. I.D. NO: 93 | |
| S307118G03 CDRH2 | SEQ. I.D. NO: 94 | |
| S307118G03 CDRH3 | SEQ. I.D. NO: 95 | |
| S307118G03 CDRL1 | SEQ. I.D. NO: 96 | |
| S307118G03 CDRL2 | SEQ. I.D. NO: 97 | |
| S307118G03 CDRL3 | SEQ. I.D. NO: 98 | |
| S307118G03 humanised H5 CDRH3 | SEQ. I.D. NO: 99 | |
| S307118G03 H0 Humanised heavy chain | SEQ. I.D. NO: 100 | SEQ. I.D. NO: 101 |
| S307118G03 H1 humanised heavy chain | SEQ. I.D. NO: 102 | SEQ. I.D. NO: 103 |
| S307118G03 H2 humanised heavy chain | SEQ. I.D. NO: 104 | SEQ. I.D. NO: 105 |
| S307118G03 H3 humanised heavy chain | SEQ. I.D. NO: 106 | SEQ. I.D. NO: 107 |
| S307118G03 H4 humanised heavy chain | SEQ. I.D. NO: 108 | SEQ. I.D. NO: 109 |
| S307118G03 H5 humanised heavy chain | SEQ. I.D. NO: 110 | SEQ. I.D. NO: 111 |
| S307118G03 L0 humanised light chain | SEQ. I.D. NO: 112 | SEQ. I.D. NO: 113 |
| S307118G03 L1 humanised light chain | SEQ. I.D. NO: 114 | SEQ. I.D. NO: 115 |
| S332121F02 murine variable heavy chain | SEQ. I.D. NO: 116 | SEQ. I.D. NO: 117 |
| S332121F02 chimeric variable heavy chain | SEQ. I.D. NO: 118 | SEQ. I.D. NO: 119 |
| S332121F02 murine variable light chain | SEQ. I.D. NO: 120 | SEQ. I.D. NO: 121 |
| S332121F02 chimeric variable light chain | SEQ. I.D. NO: 122 | SEQ. I.D. NO: 123 |
| S322110D07 murine variable heavy chain | SEQ. I.D. NO: 124 | SEQ. I.D. NO: 125 |
| S322110D07 chimeric heavy chain | SEQ. I.D. NO: 126 | SEQ. I.D. NO: 127 |
| S322110D07 murine variable light chain | SEQ. I.D. NO: 128 | SEQ. I.D. NO: 129 |
| S322110D07 chimeric light chain | SEQ. I.D. NO: 130 | SEQ. I.D. NO: 131 |
| S332126E04 murine variable heavy chain | SEQ. I.D. NO: 132 | SEQ. I.D. NO: 133 |

-continued

| Sequence Summary (Table C) | | |
|---|---|---|
| Description | Amino acid sequence | Polynucleotide sequence |
| S332126E04 Chimeric heavy chain | SEQ. I.D. NO: 134 | SEQ. I.D. NO: 135 |
| S332126E04 murine variable light chain | SEQ. I.D. NO: 136 | SEQ. I.D. NO: 137 |
| S332126E04 Chimeric light chain | SEQ. I.D. NO: 138 | SEQ. I.D. NO: 139 |
| S336105A07 murine variable heavy chain | SEQ. I.D. NO: 140 | SEQ. I.D. NO: 141 |
| S336105A07 Chimeric heavy chain | SEQ. I.D. NO: 142 | SEQ. I.D. NO: 143 |
| S336105A07 murine variable light chain | SEQ. I.D. NO: 144 | SEQ. I.D. NO: 145 |
| S336105A07 chimeric light chain | SEQ. I.D. NO: 146 | SEQ. I.D. NO: 147 |
| S335115G01 murine variable heavy chain | SEQ. I.D. NO: 148 | SEQ. I.D. NO: 149 |
| S335115G01 Chimeric heavy chain | SEQ. I.D. NO: 150 | SEQ. I.D. NO: 151 |
| S335115G01 murine variable light chain | SEQ. I.D. NO: 152 | SEQ. I.D. NO: 153 |
| S335115G01 Chimeric light chain | SEQ. I.D. NO: 154 | SEQ. I.D. NO: 155 |
| S335122F05 murine variable heavy chain | SEQ. I.D. NO: 156 | SEQ. I.D. NO: 158 |
| S335122F05 Chimeric heavy chain | SEQ. I.D. NO: 158 | SEQ. I.D. NO: 159 |
| S335122F05 murine variable light chain | SEQ. I.D. NO: 160 | SEQ. I.D. NO: 161 |
| S335122F05 Chimeric light chain | SEQ. I.D. NO: 162 | SEQ. I.D. NO: 163 |
| S332121F02 CDRH1 | SEQ. I.D. NO: 164 | |
| S332121F02 CDRH2 | SEQ. I.D. NO: 165 | |
| S332121F02 CDRH3 | SEQ. I.D. NO: 166 | |
| S332121F02 CDRL1 | SEQ. I.D. NO: 167 | |
| S332121F02 CDRL2 | SEQ. I.D. NO: 168 | |
| S332121F02 CDRL3 | SEQ. I.D. NO: 169 | |
| S322110D07 CDRH1 | SEQ. I.D. NO: 170 | |
| S322110D07 CDRH2 | SEQ. I.D. NO: 171 | |

-continued

| Sequence Summary (Table C) | | |
|---|---|---|
| Description | Amino acid sequence | Polynucleotide sequence |
| S322110D07 CDRH3 | SEQ. I.D. NO: 172 | |
| S322110D07 CDRL1 | SEQ. I.D. NO: 173 | |
| S322110D07 CDRL2 | SEQ. I.D. NO: 174 | |
| S322110D07 CDRL3 | SEQ. I.D. NO: 175 | |
| S332126E04 CDRH1 | SEQ. I.D. NO: 176 | |
| S332126E04 CDRH2 | SEQ. I.D. NO: 177 | |
| S332126E04 CDRH3 | SEQ. I.D. NO: 178 | |
| S332126E04 CDRL1 | SEQ. I.D. NO: 179 | |
| S332126E04 CDRL2 | SEQ. I.D. NO: 180 | |
| S332126E04 CDRL3 | SEQ. I.D. NO: 181 | |
| S336105A07 CDRH1 | SEQ. I.D. NO: 182 | |
| S336105A07 CDRH2 | SEQ. I.D. NO: 183 | |
| S336105A07 CDRH3 | SEQ. I.D. NO: 184 | |
| S336105A07 CDRL1 | SEQ. I.D. NO: 185 | |
| S336105A07 CDRL2 | SEQ. I.D. NO: 186 | |
| S336105A07 CDRL3 | SEQ. I.D. NO: 187 | |
| S335115G01 CDRH1 | SEQ. I.D. NO: 188 | |
| S335115G01 CDRH2 | SEQ. I.D. NO: 189 | |
| S335115G01 CDRH3 | SEQ. I.D. NO: 190 | |
| S335115G01 CDRL1 | SEQ. I.D. NO: 191 | |
| S335115G01 CDRL2 | SEQ. I.D. NO: 192 | |
| S335115G01 CDRL3 | SEQ. I.D. NO: 193 | |
| S335122F05 CDRH1 | SEQ. I.D. NO: 194 | |
| S335122F05 CDRH2 | SEQ. I.D. NO: 195 | |
| S335122F05 CDRH3 | SEQ. I.D. NO: 196 | |
| S335122F05 CDRL1 | SEQ. I.D. NO: 197 | |
| S335122F05 CDRL2 | SEQ. I.D. NO: 198 | |
| S335122F05 CDRL3 | SEQ. I.D. NO: 199 | |

SEQUENCE LISTING

CA8 CDRH1

SEQ ID 1

NYWMH

CA8 CDRH2

SEQ ID 2

ATYRGHSDTYYNQKFKG

CA8 CDRH3

SEQ ID 3

GAIYNGYDVLDN

CA8 CDRL1

SEQ ID 4

SASQDISNYLN

CA8 CDRL2

SEQ ID 5

YTSNLHS

CA8 CDRL3

SEQ ID 6

QQYRKLPWT

CA8 $V_H$ domain (murine)

SEQ ID 7

EVQLQQSGAVLARPGASVKMSCKGSGYTFTNYWMHWVKQRPGQGLEWIGATYRG

HSDTYYNQKFKGKAKLTAVTSTSTAYMELSSLTNEDSAVYYCTRGAIYNGYDVLDN

WGQGTLVTVSS

CA8 $V_H$ domain (murine) (Polynucleotide)

SEQ ID 8

GAGGTGCAGCTGCAGCAGAGCGGCGCCGTGCTGGCCAGGCCCGGAGCTAGCGTG

AAGATGAGCTGCAAGGGCAGCGGCTACACCTTCACCAACTACTGGATGCACTGG

GTGAAACAGAGGCCCGGCCAGGGACTGGAGTGGATCGGCGCCACCTACAGGGG

-continued

CCACAGCGACACCTACTACAACCAGAAGTTCAAGGGCAAGGCCAAGCTGACCGC

CGTGACCTCAACCAGCACCGCCTACATGGAACTGAGCAGCCTGACCAACGAGGA

CAGCGCCGTCTATTACTGCACCAGGGGCGCCATCTACAACGGCTACGACGTGCTG

GACAATTGGGGCCAGGGAACACTAGTGACCGTGTCCAGC

CA8 $V_L$ domain (murine)

SEQ ID 9

DIQLTQTTSSLSASLGDRVTISCSASQDISNYLNWYQQKPDGTVELVIYYTSNLHSGV

PSRFSGSGSGTDYSLTIGYLEPEDVATYYCQQYRKLPWTFGGGSKLEIKR

CA8 $V_L$ domain (murine) (Polynucleotide)

SEQ ID 10

GATATCCAGCTGACCCAGACCACAAGCAGCCTGAGCGCCTCCCTGGGCGACAGG

GTGACCATTAGCTGCAGCGCCAGCCAGGACATCAGCAACTACCTGAACTGGTAC

CAGCAGAAGCCCGACGGCACCGTGGAGCTCGTGATCTACTACACCTCCAACCTG

CACAGCGGCGTGCCCAGCAGGTTCTCTGGCAGCGGCAGCGGCACCGACTACAGC

CTGACCATCGGCTATCTGGAGCCCGAGGACGTCGCCACCTACTACTGCCAGCAGT

ACAGGAAGCTGCCCTGGACCTTCGGCGGAGGCTCTAAGCTGGAGATTAAGCGT

CA8 Humanised $V_H$ J0

SEQ ID 11

QVQLVQSGAEVKKPGSSVKVSCKASGGTFSNYWMHWVRQAPGQGLEWMGATYR

GHSDTYYNQKFKGRVTITADKSTSTAYMELSSLRSEDTAVYYCARGAIYNGYDVLD

NWGQGTLVTVSS

CA8 Humanised $V_H$ J0 (Polynucleotide)

SEQ ID 12

CAGGTGCAGCTGGTCCAGAGCGGCGCCGAAGTGAAGAAGCCCGGCAGCTCCGTG

AAAGTGAGCTGCAAGGCCAGCGGCGGCACCTTCAGCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACAAGAGCACCAGCACCGCCTACATGGAACTGAGCAGCCTCAGGAGCGAGGA

CACCGCTGTGTATTACTGCGCCAGGGGCGCCATCTACAACGGCTACGACGTGCTG

GACAACTGGGGCCAGGGCACACTAGTGACCGTGTCCAGC

CA8 Humanised $V_H$ J1

SEQ ID 13

QVQLVQSGAEVKKPGSSVKVSCKASGYTFTNYWMHWVRQAPGQGLEWMGATYR

GHSDTYYNQKFKGRVTITADKSTSTAYMELSSLRSEDTAVYYCARGAIYNGYDVLD

NWGQGTLVTVSS

CA8 Humanised $V_H$ J1 (Polynucleotide)

SEQ ID 14

CAGGTGCAGCTGGTCCAGAGCGGCGCCGAAGTGAAGAAGCCCGGCAGCTCCGTG

AAAGTGAGCTGCAAGGCCAGCGGCTACACCTTCACCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACAAGAGCACCAGCACCGCCTACATGGAACTGAGCAGCCTCAGGAGCGAGGA

CACCGCTGTGTATTACTGCGCCAGGGGCGCCATCTACAACGGCTACGACGTGCTG

GACAACTGGGGCCAGGGCACACTAGTGACCGTGTCCAGC

-continued

CA8 Humanised $V_H$ J2

SEQ ID 15

QVQLVQSGAEVKKPGSSVKVSCKASGYTFTNYWMHWVRQAPGQGLEWMGATYR

GHSDTYYNQKFKGRVTITADKSTSTAYMELSSLRSEDTAVYYCTRGAIYNGYDVLD

NWGQGTLVTVSS

CA8 Humanised $V_H$ J2 (Polynucleotide)

SEQ ID 16

CAGGTGCAGCTGGTCCAGAGCGGCGCCGAAGTGAAGAAGCCCGGCAGCTCCGTG

AAAGTGAGCTGCAAGGCCAGCGGCTACACCTTCACCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACAAGAGCACCAGCACCGCCTACATGGAACTGAGCAGCCTCAGGAGCGAGGA

CACCGCTGTGTATTACTGCACCAGGGGCGCCATCTACAACGGCTACGACGTGCTG

GACAACTGGGGCCAGGGCACACTAGTGACCGTGTCCAGC

CA8 Humanised $V_H$ J3

SEQ ID 17

QVQLVQSGAEVKKPGSSVKVSCKGSGYTFTNYWMHWVRQAPGQGLEWMGATYR

GHSDTYYNQKFKGRVTITADTSTSTAYMELSSLRSEDTAVYYCTRGAIYNGYDVLD

NWGQGTLVTVSS

CA8 Humanised $V_H$ J3 (Polynucleotide)

SEQ ID 18

CAGGTGCAGCTGGTCCAGAGCGGCGCCGAAGTGAAGAAGCCCGGCAGCTCCGTG

AAAGTGAGCTGCAAGGGCAGCGGCTACACCTTCACCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACACGAGCACCAGCACCGCCTACATGGAACTGAGCAGCCTCAGGAGCGAGGAC

ACCGCTGTGTATTACTGCACCAGGGGCGCCATCTACAACGGCTACGACGTGCTGG

ACAACTGGGGCCAGGGCACACTAGTGACCGTGTCCAGC

CA8 Humanised $V_H$ J4

SEQ ID 19

QVQLVQSGAEVKKPGSSVKVSCKGSGYTFTNYWMHWVRQAPGQGLEWIGATYRG

HSDTYYNQKFKGRATLTADTSTSTAYMELSSLRSEDTAVYYCTRGAIYNGYDVLDN

WGQGTLVTVSS

CA8 Humanised $V_H$ J4 (Polynucleotide)

SEQ ID 20

CAGGTGCAGCTGGTCCAGAGCGGCGCCGAAGTGAAGAAGCCCGGCAGCTCCGTG

AAAGTGAGCTGCAAGGGCAGCGGCTACACCTTCACCAACTACTGGATGCACTGG

GTGAGGCAGGCCCCCGGACAGGGCCTGGAGTGGATCGGCGCCACCTACAGGGGC

CACAGCGACACCTACTACAACCAGAAGTTCAAGGGCCGGGCGACCCTCACCGCC

GACACGAGCACCAGCACCGCCTACATGGAACTGAGCAGCCTCAGGAGCGAGGAC

ACCGCTGTGTATTACTGCACCAGGGGCGCCATCTACAACGGCTACGACGTGCTGG

ACAACTGGGGCCAGGGCACACTAGTGACCGTGTCCAGC

CA8 Humanised $V_H$ J5

SEQ ID 21

QVQLVQSGAEVKKPGSSVKVSCKGSGYTFTNYWMHWVRQAPGQGLEWMGATYR

GHSDTYYNQKFKGRVTITADTSTSTAYMELSSLRSEDTAVYYCTRGAIYDGYDVLD

NWGQGTLVTVSS

-continued

CA8 Humanised $V_H$ J5 (Polynucleotide)

SEQ ID 22

CAGGTGCAGCTGGTCCAGAGCGGCGCCGAAGTGAAGAAGCCCGGCAGCTCCGTG

AAAGTGAGCTGCAAGGGCAGCGGCTACACCTTCACCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACACGAGCACCAGCACCGCCTACATGGAACTGAGCAGCCTCAGGAGCGAGGAC

ACCGCTGTGTATTACTGCACCAGGGGCGCCATCTACGACGGCTACGACGTGCTGG

ACAACTGGGGCCAGGGCACACTAGTGACCGTGTCCAGC

CA8 Humanised $V_H$ J6

SEQ ID 23

QVQLVQSGAEVKKPGSSVKVSCKASGGTFSNYWMHWVRQAPGQGLEWMGATYR

GHSDTYYNQKFKGRVTITADKSTSTAYMELSSLRSEDTAVYYCARGAIYDGYDVLD

NWGQGTLVTVSS

CA8 Humanised $V_H$ J6 (Polynucleotide)

SEQ ID 24

CAGGTGCAGCTGGTCCAGAGCGGCGCCGAAGTGAAGAAGCCCGGCAGCTCCGTG

AAAGTGAGCTGCAAGGCCAGCGGCGGCACCTTCAGCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACAAGAGCACCAGCACCGCCTACATGGAACTGAGCAGCCTCAGGAGCGAGGA

CACCGCTGTGTATTACTGCGCCAGGGGCGCCATCTACGACGGCTACGACGTGCTG

GACAACTGGGGCCAGGGCACACTAGTGACCGTGTCCAGC

CA8 Humanised $V_H$ J7

SEQ ID 25

QVQLVQSGAEVKKPGSSVKVSCKASGYTFTNYWMHWVRQAPGQGLEWMGATYR

GHSDTYYNQKFKGRVTITADKSTSTAYMELSSLRSEDTAVYYCARGAIYDGYDVLD

NWGQGTLVTVSS

CA8 Humanised $V_H$ J7 (Polynucleotide)

SEQ ID 26

CAGGTGCAGCTGGTCCAGAGCGGCGCCGAAGTGAAGAAGCCCGGCAGCTCCGTG

AAAGTGAGCTGCAAGGCCAGCGGCTACACCTTCACCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACAAGAGCACCAGCACCGCCTACATGGAACTGAGCAGCCTCAGGAGCGAGGA

CACCGCTGTGTATTACTGCGCCAGGGGCGCCATCTACGACGGCTACGACGTGCTG

GACAACTGGGGCCAGGGCACACTAGTGACCGTGTCCAGC

CA8 Humanised $V_H$ J8

SEQ ID 27

QVQLVQSGAEVKKPGSSVKVSCKASGYTFTNYWMHWVRQAPGQGLEWMGATYR

GHSDTYYNQKFKGRVTITADKSTSTAYMELSSLRSEDTAVYYCTRGAIYDGYDVLD

NWGQGTLVTVSS

CA8 Humanised $V_H$ J8 (Polynucleotide)

SEQ ID 28

CAGGTGCAGCTGGTCCAGAGCGGCGCCGAAGTGAAGAAGCCCGGCAGCTCCGTG

AAAGTGAGCTGCAAGGCCAGCGGCTACACCTTCACCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

-continued

GACAAGAGCACCAGCACCGCCTACATGGAACTGAGCAGCCTCAGGAGCGAGGA

CACCGCTGTGTATTACTGCACCAGGGGCGCCATCTACGACGGCTACGACGTGCTG

GACAACTGGGGCCAGGGCACACTAGTGACCGTGTCCAGC

CA8 Humanised $V_H$ J9

SEQ ID 29

QVQLVQSGAEVKKPGSSVKVSCKGSGYTFTNYWMHWVRQAPGQGLEWIGATYRG

HSDTYYNQKFKGRATLTADTSTSTAYMELSSLRSEDTAVYYCTRGAIYDGYDVLDN

WGQGTLVTVSS

CA8 Humanised $V_H$ J9 (Polynucleotide)

SEQ ID 30

CAGGTGCAGCTGGTCCAGAGCGGCGCCGAAGTGAAGAAGCCCGGCAGCTCCGTG

AAAGTGAGCTGCAAGGGCAGCGGCTACACCTTCACCAACTACTGGATGCACTGG

GTGAGGCAGGCCCCCGGACAGGGCCTGGAGTGGATCGGCGCCACCTACAGGGGC

CACAGCGACACCTACTACAACCAGAAGTTCAAGGGCCGGGCGACCCTCACCGCC

GACACGAGCACCAGCACCGCCTACATGGAACTGAGCAGCCTCAGGAGCGAGGAC

ACCGCTGTGTATTACTGCACCAGGGGCGCCATCTACGACGGCTACGACGTGCTGG

ACAACTGGGGCCAGGGCACACTAGTGACCGTGTCCAGC

CA8 Humanised $V_L$ M0

SEQ ID 31

DIQMTQSPSSLSASVGDRVTITCSASQDISNYLNWYQQKPGKAPKLLIYYTSNLHSGV

PSRFSGSGSGTDFTLTISSLQPEDFATYYCQQYRKLPWTFGQGTKLEIKR

CA8 Humanised $V_L$ M0 (Polynucleotide)

SEQ ID 32

GACATCCAGATGACCCAGAGCCCTAGCTCACTGAGCGCCAGCGTGGGCGACAGG

GTGACCATTACCTGCTCCGCCAGCCAGGACATCAGCAACTACCTGAACTGGTACC

AGCAGAAGCCCGGCAAGGCCCCCAAGCTGCTGATCTACTACACCTCCAACCTGC

ACTCCGGCGTGCCCAGCAGGTTCAGCGGAAGCGGCAGCGGCACCGATTTCACCC

TGACCATCTCCAGCCTGCAGCCCGAGGACTTCGCCACCTACTACTGCCAGCAGTA

CAGGAAGCTCCCCTGGACTTTCGGCCAGGGCACCAAACTGGAGATCAAGCGT

CA8 Humanised $V_L$ M1

SEQ ID 33

DIQMTQSPSSLSASVGDRVTITCSASQDISNYLNWYQQKPGKAPKLLIYYTSNLHSGV

PSRFSGSGSGTDYTLTISSLQPEDFATYYCQQYRKLPWTFGQGTKLEIKR

CA8 Humanised $V_L$ M1 (Polynucleotide)

SEQ ID 34

GACATCCAGATGACCCAGAGCCCTAGCTCACTGAGCGCCAGCGTGGGCGACAGG

GTGACCATTACCTGCTCCGCCAGCCAGGACATCAGCAACTACCTGAACTGGTACC

AGCAGAAGCCCGGCAAGGCCCCCAAGCTGCTGATCTACTACACCTCCAACCTGC

ACTCCGGCGTGCCCAGCAGGTTCAGCGGAAGCGGCAGCGGCACCGATTACACCC

TGACCATCTCCAGCCTGCAGCCCGAGGACTTCGCCACCTACTACTGCCAGCAGTA

CAGGAAGCTCCCCTGGACTTTCGGCCAGGGCACCAAACTGGAGATCAAGCGT

CA8 Humanised $V_L$ M2

SEQ ID 35

DIQLTQSPSSLSASVGDRVTITCSASQDISNYLNWYQQKPGKAPELVIYYTSNLHSGV

PSRFSGSGSGTDYTLTISSLQPEDFATYYCQQYRKLPWTFGQGTKLEIKR

-continued

CA8 Humanised $V_L$ M2 (Polynucleotide)

SEQ ID 36

GACATCCAGCTGACCCAGAGCCCTAGCTCACTGAGCGCCAGCGTGGGCGACAGG

GTGACCATTACCTGCTCCGCCAGCCAGGACATCAGCAACTACCTGAACTGGTACC

AGCAGAAGCCCGGCAAGGCCCCCGAGCTGGTGATCTACTACACCTCCAACCTGC

ACTCCGGCGTGCCCAGCAGGTTCAGCGGAAGCGGCAGCGGCACCGATTACACCC

TGACCATCTCCAGCCTGCAGCCCGAGGACTTCGCCACCTACTACTGCCAGCAGTA

CAGGAAGCTCCCCTGGACTTTCGGCCAGGGCACCAAACTGGAGATCAAGCGT

Human BCMA CD33-hBCMA ECD (1-53) TEV-Fc

SEQ ID 37

MPLLLLLPLLWAGALAMLQMAGQCSQNEYFDSLLHACIPCQLRCSSNTPPLTCQRY

CNASVTNSVKGTNSGENLYFQGDPKSCDKTHTCPPCPAPELLGGPSVFLFPPKPKDTL

MISRTPEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDKSRWQQG

NVFSCSVMHEALHNHYTQKSLSLSPGK

Human BCMA CD33-hBCMA ECD (1-53) TEV-Fc (Polynucleotide)

SEQ ID 38

ATGCCGCTGCTGCTACTGCTGCCCCTGCTGTGGGCAGGGGCGCTAGCTATGCTGC

AGATGGCCGGCCAGTGCAGCCAGAACGAGTACTTCGACAGCCTGCTGCACGCCT

GCATCCCCTGCCAGCTGAGATGCAGCAGCAACACACCTCCTCTGACCTGCCAGA

GATACTGCAACGCCAGCGTGACCAACAGCGTGAAGGGCACCAACTCCGGAGAGA

ACCTGTACTTCCAAGGGGATCCCAAATCTTGTGACAAAACTCACACATGCCCACC

GTGCCCAGCACCTGAACTCCTGGGGGGACCGTCAGTCTTCCTCTTCCCCCCAAAA

CCCAAGGACACCCTCATGATCTCCCGGACCCCTGAGGTCACATGCGTGGTGGTGG

ACGTGAGCCACGAAGACCCTGAGGTCAAGTTCAACTGGTACGTGGACGGCGTGG

AGGTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAACCATC

TCCAAAGCCAAAGGGCAGCCCCGAGAGCCACAGGTGTACACCCTGCCCCCATCC

CGGGATGAGCTGACCAAGAACCAGGTCAGCCTGACCTGCCTGGTCAAAGGCTTC

TATCCCAGCGACATCGCCGTGGAGTGGGAGAGCAATGGGCAGCCGGAGAACAAC

TACAAGACCACGCCTCCCGTGCTGGACTCCGACGGCTCCTTCTTCCTCTACAGCA

AGCTCACCGTGGACAAGAGCAGGTGGCAGCAGGGGAACGTCTTCTCATGCTCCG

TGATGCATGAGGCTCTGCACAACCACTACACGCAGAAGAGCCTCTCCCTGTCTCC

GGGTAAA

Human BCMA CD33-hBCMA ECD (4-53) TEV-Fc

SEQ ID 39

MPLLLLLPLLWAGALAMAGQCSQNEYFDSLLHACIPCQLRCSSNTPPLTCQRYCNAS

VTNSVKGTNSGENLYFQGDPKSCDKTHTCPPCPAPELLGGPSVFLFPPKPKDTLMISR

TPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRWQQGNVFS

CSVMHEALHNHYTQKSLSLSPGK

-continued

Human BCMA CD33-hBCMA ECD (4-53) TEV-Fc (Polynucleotide)
SEQ ID 40
ATGCCGCTGCTGCTACTGCTGCCCCTGCTGTGGGCAGGGGCGCTAGCTATGGCCG

GCCAGTGCAGCCAGAACGAGTACTTCGACAGCCTGCTGCACGCCTGCATCCCCTG

CCAGCTGAGATGCAGCAGCAACACACCTCCTCTGACCTGCCAGAGATACTGCAA

CGCCAGCGTGACCAACAGCGTGAAGGGCACCAACTCCGGAGAGAACCTGTACTT

CCAAGGGGATCCCAAATCTTGTGACAAAACTCACACATGCCCACCGTGCCCAGC

ACCTGAACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGTGAGCC

ACGAAGACCCTGAGGTCAAGTTCAACTGGTACGTGGACGGCGTGGAGGTGCATA

ATGCCAAGACAAAGCCGCGGGAGGAGCAGTACAACAGCACGTACCGTGTGGTCA

GCGTCCTCACCGTCCTGCACCAGGACTGGCTGAATGGCAAGGAGTACAAGTGCA

AGGTCTCCAACAAAGCCCTCCCAGCCCCCATCGAGAAAACCATCTCCAAAGCCA

AAGGGCAGCCCCGAGAGCCACAGGTGTACACCCTGCCCCCATCCCGGGATGAGC

TGACCAAGAACCAGGTCAGCCTGACCTGCCTGGTCAAAGGCTTCTATCCCAGCG

ACATCGCCGTGGAGTGGGAGAGCAATGGGCAGCCGGAGAACAACTACAAGACC

ACGCCTCCCGTGCTGGACTCCGACGGCTCCTTCTTCCTCTACAGCAAGCTCACCG

TGGACAAGAGCAGGTGGCAGCAGGGGAACGTCTTCTCATGCTCCGTGATGCATG

AGGCTCTGCACAACCACTACACGCAGAAGAGCCTCTCCCTGTCTCCGGGTAAA

Cynomolgous BCMA CD33 cyno BCMA ECD (4-52) TEV-Fc
SEQ ID 41
MPLLLLLPLLWAGALAMARQCSQNEYFDSLLHDCKPCQLRCSSTPPLTCQRYCNAS

MTNSVKGMNSGENLYFQGDPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSRWQQGNV

FSCSVMHEALHNHYTQKSLSLSPGK

Cynomolgous BCMA CD33 cyno BCMA ECD (4-52) TEV-Fc
(Polynucleotide)
SEQ ID 42
ATGCCGCTGCTGCTACTGCTGCCCCTGCTGTGGGCAGGGGCGCTAGCTATGGCCA

GACAGTGCAGCCAGAACGAGTACTTCGACAGCCTGCTGCACGACTGCAAGCCCT

GCCAGCTGAGATGCAGCAGCACACCTCCTCTGACCTGCCAGAGATACTGCAACG

CCAGCATGACCAACAGCGTGAAGGGCATGAACTCCGGAGAGAACCTGTACTTCC

AAGGGGATCCCAAATCTTGTGACAAAACTCACACATGCCCACCGTGCCCAGCAC

CTGAACTCCTGGGGGGACCGTCAGTCTTCCTCTTCCCCCCAAAACCCAAGGACAC

CCTCATGATCTCCCGGACCCCTGAGGTCACATGCGTGGTGGTGGACGTGAGCCAC

GAAGACCCTGAGGTCAAGTTCAACTGGTACGTGGACGGCGTGGAGGTGCATAAT

GCCAAGACAAAGCCGCGGGAGGAGCAGTACAACAGCACGTACCGTGTGGTCAG

CGTCCTCACCGTCCTGCACCAGGACTGGCTGAATGGCAAGGAGTACAAGTGCAA

GGTCTCCAACAAAGCCCTCCCAGCCCCCATCGAGAAAACCATCTCCAAAGCCAA

AGGGCAGCCCCGAGAGCCACAGGTGTACACCCTGCCCCCATCCCGGGATGAGCT

GACCAAGAACCAGGTCAGCCTGACCTGCCTGGTCAAAGGCTTCTATCCCA

GCGACATCGCCGTGGAGTGGGAGAGCAATGGGCAGCCGGAGAACAACTACAAG

-continued

ACCACGCCTCCCGTGCTGGACTCCGACGGCTCCTTCTTCCTCTACAGCAAGCTCA

CCGTGGACAAGAGCAGGTGGCAGCAGGGGAACGTCTTCTCATGCTCCGTGATGC

ATGAGGCTCTGCACAACCACTACACGCAGAAGAGCCTCTCCCTGTCTCCGGGTAA

A

CA8 J0 Humanised heavy chain

SEQ ID 43

QVQLVQSGAEVKKPGSSVKVSCKASGGTFSNYWMHWVRQAPGQGLEWMGATYR

GHSDTYYNQKFKGRVTITADKSTSTAYMELSSLRSEDTAVYYCARGAIYNGYDVLD

NWGQGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKKVEPKSC

DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPG

K

CA8 J0 Humanised heavy chain (Polynucleotide)

SEQ ID 44

CAGGTGCAGCTGGTCCAGAGCGGCGCCGAAGTGAAGAAGCCCGGCAGCTCCGTG

AAAGTGAGCTGCAAGGCCAGCGGCGGCACCTTCAGCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACAAGAGCACCAGCACCGCCTACATGGAACTGAGCAGCCTCAGGAGCGAGGA

CACCGCTGTGTATTACTGCGCCAGGGGCGCCATCTACAACGGCTACGACGTGCTG

GACAACTGGGGCCAGGGCACACTAGTGACCGTGTCCAGCGCCAGCACCAAGGGC

CCCAGCGTGTTCCCCCTGGCCCCCAGCAGCAAGAGCACCAGCGGCGGCACAGCC

GCCCTGGGCTGCCTGGTGAAGGACTACTTCCCCGAACCGGTGACCGTGTCCTGGA

ACAGCGGAGCCCTGACCAGCGGCGTGCACACCTTCCCCGCCGTGCTGCAGAGCA

GCGGCCTGTACAGCCTGAGCAGCGTGGTGACCGTGCCCAGCAGCAGCCTGGGCA

CCCAGACCTACATCTGTAACGTGAACCACAAGCCCAGCAACACCAAGGTGGACA

AGAAGGTGGAGCCCAAGAGCTGTGACAAGACCCACACCTGCCCCCCCTGCCCTG

CCCCCGAGCTGCTGGGAGGCCCCAGCGTGTTCCTGTTCCCCCCCAAGCCTAAGGA

CACCCTGATGATCAGCAGAACCCCCGAGGTGACCTGTGTGGTGGTGGATGTGAG

CCACGAGGACCCTGAGGTGAAGTTCAACTGGTACGTGGACGGCGTGGAGGTGCA

CAATGCCAAGACCAAGCCCAGGGAGGAGCAGTACAACAGCACCTACCGGGTGGT

GTCCGTGCTGACCGTGCTGCACCAGGATTGGCTGAACGGCAAGGAGTACAAGTG

TAAGGTGTCCAACAAGGCCCTGCCTGCCCCTATCGAGAAAACCATCAGCAAGGC

CAAGGGCCAGCCCAGAGAGCCCCAGGTGTACACCCTGCCCCCTAGCAGAGATGA

GCTGACCAAGAACCAGGTGTCCCTGACCTGCCTGGTGAAGGGCTTCTACCCCAGC

GACATCGCCGTGGAGTGGGAGAGCAACGGCCAGCCCGAGAACAACTACAAGAC

CACCCCCCCTGTGCTGGACAGCGATGGCAGCTTCTTCCTGTACAGCAAGCTGACC

GTGGACAAGAGCAGATGGCAGCAGGGCAACGTGTTCAGCTGCTCCGTGATGCAC

GAGGCCCTGCACAATCACTACACCCAGAAGAGCCTGAGCCTGTCCCCTGGCAAG

-continued

CA8 J1 Humanised heavy chain

SEQ ID 45

QVQLVQSGAEVKKPGSSVKVSCKASGYTFTNYWMHWVRQAPGQGLEWMGATYR

GHSDTYYNQKFKGRVTITADKSTSTAYMELSSLRSEDTAVYYCARGAIYNGYDVLD

NWGQGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKKVEPKSC

DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPG

K

CA8 J1 Humanised heavy chain (Polynucleotide)

SEQ ID 46

CAGGTGCAGCTGGTCCAGAGCGGCGCCGAAGTGAAGAAGCCCGGCAGCTCCGTG

AAAGTGAGCTGCAAGGCCAGCGGCTACACCTTCACCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACAAGAGCACCAGCACCGCCTACATGGAACTGAGCAGCCTCAGGAGCGAGGA

CACCGCTGTGTATTACTGCGCCAGGGGCGCCATCTACAACGGCTACGACGTGCTG

GACAACTGGGGCCAGGGCACACTAGTGACCGTGTCCAGCGCCAGCACCAAGGGC

CCCAGCGTGTTCCCCCTGGCCCCCAGCAGCAAGAGCACCAGCGGCGGCACAGCC

GCCCTGGGCTGCCTGGTGAAGGACTACTTCCCCGAACCGGTGACCGTGTCCTGGA

ACAGCGGAGCCCTGACCAGCGGCGTGCACACCTTCCCCGCCGTGCTGCAGAGCA

GCGGCCTGTACAGCCTGAGCAGCGTGGTGACCGTGCCCAGCAGCAGCCTGGGCA

CCCAGACCTACATCTGTAACGTGAACCACAAGCCCAGCAACACCAAGGTGGACA

AGAAGGTGGAGCCCAAGAGCTGTGACAAGACCCACACCTGCCCCCCCTGCCCTG

CCCCCGAGCTGCTGGGAGGCCCCAGCGTGTTCCTGTTCCCCCCCAAGCCTAAGGA

CACCCTGATGATCAGCAGAACCCCCGAGGTGACCTGTGTGGTGGTGGATGTGAG

CCACGAGGACCCTGAGGTGAAGTTCAACTGGTACGTGGACGGCGTGGAGGTGCA

CAATGCCAAGACCAAGCCCAGGGAGGAGCAGTACAACAGCACCTACCGGGTGGT

GTCCGTGCTGACCGTGCTGCACCAGGATTGGCTGAACGGCAAGGAGTACAAGTG

TAAGGTGTCCAACAAGGCCCTGCCTGCCCCTATCGAGAAAACCATCAGCAAGGC

CAAGGGCCAGCCCAGAGAGCCCCAGGTGTACACCCTGCCCCCTAGCAGAGATGA

GCTGACCAAGAACCAGGTGTCCCTGACCTGCCTGGTGAAGGGCTTCTACCCCAGC

GACATCGCCGTGGAGTGGGAGAGCAACGGCCAGCCCGAGAACAACTACAAGAC

CACCCCCCCTGTGCTGGACAGCGATGGCAGCTTCTTCCTGTACAGCAAGCTGACC

GTGGACAAGAGCAGATGGCAGCAGGGCAACGTGTTCAGCTGCTCCGTGATGCAC

GAGGCCCTGCACAATCACTACACCCAGAAGAGCCTGAGCCTGTCCCCTGGCAAG

CA8 J2 Humanised heavy chain

SEQ ID 47

QVQLVQSGAEVKKPGSSVKVSCKASGYTFTNYWMHWVRQAPGQGLEWMGATYR

GHSDTYYNQKFKGRVTITADKSTSTAYMELSSLRSEDTAVYYCTRGAIYNGYDVLD

NWGQGTLVTVSSASTKGPSVFPLAPSSKSTSGGTAALGCLVKDYFPEPVTVSWNSGA

-continued

LTSGVHTFPAVLQSSGLYSLSSVVTVPSSSLGTQTYICNVNHKPSNTKVDKKVEPKSC

DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPG

K

CA8 J2 Humanised heavy chain (Polynucleotide)

SEQ ID 48

CAGGTGCAGCTGGTCCAGAGCGGCGCCGAAGTGAAGAAGCCCGGCAGCTCCGTG

AAAGTGAGCTGCAAGGCCAGCGGCTACACCTTCACCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACAAGAGCACCAGCACCGCCTACATGGAACTGAGCAGCCTCAGGAGCGAGGA

CACCGCTGTGTATTACTGCACCAGGGGCGCCATCTACAACGGCTACGACGTGCTG

GACAACTGGGGCCAGGGCACACTAGTGACCGTGTCCAGCGCCAGCACCAAGGGC

CCCAGCGTGTTCCCCCTGGCCCCCAGCAGCAAGAGCACCAGCGGCGGCACAGCC

GCCCTGGGCTGCCTGGTGAAGGACTACTTCCCCGAACCGGTGACCGTGTCCTGGA

ACAGCGGAGCCCTGACCAGCGGCGTGCACACCTTCCCCGCCGTGCTGCAGAGCA

GCGGCCTGTACAGCCTGAGCAGCGTGGTGACCGTGCCCAGCAGCAGCCTGGGCA

CCCAGACCTACATCTGTAACGTGAACCACAAGCCCAGCAACACCAAGGTGGACA

AGAAGGTGGAGCCCAAGAGCTGTGACAAGACCCACACCTGCCCCCCCTGCCCTG

CCCCCGAGCTGCTGGGAGGCCCCAGCGTGTTCCTGTTCCCCCCCAAGCCTAAGGA

CACCCTGATGATCAGCAGAACCCCCGAGGTGACCTGTGTGGTGGTGGATGTGAG

CCACGAGGACCCTGAGGTGAAGTTCAACTGGTACGTGGACGGCGTGGAGGTGCA

CAATGCCAAGACCAAGCCCAGGGAGGAGCAGTACAACAGCACCTACCGGGTGGT

GTCCGTGCTGACCGTGCTGCACCAGGATTGGCTGAACGGCAAGGAGTACAAGTG

TAAGGTGTCCAACAAGGCCCTGCCTGCCCCTATCGAGAAAACCATCAGCAAGGC

CAAGGGCCAGCCCAGAGAGCCCCAGGTGTACACCCTGCCCCCTAGCAGAGATGA

GCTGACCAAGAACCAGGTGTCCCTGACCTGCCTGGTGAAGGGCTTCTACCCCAGC

GACATCGCCGTGGAGTGGGAGAGCAACGGCCAGCCCGAGAACAACTACAAGAC

CACCCCCCCTGTGCTGGACAGCGATGGCAGCTTCTTCCTGTACAGCAAGCTGACC

GTGGACAAGAGCAGATGGCAGCAGGGCAACGTGTTCAGCTGCTCCGTGATGCAC

GAGGCCCTGCACAATCACTACACCCAGAAGAGCCTGAGCCTGTCCCCTGGCAAG

CA8 J3 Humanised heavy chain

SEQ ID 49

QVQLVQSGAEVKKPGSSVKVSCKGSGYTFTNYWMHWVRQAPGQGLEWMGATYR

GHSDTYYNQKFKGRVTITADTSTSTAYMELSSLRSEDTAVYYCTRGAIYNGYDVLD

NWGQGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKKVEPKSC

DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIE

-continued

KTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPG

K

CA8 J3 Humanised heavy chain (Polynucleotide)

SEQ ID 50

CAGGTGCAGCTGGTCCAGAGCGGCGCCGAAGTGAAGAAGCCCGGCAGCTCCGTG

AAAGTGAGCTGCAAGGGCAGCGGCTACACCTTCACCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACACGAGCACCAGCACCGCCTACATGGAACTGAGCAGCCTCAGGAGCGAGGAC

ACCGCTGTGTATTACTGCACCAGGGGCGCCATCTACAACGGCTACGACGTGCTGG

ACAACTGGGGCCAGGGCACACTAGTGACCGTGTCCAGCGCCAGCACCAAGGGCC

CCAGCGTGTTCCCCCTGGCCCCCAGCAGCAAGAGCACCAGCGGCGGCACAGCCG

CCCTGGGCTGCCTGGTGAAGGACTACTTCCCCGAACCGGTGACCGTGTCCTGGAA

CAGCGGAGCCCTGACCAGCGGCGTGCACACCTTCCCCGCCGTGCTGCAGAGCAG

CGGCCTGTACAGCCTGAGCAGCGTGGTGACCGTGCCCAGCAGCAGCCTGGGCAC

CCAGACCTACATCTGTAACGTGAACCACAAGCCCAGCAACACCAAGGTGGACAA

GAAGGTGGAGCCCAAGAGCTGTGACAAGACCCACACCTGCCCCCCCTGCCCTGC

CCCCGAGCTGCTGGGAGGCCCCAGCGTGTTCCTGTTCCCCCCCAAGCCTAAGGAC

ACCCTGATGATCAGCAGAACCCCCGAGGTGACCTGTGTGGTGGTGGATGTGAGC

CACGAGGACCCTGAGGTGAAGTTCAACTGGTACGTGGACGGCGTGGAGGTGCAC

AATGCCAAGACCAAGCCCAGGGAGGAGCAGTACAACAGCACCTACCGGGTGGT

GTCCGTGCTGACCGTGCTGCACCAGGATTGGCTGAACGGCAAGGAGTACAAGTG

TAAGGTGTCCAACAAGGCCCTGCCTGCCCCTATCGAGAAAACCATCAGCAAGGC

CAAGGGCCAGCCCAGAGAGCCCCAGGTGTACACCCTGCCCCCTAGCAGAGATGA

GCTGACCAAGAACCAGGTGTCCCTGACCTGCCTGGTGAAGGGCTTCTACCCCAGC

GACATCGCCGTGGAGTGGGAGAGCAACGGCCAGCCCGAGAACAACTACAAGAC

CACCCCCCCTGTGCTGGACAGCGATGGCAGCTTCTTCCTGTACAGCAAGCTGACC

GTGGACAAGAGCAGATGGCAGCAGGGCAACGTGTTCAGCTGCTCCGTGATGCAC

GAGGCCCTGCACAATCACTACACCCAGAAGAGCCTGAGCCTGTCCCCTGGCAAG

CA8 J4 Humanised heavy chain

SEQ ID 51

QVQLVQSGAEVKKPGSSVKVSCKGSGYTFTNYWMHWVRQAPGQGLEWIGATYRG

HSDTYYNQKFKGRATLTADTSTSTAYMELSSLRSEDTAVYYCTRGAIYNGYDVLDN

WGQGTLVTVSSASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKVDKKVEPKSCD

KTHTCPPCPAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSLSLSPGK

-continued

CA8 J4 Humanised heavy chain (Polynucleotide)

SEQ ID 52

CAGGTGCAGCTGGTCCAGAGCGGCGCCGAAGTGAAGAAGCCCGGCAGCTCCGTG
AAAGTGAGCTGCAAGGGCAGCGGCTACACCTTCACCAACTACTGGATGCACTGG
GTGAGGCAGGCCCCCGGACAGGGCCTGGAGTGGATCGGCGCCACCTACAGGGGC
CACAGCGACACCTACTACAACCAGAAGTTCAAGGGCCGGGCGACCCTCACCGCC
GACACGAGCACCAGCACCGCCTACATGGAACTGAGCAGCCTCAGGAGCGAGGAC
ACCGCTGTGTATTACTGCACCAGGGGCGCCATCTACAACGGCTACGACGTGCTGG
ACAACTGGGGCCAGGGCACACTAGTGACCGTGTCCAGCGCCAGCACCAAGGGCC
CCAGCGTGTTCCCCCTGGCCCCCAGCAGCAAGAGCACCAGCGGCGGCACAGCCG
CCCTGGGCTGCCTGGTGAAGGACTACTTCCCCGAACCGGTGACCGTGTCCTGGAA
CAGCGGAGCCCTGACCAGCGGCGTGCACACCTTCCCCGCCGTGCTGCAGAGCAG
CGGCCTGTACAGCCTGAGCAGCGTGGTGACCGTGCCCAGCAGCAGCCTGGGCAC
CCAGACCTACATCTGTAACGTGAACCACAAGCCCAGCAACACCAAGGTGGACAA
GAAGGTGGAGCCCAAGAGCTGTGACAAGACCCACACCTGCCCCCCCTGCCCTGC
CCCCGAGCTGCTGGGAGGCCCCAGCGTGTTCCTGTTCCCCCCCAAGCCTAAGGAC
ACCCTGATGATCAGCAGAACCCCCGAGGTGACCTGTGTGGTGGTGGATGTGAGC
CACGAGGACCCTGAGGTGAAGTTCAACTGGTACGTGGACGGCGTGGAGGTGCAC
AATGCCAAGACCAAGCCCAGGGAGGAGCAGTACAACAGCACCTACCGGGTGGT
GTCCGTGCTGACCGTGCTGCACCAGGATTGGCTGAACGGCAAGGAGTACAAGTG
TAAGGTGTCCAACAAGGCCCTGCCTGCCCCTATCGAGAAAACCATCAGCAAGGC
CAAGGGCCAGCCCAGAGAGCCCCAGGTGTACACCCTGCCCCCTAGCAGAGATGA
GCTGACCAAGAACCAGGTGTCCCTGACCTGCCTGGTGAAGGGCTTCTACCCCAGC
GACATCGCCGTGGAGTGGGAGAGCAACGGCCAGCCCGAGAACAACTACAAGAC
CACCCCCCCTGTGCTGGACAGCGATGGCAGCTTCTTCCTGTACAGCAAGCTGACC
GTGGACAAGAGCAGATGGCAGCAGGGCAACGTGTTCAGCTGCTCCGTGATGCAC
GAGGCCCTGCACAATCACTACACCCAGAAGAGCCTGAGCCTGTCCCCTGGCAAG

CA8 J5 Humanised heavy chain

SEQ ID 53

QVQLVQSGAEVKKPGSSVKVSCKGSGYTFTNYWMHWVRQAPGQGLEWMGATYR
GHSDTYYNQKFKGRVTITADTSTSTAYMELSSLRSEDTAVYYCTRGAIYDGYDVLD
NWGQGTLVTVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDKKVEPKSC
DKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPG
K

CA8 J5 Humanised heavy chain (Polynucleotide)

SEQ ID 54

CAGGTGCAGCTGGTCCAGAGCGGCGCCGAAGTGAAGAAGCCCGGCAGCTCCGTG
AAAGTGAGCTGCAAGGGCAGCGGCTACACCTTCACCAACTACTGGATGCACTGG
GTGAGGCAGGCCCCCGGACAGGGCCTGGAGTGGATGGGCGCCACCTACAGGGGC

-continued

CACAGCGACACCTACTACAACCAGAAGTTCAAGGGCCGGGTGACCATCACCGCC

GACACGAGCACCAGCACCGCCTACATGGAACTGAGCAGCCTCAGGAGCGAGGAC

ACCGCTGTGTATTACTGCACCAGGGGCGCCATCTACGACGGCTACGACGTGCTGG

ACAACTGGGGCCAGGGCACACTAGTGACCGTGTCCAGCGCCAGCACCAAGGGCC

CCAGCGTGTTCCCCCTGGCCCCCAGCAGCAAGAGCACCAGCGGCGGCACAGCCG

CCCTGGGCTGCCTGGTGAAGGACTACTTCCCCGAACCGGTGACCGTGTCCTGGAA

CAGCGGAGCCCTGACCAGCGGCGTGCACACCTTCCCCGCCGTGCTGCAGAGCAG

CGGCCTGTACAGCCTGAGCAGCGTGGTGACCGTGCCCAGCAGCAGCCTGGGCAC

CCAGACCTACATCTGTAACGTGAACCACAAGCCCAGCAACACCAAGGTGGACAA

GAAGGTGGAGCCCAAGAGCTGTGACAAGACCCACACCTGCCCCCCCTGCCCTGC

CCCCGAGCTGCTGGGAGGCCCCAGCGTGTTCCTGTTCCCCCCCAAGCCTAAGGAC

ACCCTGATGATCAGCAGAACCCCCGAGGTGACCTGTGTGGTGGTGGATGTGAGC

CACGAGGACCCTGAGGTGAAGTTCAACTGGTACGTGGACGGCGTGGAGGTGCAC

AATGCCAAGACCAAGCCCAGGGAGGAGCAGTACAACAGCACCTACCGGGTGGT

GTCCGTGCTGACCGTGCTGCACCAGGATTGGCTGAACGGCAAGGAGTACAAGTG

TAAGGTGTCCAACAAGGCCCTGCCTGCCCCTATCGAGAAAACCATCAGCAAGGC

CAAGGGCCAGCCCAGAGAGCCCCAGGTGTACACCCTGCCCCCTAGCAGAGATGA

GCTGACCAAGAACCAGGTGTCCCTGACCTGCCTGGTGAAGGGCTTCTACCCCAGC

GACATCGCCGTGGAGTGGGAGAGCAACGGCCAGCCCGAGAACAACTACAAGAC

CACCCCCCCTGTGCTGGACAGCGATGGCAGCTTCTTCCTGTACAGCAAGCTGACC

GTGGACAAGAGCAGATGGCAGCAGGGCAACGTGTTCAGCTGCTCCGTGATGCAC

GAGGCCCTGCACAATCACTACACCCAGAAGAGCCTGAGCCTGTCCCCTGGCAAG

CA8 J6 Humanised heavy chain

SEQ ID 55

QVQLVQSGAEVKKPGSSVKVSCKASGGTFSNYWMHWVRQAPGQGLEWMGATYR

GHSDTYYNQKFKGRVTITADKSTSTAYMELSSLRSEDTAVYYCARGAIYDGYDVLD

NWGQGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKKVEPKSC

DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPG

K

CA8 J6 Humanised heavy chain (Polynucleotide)

SEQ ID 56

CAGGTGCAGCTGGTCCAGAGCGGCGCCGAAGTGAAGAAGCCCGGCAGCTCCGTG

AAAGTGAGCTGCAAGGCCAGCGGCGGCACCTTCAGCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACAAGAGCACCAGCACCGCCTACATGGAACTGAGCAGCCTCAGGAGCGAGGA

CACCGCTGTGTATTACTGCGCCAGGGGCGCCATCTACGACGGCTACGACGTGCTG

GACAACTGGGGCCAGGGCACACTAGTGACCGTGTCCAGCGCCAGCACCAAGGGC

CCCAGCGTGTTCCCCCTGGCCCCCAGCAGCAAGAGCACCAGCGGCGGCACAGCC

-continued

GCCCTGGGCTGCCTGGTGAAGGACTACTTCCCCGAACCGGTGACCGTGTCCTGGA

ACAGCGGAGCCCTGACCAGCGGCGTGCACACCTTCCCCGCCGTGCTGCAGAGCA

GCGGCCTGTACAGCCTGAGCAGCGTGGTGACCGTGCCCAGCAGCAGCCTGGGCA

CCCAGACCTACATCTGTAACGTGAACCACAAGCCCAGCAACACCAAGGTGGACA

AGAAGGTGGAGCCCAAGAGCTGTGACAAGACCCACACCTGCCCCCCCTGCCCTG

CCCCCGAGCTGCTGGGAGGCCCCAGCGTGTTCCTGTTCCCCCCCAAGCCTAAGGA

CACCCTGATGATCAGCAGAACCCCCGAGGTGACCTGTGTGGTGGTGGATGTGAG

CCACGAGGACCCTGAGGTGAAGTTCAACTGGTACGTGGACGGCGTGGAGGTGCA

CAATGCCAAGACCAAGCCCAGGGAGGAGCAGTACAACAGCACCTACCGGGTGGT

GTCCGTGCTGACCGTGCTGCACCAGGATTGGCTGAACGGCAAGGAGTACAAGTG

TAAGGTGTCCAACAAGGCCCTGCCTGCCCCTATCGAGAAAACCATCAGCAAGGC

CAAGGGCCAGCCCAGAGAGCCCCAGGTGTACACCCTGCCCCCTAGCAGAGATGA

GCTGACCAAGAACCAGGTGTCCCTGACCTGCCTGGTGAAGGGCTTCTACCCCAGC

GACATCGCCGTGGAGTGGGAGAGCAACGGCCAGCCCGAGAACAACTACAAGAC

CACCCCCCCTGTGCTGGACAGCGATGGCAGCTTCTTCCTGTACAGCAAGCTGACC

GTGGACAAGAGCAGATGGCAGCAGGGCAACGTGTTCAGCTGCTCCGTGATGCAC

GAGGCCCTGCACAATCACTACACCCAGAAGAGCCTGAGCCTGTCCCCTGGCAAG

CA8 J7 Humanised heavy chain

SEQ ID 57

QVQLVQSGAEVKKPGSSVKVSCKASGYTFTNYWMHWVRQAPGQGLEWMGATYR

GHSDTYYNQKFKGRVTITADKSTSTAYMELSSLRSEDTAVYYCARGAIYDGYDVLD

NWGQGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKKVEPKSC

DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPG

K

CA8 J7 Humanised heavy chain (Polynucleotide)

SEQ ID 58

CAGGTGCAGCTGGTCCAGAGCGGCGCCGAAGTGAAGAAGCCCGGCAGCTCCGTG

AAAGTGAGCTGCAAGGCCAGCGGCTACACCTTCACCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACAAGAGCACCAGCACCGCCTACATGGAACTGAGCAGCCTCAGGAGCGAGGA

CACCGCTGTGTATTACTGCGCCAGGGGCGCCATCTACGACGGCTACGACGTGCTG

GACAACTGGGGCCAGGGCACACTAGTGACCGTGTCCAGCGCCAGCACCAAGGGC

CCCAGCGTGTTCCCCCTGGCCCCCAGCAGCAAGAGCACCAGCGGCGGCACAGCC

GCCCTGGGCTGCCTGGTGAAGGACTACTTCCCCGAACCGGTGACCGTGTCCTGGA

ACAGCGGAGCCCTGACCAGCGGCGTGCACACCTTCCCCGCCGTGCTGCAGAGCA

GCGGCCTGTACAGCCTGAGCAGCGTGGTGACCGTGCCCAGCAGCAGCCTGGGCA

CCCAGACCTACATCTGTAACGTGAACCACAAGCCCAGCAACACCAAGGTGGACA

-continued

AGAAGGTGGAGCCCAAGAGCTGTGACAAGACCCACACCTGCCCCCCCTGCCCTG

CCCCCGAGCTGCTGGGAGGCCCCAGCGTGTTCCTGTTCCCCCCCAAGCCTAAGGA

CACCCTGATGATCAGCAGAACCCCCGAGGTGACCTGTGTGGTGGTGGATGTGAG

CCACGAGGACCCTGAGGTGAAGTTCAACTGGTACGTGGACGGCGTGGAGGTGCA

CAATGCCAAGACCAAGCCCAGGGAGGAGCAGTACAACAGCACCTACCGGGTGGT

GTCCGTGCTGACCGTGCTGCACCAGGATTGGCTGAACGGCAAGGAGTACAAGTG

TAAGGTGTCCAACAAGGCCCTGCCTGCCCCTATCGAGAAAACCATCAGCAAGGC

CAAGGGCCAGCCCAGAGAGCCCCAGGTGTACACCCTGCCCCCTAGCAGAGATGA

GCTGACCAAGAACCAGGTGTCCCTGACCTGCCTGGTGAAGGGCTTCTACCCCAGC

GACATCGCCGTGGAGTGGGAGAGCAACGGCCAGCCCGAGAACAACTACAAGAC

CACCCCCCCTGTGCTGGACAGCGATGGCAGCTTCTTCCTGTACAGCAAGCTGACC

GTGGACAAGAGCAGATGGCAGCAGGGCAACGTGTTCAGCTGCTCCGTGATGCAC

GAGGCCCTGCACAATCACTACACCCAGAAGAGCCTGAGCCTGTCCCCTGGCAAG

CA8 J8 Humanised heavy chain

SEQ ID 59

QVQLVQSGAEVKKPGSSVKVSCKASGYTFTNYWMHWVRQAPGQGLEWMGATYR

GHSDTYYNQKFKGRVTITADKSTSTAYMELSSLRSEDTAVYYCTRGAIYDGYDVLD

NWGQGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKKVEPKSC

DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPG

K

CA8 J8 Humanised heavy chain (Polynucleotide)

SEQ ID 60

CAGGTGCAGCTGGTCCAGAGCGGCGCCGAAGTGAAGAAGCCCGGCAGCTCCGTG

AAAGTGAGCTGCAAGGCCAGCGGCTACACCTTCACCAACTACTGGATGCACTGG

GTGAGGCAGGCCCCCGGACAGGGCCTGGAGTGGATGGGCGCCACCTACAGGGGC

CACAGCGACACCTACTACAACCAGAAGTTCAAGGGCCGGGTGACCATCACCGCC

GACAAGAGCACCAGCACCGCCTACATGGAACTGAGCAGCCTCAGGAGCGAGGA

CACCGCTGTGTATTACTGCACCAGGGGCGCCATCTACGACGGCTACGACGTGCTG

GACAACTGGGGCCAGGGCACACTAGTGACCGTGTCCAGCGCCAGCACCAAGGGC

CCCAGCGTGTTCCCCCTGGCCCCCAGCAGCAAGAGCACCAGCGGCGGCACAGCC

GCCCTGGGCTGCCTGGTGAAGGACTACTTCCCCGAACCGGTGACCGTGTCCTGGA

ACAGCGGAGCCCTGACCAGCGGCGTGCACACCTTCCCCGCCGTGCTGCAGAGCA

GCGGCCTGTACAGCCTGAGCAGCGTGGTGACCGTGCCCAGCAGCAGCCTGGGCA

CCCAGACCTACATCTGTAACGTGAACCACAAGCCCAGCAACACCAAGGTGGACA

AGAAGGTGGAGCCCAAGAGCTGTGACAAGACCCACACCTGCCCCCCCTGCCCTG

CCCCCGAGCTGCTGGGAGGCCCCAGCGTGTTCCTGTTCCCCCCCAAGCCTAAGGA

CACCCTGATGATCAGCAGAACCCCCGAGGTGACCTGTGTGGTGGTGGATGTGAG

CCACGAGGACCCTGAGGTGAAGTTCAACTGGTACGTGGACGGCGTGGAGGTGCA

CAATGCCAAGACCAAGCCCAGGGAGGAGCAGTACAACAGCACCTACCGGGTGGT

-continued

GTCCGTGCTGACCGTGCTGCACCAGGATTGGCTGAACGGCAAGGAGTACAAGTG

TAAGGTGTCCAACAAGGCCCTGCCTGCCCCTATCGAGAAAACCATCAGCAAGGC

CAAGGGCCAGCCCAGAGAGCCCCAGGTGTACACCCTGCCCCCTAGCAGAGATGA

GCTGACCAAGAACCAGGTGTCCCTGACCTGCCTGGTGAAGGGCTTCTACCCCAGC

GACATCGCCGTGGAGTGGGAGAGCAACGGCCAGCCCGAGAACAACTACAAGAC

CACCCCCCCTGTGCTGGACAGCGATGGCAGCTTCTTCCTGTACAGCAAGCTGACC

GTGGACAAGAGCAGATGGCAGCAGGGCAACGTGTTCAGCTGCTCCGTGATGCAC

GAGGCCCTGCACAATCACTACACCCAGAAGAGCCTGAGCCTGTCCCCTGGCAAG

CA8 J9 Humanised heavy chain

SEQ ID 61

QVQLVQSGAEVKKPGSSVKVSCKGSGYTFTNYWMHWVRQAPGQGLEWIGATYRG

HSDTYYNQKFKGRATLTADTSTSTAYMELSSLRSEDTAVYYCTRGAIYDGYDVLDN

WGQGTLVTVSSASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKVDKKVEPKSCD

KTHTCPPCPAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSLSLSPGK

CA8 J9 Humanised heavy chain (Polynucleotide)

SEQ ID 62

CAGGTGCAGCTGGTCCAGAGCGGCGCCGAAGTGAAGAAGCCCGGCAGCTCCGTG

AAAGTGAGCTGCAAGGGCAGCGGCTACACCTTCACCAACTACTGGATGCACTGG

GTGAGGCAGGCCCCCGGACAGGGCCTGGAGTGGATCGGCGCCACCTACAGGGGC

CACAGCGACACCTACTACAACCAGAAGTTCAAGGGCCGGGCGACCCTCACCGCC

GACACGAGCACCAGCACCGCCTACATGGAACTGAGCAGCCTCAGGAGCGAGGAC

ACCGCTGTGTATTACTGCACCAGGGGCGCCATCTACGACGGCTACGACGTGCTGG

ACAACTGGGGCCAGGGCACACTAGTGACCGTGTCCAGCGCCAGCACCAAGGGCC

CCAGCGTGTTCCCCCTGGCCCCCAGCAGCAAGAGCACCAGCGGCGGCACAGCCG

CCCTGGGCTGCCTGGTGAAGGACTACTTCCCCGAACCGGTGACCGTGTCCTGGAA

CAGCGGAGCCCTGACCAGCGGCGTGCACACCTTCCCCGCCGTGCTGCAGAGCAG

CGGCCTGTACAGCCTGAGCAGCGTGGTGACCGTGCCCAGCAGCAGCCTGGGCAC

CCAGACCTACATCTGTAACGTGAACCACAAGCCCAGCAACACCAAGGTGGACAA

GAAGGTGGAGCCCAAGAGCTGTGACAAGACCCACACCTGCCCCCCCTGCCCTGC

CCCCGAGCTGCTGGGAGGCCCCAGCGTGTTCCTGTTCCCCCCCAAGCCTAAGGAC

ACCCTGATGATCAGCAGAACCCCCGAGGTGACCTGTGTGGTGGTGGATGTGAGC

CACGAGGACCCTGAGGTGAAGTTCAACTGGTACGTGGACGGCGTGGAGGTGCAC

AATGCCAAGACCAAGCCCAGGGAGGAGCAGTACAACAGCACCTACCGGGTGGT

GTCCGTGCTGACCGTGCTGCACCAGGATTGGCTGAACGGCAAGGAGTACAAGTG

TAAGGTGTCCAACAAGGCCCTGCCTGCCCCTATCGAGAAAACCATCAGCAAGGC

CAAGGGCCAGCCCAGAGAGCCCCAGGTGTACACCCTGCCCCCTAGCAGAGATGA

GCTGACCAAGAACCAGGTGTCCCTGACCTGCCTGGTGAAGGGCTTCTACCCCAGC

GACATCGCCGTGGAGTGGGAGAGCAACGGCCAGCCCGAGAACAACTACAAGAC

-continued

CACCCCCCCTGTGCTGGACAGCGATGGCAGCTTCTTCCTGTACAGCAAGCTGACC

GTGGACAAGAGCAGATGGCAGCAGGGCAACGTGTTCAGCTGCTCCGTGATGCAC

GAGGCCCTGCACAATCACTACACCCAGAAGAGCCTGAGCCTGTCCCCTGGCAAG

CA8 M0 Humanised light chain

SEQ ID 63

DIQMTQSPSSLSASVGDRVTITCSASQDISNYLNWYQQKPGKAPKLLIYYTSNLHSGV

PSRFSGSGSGTDFTLTISSLQPEDFATYYCQQYRKLPWTFGQGTKLEIKRTVAAPSVFI

FPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

CA8 M0 Humanised light chain (Polynucleotide)

SEQ ID 64

GACATCCAGATGACCCAGAGCCCTAGCTCACTGAGCGCCAGCGTGGGCGACAGG

GTGACCATTACCTGCTCCGCCAGCCAGGACATCAGCAACTACCTGAACTGGTACC

AGCAGAAGCCCGGCAAGGCCCCCAAGCTGCTGATCTACTACACCTCCAACCTGC

ACTCCGGCGTGCCCAGCAGGTTCAGCGGAAGCGGCAGCGGCACCGATTTCACCC

TGACCATCTCCAGCCTGCAGCCCGAGGACTTCGCCACCTACTACTGCCAGCAGTA

CAGGAAGCTCCCCTGGACTTTCGGCCAGGGCACCAAACTGGAGATCAAGCGTAC

GGTGGCCGCCCCCAGCGTGTTCATCTTCCCCCCCAGCGATGAGCAGCTGAAGAGC

GGCACCGCCAGCGTGGTGTGTCTGCTGAACAACTTCTACCCCCGGGAGGCCAAG

GTGCAGTGGAAGGTGGACAATGCCCTGCAGAGCGGCAACAGCCAGGAGAGCGT

GACCGAGCAGGACAGCAAGGACTCCACCTACAGCCTGAGCAGCACCCTGACCCT

GAGCAAGGCCGACTACGAGAAGCACAAGGTGTACGCCTGTGAGGTGACCCACCA

GGGCCTGTCCAGCCCCGTGACCAAGAGCTTCAACCGGGGCGAGTGC

CA8 M1 Humanised light chain

SEQ ID 65

DIQMTQSPSSLSASVGDRVTITCSASQDISNYLNWYQQKPGKAPKLLIYYTSNLHSGV

PSRFSGSGSGTDYTLTISSLQPEDFATYYCQQYRKLPWTFGQGTKLEIKRTVAAPSVFI

FPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

CA8 M1 Humanised light chain (Polynucleotide)

SEQ ID 66

GACATCCAGATGACCCAGAGCCCTAGCTCACTGAGCGCCAGCGTGGGCGACAGG

GTGACCATTACCTGCTCCGCCAGCCAGGACATCAGCAACTACCTGAACTGGTACC

AGCAGAAGCCCGGCAAGGCCCCCAAGCTGCTGATCTACTACACCTCCAACCTGC

ACTCCGGCGTGCCCAGCAGGTTCAGCGGAAGCGGCAGCGGCACCGATTACACCC

TGACCATCTCCAGCCTGCAGCCCGAGGACTTCGCCACCTACTACTGCCAGCAGTA

CAGGAAGCTCCCCTGGACTTTCGGCCAGGGCACCAAACTGGAGATCAAGCGTAC

GGTGGCCGCCCCCAGCGTGTTCATCTTCCCCCCCAGCGATGAGCAGCTGAAGAGC

GGCACCGCCAGCGTGGTGTGTCTGCTGAACAACTTCTACCCCCGGGAGGCCAAG

GTGCAGTGGAAGGTGGACAATGCCCTGCAGAGCGGCAACAGCCAGGAGAGCGT

GACCGAGCAGGACAGCAAGGACTCCACCTACAGCCTGAGCAGCACCCTGACCCT

GAGCAAGGCCGACTACGAGAAGCACAAGGTGTACGCCTGTGAGGTGACCCACCA

GGGCCTGTCCAGCCCCGTGACCAAGAGCTTCAACCGGGGCGAGTGC

-continued

CA8 M2 Humanised light chain

SEQ ID 67

DIQLTQSPSSLSASVGDRVTITCSASQDISNYLNWYQQKPGKAPELVIYYTSNLHSGV

PSRFSGSGSGTDYTLTISSLQPEDFATYYCQQYRKLPWTFGQGTKLEIKRTVAAPSVFI

FPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

CA8 M2 Humanised light chain (Polynucleotide)

SEQ ID 68

GACATCCAGCTGACCCAGAGCCCTAGCTCACTGAGCGCCAGCGTGGGCGACAGG

GTGACCATTACCTGCTCCGCCAGCCAGGACATCAGCAACTACCTGAACTGGTACC

AGCAGAAGCCCGGCAAGGCCCCCGAGCTGGTGATCTACTACACCTCCAACCTGC

ACTCCGGCGTGCCCAGCAGGTTCAGCGGAAGCGGCAGCGGCACCGATTACACCC

TGACCATCTCCAGCCTGCAGCCCGAGGACTTCGCCACCTACTACTGCCAGCAGTA

CAGGAAGCTCCCCTGGACTTTCGGCCAGGGCACCAAACTGGAGATCAAGCGTAC

GGTGGCCGCCCCCAGCGTGTTCATCTTCCCCCCCAGCGATGAGCAGCTGAAGAGC

GGCACCGCCAGCGTGGTGTGTCTGCTGAACAACTTCTACCCCCGGGAGGCCAAG

GTGCAGTGGAAGGTGGACAATGCCCTGCAGAGCGGCAACAGCCAGGAGAGCGT

GACCGAGCAGGACAGCAAGGACTCCACCTACAGCCTGAGCAGCACCCTGACCCT

GAGCAAGGCCGACTACGAGAAGCACAAGGTGTACGCCTGTGAGGTGACCCACCA

GGGCCTGTCCAGCCCCGTGACCAAGAGCTTCAACCGGGGCGAGTGC

S307118G03 mouse variable heavy

SEQ ID 69

EVQLQQSGPELVKPGASVKISCKASGYTFTDYYMKWVKQSHGKSLEWIGEIYPNNG

GITYNQKFKGKATLTVDKSSSTAYMELRSLTSEDSAVYYCANGYEFVYWGQGTLVT

VSA

S307118G03 mouse variable heavy (DNA sequence)

SEQ ID 70

GAGGTCCAGTTGCAACAATCTGGACCTGAGCTGGTGAAGCCTGGGGCTTCAGTG

AAGATATCCTGTAAGGCTTCTGGATACACATTCACTGACTACTACATGAAGTGGG

TGAAGCAGAGCCATGGAAAGAGCCTTGAGTGGATTGGAGAGATTTATCCTAATA

ATGGTGGTATTACCTACAACCAGAAGTTCAAGGGCAAGGCCACATTGACTGTAG

ACAAGTCCTCCAGCACAGCCTACATGGAGCTCCGCAGCCTGACATCTGAGGACT

CTGCAGTCTATTACTGTGCAAATGGTTACGAGTTTGTTTACTGGGGCCAAGGGAC

TCTGGTCACTGTCTCTGCA

S307118G03 mouse variable light

SEQ ID 71

DIQMTQTASSLSASLGDRVTISCSASQGISNYLNWYQQKPDGTVKLLIYYTSSLHSGV

PSRFSGSGSGTDYSLTISNLEPEDIATYYCQQYSKLPWTFGGGTKLEIKR

S307118G03 mouse variable light (DNA sequence)

SEQ ID 72

GATATCCAGATGACACAGACTGCATCCTCCCTGTCTGCCTCTCTGGGAGACAGAG

TCACCATCAGTTGCAGTGCAAGTCAGGGCATTAGCAATTATTTAAACTGGTATCA

GCAGAAACCAGATGGAACTGTTAAACTCCTGATCTATTACACATCAAGTTTACAC

TCAGGAGTCCCATCAAGGTTCAGTGGCAGTGGGTCTGGGACAGATTATTCTCTCA

CCATCAGCAACCTGGAACCTGAAGATATTGCCACTTACTATTGTCAGCAGTATAG

TAAGCTTCCGTGGACGTTCGGTGGAGGCACCAAGCTGGAAATCAAACGG

-continued

S307118G03 chimeric heavy chain

SEQ ID 73

EVQLQQSGPELVKPGASVKISCKASGYTFTDYYMKWVKQSHGKSLEWIGEIYPNNG

GITYNQKFKGKATLTVDKSSSTAYMELRSLTSEDSAVYYCANGYEFVYWGQGTLVT

VSAAKTTAPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

S307118G03 chimeric heavy chain (DNA sequence)

SEQ ID 74

GAGGTCCAGTTGCAACAATCTGGACCTGAGCTGGTGAAGCCTGGGGCTTCAGTG

AAGATATCCTGTAAGGCTTCTGGATACACATTCACTGACTACTACATGAAGTGGG

TGAAGCAGAGCCATGGAAAGAGCCTTGAGTGGATTGGAGAGATTTATCCTAATA

ATGGTGGTATTACCTACAACCAGAAGTTCAAGGGCAAGGCCACATTGACTGTAG

ACAAGTCCTCCAGCACAGCCTACATGGAGCTCCGCAGCCTGACATCTGAGGACT

CTGCAGTCTATTACTGTGCAAATGGTTACGAGTTTGTTTACTGGGGCCAAGGGAC

TCTGGTCACTGTCTCTGCAGCCAAAACAACAGCCCCCAGCGTGTTCCCCCTGGCC

CCCAGCAGCAAGAGCACCAGCGGCGGCACAGCCGCCCTGGGCTGCCTGGTGAAG

GACTACTTCCCCGAACCGGTGACCGTGTCCTGGAACAGCGGAGCCCTGACCAGC

GGCGTGCACACCTTCCCCGCCGTGCTGCAGAGCAGCGGCCTGTACAGCCTGAGC

AGCGTGGTGACCGTGCCCAGCAGCAGCCTGGGCACCCAGACCTACATCTGTAAC

GTGAACCACAAGCCCAGCAACACCAAGGTGGACAAGAAGGTGGAGCCCAAGAG

CTGTGACAAGACCCACACCTGCCCCCCCTGCCCTGCCCCCGAGCTGCTGGGAGGC

CCCAGCGTGTTCCTGTTCCCCCCCAAGCCTAAGGACACCCTGATGATCAGCAGAA

CCCCCGAGGTGACCTGTGTGGTGGTGGATGTGAGCCACGAGGACCCTGAGGTGA

AGTTCAACTGGTACGTGGACGGCGTGGAGGTGCACAATGCCAAGACCAAGCCCA

GGGAGGAGCAGTACAACAGCACCTACCGGGTGGTGTCCGTGCTGACCGTGCTGC

ACCAGGATTGGCTGAACGGCAAGGAGTACAAGTGTAAGGTGTCCAACAAGGCCC

TGCCTGCCCCTATCGAGAAAACCATCAGCAAGGCCAAGGGCCAGCCCAGAGAGC

CCCAGGTGTACACCCTGCCCCCTAGCAGAGATGAGCTGACCAAGAACCAGGTGT

CCCTGACCTGCCTGGTGAAGGGCTTCTACCCCAGCGACATCGCCGTGGAGTGGG

AGAGCAACGGCCAGCCCGAGAACAACTACAAGACCACCCCCCCTGTGCTGGACA

GCGATGGCAGCTTCTTCCTGTACAGCAAGCTGACCGTGGACAAGAGCAGATGGC

AGCAGGGCAACGTGTTCAGCTGCTCCGTGATGCACGAGGCCCTGCACAATCACT

ACACCCAGAAGAGCCTGAGCCTGTCCCCTGGCAAG

S307118G03 chimeric light chain

SEQ ID 75

DIQMTQTASSLSASLGDRVTISCSASQGISNYLNWYQQKPDGTVKLLIYYTSSLHSGV

PSRFSGSGSGTDYSLTISNLEPEDIATYYCQQYSKLPWTFGGGTKLELKRTVAAPSVFI

FPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

-continued

S307118G03 chimeric light chain (DNA sequence)

SEQ ID 76

GATATCCAGATGACACAGACTGCATCCTCCCTGTCTGCCTCTCTGGGAGACAGAG

TCACCATCAGTTGCAGTGCAAGTCAGGGCATTAGCAATTATTTAAACTGGTATCA

GCAGAAACCAGATGGAACTGTTAAACTCCTGATCTATTACACATCAAGTTTACAC

TCAGGAGTCCCATCAAGGTTCAGTGGCAGTGGGTCTGGGACAGATTATTCTCTCA

CCATCAGCAACCTGGAACCTGAAGATATTGCCACTTACTATTGTCAGCAGTATAG

TAAGCTTCCGTGGACGTTCGGTGGAGGCACCAAGCTGGAGCTGAAACGTACGGT

GGCCGCCCCCAGCGTGTTCATCTTCCCCCCCAGCGATGAGCAGCTGAAGAGCGG

CACCGCCAGCGTGGTGTGTCTGCTGAACAACTTCTACCCCCGGGAGGCCAAGGT

GCAGTGGAAGGTGGACAATGCCCTGCAGAGCGGCAACAGCCAGGAGAGCGTGA

CCGAGCAGGACAGCAAGGACTCCACCTACAGCCTGAGCAGCACCCTGACCCTGA

GCAAGGCCGACTACGAGAAGCACAAGGTGTACGCCTGTGAGGTGACCCACCAGG

GCCTGTCCAGCCCCGTGACCAAGAGCTTCAACCGGGGCGAGTGC

S307118G03 humanised H0 variable heavy

SEQ ID 77

QVQLVQSGAEVKKPGSSVKVSCKASGGTFSDYYMKWVRQAPGQGLEWMGEIYPN

NGGITYNQKFKGRVTITADKSTSTAYMELSSLRSEDTAVYYCARGYEFVYWGQGTL

VTVSS

S307118G03 humanised H0 variable heavy (DNA sequence)

SEQ ID 78

CAGGTGCAGCTGGTGCAGAGCGGCGCCGAAGTGAAGAAGCCCGGCTCCAGCGTG

AAGGTGAGCTGCAAGGCTAGCGGCGGCACCTTCAGCGACTACTACATGAAGTGG

GTGAGGCAGGCCCCCGGCCAGGGACTGGAGTGGATGGGCGAGATCTACCCCAAC

AACGGGGGCATCACCTACAACCAGAAGTTCAAGGGCAGGGTGACCATCACCGCC

GACAAAAGCACCAGCACCGCCTACATGGAACTGAGCAGCCTGAGGAGCGAGGA

CACCGCCGTGTACTACTGCGCCAGGGGCTACGAGTTCGTGTATTGGGGCCAGGG

CACACTAGTGACCGTGTCCAGC

S307118G03 humanised H1 variable heavy

SEQ ID 79

QVQLVQSGAEVKKPGSSVKVSCKASGYTFTDYYMKWVRQAPGQGLEWMGEIYPN

NGGITYNQKFKGRVTITADKSTSTAYMELSSLRSEDTAVYYCARGYEFVYWGQGTL

VTVSS

S307118G03 humanised H1 variable heavy (DNA sequence)

SEQ ID 80

CAGGTGCAGCTGGTGCAGAGCGGCGCCGAAGTGAAGAAGCCCGGCTCCAGCGTG

AAGGTGAGCTGCAAGGCTAGCGGCTACACCTTCACCGACTACTACATGAAGTGG

GTGAGGCAGGCCCCCGGCCAGGGACTGGAGTGGATGGGCGAGATCTACCCCAAC

AACGGGGGCATCACCTACAACCAGAAGTTCAAGGGCAGGGTGACCATCACCGCC

GACAAAAGCACCAGCACCGCCTACATGGAACTGAGCAGCCTGAGGAGCGAGGA

CACCGCCGTGTACTACTGCGCCAGGGGCTACGAGTTCGTGTATTGGGGCCAGGG

CACACTAGTGACCGTGTCCAGC

-continued

S307118G03 humanised H2 variable heavy
SEQ ID 81
QVQLVQSGAEVKKPGSSVKVSCKASGYTFTDYYMKWVRQAPGQGLEWMGEIYPN

NGGITYNQKFKGRVTITADKSTSTAYMELSSLRSEDTAVYYCANGYEFVYWGQGTL

VTVSS

S307118G03 humanised H2 variable heavy (DNA sequence)
SEQ ID 82
CAGGTGCAGCTGGTGCAGAGCGGCGCCGAAGTGAAGAAGCCCGGCTCCAGCGTG

AAGGTGAGCTGCAAGGCTAGCGGCTACACCTTCACCGACTACTACATGAAGTGG

GTGAGGCAGGCCCCCGGCCAGGGACTGGAGTGGATGGGCGAGATCTACCCCAAC

AACGGGGGCATCACCTACAACCAGAAGTTCAAGGGCAGGGTGACCATCACCGCC

GACAAAAGCACCAGCACCGCCTACATGGAACTGAGCAGCCTGAGGAGCGAGGA

CACCGCCGTGTACTACTGCGCCAACGGCTACGAGTTCGTGTATTGGGGCCAGGGC

ACACTAGTGACCGTGTCCAGC

S307118G03 humanised H3 variable heavy
SEQ ID 83
QVQLVQSGAEVKKPGSSVKVSCKASGYTFTDYYMKWVRQAPGQGLEWIGEIYPNN

GGITYNQKFKGRATLTVDKSTSTAYMELSSLRSEDTAVYYCANGYEFVYWGQGTLV

TVSS

S307118G03 humanised H3 variable heavy (DNA sequence)
SEQ ID 84
CAGGTGCAGCTGGTGCAGAGCGGCGCCGAAGTGAAGAAGCCCGGCTCCAGCGTG

AAGGTGAGCTGCAAGGCTAGCGGCTACACCTTCACCGACTACTACATGAAGTGG

GTGAGGCAGGCCCCCGGCCAGGGACTGGAGTGGATAGGCGAGATCTACCCCAAC

AACGGGGGCATCACCTACAACCAGAAGTTCAAGGGCAGGGCGACCCTCACCGTC

GACAAAAGCACCAGCACCGCCTACATGGAACTGAGCAGCCTGAGGAGCGAGGA

CACCGCCGTGTACTACTGCGCCAACGGCTACGAGTTCGTGTATTGGGGCCAGGGC

ACACTAGTGACCGTGTCCAGC

S307118G03 humanised H4 variable heavy
SEQ ID 85
QVQLVQSGAEVKKPGSSVKVSCKASGYTFTDYYMKWVRQAPGQGLEWMGEIYPN

NGGITYNQKFKGRVTITADKSTSTAYMELSSLRSEDTAVYYCADGYEFVYWGQGTL

VTVSS

S307118G03 humanised H4 variable heavy (DNA sequence)
SEQ ID 86
CAGGTGCAGCTGGTGCAGAGCGGCGCCGAAGTGAAGAAGCCCGGCTCCAGCGTG

AAGGTGAGCTGCAAGGCTAGCGGCTACACCTTCACCGACTACTACATGAAGTGG

GTGAGGCAGGCCCCCGGCCAGGGACTGGAGTGGATGGGCGAGATCTACCCCAAC

AACGGGGGCATCACCTACAACCAGAAGTTCAAGGGCAGGGTGACCATCACCGCC

GACAAAAGCACCAGCACCGCCTACATGGAACTGAGCAGCCTGAGGAGCGAGGA

CACCGCCGTGTACTACTGCGCCGACGGCTACGAGTTCGTGTATTGGGGCCAGGGC

ACACTAGTGACCGTGTCCAGC

S307118G03 humanised H5 variable heavy
SEQ ID 87
QVQLVQSGAEVKKPGSSVKVSCKASGYTFTDYYMKWVRQAPGQGLEWIGEIYPNN

GGITYNQKFKGRATLTVDKSTSTAYMELSSLRSEDTAVYYCANGYEFDYWGQGTLV

TVSS

-continued

S307118G03 humanised H5 variable heavy (DNA sequence)

SEQ ID 88

CAGGTGCAGCTGGTGCAGAGCGGCGCCGAAGTGAAGAAGCCCGGCTCCAGCGTG

AAGGTGAGCTGCAAGGCTAGCGGCTACACCTTCACCGACTACTACATGAAGTGG

GTGAGGCAGGCCCCCGGCCAGGGACTGGAGTGGATAGGCGAGATCTACCCCAAC

AACGGGGGCATCACCTACAACCAGAAGTTCAAGGGCAGGGCGACCCTCACCGTC

GACAAAAGCACCAGCACCGCCTACATGGAACTGAGCAGCCTGAGGAGCGAGGA

CACCGCCGTGTACTACTGCGCCAACGGCTACGAGTTCGACTATTGGGGCCAGGG

CACACTAGTGACCGTGTCCAGC

S307118G03 humanised L0 variable light

SEQ ID 89

DIQMTQSPSSLSASVGDRVTITCSASQGISNYLNWYQQKPGKAPKLLIYYTSSLHSGV

PSRFSGSGSGTDFTLTISSLQPEDFATYYCQQYSKLPWTFGQGTKLEIKR

S307118G03 humanised L0 variable light (DNA sequence)

SEQ ID 90

GACATCCAGATGACCCAGAGCCCCTCAAGCCTGAGCGCCAGCGTGGGCGACAGG

GTGACTATCACCTGCAGCGCCTCCCAGGGCATCAGCAACTACCTGAACTGGTACC

AGCAGAAGCCCGGCAAGGCCCCTAAGCTGCTGATCTACTACACCAGCAGCCTGC

ACAGCGGCGTGCCCAGCAGGTTCTCCGGCAGCGGCAGCGGAACCGACTTCACCC

TGACCATTAGCAGCCTCCAGCCCGAGGACTTCGCCACCTACTACTGCCAGCAGTA

CAGCAAGCTGCCCTGGACCTTCGGCCAGGGCACCAAACTGGAGATCAAGCGT

S307118G03 humanised L1 variable light

SEQ ID 91

DIQMTQSPSSLSASVGDRVTITCSASQGISNYLNWYQQKPGKAPKLLIYYTSSLHSGV

PSRFSGSGSGTDYTLTISSLQPEDFATYYCQQYSKLPWTFGQGTKLEIKR

S307118G03 humanised L1 variable light (DNA sequence)

SEQ ID 92

GACATCCAGATGACCCAGAGCCCCTCAAGCCTGAGCGCCAGCGTGGGCGACAGG

GTGACTATCACCTGCAGCGCCTCCCAGGGCATCAGCAACTACCTGAACTGGTACC

AGCAGAAGCCCGGCAAGGCCCCTAAGCTGCTGATCTACTACACCAGCAGCCTGC

ACAGCGGCGTGCCCAGCAGGTTCTCCGGCAGCGGCAGCGGAACCGACTACACCC

TGACCATTAGCAGCCTCCAGCCCGAGGACTTCGCCACCTACTACTGCCAGCAGTA

CAGCAAGCTGCCCTGGACCTTCGGCCAGGGCACCAAACTGGAGATCAAGCGT

S307118G03 CDRH1

SEQ ID 93

DYYMK

S307118G03 CDRH2

SEQ ID 94

EIYPNNGGITYNQKFKG

S307118G03 CDRH3

SEQ ID 95

GYEFVY

S307118G03 CDRL1

SEQ ID 96

SASQGISNYLN

S307118G03 CDRL2

SEQ ID 97

YTSSLHS

S307118G03 CDRL3

SEQ ID 98

QQYSKLPWT

-continued

S307118G03 humanised H5 CDRH3

SEQ ID 99

GYEFDY

S307118G03 humanised H0 heavy chain

SEQ ID 100

QVQLVQSGAEVKKPGSSVKVSCKASGGTFSDYYMKWVRQAPGQGLEWMGEIYPN

NGGITYNQKFKGRVTITADKSTSTAYMELSSLRSEDTAVYYCARGYEFVYWGQGTL

VTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

S307118G03 humanised H0 heavy chain (polynucleotide)

SEQ ID 101

CAGGTGCAGCTGGTGCAGAGCGGCGCCGAAGTGAAGAAGCCCGGCTCCAGCGTG

AAGGTGAGCTGCAAGGCTAGCGGCGGCACCTTCAGCGACTACTACATGAAGTGG

GTGAGGCAGGCCCCCGGCCAGGGACTGGAGTGGATGGGCGAGATCTACCCCAAC

AACGGGGGCATCACCTACAACCAGAAGTTCAAGGGCAGGGTGACCATCACCGCC

GACAAAAGCACCAGCACCGCCTACATGGAACTGAGCAGCCTGAGGAGCGAGGA

CACCGCCGTGTACTACTGCGCCAGGGGCTACGAGTTCGTGTATTGGGGCCAGGG

CACACTAGTGACCGTGTCCAGCGCCAGCACCAAGGGCCCCAGCGTGTTCCCCCTG

GCCCCCAGCAGCAAGAGCACCAGCGGCGGCACAGCCGCCCTGGGCTGCCTGGTG

AAGGACTACTTCCCCGAACCGGTGACCGTGTCCTGGAACAGCGGAGCCCTGACC

AGCGGCGTGCACACCTTCCCCGCCGTGCTGCAGAGCAGCGGCCTGTACAGCCTG

AGCAGCGTGGTGACCGTGCCCAGCAGCAGCCTGGGCACCCAGACCTACATCTGT

AACGTGAACCACAAGCCCAGCAACACCAAGGTGGACAAGAAGGTGGAGCCCAA

GAGCTGTGACAAGACCCACACCTGCCCCCCCTGCCCTGCCCCCGAGCTGCTGGGA

GGCCCCAGCGTGTTCCTGTTCCCCCCCAAGCCTAAGGACACCCTGATGATCAGCA

GAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGC

CCAGGGAGGAGCAGTACAACAGCACCTACCGGGTGGTGTCCGTGCTGACCGTGC

TGCACCAGGATTGGCTGAACGGCAAGGAGTACAAGTGTAAGGTGTCCAACAAGG

CCCTGCCTGCCCCTATCGAGAAAACCATCAGCAAGGCCAAGGGCCAGCCCAGAG

AGCCCCAGGTGTACACCCTGCCCCCTAGCAGAGATGAGCTGACCAAGAACCAGG

TGTCCCTGACCTGCCTGGTGAAGGGCTTCTACCCCAGCGACATCGCCGTGGAGTG

GGAGAGCAACGGCCAGCCCGAGAACAACTACAAGACCACCCCCCCTGTGCTGGA

CAGCGATGGCAGCTTCTTCCTGTACAGCAAGCTGACCGTGGACAAGAGCAGATG

GCAGCAGGGCAACGTGTTCAGCTGCTCCGTGATGCACGAGGCCCTGCACAATCA

CTACACCCAGAAGAGCCTGAGCCTGTCCCCTGGCAAG

S307118G03 humanised H1 heavy chain

SEQ ID 102

QVQLVQSGAEVKKPGSSVKVSCKASGYTFTDYYMKWVRQAPGQGLEWMGEIYPN

NGGITYNQKFKGRVTITADKSTSTAYMELSSLRSEDTAVYYCARGYEFVYWGQGTL

-continued

VTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

S307118G03 humanised H1 heavy chain (DNA sequence)

SEQ ID 103

CAGGTGCAGCTGGTGCAGAGCGGCGCCGAAGTGAAGAAGCCCGGCTCCAGCGTG

AAGGTGAGCTGCAAGGCTAGCGGCTACACCTTCACCGACTACTACATGAAGTGG

GTGAGGCAGGCCCCCGGCCAGGGACTGGAGTGGATGGGCGAGATCTACCCCAAC

AACGGGGGCATCACCTACAACCAGAAGTTCAAGGGCAGGGTGACCATCACCGCC

GACAAAAGCACCAGCACCGCCTACATGGAACTGAGCAGCCTGAGGAGCGAGGA

CACCGCCGTGTACTACTGCGCCAGGGGCTACGAGTTCGTGTATTGGGGCCAGGG

CACACTAGTGACCGTGTCCAGCGCCAGCACCAAGGGCCCCAGCGTGTTCCCCCTG

GCCCCCAGCAGCAAGAGCACCAGCGGCGGCACAGCCGCCCTGGGCTGCCTGGTG

AAGGACTACTTCCCCGAACCGGTGACCGTGTCCTGGAACAGCGGAGCCCTGACC

AGCGGCGTGCACACCTTCCCCGCCGTGCTGCAGAGCAGCGGCCTGTACAGCCTG

AGCAGCGTGGTGACCGTGCCCAGCAGCAGCCTGGGCACCCAGACCTACATCTGT

AACGTGAACCACAAGCCCAGCAACACCAAGGTGGACAAGAAGGTGGAGCCCAA

GAGCTGTGACAAGACCCACACCTGCCCCCCCTGCCCTGCCCCCGAGCTGCTGGGA

GGCCCCAGCGTGTTCCTGTTCCCCCCCAAGCCTAAGGACACCCTGATGATCAGCA

GAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGC

CCAGGGAGGAGCAGTACAACAGCACCTACCGGGTGGTGTCCGTGCTGACCGTGC

TGCACCAGGATTGGCTGAACGGCAAGGAGTACAAGTGTAAGGTGTCCAACAAGG

CCCTGCCTGCCCCTATCGAGAAAACCATCAGCAAGGCCAAGGGCCAGCCCAGAG

AGCCCCAGGTGTACACCCTGCCCCCTAGCAGAGATGAGCTGACCAAGAACCAGG

TGTCCCTGACCTGCCTGGTGAAGGGCTTCTACCCCAGCGACATCGCCGTGGAGTG

GGAGAGCAACGGCCAGCCCGAGAACAACTACAAGACCACCCCCCCTGTGCTGGA

CAGCGATGGCAGCTTCTTCCTGTACAGCAAGCTGACCGTGGACAAGAGCAGATG

GCAGCAGGGCAACGTGTTCAGCTGCTCCGTGATGCACGAGGCCCTGCACAATCA

CTACACCCAGAAGAGCCTGAGCCTGTCCCCTGGCAAG

S307118G03 humanised H2 heavy chain

SEQ ID 104

QVQLVQSGAEVKKPGSSVKVSCKASGYTFTDYYMKWVRQAPGQGLEWMGEIYPN

NGGITYNQKFKGRVTITADKSTSTAYMELSSLRSEDTAVYYCANGYEFVYWGQGTL

VTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

-continued

S307118G03 humanised H2 heavy chain (DNA sequence)

SEQ ID 105

CAGGTGCAGCTGGTGCAGAGCGGCGCCGAAGTGAAGAAGCCCGGCTCCAGCGTG

AAGGTGAGCTGCAAGGCTAGCGGCTACACCTTCACCGACTACTACATGAAGTGG

GTGAGGCAGGCCCCCGGCCAGGGACTGGAGTGGATGGGCGAGATCTACCCCAAC

AACGGGGGCATCACCTACAACCAGAAGTTCAAGGGCAGGGTGACCATCACCGCC

GACAAAAGCACCAGCACCGCCTACATGGAACTGAGCAGCCTGAGGAGCGAGGA

CACCGCCGTGTACTACTGCGCCAACGGCTACGAGTTCGTGTATTGGGGCCAGGGC

ACACTAGTGACCGTGTCCAGCGCCAGCACCAAGGGCCCCAGCGTGTTCCCCCTG

GCCCCCAGCAGCAAGAGCACCAGCGGCGGCACAGCCGCCCTGGGCTGCCTGGTG

AAGGACTACTTCCCCGAACCGGTGACCGTGTCCTGGAACAGCGGAGCCCTGACC

AGCGGCGTGCACACCTTCCCCGCCGTGCTGCAGAGCAGCGGCCTGTACAGCCTG

AGCAGCGTGGTGACCGTGCCCAGCAGCAGCCTGGGCACCCAGACCTACATCTGT

AACGTGAACCACAAGCCCAGCAACACCAAGGTGGACAAGAAGGTGGAGCCCAA

GAGCTGTGACAAGACCCACACCTGCCCCCCCTGCCCTGCCCCCGAGCTGCTGGGA

GGCCCCAGCGTGTTCCTGTTCCCCCCCAAGCCTAAGGACACCCTGATGATCAGCA

GAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGC

CCAGGGAGGAGCAGTACAACAGCACCTACCGGGTGGTGTCCGTGCTGACCGTGC

TGCACCAGGATTGGCTGAACGGCAAGGAGTACAAGTGTAAGGTGTCCAACAAGG

CCCTGCCTGCCCCTATCGAGAAAACCATCAGCAAGGCCAAGGGCCAGCCCAGAG

AGCCCCAGGTGTACACCCTGCCCCCTAGCAGAGATGAGCTGACCAAGAACCAGG

TGTCCCTGACCTGCCTGGTGAAGGGCTTCTACCCCAGCGACATCGCCGTGGAGTG

GGAGAGCAACGGCCAGCCCGAGAACAACTACAAGACCACCCCCCCTGTGCTGGA

CAGCGATGGCAGCTTCTTCCTGTACAGCAAGCTGACCGTGGACAAGAGCAGATG

GCAGCAGGGCAACGTGTTCAGCTGCTCCGTGATGCACGAGGCCCTGCACAATCA

CTACACCCAGAAGAGCCTGAGCCTGTCCCCTGGCAAG

S307118G03 humanised H3 heavy chain

SEQ ID 106

QVQLVQSGAEVKKPGSSVKVSCKASGYTFTDYYMKWVRQAPGQGLEWIGEIYPNN

GGITYNQKFKGRATLTVDKSTSTAYMELSSLRSEDTAVYYCANGYEFVYWGQGTLV

TVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

S307118G03 humanised H3 heavy chain (DNA sequence)

SEQ ID 107

CAGGTGCAGCTGGTGCAGAGCGGCGCCGAAGTGAAGAAGCCCGGCTCCAGCGTG

AAGGTGAGCTGCAAGGCTAGCGGCTACACCTTCACCGACTACTACATGAAGTGG

GTGAGGCAGGCCCCCGGCCAGGGACTGGAGTGGATAGGCGAGATCTACCCCAAC

AACGGGGGCATCACCTACAACCAGAAGTTCAAGGGCAGGGCGACCCTCACCGTC

-continued

GACAAAAGCACCAGCACCGCCTACATGGAACTGAGCAGCCTGAGGAGCGAGGA

CACCGCCGTGTACTACTGCGCCAACGGCTACGAGTTCGTGTATTGGGGCCAGGGC

ACACTAGTGACCGTGTCCAGCGCCAGCACCAAGGGCCCCAGCGTGTTCCCCCTG

GCCCCCAGCAGCAAGAGCACCAGCGGCGGCACAGCCGCCCTGGGCTGCCTGGTG

AAGGACTACTTCCCCGAACCGGTGACCGTGTCCTGGAACAGCGGAGCCCTGACC

AGCGGCGTGCACACCTTCCCCGCCGTGCTGCAGAGCAGCGGCCTGTACAGCCTG

AGCAGCGTGGTGACCGTGCCCAGCAGCAGCCTGGGCACCCAGACCTACATCTGT

AACGTGAACCACAAGCCCAGCAACACCAAGGTGGACAAGAAGGTGGAGCCCAA

GAGCTGTGACAAGACCCACACCTGCCCCCCCTGCCCTGCCCCCGAGCTGCTGGGA

GGCCCCAGCGTGTTCCTGTTCCCCCCCAAGCCTAAGGACACCCTGATGATCAGCA

GAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGC

CCAGGGAGGAGCAGTACAACAGCACCTACCGGGTGGTGTCCGTGCTGACCGTGC

TGCACCAGGATTGGCTGAACGGCAAGGAGTACAAGTGTAAGGTGTCCAACAAGG

CCCTGCCTGCCCCTATCGAGAAAACCATCAGCAAGGCCAAGGGCCAGCCCAGAG

AGCCCCAGGTGTACACCCTGCCCCCTAGCAGAGATGAGCTGACCAAGAACCAGG

TGTCCCTGACCTGCCTGGTGAAGGGCTTCTACCCCAGCGACATCGCCGTGGAGTG

GGAGAGCAACGGCCAGCCCGAGAACAACTACAAGACCACCCCCCCTGTGCTGGA

CAGCGATGGCAGCTTCTTCCTGTACAGCAAGCTGACCGTGGACAAGAGCAGATG

GCAGCAGGGCAACGTGTTCAGCTGCTCCGTGATGCACGAGGCCCTGCACAATCA

CTACACCCAGAAGAGCCTGAGCCTGTCCCCTGGCAAG

S307118G03 humanised H4 heavy chain

SEQ ID 108

QVQLVQSGAEVKKPGSSVKVSCKASGYTFTDYYMKWVRQAPGQGLEWMGEIYPN

NGGITYNQKFKGRVTITADKSTSTAYMELSSLRSEDTAVYYCADGYEFVYWGQGTL

VTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

S307118G03 humanised H4 heavy chain (DNA sequence)

SEQ ID 109

CAGGTGCAGCTGGTGCAGAGCGGCGCCGAAGTGAAGAAGCCCGGCTCCAGCGTG

AAGGTGAGCTGCAAGGCTAGCGGCTACACCTTCACCGACTACTACATGAAGTGG

GTGAGGCAGGCCCCCGGCCAGGGACTGGAGTGGATGGGCGAGATCTACCCCAAC

AACGGGGGCATCACCTACAACCAGAAGTTCAAGGGCAGGGTGACCATCACCGCC

GACAAAAGCACCAGCACCGCCTACATGGAACTGAGCAGCCTGAGGAGCGAGGA

CACCGCCGTGTACTACTGCGCCGACGGCTACGAGTTCGTGTATTGGGGCCAGGGC

ACACTAGTGACCGTGTCCAGCGCCAGCACCAAGGGCCCCAGCGTGTTCCCCCTG

GCCCCCAGCAGCAAGAGCACCAGCGGCGGCACAGCCGCCCTGGGCTGCCTGGTG

AAGGACTACTTCCCCGAACCGGTGACCGTGTCCTGGAACAGCGGAGCCCTGACC

AGCGGCGTGCACACCTTCCCCGCCGTGCTGCAGAGCAGCGGCCTGTACAGCCTG

-continued

AGCAGCGTGGTGACCGTGCCCAGCAGCAGCCTGGGCACCCAGACCTACATCTGT

AACGTGAACCACAAGCCCAGCAACACCAAGGTGGACAAGAAGGTGGAGCCCAA

GAGCTGTGACAAGACCCACACCTGCCCCCCCTGCCCTGCCCCCGAGCTGCTGGGA

GGCCCCAGCGTGTTCCTGTTCCCCCCCAAGCCTAAGGACACCCTGATGATCAGCA

GAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGC

CCAGGGAGGAGCAGTACAACAGCACCTACCGGGTGGTGTCCGTGCTGACCGTGC

TGCACCAGGATTGGCTGAACGGCAAGGAGTACAAGTGTAAGGTGTCCAACAAGG

CCCTGCCTGCCCCTATCGAGAAAACCATCAGCAAGGCCAAGGGCCAGCCCAGAG

AGCCCCAGGTGTACACCCTGCCCCCTAGCAGAGATGAGCTGACCAAGAACCAGG

TGTCCCTGACCTGCCTGGTGAAGGGCTTCTACCCCAGCGACATCGCCGTGGAGTG

GGAGAGCAACGGCCAGCCCGAGAACAACTACAAGACCACCCCCCCTGTGCTGGA

CAGCGATGGCAGCTTCTTCCTGTACAGCAAGCTGACCGTGGACAAGAGCAGATG

GCAGCAGGGCAACGTGTTCAGCTGCTCCGTGATGCACGAGGCCCTGCACAATCA

CTACACCCAGAAGAGCCTGAGCCTGTCCCCTGGCAAG

S307118G03 humanised H5 heavy chain

SEQ ID 110

QVQLVQSGAEVKKPGSSVKVSCKASGYTFTDYYMKWVRQAPGQGLEWIGEIYPNN

GGITYNQKFKGRATLTVDKSTSTAYMELSSLRSEDTAVYYCANGYEFDYWGQGTLV

TVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

S307118G03 humanised H5 heavy chain (DNA sequence)

SEQ ID 111

CAGGTGCAGCTGGTGCAGAGCGGCGCCGAAGTGAAGAAGCCCGGCTCCAGCGTG

AAGGTGAGCTGCAAGGCTAGCGGCTACACCTTCACCGACTACTACATGAAGTGG

GTGAGGCAGGCCCCCGGCCAGGGACTGGAGTGGATAGGCGAGATCTACCCCAAC

AACGGGGGCATCACCTACAACCAGAAGTTCAAGGGCAGGGCGACCCTCACCGTC

GACAAAAGCACCAGCACCGCCTACATGGAACTGAGCAGCCTGAGGAGCGAGGA

CACCGCCGTGTACTACTGCGCCAACGGCTACGAGTTCGACTATTGGGGCCAGGG

CACACTAGTGACCGTGTCCAGCGCCAGCACCAAGGGCCCCAGCGTGTTCCCCCTG

GCCCCCAGCAGCAAGAGCACCAGCGGCGGCACAGCCGCCCTGGGCTGCCTGGTG

AAGGACTACTTCCCCGAACCGGTGACCGTGTCCTGGAACAGCGGAGCCCTGACC

AGCGGCGTGCACACCTTCCCCGCCGTGCTGCAGAGCAGCGGCCTGTACAGCCTG

AGCAGCGTGGTGACCGTGCCCAGCAGCAGCCTGGGCACCCAGACCTACATCTGT

AACGTGAACCACAAGCCCAGCAACACCAAGGTGGACAAGAAGGTGGAGCCCAA

GAGCTGTGACAAGACCCACACCTGCCCCCCCTGCCCTGCCCCCGAGCTGCTGGGA

GGCCCCAGCGTGTTCCTGTTCCCCCCCAAGCCTAAGGACACCCTGATGATCAGCA

GAACCCCCGAGGTGACCTGTGTGGTGGTGGATGTGAGCCACGAGGACCCTGAGG

-continued

TGAAGTTCAACTGGTACGTGGACGGCGTGGAGGTGCACAATGCCAAGACCAAGC

CCAGGGAGGAGCAGTACAACAGCACCTACCGGGTGGTGTCCGTGCTGACCGTGC

TGCACCAGGATTGGCTGAACGGCAAGGAGTACAAGTGTAAGGTGTCCAACAAGG

CCCTGCCTGCCCCTATCGAGAAAACCATCAGCAAGGCCAAGGGCCAGCCCAGAG

AGCCCCAGGTGTACACCCTGCCCCCTAGCAGAGATGAGCTGACCAAGAACCAGG

TGTCCCTGACCTGCCTGGTGAAGGGCTTCTACCCCAGCGACATCGCCGTGGAGTG

GGAGAGCAACGGCCAGCCCGAGAACAACTACAAGACCACCCCCCCTGTGCTGGA

CAGCGATGGCAGCTTCTTCCTGTACAGCAAGCTGACCGTGGACAAGAGCAGATG

GCAGCAGGGCAACGTGTTCAGCTGCTCCGTGATGCACGAGGCCCTGCACAATCA

CTACACCCAGAAGAGCCTGAGCCTGTCCCCTGGCAAG

S307118G03 humanised L0 light chain

SEQ ID 112

DIQMTQSPSSLSASVGDRVTITCSASQGISNYLNWYQQKPGKAPKLLIYYTSSLHSGV

PSRFSGSGSGTDFTLTISSLQPEDFATYYCQQYSKLPWTFGQGTKLEIKRTVAAPSVFI

FPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

S307118G03 humanised L0 light chain (DNA sequence)

SEQ ID 113

GACATCCAGATGACCCAGAGCCCCTCAAGCCTGAGCGCCAGCGTGGGCGACAGG

GTGACTATCACCTGCAGCGCCTCCCAGGGCATCAGCAACTACCTGAACTGGTACC

AGCAGAAGCCCGGCAAGGCCCCTAAGCTGCTGATCTACTACACCAGCAGCCTGC

ACAGCGGCGTGCCCAGCAGGTTCTCCGGCAGCGGCAGCGGAACCGACTTCACCC

TGACCATTAGCAGCCTCCAGCCCGAGGACTTCGCCACCTACTACTGCCAGCAGTA

CAGCAAGCTGCCCTGGACCTTCGGCCAGGGCACCAAACTGGAGATCAAGCGTAC

GGTGGCCGCCCCCAGCGTGTTCATCTTCCCCCCCAGCGATGAGCAGCTGAAGAGC

GGCACCGCCAGCGTGGTGTGTCTGCTGAACAACTTCTACCCCCGGGAGGCCAAG

GTGCAGTGGAAGGTGGACAATGCCCTGCAGAGCGGCAACAGCCAGGAGAGCGT

GACCGAGCAGGACAGCAAGGACTCCACCTACAGCCTGAGCAGCACCCTGACCCT

GAGCAAGGCCGACTACGAGAAGCACAAGGTGTACGCCTGTGAGGTGACCCACCA

GGGCCTGTCCAGCCCCGTGACCAAGAGCTTCAACCGGGGCGAGTGC

S307118G03 humanised L1 light chain

SEQ ID 114

DIQMTQSPSSLSASVGDRVTITCSASQGISNYLNWYQQKPGKAPKLLIYYTSSLHSGV

PSRFSGSGSGTDYTLTISSLQPEDFATYYCQQYSKLPWTFGQGTKLEIKRTVAAPSVFI

FPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

S307118G03 humanised L1 light chain (DNA sequence)

SEQ ID 115

GACATCCAGATGACCCAGAGCCCCTCAAGCCTGAGCGCCAGCGTGGGCGACAGG

GTGACTATCACCTGCAGCGCCTCCCAGGGCATCAGCAACTACCTGAACTGGTACC

AGCAGAAGCCCGGCAAGGCCCCTAAGCTGCTGATCTACTACACCAGCAGCCTGC

ACAGCGGCGTGCCCAGCAGGTTCTCCGGCAGCGGCAGCGGAACCGACTACACCC

TGACCATTAGCAGCCTCCAGCCCGAGGACTTCGCCACCTACTACTGCCAGCAGTA

CAGCAAGCTGCCCTGGACCTTCGGCCAGGGCACCAAACTGGAGATCAAGCGTAC

GGTGGCCGCCCCCAGCGTGTTCATCTTCCCCCCCAGCGATGAGCAGCTGAAGAGC

-continued

GGCACCGCCAGCGTGGTGTGTCTGCTGAACAACTTCTACCCCCGGGAGGCCAAG

GTGCAGTGGAAGGTGGACAATGCCCTGCAGAGCGGCAACAGCCAGGAGAGCGT

GACCGAGCAGGACAGCAAGGACTCCACCTACAGCCTGAGCAGCACCCTGACCCT

GAGCAAGGCCGACTACGAGAAGCACAAGGTGTACGCCTGTGAGGTGACCCACCA

GGGCCTGTCCAGCCCCGTGACCAAGAGCTTCAACCGGGGCGAGTGC

S332121F02 murine variable heavy chain

SEQ ID 116

EVQLQQSGPVLVKPGASVKMSCEASGYTFTDYYMNWVKQSHGKTLEWIGVINPYN

GGTDYNQKFKGKATLTVDKSSSTAYMELNSLTSEDSAVYYCARSVYDYPFDYWGQ

GTLVTVSS

S332121F02 murine variable heavy chain (DNA sequence)

SEQ ID 117

GAGGTGCAGCTGCAGCAGAGCGGCCCCGTGCTGGTGAAGCCTGGAGCCAGCGTG

AAAATGAGCTGCGAAGCCAGCGGCTACACCTTCACCGACTACTACATGAACTGG

GTGAAGCAGAGCCACGGCAAGACCCTGGAGTGGATCGGCGTGATCAACCCCTAC

AACGGGGGCACCGACTACAACCAGAAGTTCAAGGGCAAGGCCACTCTGACCGTG

GACAAGAGCTCCAGCACCGCCTACATGGAACTGAACAGCCTCACCTCTGAGGAC

AGCGCCGTCTATTACTGCGCCAGGAGCGTGTACGACTACCCCTTCGACTACTGGG

GCCAGGGCACACTAGTGACCGTGTCCAGC

S332121F02 chimeric heavy chain

SEQ ID 118

EVQLQQSGPVLVKPGASVKMSCEASGYTFTDYYMNWVKQSHGKTLEWIGVINPYN

GGTDYNQKFKGKATLTVDKSSSTAYMELNSLTSEDSAVYYCARSVYDYPFDYWGQ

GTLVTVSSASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGK

S332121F02 chimeric heavy chain (DNA sequence)

SEQ ID 119

GAGGTGCAGCTGCAGCAGAGCGGCCCCGTGCTGGTGAAGCCTGGAGCCAGCGTG

AAAATGAGCTGCGAAGCCAGCGGCTACACCTTCACCGACTACTACATGAACTGG

GTGAAGCAGAGCCACGGCAAGACCCTGGAGTGGATCGGCGTGATCAACCCCTAC

AACGGGGGCACCGACTACAACCAGAAGTTCAAGGGCAAGGCCACTCTGACCGTG

GACAAGAGCTCCAGCACCGCCTACATGGAACTGAACAGCCTCACCTCTGAGGAC

AGCGCCGTCTATTACTGCGCCAGGAGCGTGTACGACTACCCCTTCGACTACTGGG

GCCAGGGCACACTAGTGACCGTGTCCAGCGCCAGCACCAAGGGCCCCAGCGTGT

TCCCCCTGGCCCCCAGCAGCAAGAGCACCAGCGGCGGCACAGCCGCCCTGGGCT

GCCTGGTGAAGGACTACTTCCCCGAACCGGTGACCGTGTCCTGGAACAGCGGAG

CCCTGACCAGCGGCGTGCACACCTTCCCCGCCGTGCTGCAGAGCAGCGGCCTGTA

CAGCCTGAGCAGCGTGGTGACCGTGCCCAGCAGCAGCCTGGGCACCCAGACCTA

CATCTGTAACGTGAACCACAAGCCCAGCAACACCAAGGTGGACAAGAAGGTGGA

GCCCAAGAGCTGTGACAAGACCCACACCTGCCCCCCCTGCCCTGCCCCCGAGCTG

-continued

CTGGGAGGCCCCAGCGTGTTCCTGTTCCCCCCCAAGCCTAAGGACACCCTGATGA

TCAGCAGAACCCCCGAGGTGACCTGTGTGGTGGTGGATGTGAGCCACGAGGACC

CTGAGGTGAAGTTCAACTGGTACGTGGACGGCGTGGAGGTGCACAATGCCAAGA

CCAAGCCCAGGGAGGAGCAGTACAACAGCACCTACCGGGTGGTGTCCGTGCTGA

CCGTGCTGCACCAGGATTGGCTGAACGGCAAGGAGTACAAGTGTAAGGTGTCCA

ACAAGGCCCTGCCTGCCCCTATCGAGAAAACCATCAGCAAGGCCAAGGGCCAGC

CCAGAGAGCCCCAGGTGTACACCCTGCCCCCTAGCAGAGATGAGCTGACCAAGA

ACCAGGTGTCCCTGACCTGCCTGGTGAAGGGCTTCTACCCCAGCGACATCGCCGT

GGAGTGGGAGAGCAACGGCCAGCCCGAGAACAACTACAAGACCACCCCCCCTGT

GCTGGACAGCGATGGCAGCTTCTTCCTGTACAGCAAGCTGACCGTGGACAAGAG

CAGATGGCAGCAGGGCAACGTGTTCAGCTGCTCCGTGATGCACGAGGCCCTGCA

CAATCACTACACCCAGAAGAGCCTGAGCCTGTCCCCTGGCAAG

S332121F02 murine variable light chain

SEQ ID 120

DIVLTQSPASLAVSLGQRATISCRASESVSIHGTHLMHWYQQKPGQPPKLLIYAASNL

ESGVPARFSGSGSETDFTLNIHPVEEEDAATYFCQQSIEDPRTFGGGTKLEIK

S332121F02 murine variable light chain (DNA sequence)

SEQ ID 121

GACATCGTCCTGACCCAGAGCCCCGCCAGCCTGGCCGTGAGCCTGGGCCAGAGG

GCCACAATCAGCTGCAGGGCCTCTGAGTCCGTGAGCATCCACGGCACCCACCTG

ATGCACTGGTATCAGCAGAAGCCCGGCCAGCCTCCCAAGCTGCTGATCTACGCC

GCCAGCAACCTGGAGAGCGGCGTGCCCGCTAGGTTCAGCGGAAGCGGCAGCGAG

ACCGACTTCACCCTGAACATCCACCCCGTGGAGGAGGAAGACGCCGCCACCTAC

TTCTGCCAGCAGAGCATCGAGGACCCCAGGACCTTCGGCGGGGGCACCAAGCTC

GAGATTAAGCGT

S332121F02 chimeric light chain

SEQ ID 122

MGWSCIILFLVATATGVHSDIVLTQSPASLAVSLGQRATISCRASESVSIHGTHLMHW

YQQKPGQPPKLLIYAASNLESGVPARFSGSGSETDFTLNIHPVEEEDAATYFCQQSIED

PRTFGGGTKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKS

FNRGEC

S332121F02 chimeric light chain (DNA sequence)

SEQ ID 123

ATGGGCTGGTCCTGCATCATCCTGTTTCTGGTGGCCACCGCCACCGGCGTGCACA

GCGACATCGTCCTGACCCAGAGCCCCGCCAGCCTGGCCGTGAGCCTGGGCCAGA

GGGCCACAATCAGCTGCAGGGCCTCTGAGTCCGTGAGCATCCACGGCACCCACC

TGATGCACTGGTATCAGCAGAAGCCCGGCCAGCCTCCCAAGCTGCTGATCTACGC

CGCCAGCAACCTGGAGAGCGGCGTGCCCGCTAGGTTCAGCGGAAGCGGCAGCGA

GACCGACTTCACCCTGAACATCCACCCCGTGGAGGAGGAAGACGCCGCCACCTA

CTTCTGCCAGCAGAGCATCGAGGACCCCAGGACCTTCGGCGGGGGCACCAAGCT

CGAGATTAAGCGTACGGTGGCCGCCCCCAGCGTGTTCATCTTCCCCCCCAGCGAT

GAGCAGCTGAAGAGCGGCACCGCCAGCGTGGTGTGTCTGCTGAACAACTTCTAC

CCCCGGGAGGCCAAGGTGCAGTGGAAGGTGGACAATGCCCTGCAGAGCGGCAA

CAGCCAGGAGAGCGTGACCGAGCAGGACAGCAAGGACTCCACCTACAGCCTGA

-continued

GCAGCACCCTGACCCTGAGCAAGGCCGACTACGAGAAGCACAAGGTGTACGCCT

GTGAGGTGACCCACCAGGGCCTGTCCAGCCCCGTGACCAAGAGCTTCAACCGGG

GCGAGTGC

S322110D07 murine variable heavy chain

SEQ ID 124

EVQLQQSGPELVKPGTSVKIPCKTSGYIFTDYSIDWVKQSHGKSLEWIGDIDPNYGDP

IYNHKFKGKATLTVDRSSSTAYMELRSLTSEDTAVYFCARRATGTDWFAFWGQGTL

VTVSS

S322110D07 murine variable heavy chain (DNA sequence)

SEQ ID 125

GAGGTGCAGCTGCAGCAGAGCGGCCCCGAGCTGGTGAAACCCGGCACCAGCGTG

AAGATCCCCTGCAAGACCTCTGGCTACATCTTCACCGACTACAGCATCGACTGGG

TGAAGCAGAGCCACGGCAAGTCTCTGGAGTGGATTGGGGACATCGACCCCAACT

ACGGCGACCCCATCTACAACCACAAGTTCAAGGGCAAGGCCACCCTGACCGTGG

ACAGGAGCAGCAGCACCGCCTACATGGAACTCAGGAGCCTGACCAGCGAGGAC

ACCGCCGTGTATTTTTGCGCCAGGAGGGCCACCGGCACTGATTGGTTCGCCTTCT

GGGGCCAGGGCACACTAGTGACCGTGTCCAGC

S322110D07 chimeric heavy chain

SEQ ID 126

EVQLQQSGPELVKPGTSVKIPCKTSGYIFTDYSIDWVKQSHGKSLEWIGDIDPNYGDP

IYNHKFKGKATLTVDRSSSTAYMELRSLTSEDTAVYFCARRATGTDWFAFWGQGTL

VTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

S322110D07 chimeric heavy chain (DNA sequence)

SEQ ID 127

GAGGTGCAGCTGCAGCAGAGCGGCCCCGAGCTGGTGAAACCCGGCACCAGCGTG

AAGATCCCCTGCAAGACCTCTGGCTACATCTTCACCGACTACAGCATCGACTGGG

TGAAGCAGAGCCACGGCAAGTCTCTGGAGTGGATTGGGGACATCGACCCCAACT

ACGGCGACCCCATCTACAACCACAAGTTCAAGGGCAAGGCCACCCTGACCGTGG

ACAGGAGCAGCAGCACCGCCTACATGGAACTCAGGAGCCTGACCAGCGAGGAC

ACCGCCGTGTATTTTTGCGCCAGGAGGGCCACCGGCACTGATTGGTTCGCCTTCT

GGGGCCAGGGCACACTAGTGACCGTGTCCAGCGCCAGCACCAAGGGCCCCAGCG

TGTTCCCCCTGGCCCCCAGCAGCAAGAGCACCAGCGGCGGCACAGCCGCCCTGG

GCTGCCTGGTGAAGGACTACTTCCCCGAACCGGTGACCGTGTCCTGGAACAGCG

GAGCCCTGACCAGCGGCGTGCACACCTTCCCCGCCGTGCTGCAGAGCAGCGGCC

TGTACAGCCTGAGCAGCGTGGTGACCGTGCCCAGCAGCAGCCTGGGCACCCAGA

CCTACATCTGTAACGTGAACCACAAGCCCAGCAACACCAAGGTGGACAAGAAGG

TGGAGCCCAAGAGCTGTGACAAGACCCACACCTGCCCCCCCTGCCCTGCCCCCG

AGCTGCTGGGAGGCCCCAGCGTGTTCCTGTTCCCCCCCAAGCCTAAGGACACCCT

GATGATCAGCAGAACCCCCGAGGTGACCTGTGTGGTGGTGGATGTGAGCCACGA

-continued

GGACCCTGAGGTGAAGTTCAACTGGTACGTGGACGGCGTGGAGGTGCACAATGC

CAAGACCAAGCCCAGGGAGGAGCAGTACAACAGCACCTACCGGGTGGTGTCCGT

GCTGACCGTGCTGCACCAGGATTGGCTGAACGGCAAGGAGTACAAGTGTAAGGT

GTCCAACAAGGCCCTGCCTGCCCCTATCGAGAAAACCATCAGCAAGGCCAAGGG

CCAGCCCAGAGAGCCCCAGGTGTACACCCTGCCCCCTAGCAGAGATGAGCTGAC

CAAGAACCAGGTGTCCCTGACCTGCCTGGTGAAGGGCTTCTACCCCAGCGACATC

GCCGTGGAGTGGGAGAGCAACGGCCAGCCCGAGAACAACTACAAGACCACCCC

CCCTGTGCTGGACAGCGATGGCAGCTTCTTCCTGTACAGCAAGCTGACCGTGGAC

AAGAGCAGATGGCAGCAGGGCAACGTGTTCAGCTGCTCCGTGATGCACGAGGCC

CTGCACAATCACTACACCCAGAAGAGCCTGAGCCTGTCCCCTGGCAAG

S322110D07 murine variable light chain

SEQ ID 128

DIQMTQSPASLSVSVGETVTITCRASENIYNNLAWYQQKQGKSPQLLVYAATILADG

VPSRFSGSGSGTQYSLKINSLQSGDFGTYYCQHFWGTPLTFGAGTKLELKR

S322110D07 murine variable light chain (DNA sequence)

SEQ ID 129

GACATCCAGATGACCCAGAGCCCCGCTAGCCTCAGCGTGTCCGTCGGCGAGACC

GTGACCATCACCTGCAGGGCCAGCGAGAACATCTACAACAACCTGGCCTGGTAT

CAGCAGAAGCAGGGCAAAAGCCCCCAGCTGCTGGTGTACGCCGCCACCATTCTG

GCCGACGGCGTGCCCAGCAGGTTCTCTGGAAGCGGCAGCGGCACCCAGTACAGC

CTGAAGATCAACAGCCTGCAGAGCGGGGACTTCGGCACCTACTACTGCCAGCAC

TTCTGGGGCACTCCCCTGACCTTCGGAGCCGGCACCAAGCTGGAGCTGAAGCGT

S322110D07 chimeric light chain

SEQ ID 130

DIQMTQSPASLSVSVGETVTITCRASENIYNNLAWYQQKQGKSPQLLVYAATILADG

VPSRFSGSGSGTQYSLKINSLQSGDFGTYYCQHFWGTPLTFGAGTKLELKRTVAAPS

VFIFPPSDEQLKSGTASVVCLLNNFYPREAKVQWKVDNALQSGNSQESVTEQDSKDS

TYSLSSTLTLSKADYEKHKVYACEVTHQGLSSPVTKSFNRGEC

S322110D07 chimeric light chain (DNA sequence)

SEQ ID 131

GACATCCAGATGACCCAGAGCCCCGCTAGCCTCAGCGTGTCCGTCGGCGAGACC

GTGACCATCACCTGCAGGGCCAGCGAGAACATCTACAACAACCTGGCCTGGTAT

CAGCAGAAGCAGGGCAAAAGCCCCCAGCTGCTGGTGTACGCCGCCACCATTCTG

GCCGACGGCGTGCCCAGCAGGTTCTCTGGAAGCGGCAGCGGCACCCAGTACAGC

CTGAAGATCAACAGCCTGCAGAGCGGGGACTTCGGCACCTACTACTGCCAGCAC

TTCTGGGGCACTCCCCTGACCTTCGGAGCCGGCACCAAGCTGGAGCTGAAGCGT

ACGGTGGCCGCCCCCAGCGTGTTCATCTTCCCCCCCAGCGATGAGCAGCTGAAGA

GCGGCACCGCCAGCGTGGTGTGTCTGCTGAACAACTTCTACCCCCGGGAGGCCA

AGGTGCAGTGGAAGGTGGACAATGCCCTGCAGAGCGGCAACAGCCAGGAGAGC

GTGACCGAGCAGGACAGCAAGGACTCCACCTACAGCCTGAGCAGCACCCTGACC

CTGAGCAAGGCCGACTACGAGAAGCACAAGGTGTACGCCTGTGAGGTGACCCAC

CAGGGCCTGTCCAGCCCCGTGACCAAGAGCTTCAACCGGGGCGAGTGC

-continued

S332126E04 murine variable heavy chain
SEQ ID 132
QVQLQQPGAELVKPGASVKLSCKASGYTFTNYWMHWVKQRPGQGLEWIGIIHPNS
GSTNYNEKFKSKATLTVDKSSSTAYMQLSSLTSEDSAVYYCARGIYDYPFAYWGQG
TLVTVSS S332126E04 murine variable heavy chain (DNA sequence)
SEQ ID 133
CAGGTGCAGCTCCAGCAGCCCGGAGCCGAACTGGTGAAGCCCGGAGCCAGCGTC
AAACTGTCCTGCAAGGCCAGCGGCTACACCTTCACCAACTACTGGATGCACTGG
GTGAAGCAGAGGCCCGGCCAGGGCCTGGAGTGGATCGGCATCATCCACCCCAAC
AGCGGGAGCACCAACTACAACGAGAAGTTCAAGAGCAAGGCCACCCTGACCGTG
GACAAGAGCAGCAGCACTGCCTACATGCAGCTGAGCAGCCTGACCAGCGAGGAC
AGCGCTGTGTACTACTGCGCCAGGGGCATCTACGACTACCCCTTCGCCTATTGGG
GCCAGGGCACACTAGTGACCGTGTCCAGC S332126E04 Chimeric heavy chain
SEQ ID 134
QVQLQQPGAELVKPGASVKLSCKASGYTFTNYWMHWVKQRPGQGLEWIGIIHPNS
GSTNYNEKFKSKATLTVDKSSSTAYMQLSSLTSEDSAVYYCARGIYDYPFAYWGQG
TLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK S332126E04 Chimeric heavy chain (DNA sequence)
SEQ ID 135
CAGGTGCAGCTCCAGCAGCCCGGAGCCGAACTGGTGAAGCCCGGAGCCAGCGTC
AAACTGTCCTGCAAGGCCAGCGGCTACACCTTCACCAACTACTGGATGCACTGG
GTGAAGCAGAGGCCCGGCCAGGGCCTGGAGTGGATCGGCATCATCCACCCCAAC
AGCGGGAGCACCAACTACAACGAGAAGTTCAAGAGCAAGGCCACCCTGACCGTG
GACAAGAGCAGCAGCACTGCCTACATGCAGCTGAGCAGCCTGACCAGCGAGGAC
AGCGCTGTGTACTACTGCGCCAGGGGCATCTACGACTACCCCTTCGCCTATTGGG
GCCAGGGCACACTAGTGACCGTGTCCAGCGCCAGCACCAAGGGCCCCAGCGTGT
TCCCCCTGGCCCCCAGCAGCAAGAGCACCAGCGGCGGCACAGCCGCCCTGGGCT
GCCTGGTGAAGGACTACTTCCCCGAACCGGTGACCGTGTCCTGGAACAGCGGAG
CCCTGACCAGCGGCGTGCACACCTTCCCCGCCGTGCTGCAGAGCAGCGGCCTGTA
CAGCCTGAGCAGCGTGGTGACCGTGCCCAGCAGCAGCCTGGGCACCCAGACCTA
CATCTGTAACGTGAACCACAAGCCCAGCAACACCAAGGTGGACAAGAAGGTGGA
GCCCAAGAGCTGTGACAAGACCCACACCTGCCCCCCCTGCCCTGCCCCCGAGCTG
CTGGGAGGCCCCAGCGTGTTCCTGTTCCCCCCCAAGCCTAAGGACACCCTGATGA
TCAGCAGAACCCCCGAGGTGACCTGTGTGGTGGTGGATGTGAGCCACGAGGACC
CTGAGGTGAAGTTCAACTGGTACGTGGACGGCGTGGAGGTGCACAATGCCAAGA
CCAAGCCCAGGGAGGAGCAGTACAACAGCACCTACCGGGTGGTGTCCGTGCTGA
CCGTGCTGCACCAGGATTGGCTGAACGGCAAGGAGTACAAGTGTAAGGTGTCCA -continued

ACAAGGCCCTGCCTGCCCCTATCGAGAAAACCATCAGCAAGGCCAAGGGCCAGC

CCAGAGAGCCCCAGGTGTACACCCTGCCCCCTAGCAGAGATGAGCTGACCAAGA

ACCAGGTGTCCCTGACCTGCCTGGTGAAGGGCTTCTACCCCAGCGACATCGCCGT

GGAGTGGGAGAGCAACGGCCAGCCCGAGAACAACTACAAGACCACCCCCCCTGT

GCTGGACAGCGATGGCAGCTTCTTCCTGTACAGCAAGCTGACCGTGGACAAGAG

CAGATGGCAGCAGGGCAACGTGTTCAGCTGCTCCGTGATGCACGAGGCCCTGCA

CAATCACTACACCCAGAAGAGCCTGAGCCTGTCCCCTGGCAAG

S332126E04 murine variable light chain

SEQ ID 136

DIVLTQSPASLAVSLGQRATISCRASESVSIHGTHLMHWYQQKPGQPPKLLIYAASNL

ESGVPARFSGSGSETDFTLNIHPVEEEDAATYFCQQSIEDPYTFGGGTKLEIKR

S332126E04 murine variable light chain (DNA sequence)

SEQ ID 137

GACATCGTGCTGACCCAGTCTCCCGCTAGCCTGGCCGTGTCTCTGGGCCAGAGGG

CCACAATCAGCTGCAGGGCCAGCGAGAGCGTCAGCATTCACGGCACCCACCTGA

TGCACTGGTACCAGCAGAAGCCCGGCCAGCCTCCCAAGCTCCTGATCTACGCCGC

CAGCAACCTGGAAAGCGGAGTGCCCGCCAGGTTCAGCGGCAGCGGCTCCGAGAC

CGACTTCACCCTGAACATCCACCCCGTGGAGGAGGAGGACGCCGCCACCTACTT

CTGCCAGCAGAGCATCGAGGACCCCTACACCTTCGGCGGCGGCACCAAGCTGGA

GATCAAGCGT

S332126E04 Chimeric light chain

SEQ ID 138

DIVLTQSPASLAVSLGQRATISCRASESVSIHGTHLMHWYQQKPGQPPKLLIYAASNL

ESGVPARFSGSGSETDFTLNIHPVEEEDAATYFCQQSIEDPYTFGGGTKLEIKRTVAAP

SVFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC

S332126E04 Chimeric light chain (DNA sequence)

SEQ ID 139

GACATCGTGCTGACCCAGTCTCCCGCTAGCCTGGCCGTGTCTCTGGGCCAGAGGG

CCACAATCAGCTGCAGGGCCAGCGAGAGCGTCAGCATTCACGGCACCCACCTGA

TGCACTGGTACCAGCAGAAGCCCGGCCAGCCTCCCAAGCTCCTGATCTACGCCGC

CAGCAACCTGGAAAGCGGAGTGCCCGCCAGGTTCAGCGGCAGCGGCTCCGAGAC

CGACTTCACCCTGAACATCCACCCCGTGGAGGAGGAGGACGCCGCCACCTACTT

CTGCCAGCAGAGCATCGAGGACCCCTACACCTTCGGCGGCGGCACCAAGCTGGA

GATCAAGCGTACGGTGGCCGCCCCCAGCGTGTTCATCTTCCCCCCCAGCGATGAG

CAGCTGAAGAGCGGCACCGCCAGCGTGGTGTGTCTGCTGAACAACTTCTACCCCC

GGGAGGCCAAGGTGCAGTGGAAGGTGGACAATGCCCTGCAGAGCGGCAACAGC

CAGGAGAGCGTGACCGAGCAGGACAGCAAGGACTCCACCTACAGCCTGAGCAG

CACCCTGACCCTGAGCAAGGCCGACTACGAGAAGCACAAGGTGTACGCCTGTGA

GGTGACCCACCAGGGCCTGTCCAGCCCCGTGACCAAGAGCTTCAACCGGGGCGA

GTGC

S336105A07 murine variable heavy chain

SEQ ID 140

EVKLLQSGGGLVQPGGSLKLSCAASGIDFSRYWMSWVRRAPGKGLEWIGEINPDRS

TINYAPSLKDKFIISRDNAKNTLYLQMSKVRSEDTALYYCAVFYYDYEGAMDYWGQ

GTSVTVSS

-continued

S336105A07 murine variable heavy chain (DNA sequence)
SEQ ID 141

GAGGTGAAGCTTCTCCAGTCTGGAGGTGGCCTGGTGCAGCCTGGAGGATCCCTG

AAACTCTCCTGTGCAGCCTCAGGAATCGATTTTAGTAGATACTGGATGAGTTGGG

TTCGGCGGGCTCCAGGGAAAGGACTAGAATGGATTGGAGAAATTAATCCAGATA

GGAGTACAATCAACTATGCACCATCTCTAAAGGATAAATTCATCATCTCCAGAGA

CAACGCCAAAAATACGCTGTACCTGCAAATGAGCAAAGTGAGATCTGAGGACAC

AGCCCTTTATTACTGTGCAGTTTTCTACTATGATTACGAGGGTGCTATGGACTACT

GGGGTCAAGGAACCTCAGTCACCGTCTCCTCA

S336105A07 Chimeric heavy chain
SEQ ID 142

EVKLLQSGGGLVQPGGSLKLSCAASGIDFSRYWMSWVRRAPGKGLEWIGEINPDRS

TINY APSLKDKFIISRDNAKNTLYLQMSKVRSEDTALYYCAVFYYDYEGAMDYWGQ

GTSVTVSSAKTTAPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGK

S336105A07 Chimeric heavy chain (DNA sequence)
SEQ ID 143

GAGGTGAAGCTTCTCCAGTCTGGAGGTGGCCTGGTGCAGCCTGGAGGATCCCTG

AAACTCTCCTGTGCAGCCTCAGGAATCGATTTTAGTAGATACTGGATGAGTTGGG

TTCGGCGGGCTCCAGGGAAAGGACTAGAATGGATTGGAGAAATTAATCCAGATA

GGAGTACAATCAACTATGCACCATCTCTAAAGGATAAATTCATCATCTCCAGAGA

CAACGCCAAAAATACGCTGTACCTGCAAATGAGCAAAGTGAGATCTGAGGACAC

AGCCCTTTATTACTGTGCAGTTTTCTACTATGATTACGAGGGTGCTATGGACTACT

GGGGTCAAGGAACCTCAGTCACCGTCTCCTCAGCCAAAACAACAGCCCCCAGCG

TGTTCCCCCTGGCCCCCAGCAGCAAGAGCACCAGCGGCGGCACAGCCGCCCTGG

GCTGCCTGGTGAAGGACTACTTCCCCGAACCGGTGACCGTGTCCTGGAACAGCG

GAGCCCTGACCAGCGGCGTGCACACCTTCCCCGCCGTGCTGCAGAGCAGCGGCC

TGTACAGCCTGAGCAGCGTGGTGACCGTGCCCAGCAGCAGCCTGGGCACCCAGA

CCTACATCTGTAACGTGAACCACAAGCCCAGCAACACCAAGGTGGACAAGAAGG

TGGAGCCCAAGAGCTGTGACAAGACCCACACCTGCCCCCCCTGCCCTGCCCCCG

AGCTGCTGGGAGGCCCCAGCGTGTTCCTGTTCCCCCCCAAGCCTAAGGACACCCT

GATGATCAGCAGAACCCCCGAGGTGACCTGTGTGGTGGTGGATGTGAGCCACGA

GGACCCTGAGGTGAAGTTCAACTGGTACGTGGACGGCGTGGAGGTGCACAATGC

CAAGACCAAGCCCAGGGAGGAGCAGTACAACAGCACCTACCGGGTGGTGTCCGT

GCTGACCGTGCTGCACCAGGATTGGCTGAACGGCAAGGAGTACAAGTGTAAGGT

GTCCAACAAGGCCCTGCCTGCCCCTATCGAGAAAACCATCAGCAAGGCCAAGGG

CCAGCCCAGAGAGCCCCAGGTGTACACCCTGCCCCCTAGCAGAGATGAGCTGAC

CAAGAACCAGGTGTCCCTGACCTGCCTGGTGAAGGGCTTCTACCCCAGCGACATC

GCCGTGGAGTGGGAGAGCAACGGCCAGCCCGAGAACAACTACAAGACCACCCC

-continued

CCCTGTGCTGGACAGCGATGGCAGCTTCTTCCTGTACAGCAAGCTGACCGTGGAC

AAGAGCAGATGGCAGCAGGGCAACGTGTTCAGCTGCTCCGTGATGCACGAGGCC

CTGCACAATCACTACACCCAGAAGAGCCTGAGCCTGTCCCCTGGCAAG

S336105A07 murine varaible light chain

SEQ ID 144

DIVMTQSQKFMSTSVGDRVSVTCKASQNVDTNVAWYQQKPGQSPKALIYSASYRFS

GVPDRFTGSGSGTDFTLTISNVQSEDLAEYFCQQYNSFPFTFGSGTKLEIKR

S336105A07 murine variable light chain (DNA sequence)

SEQ ID 145

GACATTGTGATGACCCAGTCTCAAAAATTCATGTCCACATCAGTAGGAGACAGG

GTCAGCGTCACCTGCAAGGCCAGTCAGAATGTGGATACTAATGTAGCCTGGTATC

AACAAAAACCAGGGCAATCTCCTAAAGCACTGATTTACTCGGCATCCTACCGGTT

CAGTGGAGTCCCTGATCGCTTCACAGGCAGTGGATCTGGGACAGATTTCACTCTC

ACCATCAGCAATGTGCAGTCTGAAGACTTGGCAGAGTATTTCTGTCAGCAATATA

ACAGCTTTCCATTCACGTTCGGCTCGGGGACAAAGTTGGAAATAAAACGT

S336105A07 chimeric light chain

SEQ ID 146

DIVMTQSQKFMSTSVGDRVSVTCKASQNVDTNVAWYQQKPGQSPKALIYSASYRFS

GVPDRFTGSGSGTDFTLTISNVQSEDLAEYFCQQYNSFPFTFGSGTKLEIKRTVAAPSV

FIFPPSDEQLKSGTASVVCLLNNFYPREAKVQWKVDNALQSGNSQESVTEQDSKDST

YSLSSTLTLSKADYEKHKVYACEVTHQGLSSPVTKSFNRGEC

S336105A07 chimeric light chain (DNA sequence)

SEQ ID 147

GACATTGTGATGACCCAGTCTCAAAAATTCATGTCCACATCAGTAGGAGACAGG

GTCAGCGTCACCTGCAAGGCCAGTCAGAATGTGGATACTAATGTAGCCTGGTATC

AACAAAAACCAGGGCAATCTCCTAAAGCACTGATTTACTCGGCATCCTACCGGTT

CAGTGGAGTCCCTGATCGCTTCACAGGCAGTGGATCTGGGACAGATTTCACTCTC

ACCATCAGCAATGTGCAGTCTGAAGACTTGGCAGAGTATTTCTGTCAGCAATATA

ACAGCTTTCCATTCACGTTCGGCTCGGGGACAAAGTTGGAAATAAAACGTACGG

TGGCCGCCCCCAGCGTGTTCATCTTCCCCCCCAGCGATGAGCAGCTGAAGAGCGG

CACCGCCAGCGTGGTGTGTCTGCTGAACAACTTCTACCCCCGGGAGGCCAAGGT

GCAGTGGAAGGTGGACAATGCCCTGCAGAGCGGCAACAGCCAGGAGAGCGTGA

CCGAGCAGGACAGCAAGGACTCCACCTACAGCCTGAGCAGCACCCTGACCCTGA

GCAAGGCCGACTACGAGAAGCACAAGGTGTACGCCTGTGAGGTGACCCACCAGG

GCCTGTCCAGCCCCGTGACCAAGAGCTTCAACCGGGGCGAGTGC

S335115G01 murine variable heavy chain

SEQ ID 148

PVQLQQPGTELVRPGTSVKLSCKASGYTFTSYWMHWVKQRPGQGLEWIGVIDPSDS

YTNYNQKFKGKATLTVDTSSSTAYMQLSSLTSEDSAVYYCARQVFDYPMDYWGQG

TSVTVSS

S335115G01 murine variable heavy chain (DNA sequence)

SEQ ID 149

CCGGTCCAACTGCAGCAGCCTGGGACTGAGCTGGTGAGGCCTGGGACTTCAGTG

AAGTTGTCCTGCAAGGCTTCTGGCTACACCTTCACCAGCTACTGGATGCACTGGG

TAAAGCAGAGGCCTGGACAAGGCCTTGAGTGGATCGGAGTGATTGATCCTTCTG

ATAGTTATACTAACTACAATCAAAAGTTCAAGGGCAAGGCCACATTGACTGTAG

ACACATCCTCCAGCACAGCCTACATGCAGCTCAGCAGCCTGACATCTGAGGACTC

-continued

TGCGGTCTATTACTGTGCAAGACAGGTGTTTGACTATCCTATGGACTACTGGGGT

CAAGGAACCTCAGTCACCGTCTCCTCA

S335115G01 Chimeric heavy chain

SEQ ID 150

PVQLQQPGTELVRPGTSVKLSCKASGYTFTSHWMHWVKQRPGQGLEWIGVIDPSDS

YTNYNQKFKGKATLTVDTSSSTAYMQLSSLTSEDSAVYYCARQVFDYPMDYWGQG

TLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK

S335115G01 Chimeric heavy chain (DNA sequence)

SEQ ID 151

CCGGTCCAACTGCAGCAGCCTGGGACTGAGCTGGTGAGGCCTGGGACTTCAGTG

AAGTTGTCCTGCAAGGCTTCTGGCTACACCTTCACCAGCCACTGGATGCACTGGG

TAAAGCAGAGGCCTGGACAAGGCCTTGAGTGGATCGGAGTGATTGATCCTTCTG

ATAGTTATACTAACTACAATCAAAAGTTCAAGGGCAAGGCCACATTGACTGTAG

ACACATCCTCCAGCACAGCCTACATGCAGCTCAGCAGCCTGACATCTGAGGACTC

TGCGGTCTATTACTGTGCAAGACAGGTGTTTGACTATCCTATGGACTACTGGGGT

CAAGGAACACTAGTGACCGTGTCCAGCGCCAGCACCAAGGGCCCCAGCGTGTTC

CCCCTGGCCCCCAGCAGCAAGAGCACCAGCGGCGGCACAGCCGCCCTGGGCTGC

CTGGTGAAGGACTACTTCCCCGAACCGGTGACCGTGTCCTGGAACAGCGGAGCC

CTGACCAGCGGCGTGCACACCTTCCCCGCCGTGCTGCAGAGCAGCGGCCTGTAC

AGCCTGAGCAGCGTGGTGACCGTGCCCAGCAGCAGCCTGGGCACCCAGACCTAC

ATCTGTAACGTGAACCACAAGCCCAGCAACACCAAGGTGGACAAGAAGGTGGA

GCCCAAGAGCTGTGACAAGACCCACACCTGCCCCCCCTGCCCTGCCCCCGAGCTG

CTGGGAGGCCCCAGCGTGTTCCTGTTCCCCCCCAAGCCTAAGGACACCCTGATGA

TCAGCAGAACCCCCGAGGTGACCTGTGTGGTGGTGGATGTGAGCCACGAGGACC

CTGAGGTGAAGTTCAACTGGTACGTGGACGGCGTGGAGGTGCACAATGCCAAGA

CCAAGCCCAGGGAGGAGCAGTACAACAGCACCTACCGGGTGGTGTCCGTGCTGA

CCGTGCTGCACCAGGATTGGCTGAACGGCAAGGAGTACAAGTGTAAGGTGTCCA

ACAAGGCCCTGCCTGCCCCTATCGAGAAAACCATCAGCAAGGCCAAGGGCCAGC

CCAGAGAGCCCCAGGTGTACACCCTGCCCCCTAGCAGAGATGAGCTGACCAAGA

ACCAGGTGTCCCTGACCTGCCTGGTGAAGGGCTTCTACCCCAGCGACATCGCCGT

GGAGTGGGAGAGCAACGGCCAGCCCGAGAACAACTACAAGACCACCCCCCCTGT

GCTGGACAGCGATGGCAGCTTCTTCCTGTACAGCAAGCTGACCGTGGACAAGAG

CAGATGGCAGCAGGGCAACGTGTTCAGCTGCTCCGTGATGCACGAGGCCCTGCA

CAATCACTACACCCAGAAGAGCCTGAGCCTGTCCCCTGGCAAG

S335115G01 murine variable light chain

SEQ ID 152

DIVLTQSPASLAVSLGQRATISCRASESVSIHGTHLMHWYQQKPGQPPKLLIYAASNL

ESGVPARFSGSGSETDFTLNIHPVEEEDAATYFCQQSIEDPWTFGGGTKLEIKR

-continued

S335115G01 murine variable light chain (DNA sequence)

SEQ ID 153

GACATTGTGCTGACCCAATCTCCAGCTTCTTTGGCTGTGTCTCTAGGGCAGAGGG

CCACCATCTCCTGCAGAGCCAGTGAAAGTGTCAGTATTCATGGTACTCATTTAAT

GCACTGGTACCAACAGAAACCAGGACAGCCACCCAAACTCCTCATCTATGCTGC

ATCCAACCTAGAATCTGGAGTCCCTGCCAGGTTCAGTGGCAGTGGGTCTGAGAC

AGACTTCACCCTCAACATCCATCCTGTGGAGGAGGAGGATGCTGCAACCTATTTC

TGTCAGCAAAGTATTGAGGATCCGTGGACGTTCGGTGGAGGCACCAAGCTGGAA

ATCAAACGT

S335115G01 Chimeric light chain

SEQ ID 154

DIVLTQSPASLAVSLGQRATISCRASESVSIHGTHLMHWYQQKPGQPPKLLIYAASNL

ESGVPARFSGSGSETDFTLNIHPVEEEDAATYFCQQSIEDPWTFGGGTKLEINRTVAA

PSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC

S335115G01 Chimeric light chain (DNA sequence)

SEQ ID 155

GACATTGTGCTGACCCAATCTCCAGCTTCTTTGGCTGTGTCTCTAGGGCAGAGGG

CCACCATCTCCTGCAGAGCCAGTGAAAGTGTCAGTATTCATGGTACTCATTTAAT

GCACTGGTACCAACAGAAACCAGGACAGCCACCCAAACTCCTCATCTATGCTGC

ATCCAACCTAGAATCTGGAGTCCCTGCCAGGTTCAGTGGCAGTGGGTCTGAGAC

AGACTTCACCCTCAACATCCATCCTGTGGAGGAGGAGGATGCTGCAACCTATTTC

TGTCAGCAAAGTATTGAGGATCCGTGGACGTTCGGTGGAGGCACCAAGCTGGAA

ATCAATCGTACGGTGGCCGCCCCCAGCGTGTTCATCTTCCCCCCCAGCGATGAGC

AGCTGAAGAGCGGCACCGCCAGCGTGGTGTGTCTGCTGAACAACTTCTACCCCC

GGGAGGCCAAGGTGCAGTGGAAGGTGGACAATGCCCTGCAGAGCGGCAACAGC

CAGGAGAGCGTGACCGAGCAGGACAGCAAGGACTCCACCTACAGCCTGAGCAG

CACCCTGACCCTGAGCAAGGCCGACTACGAGAAGCACAAGGTGTACGCCTGTGA

GGTGACCCACCAGGGCCTGTCCAGCCCCGTGACCAAGAGCTTCAACCGGGGCGA

GTGC

S335122F05 murine variable heavy chain

SEQ ID 156

QVQLQQSGAELVRPGASVTLSCKASGYTFTDYEMHWVKQTPVHGLEWIGAIDPETG

GTAYNQKFKGKAILTADKSSSTAYMELRSLTSEDSAVYYCTRSIYDYYFDYWGQGT

TLTVSS

S335122F05 murine variable heavy chain (DNA sequence)

SEQ ID 157

CAGGTTCAACTGCAGCAGTCTGGGGCTGAGCTGGTGAGGCCTGGGGCTTCAGTG

ACGCTGTCCTGCAAGGCTTCGGGCTACACATTTACTGACTATGAAATGCACTGGG

TGAAGCAGACACCTGTGCATGGCCTGGAATGGATTGGAGCTATTGATCCTGAAA

CTGGTGGTACTGCCTACAATCAGAAGTTCAAGGGCAAGGCCATACTGACTGCAG

ACAAATCCTCCAGCACAGCCTACATGGAGCTCCGCAGCCTGACATCTGAGGACT

CTGCCGTCTATTACTGTACAAGATCGATTTATGATTACTACTTTGACTACTGGGGC

CAAGGCACCACTCTCACAGTCTCCTCA

-continued

S335122F05 Chimeric heavy chain

SEQ ID 158

QVQLQQSGAELVRPGASVTLSCKASGYTFTDYEMHWVKQTPVHGLEWIGAIDPETG

GTAYNQKFKGKAILTADKSSSTAYMELRSLTSEDSAVYYCTRSIYDYYFDYWGQGT

TLTVSSAKTTPPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

S335122F05 Chimeric heavy chain (DNA sequence)

SEQ ID 159

CAGGTTCAACTGCAGCAGTCTGGGGCTGAGCTGGTGAGGCCTGGGGCTTCAGTG

ACGCTGTCCTGCAAGGCTTCGGGCTACACATTTACTGACTATGAAATGCACTGGG

TGAAGCAGACACCTGTGCATGGCCTGGAATGGATTGGAGCTATTGATCCTGAAA

CTGGTGGTACTGCCTACAATCAGAAGTTCAAGGGCAAGGCCATACTGACTGCAG

ACAAATCCTCCAGCACAGCCTACATGGAGCTCCGCAGCCTGACATCTGAGGACT

CTGCCGTCTATTACTGTACAAGATCGATTTATGATTACTACTTTGACTACTGGGGC

CAAGGCACCACTCTCACAGTCTCCTCAGCCAAAACGACACCCCCCAGCGTGTTCC

CCCTGGCCCCCAGCAGCAAGAGCACCAGCGGCGGCACAGCCGCCCTGGGCTGCC

TGGTGAAGGACTACTTCCCCGAACCGGTGACCGTGTCCTGGAACAGCGGAGCCC

TGACCAGCGGCGTGCACACCTTCCCCGCCGTGCTGCAGAGCAGCGGCCTGTACA

GCCTGAGCAGCGTGGTGACCGTGCCCAGCAGCAGCCTGGGCACCCAGACCTACA

TCTGTAACGTGAACCACAAGCCCAGCAACACCAAGGTGGACAAGAAGGTGGAGC

CCAAGAGCTGTGACAAGACCCACACCTGCCCCCCCTGCCCTGCCCCCGAGCTGCT

GGGAGGCCCCAGCGTGTTCCTGTTCCCCCCCAAGCCTAAGGACACCCTGATGATC

AGCAGAACCCCCGAGGTGACCTGTGTGGTGGTGGATGTGAGCCACGAGGACCCT

GAGGTGAAGTTCAACTGGTACGTGGACGGCGTGGAGGTGCACAATGCCAAGACC

AAGCCCAGGGAGGAGCAGTACAACAGCACCTACCGGGTGGTGTCCGTGCTGACC

GTGCTGCACCAGGATTGGCTGAACGGCAAGGAGTACAAGTGTAAGGTGTCCAAC

AAGGCCCTGCCTGCCCCTATCGAGAAAACCATCAGCAAGGCCAAGGGCCAGCCC

AGAGAGCCCCAGGTGTACACCCTGCCCCCTAGCAGAGATGAGCTGACCAAGAAC

CAGGTGTCCCTGACCTGCCTGGTGAAGGGCTTCTACCCCAGCGACATCGCCGTGG

AGTGGGAGAGCAACGGCCAGCCCGAGAACAACTACAAGACCACCCCCCCTGTGC

TGGACAGCGATGGCAGCTTCTTCCTGTACAGCAAGCTGACCGTGGACAAGAGCA

GATGGCAGCAGGGCAACGTGTTCAGCTGCTCCGTGATGCACGAGGCCCTGCACA

ATCACTACACCCAGAAGAGCCTGAGCCTGTCCCCTGGCAAG

S335122F05 murine variable light chain

SEQ ID 160

DIVLTQSPASLAVSLGQRATISCRASESVSIHGTHLMHWYQQKPGQPPKLLIYAASNL

ESGVPARFSGGGSETDFTLNIHPVEEEDGATYFCQQSIEYPRTFGGGTKLEINR

-continued

S335122F05 murine variable light chain (DNA sequence)
SEQ ID 161
GACATTGTGCTGACCCAATCTCCAGCTTCTTTGGCTGTGTCTCTAGGGCAGAGGG
CCACCATCTCCTGCAGAGCCAGTGAAAGTGTCAGTATTCATGGTACTCATTTAAT
GCACTGGTACCAACAGAAACCAGGACAGCCACCCAAACTCCTCATCTATGCTGC
ATCCAACCTAGAATCTGGAGTCCCTGCCAGGTTCAGTGGCGGTGGGTCTGAGAC
AGACTTCACCCTCAACATCCATCCTGTGGAGGAGGAGGATGGTGCAACCTATTTC
TGTCAGCAAAGTATTGAGTATCCTCGGACGTTCGGTGGAGGCACCAAGCTGGAA
ATCAATCGT S335122F05 Chimeric light chain
SEQ ID 162
DIVLTQSPASLAVSLGQRATISCRASESVSIHGTHLMHWYQQKPGQPPKLLIYAASNL
ESGVPARFSGGGSETDFTLNIHPVEEEDGATYFCQQSIEYPRTFGGGTKLEINRTVAAP
SVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC S335122F05 Chimeric light chain (DNA sequence)
SEQ ID 163
GACATTGTGCTGACCCAATCTCCAGCTTCTTTGGCTGTGTCTCTAGGGCAGAGGG
CCACCATCTCCTGCAGAGCCAGTGAAAGTGTCAGTATTCATGGTACTCATTTAAT
GCACTGGTACCAACAGAAACCAGGACAGCCACCCAAACTCCTCATCTATGCTGC
ATCCAACCTAGAATCTGGAGTCCCTGCCAGGTTCAGTGGCGGTGGGTCTGAGAC
AGACTTCACCCTCAACATCCATCCTGTGGAGGAGGAGGATGGTGCAACCTATTTC
TGTCAGCAAAGTATTGAGTATCCTCGGACGTTCGGTGGAGGCACCAAGCTGGAA
ATCAATCGTACGGTGGCCGCCCCCAGCGTGTTCATCTTCCCCCCCAGCGATGAGC
AGCTGAAGAGCGGCACCGCCAGCGTGGTGTGTCTGCTGAACAACTTCTACCCCC
GGGAGGCCAAGGTGCAGTGGAAGGTGGACAATGCCCTGCAGAGCGGCAACAGC
CAGGAGAGCGTGACCGAGCAGGACAGCAAGGACTCCACCTACAGCCTGAGCAG
CACCCTGACCCTGAGCAAGGCCGACTACGAGAAGCACAAGGTGTACGCCTGTGA
GGTGACCCACCAGGGCCTGTCCAGCCCCGTGACCAAGAGCTTCAACCGGGGCGA
GTGC

S332121F02 CDRH1
SEQ.I.D.NO: 164
DYYNM

S332121F02 CDRH2
SEQ.I.D.NO: 165
VINPYNGGTDYNQKFG

S332121F02 CDRH3
SEQ.I.D.NO: 166
SVYDYPFDY

S332121F02 CDRL1
SEQ.I.D.NO: 167
RASESVSIHGTHLMH

S332121F02 CDRL2
SEQ.I.D.NO: 168
AASNLES

S332121F02 CDRL3
SEQ.I.D.NO: 169
QQSIEDPRT

-continued

S322110D07 CDRH1
DYSID SEQ.I.D.NO: 170

S322110D07 CDRH2
DIDPNYGDPIYNHKFKG SEQ.I.D.NO: 171

S322110D07 CDRH3
RATGTDWFAF SEQ.I.D.NO: 172

S322110D07CDRL1
RASENIYNNLA SEQ.I.D.NO: 173

S322110D07 CDRL2
AATILAD SEQ.I.D.NO: 174

S322110D07 CDRL3
QHFWGTPLT SEQ.I.D.NO: 175

S332126E04CDRH1
NYWMH SEQ.I.D.NO: 176

S332126E04 CDRH2
IIHPNSGSTNYNEKFKS SEQ.I.D.NO: 177

S332126E04 CDRH3
GIYDYPFAY SEQ.I.D.NO: 178

S332126E04 CDRL1
RASESVSIHGTHLMH SEQ.I.D.NO: 179

S332126E04 CDRL2
AASNLES SEQ.I.D.NO: 180

S332126E04 CDRL3
QQSIEDPYT SEQ.I.D.NO: 181

S336105A07 CDRH1
RYWMS SEQ.I.D.NO: 182

S336105A07 CDRH2
EINPDRSTINYAPSLKD SEQ.I.D.NO: 183

S336105A07 CDRH3
FYYDYEGAMDY SEQ.I.D.NO: 184

S336105A07 CDRL1
KASQNVDTNVA SEQ.I.D.NO: 185

S336105A07 CDRL2
SASYRFS SEQ.I.D.NO: 186

S336105A07 CDRL3
QQYNSFPFT SEQ.I.D.NO: 187

S335115G01 CDRH1
SYWMH SEQ.I.D.NO: 188

S335115G01 CDRH2
VIDPSDSYTNYNQKFKG SEQ.I.D.NO: 189

-continued

S335115G01 CDRH3
SEQ.I.D.NO: 190
QVFDYPMDY

S335115G01 CDRL1
SEQ.I.D.NO: 191
RASESVSIHGTHLMH

S335115G01 CDRL2
SEQ.I.D.NO: 192
AASNLES

S335115G01 CDRL3
SEQ.I.D.NO: 193
QQSIEDPWT

S335122F05 CDRH1
SEQ.I.D.NO: 194
DYEMH

S335122F05 CDRH2
SEQ.I.D.NO: 195
AIDPETGGTAYNQKFKG

S335122F05 CDRH3
SEQ.I.D.NO: 196
SIYDYYFDY

S335122F05 CDRL1
SEQ.I.D.NO: 197
RASESVSIHGTHLMH

S335122F05 CDRL2
SEQ.I.D.NO: 198
AASNLES

S335122F05 CDRL3
SEQ.I.D.NO: 199
QQSIEYPRT

SEQUENCE LISTING

```
Sequence total quantity: 199
SEQ ID NO: 1           moltype = AA  length = 5
FEATURE                Location/Qualifiers
source                 1..5
                       mol_type = protein
                       organism = Mus musculus
SEQUENCE: 1
NYWMH                                                        5

SEQ ID NO: 2           moltype = AA  length = 17
FEATURE                Location/Qualifiers
source                 1..17
                       mol_type = protein
                       organism = Mus musculus
SEQUENCE: 2
ATYRGHSDTY YNQKFKG                                           17

SEQ ID NO: 3           moltype = AA  length = 12
FEATURE                Location/Qualifiers
source                 1..12
                       mol_type = protein
                       organism = Mus musculus
SEQUENCE: 3
GAIYNGYDVL DN                                                12

SEQ ID NO: 4           moltype = AA  length = 11
FEATURE                Location/Qualifiers
source                 1..11
                       mol_type = protein
                       organism = Mus musculus
SEQUENCE: 4
SASQDISNYL N                                                 11

SEQ ID NO: 5           moltype = AA  length = 7
FEATURE                Location/Qualifiers
```

-continued

```
source                  1..7
                        mol_type = protein
                        organism = Mus musculus
SEQUENCE: 5
YTSNLHS                                                           7

SEQ ID NO: 6            moltype = AA  length = 9
FEATURE                 Location/Qualifiers
source                  1..9
                        mol_type = protein
                        organism = Mus musculus
SEQUENCE: 6
QQYRKLPWT                                                         9

SEQ ID NO: 7            moltype = AA  length = 121
FEATURE                 Location/Qualifiers
source                  1..121
                        mol_type = protein
                        organism = Mus musculus
SEQUENCE: 7
EVQLQQSGAV LARPGASVKM SCKGSGYTFT NYWMHWVKQR PGQGLEWIGA TYRGHSDTYY  60
NQKFKGKAKL TAVTSTSTAY MELSSLTNED SAVYYCTRGA IYNGYDVLDN WGQGTLVTVS  120
S                                                                 121

SEQ ID NO: 8            moltype = DNA  length = 363
FEATURE                 Location/Qualifiers
source                  1..363
                        mol_type = genomic DNA
                        organism = Mus musculus
SEQUENCE: 8
gaggtgcagc tgcagcagag cggcgccgtg ctggccaggc ccggagctag cgtgaagatg  60
agctgcaagg gcagcggcta caccttcacc aactactgga tgcactgggt gaaacagagg  120
cccggccagg gactggagtg gatcggcgcc acctacaggg gccacagcga cacctactac  180
aaccagaagt tcaagggcaa ggccaagctg accgccgtga cctcaaccag caccgcctac  240
atggaactga gcagcctgac caacgaggac agcgccgtct attactgcac caggggcgcc  300
atctacaacg gctacgacgt gctggacaat tggggccagg gaacactagt gaccgtgtcc  360
agc                                                               363

SEQ ID NO: 9            moltype = AA  length = 108
FEATURE                 Location/Qualifiers
source                  1..108
                        mol_type = protein
                        organism = Mus musculus
SEQUENCE: 9
DIQLTQTTSS LSASLGDRVT ISCSASQDIS NYLNWYQQKP DGTVELVIYY TSNLHSGVPS  60
RFSGSGSGTD YSLTIGYLEP EDVATYYCQQ YRKLPWTFGG GSKLEIKR              108

SEQ ID NO: 10           moltype = DNA  length = 324
FEATURE                 Location/Qualifiers
source                  1..324
                        mol_type = genomic DNA
                        organism = Mus musculus
SEQUENCE: 10
gatatccagc tgacccagac cacaagcagc ctgagcgcct ccctgggcga cagggtgacc  60
attagctgca gcgccagcca ggacatcagc aactacctga actggtacca gcagaagccc  120
gacggcaccg tggagctcgt gatctactac acctccaacc tgcacagcgg cgtgcccagc  180
aggttctctg gcagcggcag cggcaccgac tacagcctga ccatcggcta tctggagccc  240
gaggacgtcg ccacctacta ctgccagcag tacaggaagc tgccctggac cttcggcgga  300
ggctctaagc tggagattaa gcgt                                        324

SEQ ID NO: 11           moltype = AA  length = 121
FEATURE                 Location/Qualifiers
REGION                  1..121
                        note = Humansed antibody sequence
source                  1..121
                        mol_type = protein
                        organism = synthetic construct
SEQUENCE: 11
QVQLVQSGAE VKKPGSSVKV SCKASGGTFS NYWMHWVRQA PGQGLEWMGA TYRGHSDTYY  60
NQKFKGRVTI TADKSTSTAY MELSSLRSED TAVYYCARGA IYNGYDVLDN WGQGTLVTVS  120
S                                                                 121

SEQ ID NO: 12           moltype = DNA  length = 363
FEATURE                 Location/Qualifiers
misc_feature            1..363
                        note = Humansed antibody sequence
source                  1..363
                        mol_type = other DNA
                        organism = synthetic construct
```

-continued

```
SEQUENCE: 12
caggtgcagc tggtccagag cggcgccgaa gtgaagaagc ccggcagctc cgtgaaagtg  60
agctgcaagg ccagcggcgg caccttcagc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca agagcaccag caccgcctac  240
atggaactga gcagcctcag gagcgaggac accgctgtgt attactgcgc caggggcgcc  300
atctacaacg gctacgacgt gctggacaac tggggccagg gcacactagt gaccgtgtcc  360
agc                                                                363

SEQ ID NO: 13          moltype = AA  length = 121
FEATURE                Location/Qualifiers
REGION                 1..121
                       note = Humansed antibody sequence
source                 1..121
                       mol_type = protein
                       organism = synthetic construct
SEQUENCE: 13
QVQLVQSGAE VKKPGSSVKV SCKASGYTFT NYWMHWVRQA PGQGLEWMGA TYRGHSDTYY  60
NQKFKGRVTI TADKSTSTAY MELSSLRSED TAVYYCARGA IYNGYDVLDN WGQGTLVTVS  120
S                                                                  121

SEQ ID NO: 14          moltype = DNA  length = 363
FEATURE                Location/Qualifiers
misc_feature           1..363
                       note = Humansed antibody sequence
source                 1..363
                       mol_type = other DNA
                       organism = synthetic construct
SEQUENCE: 14
caggtgcagc tggtccagag cggcgccgaa gtgaagaagc ccggcagctc cgtgaaagtg  60
agctgcaagg ccagcggcta caccttcacc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca agagcaccag caccgcctac  240
atggaactga gcagcctcag gagcgaggac accgctgtgt attactgcgc caggggcgcc  300
atctacaacg gctacgacgt gctggacaac tggggccagg gcacactagt gaccgtgtcc  360
agc                                                                363

SEQ ID NO: 15          moltype = AA  length = 121
FEATURE                Location/Qualifiers
REGION                 1..121
                       note = Humansed antibody sequence
source                 1..121
                       mol_type = protein
                       organism = synthetic construct
SEQUENCE: 15
QVQLVQSGAE VKKPGSSVKV SCKASGYTFT NYWMHWVRQA PGQGLEWMGA TYRGHSDTYY  60
NQKFKGRVTI TADKSTSTAY MELSSLRSED TAVYYCTRGA IYNGYDVLDN WGQGTLVTVS  120
S                                                                  121

SEQ ID NO: 16          moltype = DNA  length = 363
FEATURE                Location/Qualifiers
misc_feature           1..363
                       note = Humansed antibody sequence
source                 1..363
                       mol_type = other DNA
                       organism = synthetic construct
SEQUENCE: 16
caggtgcagc tggtccagag cggcgccgaa gtgaagaagc ccggcagctc cgtgaaagtg  60
agctgcaagg ccagcggcta caccttcacc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca agagcaccag caccgcctac  240
atggaactga gcagcctcag gagcgaggac accgctgtgt attactgcac caggggcgcc  300
atctacaacg gctacgacgt gctggacaac tggggccagg gcacactagt gaccgtgtcc  360
agc                                                                363

SEQ ID NO: 17          moltype = AA  length = 121
FEATURE                Location/Qualifiers
REGION                 1..121
                       note = Humansed antibody sequence
source                 1..121
                       mol_type = protein
                       organism = synthetic construct
SEQUENCE: 17
QVQLVQSGAE VKKPGSSVKV SCKGSGYTFT NYWMHWVRQA PGQGLEWMGA TYRGHSDTYY  60
NQKFKGRVTI TADTSTSTAY MELSSLRSED TAVYYCTRGA IYNGYDVLDN WGQGTLVTVS  120
S                                                                  121

SEQ ID NO: 18          moltype = DNA  length = 363
FEATURE                Location/Qualifiers
```

```
misc_feature           1..363
                       note = Humansed antibody sequence
source                 1..363
                       mol_type = other DNA
                       organism = synthetic construct
SEQUENCE: 18
caggtgcagc tggtccagag cggcgccgaa gtgaagaagc ccggcagctc cgtgaaagtg  60
agctgcaagg gcagcggcta caccttcacc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca cgagcaccag caccgcctac  240
atggaactga gcagcctcag gagcgaggac accgctgtgt attactgcac caggggcgcc  300
atctacaacg gctacgacgt gctggacaac tggggccagg gcacactagt gaccgtgtcc  360
agc                                                                363

SEQ ID NO: 19          moltype = AA  length = 121
FEATURE                Location/Qualifiers
REGION                 1..121
                       note = Humansed antibody sequence
source                 1..121
                       mol_type = protein
                       organism = synthetic construct
SEQUENCE: 19
QVQLVQSGAE VKKPGSSVKV SCKGSGYTFT NYWMHWVRQA PGQGLEWIGA TYRGHSDTYY  60
NQKFKGRATL TADTSTSTAY MELSSLRSED TAVYYCTRGA IYNGYDVLDN WGQGTLVTVS  120
S                                                                  121

SEQ ID NO: 20          moltype = DNA  length = 363
FEATURE                Location/Qualifiers
misc_feature           1..363
                       note = Humansed antibody sequence
source                 1..363
                       mol_type = other DNA
                       organism = synthetic construct
SEQUENCE: 20
caggtgcagc tggtccagag cggcgccgaa gtgaagaagc ccggcagctc cgtgaaagtg  60
agctgcaagg gcagcggcta caccttcacc aactactgga tgcactgggt gaggcaggcc  120
cccggacagg gcctggagtg gatcggcgcc acctacaggg gccacagcga cacctactac  180
aaccagaagt tcaagggccg ggcgaccctc accgccgaca cgagcaccag caccgcctac  240
atggaactga gcagcctcag gagcgaggac accgctgtgt attactgcac caggggcgcc  300
atctacaacg gctacgacgt gctggacaac tggggccagg gcacactagt gaccgtgtcc  360
agc                                                                363

SEQ ID NO: 21          moltype = AA  length = 121
FEATURE                Location/Qualifiers
REGION                 1..121
                       note = Humansed antibody sequence
source                 1..121
                       mol_type = protein
                       organism = synthetic construct
SEQUENCE: 21
QVQLVQSGAE VKKPGSSVKV SCKGSGYTFT NYWMHWVRQA PGQGLEWMGA TYRGHSDTYY  60
NQKFKGRVTI TADTSTSTAY MELSSLRSED TAVYYCTRGA IYDGYDVLDN WGQGTLVTVS  120
S                                                                  121

SEQ ID NO: 22          moltype = DNA  length = 363
FEATURE                Location/Qualifiers
misc_feature           1..363
                       note = Humansed antibody sequence
source                 1..363
                       mol_type = other DNA
                       organism = synthetic construct
SEQUENCE: 22
caggtgcagc tggtccagag cggcgccgaa gtgaagaagc ccggcagctc cgtgaaagtg  60
agctgcaagg gcagcggcta caccttcacc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca cgagcaccag caccgcctac  240
atggaactga gcagcctcag gagcgaggac accgctgtgt attactgcac caggggcgcc  300
atctacgacg gctacgacgt gctggacaac tggggccagg gcacactagt gaccgtgtcc  360
agc                                                                363

SEQ ID NO: 23          moltype = AA  length = 121
FEATURE                Location/Qualifiers
REGION                 1..121
                       note = Humansed antibody sequence
source                 1..121
                       mol_type = protein
                       organism = synthetic construct
SEQUENCE: 23
QVQLVQSGAE VKKPGSSVKV SCKASGGTFS NYWMHWVRQA PGQGLEWMGA TYRGHSDTYY  60
```

```
NQKFKGRVTI TADKSTSTAY MELSSLRSED TAVYYCARGA IYDGYDVLDN WGQGTLVTVS  120
S                                                                 121

SEQ ID NO: 24          moltype = DNA  length = 363
FEATURE                Location/Qualifiers
misc_feature           1..363
                       note = Humansed antibody sequence
source                 1..363
                       mol_type = other DNA
                       organism = synthetic construct
SEQUENCE: 24
caggtgcagc tggtccagag cggcgccgaa gtgaagaagc ccggcagctc cgtgaaagtg  60
agctgcaagg ccagcggcgg caccttcagc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca agagcaccag caccgcctac  240
atggaactga gcagcctcag gagcgaggac accgctgtgt attactgcgc caggggcgcc  300
atctacgacg gctacgacgt gctggacaac tggggccagg gcacactagt gaccgtgtcc  360
agc                                                               363

SEQ ID NO: 25          moltype = AA  length = 121
FEATURE                Location/Qualifiers
REGION                 1..121
                       note = Humansed antibody sequence
source                 1..121
                       mol_type = protein
                       organism = synthetic construct
SEQUENCE: 25
QVQLVQSGAE VKKPGSSVKV SCKASGYTFT NYWMHWVRQA PGQGLEWMGA TYRGHSDTYY  60
NQKFKGRVTI TADKSTSTAY MELSSLRSED TAVYYCARGA IYDGYDVLDN WGQGTLVTVS  120
S                                                                 121

SEQ ID NO: 26          moltype = DNA  length = 363
FEATURE                Location/Qualifiers
misc_feature           1..363
                       note = Humansed antibody sequence
source                 1..363
                       mol_type = other DNA
                       organism = synthetic construct
SEQUENCE: 26
caggtgcagc tggtccagag cggcgccgaa gtgaagaagc ccggcagctc cgtgaaagtg  60
agctgcaagg ccagcggcta caccttcacc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca agagcaccag caccgcctac  240
atggaactga gcagcctcag gagcgaggac accgctgtgt attactgcgc caggggcgcc  300
atctacgacg gctacgacgt gctggacaac tggggccagg gcacactagt gaccgtgtcc  360
agc                                                               363

SEQ ID NO: 27          moltype = AA  length = 121
FEATURE                Location/Qualifiers
REGION                 1..121
                       note = Humansed antibody sequence
source                 1..121
                       mol_type = protein
                       organism = synthetic construct
SEQUENCE: 27
QVQLVQSGAE VKKPGSSVKV SCKASGYTFT NYWMHWVRQA PGQGLEWMGA TYRGHSDTYY  60
NQKFKGRVTI TADKSTSTAY MELSSLRSED TAVYYCTRGA IYDGYDVLDN WGQGTLVTVS  120
S                                                                 121

SEQ ID NO: 28          moltype = DNA  length = 363
FEATURE                Location/Qualifiers
misc_feature           1..363
                       note = Humansed antibody sequence
source                 1..363
                       mol_type = other DNA
                       organism = synthetic construct
SEQUENCE: 28
caggtgcagc tggtccagag cggcgccgaa gtgaagaagc ccggcagctc cgtgaaagtg  60
agctgcaagg ccagcggcta caccttcacc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca agagcaccag caccgcctac  240
atggaactga gcagcctcag gagcgaggac accgctgtgt attactgcac caggggcgcc  300
atctacgacg gctacgacgt gctggacaac tggggccagg gcacactagt gaccgtgtcc  360
agc                                                               363

SEQ ID NO: 29          moltype = AA  length = 121
FEATURE                Location/Qualifiers
REGION                 1..121
                       note = Humansed antibody sequence
```

```
source                  1..121
                        mol_type = protein
                        organism = synthetic construct
SEQUENCE: 29
QVQLVQSGAE VKKPGSSVKV SCKGSGYTFT NYWMHWVRQA PGQGLEWIGA TYRGHSDTYY  60
NQKFKGRATL TADTSTSTAY MELSSLRSED TAVYYCTRGA IYDGYDVLDN WGQGTLVTVS  120
S                                                                 121

SEQ ID NO: 30           moltype = DNA  length = 363
FEATURE                 Location/Qualifiers
misc_feature            1..363
                        note = Humansed antibody sequence
source                  1..363
                        mol_type = other DNA
                        organism = synthetic construct
SEQUENCE: 30
caggtgcagc tggtccagag cggcgccgaa gtgaagaagc ccggcagctc cgtgaaagtg  60
agctgcaagg gcagcggcta caccttcacc aactactgga tgcactgggt gaggcaggcc  120
cccggacagg gcctggagtg gatcggcgcc acctacaggg gccacagcga cacctactac  180
aaccagaagt tcaagggccg ggcgaccctc accgccgaca cgagcaccag caccgcctac  240
atggaactga gcagcctcag gagcgaggac accgctgtgt attactgcac caggggcgcc  300
atctacgacg gctacgacgt gctggacaac tggggccagg gcacactagt gaccgtgtcc  360
agc                                                               363

SEQ ID NO: 31           moltype = AA  length = 108
FEATURE                 Location/Qualifiers
REGION                  1..108
                        note = Humansed antibody sequence
source                  1..108
                        mol_type = protein
                        organism = synthetic construct
SEQUENCE: 31
DIQMTQSPSS LSASVGDRVT ITCSASQDIS NYLNWYQQKP GKAPKLLIYY TSNLHSGVPS  60
RFSGSGSGTD FTLTISSLQP EDFATYYCQQ YRKLPWTFGQ GTKLEIKR              108

SEQ ID NO: 32           moltype = DNA  length = 324
FEATURE                 Location/Qualifiers
misc_feature            1..324
                        note = Humansed antibody sequence
source                  1..324
                        mol_type = other DNA
                        organism = synthetic construct
SEQUENCE: 32
gacatccaga tgacccagag ccctagctca ctgagcgcca gcgtgggcga cagggtgacc  60
attacctgct ccgccagcca ggacatcagc aactacctga actggtacca gcagaagccc  120
ggcaaggccc ccaagctgct gatctactac acctccaacc tgcactccgg cgtgcccagc  180
aggttcagcg gaagcggcag cggcaccgat ttcaccctga ccatctccag cctgcagccc  240
gaggacttcg ccacctacta ctgccagcag tacaggaagc tcccctggac tttcggccag  300
ggcaccaaac tggagatcaa gcgt                                        324

SEQ ID NO: 33           moltype = AA  length = 108
FEATURE                 Location/Qualifiers
REGION                  1..108
                        note = Humansed antibody sequence
source                  1..108
                        mol_type = protein
                        organism = synthetic construct
SEQUENCE: 33
DIQMTQSPSS LSASVGDRVT ITCSASQDIS NYLNWYQQKP GKAPKLLIYY TSNLHSGVPS  60
RFSGSGSGTD YTLTISSLQP EDFATYYCQQ YRKLPWTFGQ GTKLEIKR              108

SEQ ID NO: 34           moltype = DNA  length = 324
FEATURE                 Location/Qualifiers
misc_feature            1..324
                        note = Humansed antibody sequence
source                  1..324
                        mol_type = other DNA
                        organism = synthetic construct
SEQUENCE: 34
gacatccaga tgacccagag ccctagctca ctgagcgcca gcgtgggcga cagggtgacc  60
attacctgct ccgccagcca ggacatcagc aactacctga actggtacca gcagaagccc  120
ggcaaggccc ccaagctgct gatctactac acctccaacc tgcactccgg cgtgcccagc  180
aggttcagcg gaagcggcag cggcaccgat tacaccctga ccatctccag cctgcagccc  240
gaggacttcg ccacctacta ctgccagcag tacaggaagc tcccctggac tttcggccag  300
ggcaccaaac tggagatcaa gcgt                                        324

SEQ ID NO: 35           moltype = AA  length = 108
FEATURE                 Location/Qualifiers
REGION                  1..108
```

```
                         note = Humansed antibody sequence
source                   1..108
                         mol_type = protein
                         organism = synthetic construct
SEQUENCE: 35
DIQLTQSPSS LSASVGDRVT ITCSASQDIS NYLNWYQQKP GKAPELVIYY TSNLHSGVPS  60
RFSGSGSGTD YTLTISSLQP EDFATYYCQQ YRKLPWTFGQ GTKLEIKR              108

SEQ ID NO: 36            moltype = DNA  length = 324
FEATURE                  Location/Qualifiers
misc_feature             1..324
                         note = Humansed antibody sequence
source                   1..324
                         mol_type = other DNA
                         organism = synthetic construct
SEQUENCE: 36
gacatccagc tgacccagag ccctagctca ctgagcgcca gcgtgggcga cagggtgacc  60
attacctgct ccgccagcca ggacatcagc aactacctga actggtacca gcagaagccc  120
ggcaaggccc ccgagctggt gatctactac acctccaacc tgcactccgg cgtgcccagc  180
aggttcagcg gaagcggcag cggcaccgat tacaccctga ccatctccag cctgcagccc  240
gaggacttcg ccacctacta ctgccagcag tacaggaagc tcccctggac tttcggccag  300
ggcaccaaac tggagatcaa gcgt                                        324

SEQ ID NO: 37            moltype = AA  length = 310
FEATURE                  Location/Qualifiers
source                   1..310
                         mol_type = protein
                         organism = Homo sapiens
SEQUENCE: 37
MPLLLLLPLL WAGALAMLQM AGQCSQNEYF DSLLHACIPC QLRCSSNTPP LTCQRYCNAS  60
VTNSVKGTNS GENLYFQGDP KSCDKTHTCP PCPAPELLGG PSVFLFPPKP KDTLMISRTP  120
EVTCVVVDVS HEDPEVKFNW YVDGVEVHNA KTKPREEQYN STYRVVSVLT VLHQDWLNGK  180
EYKCKVSNKA LPAPIEKTIS KAKGQPREPQ VYTLPPSRDE LTKNQVSLTC LVKGFYPSDI  240
AVEWESNGQP ENNYKTTPPV LDSDGSFFLY SKLTVDKSRW QQGNVFSCSV MHEALHNHYT  300
QKSLSLSPGK                                                        310

SEQ ID NO: 38            moltype = DNA  length = 930
FEATURE                  Location/Qualifiers
source                   1..930
                         mol_type = genomic DNA
                         organism = Homo sapiens
SEQUENCE: 38
atgccgctgc tgctactgct gcccctgctg tgggcagggg cgctagctat gctgcagatg  60
gccggccagt gcagccagaa cgagtacttc gacagcctgc tgcacgcctg catcccctgc  120
cagctgagat gcagcagcaa cacacctcct ctgacctgcc agagatactg caacgccagc  180
gtgaccaaca gcgtgaaggg caccaactcc ggagagaacc tgtacttcca aggggatccc  240
aaatcttgtg acaaaactca cacatgccca ccgtgcccag cacctgaact cctgggggga  300
ccgtcagtct tcctcttccc cccaaaaccc aaggacaccc tcatgatctc ccggacccct  360
gaggtcacat gcgtggtggt ggacgtgagc cacgaagacc ctgaggtcaa gttcaactgg  420
tacgtggacg gcgtggaggt gcataatgcc aagacaaagc cgcgggagga gcagtacaac  480
agcacgtacc gtgtggtcag cgtcctcacc gtcctgcacc aggactggct gaatggcaag  540
gagtacaagt gcaaggtctc caacaaagcc ctcccagccc ccatcgagaa aaccatctcc  600
aaagccaaag ggcagccccg agagccacag gtgtacaccc tgcccccatc ccgggatgag  660
ctgaccaaga accaggtcag cctgacctgc ctggtcaaag gcttctatcc cagcgacatc  720
gccgtggagt gggagagcaa tgggcagccg gagaacaact acaagaccac gcctcccgtg  780
ctggactccg acggctcctt cttcctctac agcaagctca ccgtggacaa gagcaggtgg  840
cagcagggga acgtcttctc atgctccgtg atgcatgagg ctctgcacaa ccactacacg  900
cagaagagcc tctccctgtc tccgggtaaa                                  930

SEQ ID NO: 39            moltype = AA  length = 307
FEATURE                  Location/Qualifiers
source                   1..307
                         mol_type = protein
                         organism = Homo sapiens
SEQUENCE: 39
MPLLLLLPLL WAGALAMAGQ CSQNEYFDSL LHACIPCQLR CSSNTPPLTC QRYCNASVTN  60
SVKGTNSGEN LYFQGDPKSC DKTHTCPPCP APELLGGPSV FLFPPKPKDT LMISRTPEVT  120
CVVVDVSHED PEVKFNWYVD GVEVHNAKTK PREEQYNSTY RVVSVLTVLH QDWLNGKEYK  180
CKVSNKALPA PIEKTISKAK GQPREPQVYT LPPSRDELTK NQVSLTCLVK GFYPSDIAVE  240
WESNGQPENN YKTTPPVLDS DGSFFLYSKL TVDKSRWQQG NVFSCSVMHE ALHNHYTQKS  300
LSLSPGK                                                           307

SEQ ID NO: 40            moltype = DNA  length = 921
FEATURE                  Location/Qualifiers
source                   1..921
                         mol_type = genomic DNA
                         organism = Homo sapiens
SEQUENCE: 40
atgccgctgc tgctactgct gcccctgctg tgggcagggg cgctagctat ggccggccag  60
```

-continued

```
tgcagccaga acgagtactt cgacagcctg ctgcacgcct gcatcccctg ccagctgaga  120
tgcagcagca acacacctcc tctgacctgc cagagatact gcaacgccag cgtgaccaac  180
agcgtgaagg gcaccaactc cggagagaac ctgtacttcc aaggggatcc caaatcttgt  240
gacaaaactc acacatgccc accgtgccca gcacctgaac tcctgggggg accgtcagtc  300
ttcctcttcc ccccaaaacc caaggacacc ctcatgatct cccggacccc tgaggtcaca  360
tgcgtggtgg tggacgtgag ccacgaagac cctgaggtca agttcaactg gtacgtggac  420
ggcgtggagg tgcataatgc caagacaaag ccgcgggagg agcagtacaa cagcacgtac  480
cgtgtggtca gcgtcctcac cgtcctgcac caggactggc tgaatggcaa ggagtacaag  540
tgcaaggtct ccaacaaagc cctcccagcc cccatcgaga aaaccatctc caaagccaaa  600
gggcagcccc gagagccaca ggtgtacacc ctgcccccat cccgggatga gctgaccaag  660
aaccaggtca gcctgacctg cctggtcaaa ggcttctatc ccagcgacat cgccgtggag  720
tgggagagca atgggcagcc ggagaacaac tacaagacca cgcctcccgt gctggactcc  780
gacggctcct tcttcctcta cagcaagctc accgtggaca agagcaggtg gcagcagggg  840
aacgtcttct catgctccgt gatgcatgag gctctgcaca accactacac gcagaagagc  900
ctctccctgt ctccgggtaa a                                            921
```

```
SEQ ID NO: 41          moltype = AA  length = 306
FEATURE                Location/Qualifiers
source                 1..306
                       mol_type = protein
                       organism = Cynomolgus macaque
SEQUENCE: 41
MPLLLLLPLL WAGALAMARQ CSQNEYFDSL LHDCKPCQLR CSSTPPLTCQ RYCNASMTNS  60
VKGMNSGENL YFQGDPKSCD KTHTCPPCPA PELLGGPSVF LFPPKPKDTL MISRTPEVTC  120
VVVDVSHEDP EVKFNWYVDG VEVHNAKTKP REEQYNSTYR VVSVLTVLHQ DWLNGKEYKC  180
KVSNKALPAP IEKTISKAKG QPREPQVYTL PPSRDELTKN QVSLTCLVKG FYPSDIAVEW  240
ESNGQPENNY KTTPPVLDSD GSFFLYSKLT VDKSRWQQGN VFSCSVMHEA LHNHYTQKSL  300
SLSPGK                                                             306
```

```
SEQ ID NO: 42          moltype = DNA  length = 918
FEATURE                Location/Qualifiers
source                 1..918
                       mol_type = genomic DNA
                       organism = Cynomolgus macaque
SEQUENCE: 42
atgccgctgc tgctactgct gcccctgctg tgggcagggg cgctagctat ggccagacag  60
tgcagccaga acgagtactt cgacagcctg ctgcacgact gcaagccctg ccagctgaga  120
tgcagcagca cacctcctct gacctgccag agatactgca acgccagcat gaccaacagc  180
gtgaagggca tgaactccgg agagaacctg tacttccaag gggatcccaa atcttgtgac  240
aaaactcaca catgcccacc gtgcccagca cctgaactcc tggggggacc gtcagtcttc  300
ctcttccccc caaaacccaa ggacaccctc atgatctccc ggacccctga ggtcacatgc  360
gtggtggtgg acgtgagcca cgaagaccct gaggtcaagt tcaactggta cgtggacggc  420
gtggaggtgc ataatgccaa gacaaagccg cgggaggagc agtacaacag cacgtaccgt  480
gtggtcagcg tcctcaccgt cctgcaccag gactggctga atggcaagga gtacaagtgc  540
aaggtctcca acaaagccct cccagccccc atcgagaaaa ccatctccaa agccaaaggg  600
cagccccgag agccacaggt gtacaccctg cccccatccc gggatgagct gaccaagaac  660
caggtcagcc tgacctgcct ggtcaaaggc ttctatccca gcgacatcgc cgtggagtgg  720
gagagcaatg ggcagccgga gaacaactac aagaccacgc ctcccgtgct ggactccgac  780
ggctccttct tcctctacag caagctcacc gtggacaaga gcaggtggca gcaggggaac  840
gtcttctcat gctccgtgat gcatgaggct ctgcacaacc actacacgca gaagagcctc  900
tccctgtctc cgggtaaa                                                918
```

```
SEQ ID NO: 43          moltype = AA  length = 451
FEATURE                Location/Qualifiers
REGION                 1..451
                       note = Humansed antibody sequence
source                 1..451
                       mol_type = protein
                       organism = synthetic construct
SEQUENCE: 43
QVQLVQSGAE VKKPGSSVKV SCKASGGTFS NYWMHWVRQA PGQGLEWMGA TYRGHSDTYY  60
NQKFKGRVTI TADKSTSTAY MELSSLRSED TAVYYCARGA IYNGYDVLDN WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451
```

```
SEQ ID NO: 44          moltype = DNA  length = 1353
FEATURE                Location/Qualifiers
misc_feature           1..1353
                       note = Humansed antibody sequence
source                 1..1353
                       mol_type = other DNA
                       organism = synthetic construct
SEQUENCE: 44
caggtgcagc tggtccagag cggcgccgaa gtgaagaagc ccggcagctc cgtgaaagtg  60
agctgcaagg ccagcggcgg caccttcagc aactactgga tgcactgggt gaggcaggcc  120
```

-continued

```
cccggacagg gcctggagtg gatgggcgcc acctacaggg gccacagcga cacctactac  180
aaccagaagt tcaagggccg ggtgaccatc accgccgaca agagcaccag caccgcctac  240
atggaactga gcagcctcag gagcgaggac accgctgtgt attactgcgc caggggcgcc  300
atctacaacg gctacgacgt gctggacaac tggggccagg gcacactagt gaccgtgtcc  360
agcgccagca ccaagggccc cagcgtgttc cccctggccc ccagcagcaa gagcaccagc  420
ggcggcacag ccgccctggg ctgcctggtg aaggactact tccccgaacc ggtgaccgtg  480
tcctggaaca gcggagccct gaccagcggc gtgcacacct tccccgccgt gctgcagagc  540
agcggcctgt acagcctgag cagcgtggtg accgtgccca gcagcagcct gggcacccag  600
acctacatct gtaacgtgaa ccacaagccc agcaacacca aggtggacaa gaaggtggag  660
cccaagagct gtgacaagac ccacacctgc ccccccctgcc ctgcccccga gctgctggga  720
ggccccagcg tgttcctgtt cccccccaag cctaaggaca ccctgatgat cagcagaacc  780
cccgaggtga cctgtgtggt ggtggatgtg agccacgagg accctgaggt gaagttcaac  840
tggtacgtgg acggcgtgga ggtgcacaat gccaagacca agcccaggga ggagcagtac  900
aacagcacct accgggtggt gtccgtgctg accgtgctgc accaggattg gctgaacggc  960
aaggagtaca agtgtaaggt gtccaacaag gccctgcctg cccctatcga gaaaaccatc  1020
agcaaggcca agggccagcc cagagagccc caggtgtaca ccctgccccc tagcagagat  1080
gagctgacca agaaccaggt gtccctgacc tgcctggtga agggcttcta ccccagcgac  1140
atcgccgtgg agtgggagag caacggccag cccgagaaca actacaagac caccccccct  1200
gtgctggaca gcgatggcag cttcttcctg tacagcaagc tgaccgtgga caagagcaga  1260
tggcagcagg gcaacgtgtt cagctgctcc gtgatgcacg aggccctgca caatcactac  1320
acccagaaga gcctgagcct gtcccctggc aag                              1353

SEQ ID NO: 45          moltype = AA  length = 451
FEATURE                Location/Qualifiers
REGION                 1..451
                       note = Humansed antibody sequence
source                 1..451
                       mol_type = protein
                       organism = synthetic construct
SEQUENCE: 45
QVQLVQSGAE VKKPGSSVKV SCKASGYTFT NYWMHWVRQA PGQGLEWMGA TYRGHSDTYY  60
NQKFKGRVTI TADKSTSTAY MELSSLRSED TAVYYCARGA IYNGYDVLDN WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 46          moltype = DNA  length = 1353
FEATURE                Location/Qualifiers
misc_feature           1..1353
                       note = Humansed antibody sequence
source                 1..1353
                       mol_type = other DNA
                       organism = synthetic construct
SEQUENCE: 46
caggtgcagc tggtccagag cggcgccgaa gtgaagaagc ccggcagctc cgtgaaagtg  60
agctgcaagg ccagcggcta caccttcacc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca agagcaccag caccgcctac  240
atggaactga gcagcctcag gagcgaggac accgctgtgt attactgcgc caggggcgcc  300
atctacaacg gctacgacgt gctggacaac tggggccagg gcacactagt gaccgtgtcc  360
agcgccagca ccaagggccc cagcgtgttc cccctggccc ccagcagcaa gagcaccagc  420
ggcggcacag ccgccctggg ctgcctggtg aaggactact tccccgaacc ggtgaccgtg  480
tcctggaaca gcggagccct gaccagcggc gtgcacacct tccccgccgt gctgcagagc  540
agcggcctgt acagcctgag cagcgtggtg accgtgccca gcagcagcct gggcacccag  600
acctacatct gtaacgtgaa ccacaagccc agcaacacca aggtggacaa gaaggtggag  660
cccaagagct gtgacaagac ccacacctgc ccccccctgcc ctgcccccga gctgctggga  720
ggccccagcg tgttcctgtt cccccccaag cctaaggaca ccctgatgat cagcagaacc  780
cccgaggtga cctgtgtggt ggtggatgtg agccacgagg accctgaggt gaagttcaac  840
tggtacgtgg acggcgtgga ggtgcacaat gccaagacca agcccaggga ggagcagtac  900
aacagcacct accgggtggt gtccgtgctg accgtgctgc accaggattg gctgaacggc  960
aaggagtaca agtgtaaggt gtccaacaag gccctgcctg cccctatcga gaaaaccatc  1020
agcaaggcca agggccagcc cagagagccc caggtgtaca ccctgccccc tagcagagat  1080
gagctgacca agaaccaggt gtccctgacc tgcctggtga agggcttcta ccccagcgac  1140
atcgccgtgg agtgggagag caacggccag cccgagaaca actacaagac caccccccct  1200
gtgctggaca gcgatggcag cttcttcctg tacagcaagc tgaccgtgga caagagcaga  1260
tggcagcagg gcaacgtgtt cagctgctcc gtgatgcacg aggccctgca caatcactac  1320
acccagaaga gcctgagcct gtcccctggc aag                              1353

SEQ ID NO: 47          moltype = AA  length = 451
FEATURE                Location/Qualifiers
REGION                 1..451
                       note = Humansed antibody sequence
source                 1..451
                       mol_type = protein
                       organism = synthetic construct
SEQUENCE: 47
```

-continued

```
QVQLVQSGAE VKKPGSSVKV SCKASGYTFT NYWMHWVRQA PGQGLEWMGA TYRGHSDTYY  60
NQKFKGRVTI TADKSTSTAY MELSSLRSED TAVYYCTRGA IYNGYDVLDN WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 48          moltype = DNA  length = 1353
FEATURE                Location/Qualifiers
misc_feature           1..1353
                       note = Humansed antibody sequence
source                 1..1353
                       mol_type = other DNA
                       organism = synthetic construct
SEQUENCE: 48
caggtgcagc tggtccagag cggcgccgaa gtgaagaagc ccggcagctc cgtgaaagtg  60
agctgcaagg ccagcggcta caccttcacc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca agagcaccag caccgcctac  240
atggaactga gcagcctcag gagcgaggac accgctgtgt attactgcac caggggcgcc  300
atctacaacg gctacgacgt gctggacaac tggggccagg gcacactagt gaccgtgtcc  360
agcgccagca ccaagggccc cagcgtgttc cccctggccc ccagcagcaa gagcaccagc  420
ggcggcacag ccgccctggg ctgcctggtg aaggactact tccccgaacc ggtgaccgtg  480
tcctggaaca gcggagccct gaccagcggc gtgcacacct tccccgccgt gctgcagagc  540
agcggcctgt acagcctgag cagcgtggtg accgtgccca gcagcagcct gggcacccag  600
acctacatct gtaacgtgaa ccacaagccc agcaacacca aggtggacaa gaaggtggag  660
cccaagagct gtgacaagac ccacacctgc ccccccctgcc ctgcccccga gctgctggga  720
ggccccagcg tgttcctgtt cccccccaag cctaaggaca ccctgatgat cagcagaacc  780
cccgaggtga cctgtgtggt ggtggatgtg agccacgagg accctgaggt gaagttcaac  840
tggtacgtgg acggcgtgga ggtgcacaat gccaagacca agcccaggga ggagcagtac  900
aacagcacct accgggtggt gtccgtgctg accgtgctgc accaggattg gctgaacggc  960
aaggagtaca agtgtaaggt gtccaacaag gccctgcctg cccctatcga gaaaaccatc  1020
agcaaggcca agggccagcc cagagagccc caggtgtaca ccctgccccc tagcagagat  1080
gagctgacca agaaccaggt gtccctgacc tgcctggtga agggcttcta ccccagcgac  1140
atcgccgtgg agtgggagag caacggccag cccgagaaca actacaagac caccccccct  1200
gtgctggaca gcgatggcag cttcttcctg tacagcaagc tgaccgtgga caagagcaga  1260
tggcagcagg gcaacgtgtt cagctgctcc gtgatgcacg aggccctgca caatcactac  1320
acccagaaga gcctgagcct gtcccctggc aag                              1353

SEQ ID NO: 49          moltype = AA  length = 451
FEATURE                Location/Qualifiers
REGION                 1..451
                       note = Humansed antibody sequence
source                 1..451
                       mol_type = protein
                       organism = synthetic construct
SEQUENCE: 49
QVQLVQSGAE VKKPGSSVKV SCKGSGYTFT NYWMHWVRQA PGQGLEWMGA TYRGHSDTYY  60
NQKFKGRVTI TADTSTSTAY MELSSLRSED TAVYYCTRGA IYNGYDVLDN WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 50          moltype = DNA  length = 1353
FEATURE                Location/Qualifiers
misc_feature           1..1353
                       note = Humansed antibody sequence
source                 1..1353
                       mol_type = other DNA
                       organism = synthetic construct
SEQUENCE: 50
caggtgcagc tggtccagag cggcgccgaa gtgaagaagc ccggcagctc cgtgaaagtg  60
agctgcaagg gcagcggcta caccttcacc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca cgagcaccag caccgcctac  240
atggaactga gcagcctcag gagcgaggac accgctgtgt attactgcac caggggcgcc  300
atctacaacg gctacgacgt gctggacaac tggggccagg gcacactagt gaccgtgtcc  360
agcgccagca ccaagggccc cagcgtgttc cccctggccc ccagcagcaa gagcaccagc  420
ggcggcacag ccgccctggg ctgcctggtg aaggactact tccccgaacc ggtgaccgtg  480
tcctggaaca gcggagccct gaccagcggc gtgcacacct tccccgccgt gctgcagagc  540
agcggcctgt acagcctgag cagcgtggtg accgtgccca gcagcagcct gggcacccag  600
acctacatct gtaacgtgaa ccacaagccc agcaacacca aggtggacaa gaaggtggag  660
cccaagagct gtgacaagac ccacacctgc ccccccctgcc ctgcccccga gctgctggga  720
ggccccagcg tgttcctgtt cccccccaag cctaaggaca ccctgatgat cagcagaacc  780
```

-continued

```
cccgaggtga cctgtgtggt ggtggatgtg agccacgagg accctgaggt gaagttcaac  840
tggtacgtgg acggcgtgga ggtgcacaat gccaagacca agcccaggga ggagcagtac  900
aacagcacct accgggtggt gtccgtgctg accgtgctgc accaggattg gctgaacggc  960
aaggagtaca agtgtaaggt gtccaacaag gccctgcctg cccctatcga gaaaaccatc  1020
agcaaggcca agggccagcc cagagagccc caggtgtaca ccctgccccc tagcagagat  1080
gagctgacca agaaccaggt gtccctgacc tgcctggtga agggcttcta ccccagcgac  1140
atcgccgtgg agtgggagag caacggccag cccgagaaca actacaagac caccccccct  1200
gtgctggaca gcgatggcag cttcttcctg tacagcaagc tgaccgtgga caagagcaga  1260
tggcagcagg gcaacgtgtt cagctgctcc gtgatgcacg aggccctgca caatcactac  1320
acccagaaga gcctgagcct gtcccctggc aag                               1353

SEQ ID NO: 51          moltype = AA  length = 451
FEATURE                Location/Qualifiers
REGION                 1..451
                       note = Humansed antibody sequence
source                 1..451
                       mol_type = protein
                       organism = synthetic construct
SEQUENCE: 51
QVQLVQSGAE VKKPGSSVKV SCKGSGYTFT NYWMHWVRQA PGQGLEWIGA TYRGHSDTYY  60
NQKFKGRATL TADTSTSTAY MELSSLRSED TAVYYCTRGA IYNGYDVLDN WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 52          moltype = DNA  length = 1353
FEATURE                Location/Qualifiers
misc_feature           1..1353
                       note = Humansed antibody sequence
source                 1..1353
                       mol_type = other DNA
                       organism = synthetic construct
SEQUENCE: 52
caggtgcagc tggtccagag cggcgccgaa gtgaagaagc ccggcagctc cgtgaaagtg  60
agctgcaagg gcagcggcta caccttcacc aactactgga tgcactgggt gaggcaggcc  120
cccggacagg gcctggagtg gatcggcgcc acctacaggg gccacagcga cacctactac  180
aaccagaagt tcaagggccg ggcgaccctc accgccgaca cgagcaccag caccgcctac  240
atggaactga gcagcctcag gagcgaggac accgctgtgt attactgcac caggggcgcc  300
atctacaacg gctacgacgt gctggacaac tggggccagg gcacactagt gaccgtgtcc  360
agcgccagca ccaagggccc cagcgtgttc cccctggccc ccagcagcaa gagcaccagc  420
ggcggcacag ccgccctggg ctgcctggtg aaggactact tccccgaacc ggtgaccgtg  480
tcctggaaca gcggagccct gaccagcggc gtgcacacct tccccgccgt gctgcagagc  540
agcggcctgt acagcctgag cagcgtggtg accgtgccca gcagcagcct gggcacccag  600
acctacatct gtaacgtgaa ccacaagccc agcaacacca aggtggacaa gaaggtggag  660
cccaagagct gtgacaagac ccacacctgc ccccctgcc ctgcccccga gctgctggga  720
ggccccagcg tgttcctgtt cccccccaag cctaaggaca ccctgatgat cagcagaacc  780
cccgaggtga cctgtgtggt ggtggatgtg agccacgagg accctgaggt gaagttcaac  840
tggtacgtgg acggcgtgga ggtgcacaat gccaagacca agcccaggga ggagcagtac  900
aacagcacct accgggtggt gtccgtgctg accgtgctgc accaggattg gctgaacggc  960
aaggagtaca agtgtaaggt gtccaacaag gccctgcctg cccctatcga gaaaaccatc  1020
agcaaggcca agggccagcc cagagagccc caggtgtaca ccctgccccc tagcagagat  1080
gagctgacca agaaccaggt gtccctgacc tgcctggtga agggcttcta ccccagcgac  1140
atcgccgtgg agtgggagag caacggccag cccgagaaca actacaagac caccccccct  1200
gtgctggaca gcgatggcag cttcttcctg tacagcaagc tgaccgtgga caagagcaga  1260
tggcagcagg gcaacgtgtt cagctgctcc gtgatgcacg aggccctgca caatcactac  1320
acccagaaga gcctgagcct gtcccctggc aag                               1353

SEQ ID NO: 53          moltype = AA  length = 451
FEATURE                Location/Qualifiers
REGION                 1..451
                       note = Humansed antibody sequence
source                 1..451
                       mol_type = protein
                       organism = synthetic construct
SEQUENCE: 53
QVQLVQSGAE VKKPGSSVKV SCKGSGYTFT NYWMHWVRQA PGQGLEWMGA TYRGHSDTYY  60
NQKFKGRVTI TADTSTSTAY MELSSLRSED TAVYYCTRGA IYDGYDVLDN WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 54          moltype = DNA  length = 1353
FEATURE                Location/Qualifiers
```

```
misc_feature            1..1353
                        note = Humansed antibody sequence
source                  1..1353
                        mol_type = other DNA
                        organism = synthetic construct
SEQUENCE: 54
caggtgcagc tggtccagag cggcgccgaa gtgaagaagc ccggcagctc cgtgaaagtg  60
agctgcaagg gcagcggcta caccttcacc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca cgagcaccag caccgcctac  240
atggaactga gcagcctcag gagcgaggac accgctgtgt attactgcac caggggcgcc  300
atctacgacg gctacgacgt gctggacaac tggggccagg gcacactagt gaccgtgtcc  360
agcgccagca ccaagggccc cagcgtgttc cccctggccc ccagcagcaa gagcaccagc  420
ggcggcacag ccgccctggg ctgcctggtg aaggactact tccccgaacc ggtgaccgtg  480
tcctggaaca gcggagccct gaccagcggc gtgcacacct tccccgccgt gctgcagagc  540
agcggcctgt acagcctgag cagcgtggtg accgtgccca gcagcagcct gggcacccag  600
acctacatct gtaacgtgaa ccacaagccc agcaacacca aggtggacaa gaaggtggag  660
cccaagagct gtgacaagac ccacacctgc ccccctgcc ctgcccccga gctgctggga  720
ggccccagcg tgttcctgtt cccccccaag cctaaggaca ccctgatgat cagcagaacc  780
cccgaggtga cctgtgtggt ggtggatgtg agccacgagg accctgaggt gaagttcaac  840
tggtacgtgg acggcgtgga ggtgcacaat gccaagacca agcccaggga ggagcagtac  900
aacagcacct accgggtggt gtccgtgctg accgtgctgc accaggattg gctgaacggc  960
aaggagtaca agtgtaaggt gtccaacaag gccctgcctg cccctatcga gaaaaccatc  1020
agcaaggcca agggccagcc cagagagccc caggtgtaca ccctgccccc tagcagagat  1080
gagctgacca agaaccaggt gtccctgacc tgcctggtga agggcttcta ccccagcgac  1140
atcgccgtgg agtgggagag caacggccag cccgagaaca actacaagac caccccccct  1200
gtgctggaca gcgatggcag cttcttcctg tacagcaagc tgaccgtgga caagagcaga  1260
tggcagcagg gcaacgtgtt cagctgctcc gtgatgcacg aggccctgca caatcactac  1320
acccagaaga gcctgagcct gtcccctggc aag                               1353

SEQ ID NO: 55           moltype = AA  length = 451
FEATURE                 Location/Qualifiers
REGION                  1..451
                        note = Humansed antibody sequence
source                  1..451
                        mol_type = protein
                        organism = synthetic construct
SEQUENCE: 55
QVQLVQSGAE VKKPGSSVKV SCKASGGTFS NYWMHWVRQA PGQGLEWMGA TYRGHSDTYY  60
NQKFKGRVTI TADKSTSTAY MELSSLRSED TAVYYCARGA IYDGYDVLDN WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 56           moltype = DNA  length = 1353
FEATURE                 Location/Qualifiers
misc_feature            1..1353
                        note = Humansed antibody sequence
source                  1..1353
                        mol_type = other DNA
                        organism = synthetic construct
SEQUENCE: 56
caggtgcagc tggtccagag cggcgccgaa gtgaagaagc ccggcagctc cgtgaaagtg  60
agctgcaagg ccagcggcgg caccttcagc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca agagcaccag caccgcctac  240
atggaactga gcagcctcag gagcgaggac accgctgtgt attactgcgc caggggcgcc  300
atctacgacg gctacgacgt gctggacaac tggggccagg gcacactagt gaccgtgtcc  360
agcgccagca ccaagggccc cagcgtgttc cccctggccc ccagcagcaa gagcaccagc  420
ggcggcacag ccgccctggg ctgcctggtg aaggactact tccccgaacc ggtgaccgtg  480
tcctggaaca gcggagccct gaccagcggc gtgcacacct tccccgccgt gctgcagagc  540
agcggcctgt acagcctgag cagcgtggtg accgtgccca gcagcagcct gggcacccag  600
acctacatct gtaacgtgaa ccacaagccc agcaacacca aggtggacaa gaaggtggag  660
cccaagagct gtgacaagac ccacacctgc ccccctgcc ctgcccccga gctgctggga  720
ggccccagcg tgttcctgtt cccccccaag cctaaggaca ccctgatgat cagcagaacc  780
cccgaggtga cctgtgtggt ggtggatgtg agccacgagg accctgaggt gaagttcaac  840
tggtacgtgg acggcgtgga ggtgcacaat gccaagacca agcccaggga ggagcagtac  900
aacagcacct accgggtggt gtccgtgctg accgtgctgc accaggattg gctgaacggc  960
aaggagtaca agtgtaaggt gtccaacaag gccctgcctg cccctatcga gaaaaccatc  1020
agcaaggcca agggccagcc cagagagccc caggtgtaca ccctgccccc tagcagagat  1080
gagctgacca agaaccaggt gtccctgacc tgcctggtga agggcttcta ccccagcgac  1140
atcgccgtgg agtgggagag caacggccag cccgagaaca actacaagac caccccccct  1200
gtgctggaca gcgatggcag cttcttcctg tacagcaagc tgaccgtgga caagagcaga  1260
tggcagcagg gcaacgtgtt cagctgctcc gtgatgcacg aggccctgca caatcactac  1320
acccagaaga gcctgagcct gtcccctggc aag                               1353
```

-continued

```
SEQ ID NO: 57          moltype = AA  length = 451
FEATURE                Location/Qualifiers
REGION                 1..451
                       note = Humansed antibody sequence
source                 1..451
                       mol_type = protein
                       organism = synthetic construct
SEQUENCE: 57
QVQLVQSGAE VKKPGSSVKV SCKASGYTFT NYWMHWVRQA PGQGLEWMGA TYRGHSDTYY  60
NQKFKGRVTI TADKSTSTAY MELSSLRSED TAVYYCARGA IYDGYDVLDN WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 58          moltype = DNA  length = 1353
FEATURE                Location/Qualifiers
misc_feature           1..1353
                       note = Humansed antibody sequence
source                 1..1353
                       mol_type = other DNA
                       organism = synthetic construct
SEQUENCE: 58
caggtgcagc tggtccagag cggcgccgaa gtgaagaagc ccggcagctc cgtgaaagtg  60
agctgcaagg ccagcggcta caccttcacc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca agagcaccag caccgcctac  240
atggaactga gcagcctcag gagcgaggac accgctgtgt attactgcgc caggggcgcc  300
atctacgacg gctacgacgt gctggacaac tggggccagg gcacactagt gaccgtgtcc  360
agcgccagca ccaagggccc cagcgtgttc cccctggccc ccagcagcaa gagcaccagc  420
ggcggcacag ccgccctggg ctgcctggtg aaggactact tccccgaacc ggtgaccgtg  480
tcctggaaca gcggagccct gaccagcggc gtgcacacct tccccgccgt gctgcagagc  540
agcggcctgt acagcctgag cagcgtggtg accgtgccca gcagcagcct gggcacccag  600
acctacatct gtaacgtgaa ccacaagccc agcaacacca aggtggacaa gaaggtggag  660
cccaagagct gtgacaagac ccacacctgc ccccctgcc ctgcccccga gctgctggga  720
ggccccagcg tgttcctgtt cccccccaag cctaaggaca ccctgatgat cagcagaacc  780
cccgaggtga cctgtgtggt ggtggatgtg agccacgagg accctgaggt gaagttcaac  840
tggtacgtgg acggcgtgga ggtgcacaat gccaagacca agcccaggga ggagcagtac  900
aacagcacct accgggtggt gtccgtgctg accgtgctgc accaggattg gctgaacggc  960
aaggagtaca agtgtaaggt gtccaacaag gccctgcctg cccctatcga gaaaaccatc  1020
agcaaggcca agggccagcc cagagagccc caggtgtaca ccctgccccc tagcagagat  1080
gagctgacca agaaccaggt gtccctgacc tgcctggtga agggcttcta ccccagcgac  1140
atcgccgtgg agtgggagag caacggccag cccgagaaca actacaagac caccccccct  1200
gtgctggaca gcgatggcag cttcttcctg tacagcaagc tgaccgtgga caagagcaga  1260
tggcagcagg gcaacgtgtt cagctgctcc gtgatgcacg aggccctgca caatcactac  1320
acccagaaga gcctgagcct gtcccctggc aag                               1353

SEQ ID NO: 59          moltype = AA  length = 451
FEATURE                Location/Qualifiers
REGION                 1..451
                       note = Humansed antibody sequence
source                 1..451
                       mol_type = protein
                       organism = synthetic construct
SEQUENCE: 59
QVQLVQSGAE VKKPGSSVKV SCKASGYTFT NYWMHWVRQA PGQGLEWMGA TYRGHSDTYY  60
NQKFKGRVTI TADKSTSTAY MELSSLRSED TAVYYCTRGA IYDGYDVLDN WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 60          moltype = DNA  length = 1353
FEATURE                Location/Qualifiers
misc_feature           1..1353
                       note = Humansed antibody sequence
source                 1..1353
                       mol_type = other DNA
                       organism = synthetic construct
SEQUENCE: 60
caggtgcagc tggtccagag cggcgccgaa gtgaagaagc ccggcagctc cgtgaaagtg  60
agctgcaagg ccagcggcta caccttcacc aactactgga tgcactgggt gaggcaggcc  120
cccggacagg gcctggagtg gatgggcgcc acctacaggg gccacagcga cacctactac  180
aaccagaagt tcaagggccg ggtgaccatc accgccgaca agagcaccag caccgcctac  240
atggaactga gcagcctcag gagcgaggac accgctgtgt attactgcac caggggcgcc  300
```

-continued

```
atctacgacg gctacgacgt gctggacaac tggggccagg gcacactagt gaccgtgtcc  360
agcgccagca ccaagggccc cagcgtgttc cccctggccc ccagcagcaa gagcaccagc  420
ggcggcacag ccgccctggg ctgcctggtg aaggactact tccccgaacc ggtgaccgtg  480
tcctggaaca gcggagccct gaccagcggc gtgcacacct tccccgccgt gctgcagagc  540
agcggcctgt acagcctgag cagcgtggtg accgtgccca gcagcagcct gggcacccag  600
acctacatct gtaacgtgaa ccacaagccc agcaacacca aggtggacaa gaaggtggag  660
cccaagagct gtgacaagac ccacacctgc ccccctgcc ctgcccccga gctgctggga  720
ggccccagcg tgttcctgtt ccccccaag cctaaggaca ccctgatgat cagcagaacc  780
cccgaggtga cctgtgtggt ggtggatgtg agccacgagg accctgaggt gaagttcaac  840
tggtacgtgg acggcgtgga ggtgcacaat gccaagacca agcccaggga ggagcagtac  900
aacagcacct accgggtggt gtccgtgctg accgtgctgc accaggattg gctgaacggc  960
aaggagtaca agtgtaaggt gtccaacaag gccctgcctg cccctatcga gaaaaccatc  1020
agcaaggcca agggccagcc cagagagccc caggtgtaca ccctgccccc tagcagagat  1080
gagctgacca agaaccaggt gtccctgacc tgcctggtga agggcttcta ccccagcgac  1140
atcgccgtgg agtgggagag caacggccag cccgagaaca actacaagac caccccccct  1200
gtgctggaca gcgatggcag cttcttcctg tacagcaagc tgaccgtgga caagagcaga  1260
tggcagcagg gcaacgtgtt cagctgctcc gtgatgcacg aggccctgca caatcactac  1320
acccagaaga gcctgagcct gtcccctggc aag                                1353

SEQ ID NO: 61          moltype = AA  length = 451
FEATURE                Location/Qualifiers
REGION                 1..451
                       note = Humansed antibody sequence
source                 1..451
                       mol_type = protein
                       organism = synthetic construct
SEQUENCE: 61
QVQLVQSGAE VKKPGSSVKV SCKGSGYTFT NYWMHWVRQA PGQGLEWIGA TYRGHSDTYY  60
NQKFKGRATL TADTSTSTAY MELSSLRSED TAVYYCTRGA IYDGYDVLDN WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 62          moltype = DNA  length = 1353
FEATURE                Location/Qualifiers
misc_feature           1..1353
                       note = Humansed antibody sequence
source                 1..1353
                       mol_type = other DNA
                       organism = synthetic construct
SEQUENCE: 62
caggtgcagc tggtccagag cggcgccgaa gtgaagaagc ccggcagctc cgtgaaagtg  60
agctgcaagg gcagcggcta caccttcacc aactactgga tgcactgggt gaggcaggcc  120
cccggacagg gcctggagtg gatcggcgcc acctacaggg gccacagcga cacctactac  180
aaccagaagt tcaagggccg ggcgaccctc accgccgaca cgagcaccag caccgcctac  240
atggaactga gcagcctcag gagcgaggac accgctgtgt attactgcac cagggggcgcc  300
atctacgacg gctacgacgt gctggacaac tggggccagg gcacactagt gaccgtgtcc  360
agcgccagca ccaagggccc cagcgtgttc cccctggccc ccagcagcaa gagcaccagc  420
ggcggcacag ccgccctggg ctgcctggtg aaggactact tccccgaacc ggtgaccgtg  480
tcctggaaca gcggagccct gaccagcggc gtgcacacct tccccgccgt gctgcagagc  540
agcggcctgt acagcctgag cagcgtggtg accgtgccca gcagcagcct gggcacccag  600
acctacatct gtaacgtgaa ccacaagccc agcaacacca aggtggacaa gaaggtggag  660
cccaagagct gtgacaagac ccacacctgc ccccctgcc ctgcccccga gctgctggga  720
ggccccagcg tgttcctgtt ccccccaag cctaaggaca ccctgatgat cagcagaacc  780
cccgaggtga cctgtgtggt ggtggatgtg agccacgagg accctgaggt gaagttcaac  840
tggtacgtgg acggcgtgga ggtgcacaat gccaagacca agcccaggga ggagcagtac  900
aacagcacct accgggtggt gtccgtgctg accgtgctgc accaggattg gctgaacggc  960
aaggagtaca agtgtaaggt gtccaacaag gccctgcctg cccctatcga gaaaaccatc  1020
agcaaggcca agggccagcc cagagagccc caggtgtaca ccctgccccc tagcagagat  1080
gagctgacca agaaccaggt gtccctgacc tgcctggtga agggcttcta ccccagcgac  1140
atcgccgtgg agtgggagag caacggccag cccgagaaca actacaagac caccccccct  1200
gtgctggaca gcgatggcag cttcttcctg tacagcaagc tgaccgtgga caagagcaga  1260
tggcagcagg gcaacgtgtt cagctgctcc gtgatgcacg aggccctgca caatcactac  1320
acccagaaga gcctgagcct gtcccctggc aag                                1353

SEQ ID NO: 63          moltype = AA  length = 214
FEATURE                Location/Qualifiers
REGION                 1..214
                       note = Humansed antibody sequence
source                 1..214
                       mol_type = protein
                       organism = synthetic construct
SEQUENCE: 63
DIQMTQSPSS LSASVGDRVT ITCSASQDIS NYLNWYQQKP GKAPKLLIYY TSNLHSGVPS  60
RFSGSGSGTD FTLTISSLQP EDFATYYCQQ YRKLPWTFGQ GTKLEIKRTV AAPSVFIFPP  120
SDEQLKSGTA SVVCLLNNFY PREAKVQWKV DNALQSGNSQ ESVTEQDSKD STYSLSSTLT  180
```

```
LSKADYEKHK VYACEVTHQG LSSPVTKSFN RGEC                            214

SEQ ID NO: 64          moltype = DNA  length = 642
FEATURE                Location/Qualifiers
misc_feature           1..642
                       note = Humansed antibody sequence
source                 1..642
                       mol_type = other DNA
                       organism = synthetic construct
SEQUENCE: 64
gacatccaga tgacccagag ccctagctca ctgagcgcca gcgtgggcga cagggtgacc  60
attacctgct ccgccagcca ggacatcagc aactacctga actggtacca gcagaagccc  120
ggcaaggccc ccaagctgct gatctactac acctccaacc tgcactccgg cgtgcccagc  180
aggttcagcg gaagcggcag cggcaccgat ttcaccctga ccatctccag cctgcagccc  240
gaggacttcg ccacctacta ctgccagcag tacaggaagc tcccctggac tttcggccag  300
ggcaccaaac tggagatcaa gcgtacggtg gccgccccca gcgtgttcat cttccccccc  360
agcgatgagc agctgaagag cggcaccgcc agcgtggtgt gtctgctgaa caacttctac  420
cccCgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                    642

SEQ ID NO: 65          moltype = AA  length = 214
FEATURE                Location/Qualifiers
REGION                 1..214
                       note = Humansed antibody sequence
source                 1..214
                       mol_type = protein
                       organism = synthetic construct
SEQUENCE: 65
DIQMTQSPSS LSASVGDRVT ITCSASQDIS NYLNWYQQKP GKAPKLLIYY TSNLHSGVPS  60
RFSGSGSGTD YTLTISSLQP EDFATYYCQQ YRKLPWTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 66          moltype = DNA  length = 642
FEATURE                Location/Qualifiers
misc_feature           1..642
                       note = Humansed antibody sequence
source                 1..642
                       mol_type = other DNA
                       organism = synthetic construct
SEQUENCE: 66
gacatccaga tgacccagag ccctagctca ctgagcgcca gcgtgggcga cagggtgacc  60
attacctgct ccgccagcca ggacatcagc aactacctga actggtacca gcagaagccc  120
ggcaaggccc ccaagctgct gatctactac acctccaacc tgcactccgg cgtgcccagc  180
aggttcagcg gaagcggcag cggcaccgat tacaccctga ccatctccag cctgcagccc  240
gaggacttcg ccacctacta ctgccagcag tacaggaagc tcccctggac tttcggccag  300
ggcaccaaac tggagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                    642

SEQ ID NO: 67          moltype = AA  length = 214
FEATURE                Location/Qualifiers
REGION                 1..214
                       note = Humansed antibody sequence
source                 1..214
                       mol_type = protein
                       organism = synthetic construct
SEQUENCE: 67
DIQLTQSPSS LSASVGDRVT ITCSASQDIS NYLNWYQQKP GKAPELVIYY TSNLHSGVPS  60
RFSGSGSGTD YTLTISSLQP EDFATYYCQQ YRKLPWTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 68          moltype = DNA  length = 642
FEATURE                Location/Qualifiers
misc_feature           1..642
                       note = Humansed antibody sequence
source                 1..642
                       mol_type = other DNA
                       organism = synthetic construct
SEQUENCE: 68
gacatccagc tgacccagag ccctagctca ctgagcgcca gcgtgggcga cagggtgacc  60
attacctgct ccgccagcca ggacatcagc aactacctga actggtacca gcagaagccc  120
ggcaaggccc ccgagctggt gatctactac acctccaacc tgcactccgg cgtgcccagc  180
```

```
aggttcagcg gaagcggcag cggcaccgat tacaccctga ccatctccag cctgcagccc  240
gaggacttcg ccacctacta ctgccagcag tacaggaagc tcccctggac tttcggccag  300
ggcaccaaac tggagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                    642

SEQ ID NO: 69          moltype = AA  length = 115
FEATURE                Location/Qualifiers
source                 1..115
                       mol_type = protein
                       organism = Mus musculus
SEQUENCE: 69
EVQLQQSGPE LVKPGASVKI SCKASGYTFT DYYMKWVKQS HGKSLEWIGE IYPNNGGITY  60
NQKFKGKATL TVDKSSSTAY MELRSLTSED SAVYYCANGY EFVYWGQGTL VTVSA       115

SEQ ID NO: 70          moltype = DNA  length = 345
FEATURE                Location/Qualifiers
source                 1..345
                       mol_type = genomic DNA
                       organism = Mus musculus
SEQUENCE: 70
gaggtccagt tgcaacaatc tggacctgag ctggtgaagc ctggggcttc agtgaagata  60
tcctgtaagg cttctggata cacattcact gactactaca tgaagtgggt gaagcagagc  120
catggaaaga gccttgagtg gattggagag atttatccta ataatggtgg tattacctac  180
aaccagaagt tcaagggcaa ggccacattg actgtagaca agtcctccag cacagcctac  240
atggagctcc gcagcctgac atctgaggac tctgcagtct attactgtgc aaatggttac  300
gagtttgttt actggggcca agggactctg gtcactgtct ctgca                 345

SEQ ID NO: 71          moltype = AA  length = 108
FEATURE                Location/Qualifiers
source                 1..108
                       mol_type = protein
                       organism = Mus musculus
SEQUENCE: 71
DIQMTQTASS LSASLGDRVT ISCSASQGIS NYLNWYQQKP DGTVKLLIYY TSSLHSGVPS  60
RFSGSGSGTD YSLTISNLEP EDIATYYCQQ YSKLPWTFGG GTKLEIKR               108

SEQ ID NO: 72          moltype = DNA  length = 324
FEATURE                Location/Qualifiers
source                 1..324
                       mol_type = genomic DNA
                       organism = Mus musculus
SEQUENCE: 72
gatatccaga tgacacagac tgcatcctcc ctgtctgcct ctctgggaga cagagtcacc  60
atcagttgca gtgcaagtca gggcattagc aattatttaa actggtatca gcagaaacca  120
gatggaactg ttaaactcct gatctattac acatcaagtt tacactcagg agtcccatca  180
aggttcagtg gcagtgggtc tgggacagat tattctctca ccatcagcaa cctggaacct  240
gaagatattg ccacttacta ttgtcagcag tatagtaagc ttccgtggac gttcggtgga  300
ggcaccaagc tggaaatcaa acgg                                        324

SEQ ID NO: 73          moltype = AA  length = 445
FEATURE                Location/Qualifiers
REGION                 1..445
                       note = Chimeric antibody sequence
source                 1..445
                       mol_type = protein
                       organism = synthetic construct
SEQUENCE: 73
EVQLQQSGPE LVKPGASVKI SCKASGYTFT DYYMKWVKQS HGKSLEWIGE IYPNNGGITY  60
NQKFKGKATL TVDKSSSTAY MELRSLTSED SAVYYCANGY EFVYWGQGTL VTVSAAKTTA  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                       445

SEQ ID NO: 74          moltype = DNA  length = 1335
FEATURE                Location/Qualifiers
misc_feature           1..1335
                       note = Chimeric antibody sequence
source                 1..1335
                       mol_type = other DNA
                       organism = synthetic construct
SEQUENCE: 74
gaggtccagt tgcaacaatc tggacctgag ctggtgaagc ctggggcttc agtgaagata  60
```

```
tcctgtaagg cttctggata cacattcact gactactaca tgaagtgggt gaagcagagc  120
catggaaaga gccttgagtg gattggagag atttatccta ataatggtgg tattacctac  180
aaccagaagt tcaagggcaa ggccacattg actgtagaca agtcctccag cacagcctac  240
atggagctcc gcagcctgac atctgaggac tctgcagtct attactgtgc aaatggttac  300
gagtttgttt actggggcca agggactctg gtcactgtct ctgcagccaa aacaacagcc  360
cccagcgtgt tccccctggc ccccagcagc aagagcacca gcggcggcac agccgccctg  420
ggctgcctgg tgaaggacta cttccccgaa ccggtgaccg tgtcctggaa cagcggagcc  480
ctgaccagcg gcgtgcacac cttccccgcc gtgctgcaga gcagcggcct gtacagcctg  540
agcagcgtgg tgaccgtgcc cagcagcagc ctgggcaccc agacctacat ctgtaacgtg  600
aaccacaagc ccagcaacac caaggtggac aagaaggtgg agcccaagag ctgtgacaag  660
acccacacct gccccccctg ccctgccccc gagctgctgg gaggccccag cgtgttcctg  720
ttccccccca agcctaagga caccctgatg atcagcagaa cccccgaggt gacctgtgtg  780
gtggtggatg tgagccacga ggaccctgag gtgaagttca actggtacgt ggacggcgtg  840
gaggtgcaca atgccaagac caagcccagg gaggagcagt acaacagcac ctaccgggtg  900
gtgtccgtgc tgaccgtgct gcaccaggat tggctgaacg gcaaggagta caagtgtaag  960
gtgtccaaca aggccctgcc tgcccctatc gagaaaacca tcagcaaggc caagggccag  1020
cccagagagc cccaggtgta caccctgccc cctagcagag atgagctgac caagaaccag  1080
gtgtccctga cctgcctggt gaagggcttc taccccagcg acatcgccgt ggagtgggag  1140
agcaacggcc agcccgagaa caactacaag accacccccc ctgtgctgga cagcgatggc  1200
agcttcttcc tgtacagcaa gctgaccgtg gacaagagca gatggcagca gggcaacgtg  1260
ttcagctgct ccgtgatgca cgaggccctg cacaatcact acacccagaa gagcctgagc  1320
ctgtcccctg gcaag                                                   1335

SEQ ID NO: 75          moltype = AA  length = 214
FEATURE                Location/Qualifiers
REGION                 1..214
                       note = Chimeric antibody sequence
source                 1..214
                       mol_type = protein
                       organism = synthetic construct
SEQUENCE: 75
DIQMTQTASS LSASLGDRVT ISCSASQGIS NYLNWYQQKP DGTVKLLIYY TSSLHSGVPS  60
RFSGSGSGTD YSLTISNLEP EDIATYYCQQ YSKLPWTFGG GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 76          moltype = DNA  length = 642
FEATURE                Location/Qualifiers
misc_feature           1..642
                       note = Chimeric antibody sequence
source                 1..642
                       mol_type = other DNA
                       organism = synthetic construct
SEQUENCE: 76
gatatccaga tgacacagac tgcatcctcc ctgtctgcct ctctgggaga cagagtcacc  60
atcagttgca gtgcaagtca gggcattagc aattatttaa actggtatca gcagaaacca  120
gatggaactg ttaaactcct gatctattac acatcaagtt tacactcagg agtcccatca  180
aggttcagtg gcagtgggtc tgggacagat tattctctca ccatcagcaa cctggaacct  240
gaagatattg ccacttacta ttgtcagcag tatagtaagc ttccgtggac gttcggtgga  300
ggcaccaagc tggagctgaa acgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                     642

SEQ ID NO: 77          moltype = AA  length = 115
FEATURE                Location/Qualifiers
REGION                 1..115
                       note = Humansed antibody sequence
source                 1..115
                       mol_type = protein
                       organism = synthetic construct
SEQUENCE: 77
QVQLVQSGAE VKKPGSSVKV SCKASGGTFS DYYMKWVRQA PGQGLEWMGE IYPNNGGITY  60
NQKFKGRVTI TADKSTSTAY MELSSLRSED TAVYYCARGY EFVYWGQGTL VTVSS       115

SEQ ID NO: 78          moltype = DNA  length = 345
FEATURE                Location/Qualifiers
misc_feature           1..345
                       note = Humansed antibody sequence
source                 1..345
                       mol_type = other DNA
                       organism = synthetic construct
SEQUENCE: 78
caggtgcagc tggtgcagag cggcgccgaa gtgaagaagc ccggctccag cgtgaaggtg  60
agctgcaagg ctagcggcgg caccttcagc gactactaca tgaagtgggt gaggcaggcc  120
cccggccagg gactggagtg gatgggcgag atctacccca acaacggggg catcacctac  180
aaccagaagt tcaagggcag ggtgaccatc accgccgaca aaagcaccag caccgcctac  240
```

-continued

```
atggaactga gcagcctgag gagcgaggac accgccgtgt actactgcgc caggggctac  300
gagttcgtgt attggggcca gggcacacta gtgaccgtgt ccagc                  345

SEQ ID NO: 79           moltype = AA  length = 115
FEATURE                 Location/Qualifiers
REGION                  1..115
                        note = Humansed antibody sequence
source                  1..115
                        mol_type = protein
                        organism = synthetic construct
SEQUENCE: 79
QVQLVQSGAE VKKPGSSVKV SCKASGYTFT DYYMKWVRQA PGQGLEWMGE IYPNNGGITY  60
NQKFKGRVTI TADKSTSTAY MELSSLRSED TAVYYCARGY EFVYWGQGTL VTVSS       115

SEQ ID NO: 80           moltype = DNA  length = 345
FEATURE                 Location/Qualifiers
misc_feature            1..345
                        note = Humansed antibody sequence
source                  1..345
                        mol_type = other DNA
                        organism = synthetic construct
SEQUENCE: 80
caggtgcagc tggtgcagag cggcgccgaa gtgaagaagc ccggctccag cgtgaaggtg  60
agctgcaagg ctagcggcta caccttcacc gactactaca tgaagtgggt gaggcaggcc  120
cccggccagg gactggagtg gatgggcgag atctacccca acaacggggg catcacctac  180
aaccagaagt tcaagggcag ggtgaccatc accgccgaca aaagcaccag caccgcctac  240
atggaactga gcagcctgag gagcgaggac accgccgtgt actactgcgc caggggctac  300
gagttcgtgt attggggcca gggcacacta gtgaccgtgt ccagc                  345

SEQ ID NO: 81           moltype = AA  length = 115
FEATURE                 Location/Qualifiers
REGION                  1..115
                        note = Humansed antibody sequence
source                  1..115
                        mol_type = protein
                        organism = synthetic construct
SEQUENCE: 81
QVQLVQSGAE VKKPGSSVKV SCKASGYTFT DYYMKWVRQA PGQGLEWMGE IYPNNGGITY  60
NQKFKGRVTI TADKSTSTAY MELSSLRSED TAVYYCANGY EFVYWGQGTL VTVSS       115

SEQ ID NO: 82           moltype = DNA  length = 345
FEATURE                 Location/Qualifiers
misc_feature            1..345
                        note = Humansed antibody sequence
source                  1..345
                        mol_type = other DNA
                        organism = synthetic construct
SEQUENCE: 82
caggtgcagc tggtgcagag cggcgccgaa gtgaagaagc ccggctccag cgtgaaggtg  60
agctgcaagg ctagcggcta caccttcacc gactactaca tgaagtgggt gaggcaggcc  120
cccggccagg gactggagtg gatgggcgag atctacccca acaacggggg catcacctac  180
aaccagaagt tcaagggcag ggtgaccatc accgccgaca aaagcaccag caccgcctac  240
atggaactga gcagcctgag gagcgaggac accgccgtgt actactgcgc caacggctac  300
gagttcgtgt attggggcca gggcacacta gtgaccgtgt ccagc                  345

SEQ ID NO: 83           moltype = AA  length = 115
FEATURE                 Location/Qualifiers
REGION                  1..115
                        note = Humansed antibody sequence
source                  1..115
                        mol_type = protein
                        organism = synthetic construct
SEQUENCE: 83
QVQLVQSGAE VKKPGSSVKV SCKASGYTFT DYYMKWVRQA PGQGLEWIGE IYPNNGGITY  60
NQKFKGRATL TVDKSTSTAY MELSSLRSED TAVYYCANGY EFVYWGQGTL VTVSS       115

SEQ ID NO: 84           moltype = DNA  length = 345
FEATURE                 Location/Qualifiers
misc_feature            1..345
                        note = Humansed antibody sequence
source                  1..345
                        mol_type = other DNA
                        organism = synthetic construct
SEQUENCE: 84
caggtgcagc tggtgcagag cggcgccgaa gtgaagaagc ccggctccag cgtgaaggtg  60
agctgcaagg ctagcggcta caccttcacc gactactaca tgaagtgggt gaggcaggcc  120
cccggccagg gactggagtg gataggcgag atctacccca acaacggggg catcacctac  180
aaccagaagt tcaagggcag ggcgaccctc accgtcgaca aaagcaccag caccgcctac  240
atggaactga gcagcctgag gagcgaggac accgccgtgt actactgcgc caacggctac  300
```

-continued

```
gagttcgtgt attggggcca gggcacacta gtgaccgtgt ccagc                345

SEQ ID NO: 85          moltype = AA  length = 115
FEATURE                Location/Qualifiers
REGION                 1..115
                       note = Humansed antibody sequence
source                 1..115
                       mol_type = protein
                       organism = synthetic construct
SEQUENCE: 85
QVQLVQSGAE VKKPGSSVKV SCKASGYTFT DYYMKWVRQA PGQGLEWMGE IYPNNGGITY  60
NQKFKGRVTI TADKSTSTAY MELSSLRSED TAVYYCADGY EFVYWGQGTL VTVSS       115

SEQ ID NO: 86          moltype = DNA  length = 345
FEATURE                Location/Qualifiers
misc_feature           1..345
                       note = Humansed antibody sequence
source                 1..345
                       mol_type = other DNA
                       organism = synthetic construct
SEQUENCE: 86
caggtgcagc tggtgcagag cggcgccgaa gtgaagaagc ccggctccag cgtgaaggtg  60
agctgcaagg ctagcggcta caccttcacc gactactaca tgaagtgggt gaggcaggcc  120
cccggccagg gactggagtg gatgggcgag atctacccca acaacggggg catcacctac  180
aaccagaagt tcaagggcag ggtgaccatc accgccgaca aaagcaccag caccgcctac  240
atggaactga gcagcctgag gagcgaggac accgccgtgt actactgcgc cgacggctac  300
gagttcgtgt attggggcca gggcacacta gtgaccgtgt ccagc                345

SEQ ID NO: 87          moltype = AA  length = 115
FEATURE                Location/Qualifiers
REGION                 1..115
                       note = Humansed antibody sequence
source                 1..115
                       mol_type = protein
                       organism = synthetic construct
SEQUENCE: 87
QVQLVQSGAE VKKPGSSVKV SCKASGYTFT DYYMKWVRQA PGQGLEWIGE IYPNNGGITY  60
NQKFKGRATL TVDKSTSTAY MELSSLRSED TAVYYCANGY EFDYWGQGTL VTVSS       115

SEQ ID NO: 88          moltype = DNA  length = 345
FEATURE                Location/Qualifiers
misc_feature           1..345
                       note = Humansed antibody sequence
source                 1..345
                       mol_type = other DNA
                       organism = synthetic construct
SEQUENCE: 88
caggtgcagc tggtgcagag cggcgccgaa gtgaagaagc ccggctccag cgtgaaggtg  60
agctgcaagg ctagcggcta caccttcacc gactactaca tgaagtgggt gaggcaggcc  120
cccggccagg gactggagtg gataggcgag atctacccca acaacggggg catcacctac  180
aaccagaagt tcaagggcag ggcgaccctc accgtcgaca aaagcaccag caccgcctac  240
atggaactga gcagcctgag gagcgaggac accgccgtgt actactgcgc caacggctac  300
gagttcgact attggggcca gggcacacta gtgaccgtgt ccagc                345

SEQ ID NO: 89          moltype = AA  length = 108
FEATURE                Location/Qualifiers
REGION                 1..108
                       note = Humansed antibody sequence
source                 1..108
                       mol_type = protein
                       organism = synthetic construct
SEQUENCE: 89
DIQMTQSPSS LSASVGDRVT ITCSASQGIS NYLNWYQQKP GKAPKLLIYY TSSLHSGVPS  60
RFSGSGSGTD FTLTISSLQP EDFATYYCQQ YSKLPWTFGQ GTKLEIKR             108

SEQ ID NO: 90          moltype = DNA  length = 324
FEATURE                Location/Qualifiers
misc_feature           1..324
                       note = Humansed antibody sequence
source                 1..324
                       mol_type = other DNA
                       organism = synthetic construct
SEQUENCE: 90
gacatccaga tgacccagag cccctcaagc ctgagcgcca gcgtgggcga cagggtgact  60
atcacctgca gcgcctccca gggcatcagc aactacctga actggtacca gcagaagccc  120
ggcaaggccc ctaagctgct gatctactac accagcagcc tgcacagcgg cgtgcccagc  180
aggttctccg gcagcggcag cggaaccgac ttcaccctga ccattagcag cctccagccc  240
gaggacttcg ccacctacta ctgccagcag tacagcaagc tgccctggac cttcggccag  300
ggcaccaaac tggagatcaa gcgt                                       324
```

```
SEQ ID NO: 91          moltype = AA  length = 108
FEATURE                Location/Qualifiers
REGION                 1..108
                       note = Humansed antibody sequence
source                 1..108
                       mol_type = protein
                       organism = synthetic construct
SEQUENCE: 91
DIQMTQSPSS LSASVGDRVT ITCSASQGIS NYLNWYQQKP GKAPKLLIYY TSSLHSGVPS  60
RFSGSGSGTD YTLTISSLQP EDFATYYCQQ YSKLPWTFGQ GTKLEIKR               108

SEQ ID NO: 92          moltype = DNA  length = 324
FEATURE                Location/Qualifiers
misc_feature           1..324
                       note = Humansed antibody sequence
source                 1..324
                       mol_type = other DNA
                       organism = synthetic construct
SEQUENCE: 92
gacatccaga tgacccagag cccctcaagc ctgagcgcca gcgtgggcga cagggtgact  60
atcacctgca gcgcctccca gggcatcagc aactacctga actggtacca gcagaagccc  120
ggcaaggccc ctaagctgct gatctactac accagcagcc tgcacagcgg cgtgcccagc  180
aggttctccg gcagcggcag cggaaccgac tacaccctga ccattagcag cctccagccc  240
gaggacttcg ccacctacta ctgccagcag tacagcaagc tgccctggac cttcggccag  300
ggcaccaaac tggagatcaa gcgt                                         324

SEQ ID NO: 93          moltype = AA  length = 5
FEATURE                Location/Qualifiers
source                 1..5
                       mol_type = protein
                       organism = Mus musculus
SEQUENCE: 93
DYYMK                                                              5

SEQ ID NO: 94          moltype = AA  length = 17
FEATURE                Location/Qualifiers
source                 1..17
                       mol_type = protein
                       organism = Mus musculus
SEQUENCE: 94
EIYPNNGGIT YNQKFKG                                                 17

SEQ ID NO: 95          moltype = AA  length = 6
FEATURE                Location/Qualifiers
source                 1..6
                       mol_type = protein
                       organism = Mus musculus
SEQUENCE: 95
GYEFVY                                                             6

SEQ ID NO: 96          moltype = AA  length = 11
FEATURE                Location/Qualifiers
source                 1..11
                       mol_type = protein
                       organism = Mus musculus
SEQUENCE: 96
SASQGISNYL N                                                       11

SEQ ID NO: 97          moltype = AA  length = 7
FEATURE                Location/Qualifiers
source                 1..7
                       mol_type = protein
                       organism = Mus musculus
SEQUENCE: 97
YTSSLHS                                                            7

SEQ ID NO: 98          moltype = AA  length = 9
FEATURE                Location/Qualifiers
source                 1..9
                       mol_type = protein
                       organism = Mus musculus
SEQUENCE: 98
QQYSKLPWT                                                          9

SEQ ID NO: 99          moltype = AA  length = 6
FEATURE                Location/Qualifiers
REGION                 1..6
                       note = Humansed antibody sequence
```

```
source                  1..6
                        mol_type = protein
                        organism = synthetic construct
SEQUENCE: 99
GYEFDY                                                                      6

SEQ ID NO: 100          moltype = AA  length = 445
FEATURE                 Location/Qualifiers
REGION                  1..445
                        note = Humansed antibody sequence
source                  1..445
                        mol_type = protein
                        organism = synthetic construct
SEQUENCE: 100
QVQLVQSGAE VKKPGSSVKV SCKASGGTFS DYYMKWVRQA PGQGLEWMGE IYPNNGGITY  60
NQKFKGRVTI TADKSTSTAY MELSSLRSED TAVYYCARGY EFVYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                         445

SEQ ID NO: 101          moltype = DNA  length = 1335
FEATURE                 Location/Qualifiers
misc_feature            1..1335
                        note = Humansed antibody sequence
source                  1..1335
                        mol_type = other DNA
                        organism = synthetic construct
SEQUENCE: 101
caggtgcagc tggtgcagag cggcgccgaa gtgaagaagc ccggctccag cgtgaaggtg  60
agctgcaagg ctagcggcgg caccttcagc gactactaca tgaagtgggt gaggcaggcc  120
cccggccagg gactggagtg gatgggcgag atctacccca acaacggggg catcacctac  180
aaccagaagt tcaagggcag ggtgaccatc accgccgaca aaagcaccag caccgcctac  240
atggaactga gcagcctgag gagcgaggac accgccgtgt actactgcgc caggggctac  300
gagttcgtgt attggggcca gggcacacta gtgaccgtgt ccagcgccag caccaagggc  360
cccagcgtgt tccccctggc ccccagcagc aagagcacca gcggcggcac agccgccctg  420
ggctgcctgg tgaaggacta cttccccgaa ccggtgaccg tgtcctggaa cagcggagcc  480
ctgaccagcg gcgtgcacac cttccccgcc gtgctgcaga gcagcggcct gtacagcctg  540
agcagcgtgg tgaccgtgcc cagcagcagc ctgggcaccc agacctacat ctgtaacgtg  600
aaccacaagc ccagcaacac caaggtggac aagaaggtgg agcccaagag ctgtgacaag  660
acccacacct gccccccctg ccctgccccc gagctgctgg gaggccccag cgtgttcctg  720
ttccccccca agcctaagga caccctgatg atcagcagaa cccccgaggt gacctgtgtg  780
gtggtggatg tgagccacga ggaccctgag gtgaagttca actggtacgt ggacggcgtg  840
gaggtgcaca atgccaagac caagcccagg gaggagcagt acaacagcac ctaccgggtg  900
gtgtccgtgc tgaccgtgct gcaccaggat tggctgaacg gcaaggagta caagtgtaag  960
gtgtccaaca aggccctgcc tgcccctatc gagaaaacca tcagcaaggc caagggccag  1020
cccagagagc cccaggtgta caccctgccc cctagcagag atgagctgac caagaaccag  1080
gtgtccctga cctgcctggt gaagggcttc taccccagcg acatcgccgt ggagtgggag  1140
agcaacggcc agcccgagaa caactacaag accacccccc ctgtgctgga cagcgatggc  1200
agcttcttcc tgtacagcaa gctgaccgtg gacaagagca gatggcagca gggcaacgtg  1260
ttcagctgct ccgtgatgca cgaggccctg cacaatcact acacccagaa gagcctgagc  1320
ctgtcccctg gcaag                                                    1335

SEQ ID NO: 102          moltype = AA  length = 445
FEATURE                 Location/Qualifiers
REGION                  1..445
                        note = Humansed antibody sequence
source                  1..445
                        mol_type = protein
                        organism = synthetic construct
SEQUENCE: 102
QVQLVQSGAE VKKPGSSVKV SCKASGYTFT DYYMKWVRQA PGQGLEWMGE IYPNNGGITY  60
NQKFKGRVTI TADKSTSTAY MELSSLRSED TAVYYCARGY EFVYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                         445

SEQ ID NO: 103          moltype = DNA  length = 1335
FEATURE                 Location/Qualifiers
misc_feature            1..1335
                        note = Humansed antibody sequence
source                  1..1335
                        mol_type = other DNA
                        organism = synthetic construct
```

SEQUENCE: 103
caggtgcagc tggtgcagag cggcgccgaa gtgaagaagc ccggctccag cgtgaaggtg 60
agctgcaagg ctagcggcta caccttcacc gactactaca tgaagtgggt gaggcaggcc 120
cccggccagg gactggagtg gatgggcgag atctacccca acaacggggg catcacctac 180
aaccagaagt tcaagggcag ggtgaccatc accgccgaca aaagcaccag caccgcctac 240
atggaactga gcagcctgag gagcgaggac accgccgtgt actactgcgc caggggctac 300
gagttcgtgt attggggcca gggcacacta gtgaccgtgt ccagcgccag caccaagggc 360
cccagcgtgt tccccctggc ccccagcagc aagagcacca gcggcggcac agccgccctg 420
ggctgcctgg tgaaggacta cttccccgaa ccggtgaccg tgtcctggaa cagcggagcc 480
ctgaccagcg gcgtgcacac cttccccgcc gtgctgcaga gcagcggcct gtacagcctg 540
agcagcgtgg tgaccgtgcc cagcagcagc ctgggcaccc agacctacat ctgtaacgtg 600
aaccacaagc ccagcaacac caaggtggac aagaaggtgg agcccaagag ctgtgacaag 660
acccacacct gcccccctg ccctgccccc gagctgctgg gaggccccag cgtgttcctg 720
ttcccccca agcctaagga caccctgatg atcagcagaa cccccgaggt gacctgtgtg 780
gtggtggatg tgagccacga ggaccctgag gtgaagttca actggtacgt ggacggcgtg 840
gaggtgcaca atgccaagac caagcccagg gaggagcagt acaacagcac ctaccgggtg 900
gtgtccgtgc tgaccgtgct gcaccaggat tggctgaacg gcaaggagta caagtgtaag 960
gtgtccaaca aggccctgcc tgcccctatc gagaaaacca tcagcaaggc caagggccag 1020
cccagagagc cccaggtgta caccctgccc cctagcagag atgagctgac caagaaccag 1080
gtgtccctga cctgcctggt gaagggcttc taccccagcg acatcgccgt ggagtgggag 1140
agcaacggcc agcccgagaa caactacaag accacccccc ctgtgctgga cagcgatggc 1200
agcttcttcc tgtacagcaa gctgaccgtg gacaagagca gatggcagca gggcaacgtg 1260
ttcagctgct ccgtgatgca cgaggccctg cacaatcact acacccagaa gagcctgagc 1320
ctgtcccctg gcaag 1335

SEQ ID NO: 104 moltype = AA length = 445
FEATURE Location/Qualifiers
REGION 1..445
note = Humansed antibody sequence
source 1..445
mol_type = protein
organism = synthetic construct
SEQUENCE: 104
QVQLVQSGAE VKKPGSSVKV SCKASGYTFT DYYMKWVRQA PGQGLEWMGE IYPNNGGITY 60
NQKFKGRVTI TADKSTSTAY MELSSLRSED TAVYYCANGY EFVYWGQGTL VTVSSASTKG 120
PSVFPLAPSS KSTSGGTAAL GCLVKDYFPE PVTVSWNSGA LTSGVHTFPA VLQSSGLYSL 180
SSVVTVPSSS LGTQTYICNV NHKPSNTKVD KKVEPKSCDK THTCPPCPAP ELLGGPSVFL 240
FPPKPKDTLM ISRTPEVTCV VVDVSHEDPE VKFNWYVDGV EVHNAKTKPR EEQYNSTYRV 300
VSVLTVLHQD WLNGKEYKCK VSNKALPAPI EKTISKAKGQ PREPQVYTLP PSRDELTKNQ 360
VSLTCLVKGF YPSDIAVEWE SNGQPENNYK TTPPVLDSDG SFFLYSKLTV DKSRWQQGNV 420
FSCSVMHEAL HNHYTQKSLS LSPGK 445

SEQ ID NO: 105 moltype = DNA length = 1335
FEATURE Location/Qualifiers
misc_feature 1..1335
note = Humansed antibody sequence
source 1..1335
mol_type = other DNA
organism = synthetic construct
SEQUENCE: 105
caggtgcagc tggtgcagag cggcgccgaa gtgaagaagc ccggctccag cgtgaaggtg 60
agctgcaagg ctagcggcta caccttcacc gactactaca tgaagtgggt gaggcaggcc 120
cccggccagg gactggagtg gatgggcgag atctacccca acaacggggg catcacctac 180
aaccagaagt tcaagggcag ggtgaccatc accgccgaca aaagcaccag caccgcctac 240
atggaactga gcagcctgag gagcgaggac accgccgtgt actactgcgc caacggctac 300
gagttcgtgt attggggcca gggcacacta gtgaccgtgt ccagcgccag caccaagggc 360
cccagcgtgt tccccctggc ccccagcagc aagagcacca gcggcggcac agccgccctg 420
ggctgcctgg tgaaggacta cttccccgaa ccggtgaccg tgtcctggaa cagcggagcc 480
ctgaccagcg gcgtgcacac cttccccgcc gtgctgcaga gcagcggcct gtacagcctg 540
agcagcgtgg tgaccgtgcc cagcagcagc ctgggcaccc agacctacat ctgtaacgtg 600
aaccacaagc ccagcaacac caaggtggac aagaaggtgg agcccaagag ctgtgacaag 660
acccacacct gcccccctg ccctgccccc gagctgctgg gaggccccag cgtgttcctg 720
ttcccccca agcctaagga caccctgatg atcagcagaa cccccgaggt gacctgtgtg 780
gtggtggatg tgagccacga ggaccctgag gtgaagttca actggtacgt ggacggcgtg 840
gaggtgcaca atgccaagac caagcccagg gaggagcagt acaacagcac ctaccgggtg 900
gtgtccgtgc tgaccgtgct gcaccaggat tggctgaacg gcaaggagta caagtgtaag 960
gtgtccaaca aggccctgcc tgcccctatc gagaaaacca tcagcaaggc caagggccag 1020
cccagagagc cccaggtgta caccctgccc cctagcagag atgagctgac caagaaccag 1080
gtgtccctga cctgcctggt gaagggcttc taccccagcg acatcgccgt ggagtgggag 1140
agcaacggcc agcccgagaa caactacaag accacccccc ctgtgctgga cagcgatggc 1200
agcttcttcc tgtacagcaa gctgaccgtg gacaagagca gatggcagca gggcaacgtg 1260
ttcagctgct ccgtgatgca cgaggccctg cacaatcact acacccagaa gagcctgagc 1320
ctgtcccctg gcaag 1335

SEQ ID NO: 106 moltype = AA length = 445
FEATURE Location/Qualifiers
REGION 1..445
note = Humansed antibody sequence
source 1..445

```
                         mol_type = protein
                         organism = synthetic construct
SEQUENCE: 106
QVQLVQSGAE VKKPGSSVKV SCKASGYTFT DYYMKWVRQA PGQGLEWIGE IYPNNGGITY  60
NQKFKGRATL TVDKSTSTAY MELSSLRSED TAVYYCANGY EFVYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                     445

SEQ ID NO: 107           moltype = DNA  length = 1335
FEATURE                  Location/Qualifiers
misc_feature             1..1335
                         note = Humansed antibody sequence
source                   1..1335
                         mol_type = other DNA
                         organism = synthetic construct
SEQUENCE: 107
caggtgcagc tggtgcagag cggcgccgaa gtgaagaagc ccggctccag cgtgaaggtg  60
agctgcaagg ctagcggcta caccttcacc gactactaca tgaagtgggt gaggcaggcc  120
cccggccagg gactggagtg gataggcgag atctacccca acaacggggg catcacctac  180
aaccagaagt tcaagggcag ggcgaccctc accgtcgaca aaagcaccag caccgcctac  240
atggaactga gcagcctgag gagcgaggac accgccgtgt actactgcgc caacggctac  300
gagttcgtgt attggggcca gggcacacta gtgaccgtgt ccagcgccag caccaagggc  360
cccagcgtgt tccccctggc ccccagcagc aagagcacca gcggcggcac agccgccctg  420
ggctgcctgg tgaaggacta cttccccgaa ccggtgaccg tgtcctggaa cagcggagcc  480
ctgaccagcg gcgtgcacac cttccccgcc gtgctgcaga gcagcggcct gtacagcctg  540
agcagcgtgg tgaccgtgcc cagcagcagc ctgggcaccc agacctacat ctgtaacgtg  600
aaccacaagc ccagcaacac caaggtggac aagaaggtgg agcccaagag ctgtgacaag  660
acccacacct gccccccctg ccctgccccc gagctgctgg gaggccccag cgtgttcctg  720
ttccccccca agcctaagga caccctgatg atcagcagaa cccccgaggt gacctgtgtg  780
gtggtggatg tgagccacga ggaccctgag gtgaagttca actggtacgt ggacggcgtg  840
gaggtgcaca atgccaagac caagcccagg gaggagcagt acaacagcac ctaccgggtg  900
gtgtccgtgc tgaccgtgct gcaccaggat tggctgaacg gcaaggagta caagtgtaag  960
gtgtccaaca aggccctgcc tgcccctatc gagaaaacca tcagcaaggc caagggccag  1020
cccagagagc cccaggtgta caccctgccc cctagcagag atgagctgac caagaaccag  1080
gtgtccctga cctgcctggt gaagggcttc taccccagcg acatcgccgt ggagtgggag  1140
agcaacggcc agcccgagaa caactacaag accacccccc ctgtgctgga cagcgatggc  1200
agcttcttcc tgtacagcaa gctgaccgtg gacaagagca gatggcagca gggcaacgtg  1260
ttcagctgct ccgtgatgca cgaggccctg cacaatcact acacccagaa gagcctgagc  1320
ctgtcccctg gcaag                                                1335

SEQ ID NO: 108           moltype = AA  length = 445
FEATURE                  Location/Qualifiers
REGION                   1..445
                         note = Humansed antibody sequence
source                   1..445
                         mol_type = protein
                         organism = synthetic construct
SEQUENCE: 108
QVQLVQSGAE VKKPGSSVKV SCKASGYTFT DYYMKWVRQA PGQGLEWMGE IYPNNGGITY  60
NQKFKGRVTI TADKSTSTAY MELSSLRSED TAVYYCADGY EFVYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                     445

SEQ ID NO: 109           moltype = DNA  length = 1335
FEATURE                  Location/Qualifiers
misc_feature             1..1335
                         note = Humansed antibody sequence
source                   1..1335
                         mol_type = other DNA
                         organism = synthetic construct
SEQUENCE: 109
caggtgcagc tggtgcagag cggcgccgaa gtgaagaagc ccggctccag cgtgaaggtg  60
agctgcaagg ctagcggcta caccttcacc gactactaca tgaagtgggt gaggcaggcc  120
cccggccagg gactggagtg gatgggcgag atctacccca acaacggggg catcacctac  180
aaccagaagt tcaagggcag ggtgaccatc accgccgaca aaagcaccag caccgcctac  240
atggaactga gcagcctgag gagcgaggac accgccgtgt actactgcgc cgacggctac  300
gagttcgtgt attggggcca gggcacacta gtgaccgtgt ccagcgccag caccaagggc  360
cccagcgtgt tccccctggc ccccagcagc aagagcacca gcggcggcac agccgccctg  420
ggctgcctgg tgaaggacta cttccccgaa ccggtgaccg tgtcctggaa cagcggagcc  480
ctgaccagcg gcgtgcacac cttccccgcc gtgctgcaga gcagcggcct gtacagcctg  540
agcagcgtgg tgaccgtgcc cagcagcagc ctgggcaccc agacctacat ctgtaacgtg  600
```

```
aaccacaagc ccagcaacac caaggtggac aagaaggtgg agcccaagag ctgtgacaag  660
acccacacct gcccccctg ccctgccccc gagctgctgg gaggccccag cgtgttcctg  720
ttcccccca agcctaagga caccctgatg atcagcagaa cccccgaggt gacctgtgtg  780
gtggtggatg tgagccacga ggaccctgag gtgaagttca actggtacgt ggacggcgtg  840
gaggtgcaca atgccaagac caagcccagg gaggagcagt acaacagcac ctaccgggtg  900
gtgtccgtgc tgaccgtgct gcaccaggat tggctgaacg gcaaggagta caagtgtaag  960
gtgtccaaca aggccctgcc tgcccctatc gagaaaacca tcagcaaggc caagggccag  1020
cccagagagc cccaggtgta caccctgccc cctagcagag atgagctgac caagaaccag  1080
gtgtccctga cctgcctggt gaagggcttc taccccagcg acatcgccgt ggagtgggag  1140
agcaacggcc agcccgagaa caactacaag accacccccc ctgtgctgga cagcgatggc  1200
agcttcttcc tgtacagcaa gctgaccgtg gacaagagca gatggcagca gggcaacgtg  1260
ttcagctgct ccgtgatgca cgaggccctg cacaatcact acacccagaa gagcctgagc  1320
ctgtcccctg gcaag                                                   1335

SEQ ID NO: 110         moltype = AA  length = 445
FEATURE                Location/Qualifiers
REGION                 1..445
                       note = Humansed antibody sequence
source                 1..445
                       mol_type = protein
                       organism = synthetic construct
SEQUENCE: 110
QVQLVQSGAE VKKPGSSVKV SCKASGYTFT DYYMKWVRQA PGQGLEWIGE IYPNNGGITY  60
NQKFKGRATL TVDKSTSTAY MELSSLRSED TAVYYCANGY EFDYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                        445

SEQ ID NO: 111         moltype = DNA  length = 1335
FEATURE                Location/Qualifiers
misc_feature           1..1335
                       note = Humansed antibody sequence
source                 1..1335
                       mol_type = other DNA
                       organism = synthetic construct
SEQUENCE: 111
caggtgcagc tggtgcagag cggcgccgaa gtgaagaagc ccggctccag cgtgaaggtg  60
agctgcaagg ctagcggcta caccttcacc gactactaca tgaagtgggt gaggcaggcc  120
cccggccagg gactggagtg gataggcgag atctacccca acaacggggg catcacctac  180
aaccagaagt tcaagggcag ggcgaccctc accgtcgaca aaagcaccag caccgcctac  240
atggaactga gcagcctgag gagcgaggac accgccgtgt actactgcgc caacggctac  300
gagttcgact attggggcca gggcacacta gtgaccgtgt ccagcgccag caccaagggc  360
cccagcgtgt tccccctggc ccccagcagc aagagcacca gcggcggcac agccgccctg  420
ggctgcctgg tgaaggacta cttccccgaa ccggtgaccg tgtcctggaa cagcggagcc  480
ctgaccagcg gcgtgcacac cttccccgcc gtgctgcaga gcagcggcct gtacagcctg  540
agcagcgtgg tgaccgtgcc cagcagcagc ctgggcaccc agacctacat ctgtaacgtg  600
aaccacaagc ccagcaacac caaggtggac aagaaggtgg agcccaagag ctgtgacaag  660
acccacacct gcccccctg ccctgccccc gagctgctgg gaggccccag cgtgttcctg  720
ttcccccca agcctaagga caccctgatg atcagcagaa cccccgaggt gacctgtgtg  780
gtggtggatg tgagccacga ggaccctgag gtgaagttca actggtacgt ggacggcgtg  840
gaggtgcaca atgccaagac caagcccagg gaggagcagt acaacagcac ctaccgggtg  900
gtgtccgtgc tgaccgtgct gcaccaggat tggctgaacg gcaaggagta caagtgtaag  960
gtgtccaaca aggccctgcc tgcccctatc gagaaaacca tcagcaaggc caagggccag  1020
cccagagagc cccaggtgta caccctgccc cctagcagag atgagctgac caagaaccag  1080
gtgtccctga cctgcctggt gaagggcttc taccccagcg acatcgccgt ggagtgggag  1140
agcaacggcc agcccgagaa caactacaag accacccccc ctgtgctgga cagcgatggc  1200
agcttcttcc tgtacagcaa gctgaccgtg gacaagagca gatggcagca gggcaacgtg  1260
ttcagctgct ccgtgatgca cgaggccctg cacaatcact acacccagaa gagcctgagc  1320
ctgtcccctg gcaag                                                   1335

SEQ ID NO: 112         moltype = AA  length = 214
FEATURE                Location/Qualifiers
REGION                 1..214
                       note = Humansed antibody sequence
source                 1..214
                       mol_type = protein
                       organism = synthetic construct
SEQUENCE: 112
DIQMTQSPSS LSASVGDRVT ITCSASQGIS NYLNWYQQKP GKAPKLLIYY TSSLHSGVPS  60
RFSGSGSGTD FTLTISSLQP EDFATYYCQQ YSKLPWTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 113         moltype = DNA  length = 642
FEATURE                Location/Qualifiers
misc_feature           1..642
```

```
                         note = Humansed antibody sequence
source                   1..642
                         mol_type = other DNA
                         organism = synthetic construct
SEQUENCE: 113
gacatccaga tgacccagag cccctcaagc ctgagcgcca gcgtgggcga cagggtgact  60
atcacctgca gcgcctccca gggcatcagc aactacctga actggtacca gcagaagccc  120
ggcaaggccc ctaagctgct gatctactac accagcagcc tgcacagcgg cgtgcccagc  180
aggttctccg gcagcggcag cggaaccgac ttcaccctga ccattagcag cctccagccc  240
gaggacttcg ccacctacta ctgccagcag tacagcaagc tgccctggac cttcggccag  300
ggcaccaaac tggagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                    642

SEQ ID NO: 114           moltype = AA  length = 214
FEATURE                  Location/Qualifiers
REGION                   1..214
                         note = Humansed antibody sequence
source                   1..214
                         mol_type = protein
                         organism = synthetic construct
SEQUENCE: 114
DIQMTQSPSS LSASVGDRVT ITCSASQGIS NYLNWYQQKP GKAPKLLIYY TSSLHSGVPS  60
RFSGSGSGTD YTLTISSLQP EDFATYYCQQ YSKLPWTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 115           moltype = DNA  length = 642
FEATURE                  Location/Qualifiers
misc_feature             1..642
                         note = Humansed antibody sequence
source                   1..642
                         mol_type = other DNA
                         organism = synthetic construct
SEQUENCE: 115
gacatccaga tgacccagag cccctcaagc ctgagcgcca gcgtgggcga cagggtgact  60
atcacctgca gcgcctccca gggcatcagc aactacctga actggtacca gcagaagccc  120
ggcaaggccc ctaagctgct gatctactac accagcagcc tgcacagcgg cgtgcccagc  180
aggttctccg gcagcggcag cggaaccgac tacaccctga ccattagcag cctccagccc  240
gaggacttcg ccacctacta ctgccagcag tacagcaagc tgccctggac cttcggccag  300
ggcaccaaac tggagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                    642

SEQ ID NO: 116           moltype = AA  length = 118
FEATURE                  Location/Qualifiers
source                   1..118
                         mol_type = protein
                         organism = Mus musculus
SEQUENCE: 116
EVQLQQSGPV LVKPGASVKM SCEASGYTFT DYYMNWVKQS HGKTLEWIGV INPYNGGTDY  60
NQKFKGKATL TVDKSSSTAY MELNSLTSED SAVYYCARSV YDYPFDYWGQ GTLVTVSS   118

SEQ ID NO: 117           moltype = DNA  length = 354
FEATURE                  Location/Qualifiers
source                   1..354
                         mol_type = genomic DNA
                         organism = Mus musculus
SEQUENCE: 117
gaggtgcagc tgcagcagag cggccccgtg ctggtgaagc ctggagccag cgtgaaaatg  60
agctgcgaag ccagcggcta caccttcacc gactactaca tgaactgggt gaagcagagc  120
cacggcaaga ccctggagtg gatcggcgtg atcaacccct acaacggggg caccgactac  180
aaccagaagt tcaagggcaa ggccactctg accgtggaca agagctccag caccgcctac  240
atggaactga acagcctcac ctctgaggac agcgccgtct attactgcgc caggagcgtg  300
tacgactacc ccttcgacta ctggggccag ggcacactag tgaccgtgtc cagc        354

SEQ ID NO: 118           moltype = AA  length = 448
FEATURE                  Location/Qualifiers
REGION                   1..448
                         note = Chimeric antibody sequence
source                   1..448
                         mol_type = protein
                         organism = synthetic construct
```

-continued

```
SEQUENCE: 118
EVQLQQSGPV LVKPGASVKM SCEASGYTFT DYYMNWVKQS HGKTLEWIGV INPYNGGTDY  60
NQKFKGKATL TVDKSSSTAY MELNSLTSED SAVYYCARSV YDYPFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 119          moltype = DNA  length = 1344
FEATURE                 Location/Qualifiers
misc_feature            1..1344
                        note = Chimeric antibody sequence
source                  1..1344
                        mol_type = other DNA
                        organism = synthetic construct
SEQUENCE: 119
gaggtgcagc tgcagcagag cggccccgtg ctggtgaagc ctggagccag cgtgaaaatg  60
agctgcgaag ccagcggcta caccttcacc gactactaca tgaactgggt gaagcagagc  120
cacggcaaga ccctggagtg gatcggcgtg atcaacccct acaacggggg caccgactac  180
aaccagaagt tcaagggcaa ggccactctg accgtggaca agagctccag caccgcctac  240
atggaactga acagcctcac ctctgaggac agcgccgtct attactgcgc caggagcgtg  300
tacgactacc ccttcgacta ctggggccag ggcacactag tgaccgtgtc cagcgccagc  360
accaagggcc ccagcgtgtt cccccctggcc cccagcagca agagcaccag cggcggcaca  420
gccgccctgg gctgcctggt gaaggactac ttccccgaac cggtgaccgt gtcctggaac  480
agcggagccc tgaccagcgg cgtgcacacc ttccccgccg tgctgcagag cagcggcctg  540
tacagcctga gcagcgtggt gaccgtgccc agcagcagcc tgggcaccca gacctacatc  600
tgtaacgtga accacaagcc cagcaacacc aaggtggaca agaaggtgga gcccaagagc  660
tgtgacaaga cccacacctg ccccccctgc cctgcccccg agctgctggg aggccccagc  720
gtgttcctgt tcccccccaa gcctaaggac accctgatga tcagcagaac ccccgaggtg  780
acctgtgtgg tggtggatgt gagccacgag gaccctgagg tgaagttcaa ctggtacgtg  840
gacggcgtgg aggtgcacaa tgccaagacc aagcccaggg aggagcagta caacagcacc  900
taccgggtgg tgtccgtgct gaccgtgctg caccaggatt ggctgaacgg caaggagtac  960
aagtgtaagg tgtccaacaa ggccctgcct gcccctatcg agaaaaccat cagcaaggcc  1020
aagggccagc ccagagagcc ccaggtgtac accctgcccc ctagcagaga tgagctgacc  1080
aagaaccagg tgtccctgac ctgcctggtg aagggcttct accccagcga catcgccgtg  1140
gagtgggaga gcaacggcca gcccgagaac aactacaaga ccaccccccc tgtgctggac  1200
agcgatggca gcttcttcct gtacagcaag ctgaccgtgg acaagagcag atggcagcag  1260
ggcaacgtgt tcagctgctc cgtgatgcac gaggccctgc acaatcacta cacccagaag  1320
agcctgagcc tgtcccctgg caag                                        1344

SEQ ID NO: 120          moltype = AA  length = 111
FEATURE                 Location/Qualifiers
source                  1..111
                        mol_type = protein
                        organism = Mus musculus
SEQUENCE: 120
DIVLTQSPAS LAVSLGQRAT ISCRASESVS IHGTHLMHWY QQKPGQPPKL LIYAASNLES  60
GVPARFSGSG SETDFTLNIH PVEEEDAATY FCQQSIEDPR TFGGGTKLEI K           111

SEQ ID NO: 121          moltype = DNA  length = 336
FEATURE                 Location/Qualifiers
source                  1..336
                        mol_type = genomic DNA
                        organism = Mus musculus
SEQUENCE: 121
gacatcgtcc tgacccagag ccccgccagc ctggccgtga gcctgggcca gagggccaca  60
atcagctgca gggcctctga gtccgtgagc atccacggca cccacctgat gcactggtat  120
cagcagaagc ccggccagcc tcccaagctg ctgatctacg ccgccagcaa cctggagagc  180
ggcgtgcccg ctaggttcag cggaagcggc agcgagaccg acttcaccct gaacatccac  240
cccgtggagg aggaagacgc cgccacctac ttctgccagc agagcatcga ggaccccagg  300
accttcggcg ggggcaccaa gctcgagatt aagcgt                           336

SEQ ID NO: 122          moltype = AA  length = 237
FEATURE                 Location/Qualifiers
REGION                  1..237
                        note = Chimeric antibody sequence
source                  1..237
                        mol_type = protein
                        organism = synthetic construct
SEQUENCE: 122
MGWSCIILFL VATATGVHSD IVLTQSPASL AVSLGQRATI SCRASESVSI HGTHLMHWYQ  60
QKPGQPPKLL IYAASNLESG VPARFSGSGS ETDFTLNIHP VEEEDAATYF CQQSIEDPRT  120
FGGGTKLEIK RTVAAPSVFI FPPSDEQLKS GTASVVCLLN NFYPREAKVQ WKVDNALQSG  180
NSQESVTEQD SKDSTYSLSS TLTLSKADYE KHKVYACEVT HQGLSSPVTK SFNRGEC     237

SEQ ID NO: 123          moltype = DNA  length = 711
FEATURE                 Location/Qualifiers
```

-continued

```
misc_feature          1..711
                      note = Chimeric antibody sequence
source                1..711
                      mol_type = other DNA
                      organism = synthetic construct
SEQUENCE: 123
atgggctggt cctgcatcat cctgtttctg gtggccaccg ccaccggcgt gcacagcgac  60
atcgtcctga cccagagccc cgccagcctg gccgtgagcc tgggccagag ggccacaatc  120
agctgcaggg cctctgagtc cgtgagcatc cacggcaccc acctgatgca ctggtatcag  180
cagaagcccg gccagcctcc caagctgctg atctacgccg ccagcaacct ggagagcggc  240
gtgcccgcta ggttcagcgg aagcggcagc gagaccgact tcaccctgaa catccacccc  300
gtggaggagg aagacgccgc cacctacttc tgccagcaga gcatcgagga ccccaggacc  360
ttcggcgggg gcaccaagct cgagattaag cgtacggtgg ccgcccccag cgtgttcatc  420
ttccccccca gcgatgagca gctgaagagc ggcaccgcca gcgtggtgtg tctgctgaac  480
aacttctacc cccgggaggc caaggtgcag tggaaggtgg acaatgccct gcagagcggc  540
aacagccagg agagcgtgac cgagcaggac agcaaggact ccacctacag cctgagcagc  600
accctgaccc tgagcaaggc cgactacgag aagcacaagg tgtacgcctg tgaggtgacc  660
caccagggcc tgtccagccc cgtgaccaag agcttcaacc ggggcgagtg c           711

SEQ ID NO: 124        moltype = AA  length = 119
FEATURE               Location/Qualifiers
source                1..119
                      mol_type = protein
                      organism = Mus musculus
SEQUENCE: 124
EVQLQQSGPE LVKPGTSVKI PCKTSGYIFT DYSIDWVKQS HGKSLEWIGD IDPNYGDPIY  60
NHKFKGKATL TVDRSSSTAY MELRSLTSED TAVYFCARRA TGTDWFAFWG QGTLVTVSS   119

SEQ ID NO: 125        moltype = DNA  length = 357
FEATURE               Location/Qualifiers
source                1..357
                      mol_type = genomic DNA
                      organism = Mus musculus
SEQUENCE: 125
gaggtgcagc tgcagcagag cggccccgag ctggtgaaac ccggcaccag cgtgaagatc  60
ccctgcaaga cctctggcta catcttcacc gactacagca tcgactgggt gaagcagagc  120
cacggcaagt ctctggagtg gattggggac atcgacccca actacggcga ccccatctac  180
aaccacaagt tcaagggcaa ggccaccctg accgtggaca ggagcagcag caccgcctac  240
atggaactca ggagcctgac cagcgaggac accgccgtgt atttttgcgc caggagggcc  300
accggcactg attggttcgc cttctggggc cagggcacac tagtgaccgt gtccagc     357

SEQ ID NO: 126        moltype = AA  length = 449
FEATURE               Location/Qualifiers
REGION                1..449
                      note = Chimeric antibody sequence
source                1..449
                      mol_type = protein
                      organism = synthetic construct
SEQUENCE: 126
EVQLQQSGPE LVKPGTSVKI PCKTSGYIFT DYSIDWVKQS HGKSLEWIGD IDPNYGDPIY  60
NHKFKGKATL TVDRSSSTAY MELRSLTSED TAVYFCARRA TGTDWFAFWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 127        moltype = DNA  length = 1347
FEATURE               Location/Qualifiers
misc_feature          1..1347
                      note = Chimeric antibody sequence
source                1..1347
                      mol_type = other DNA
                      organism = synthetic construct
SEQUENCE: 127
gaggtgcagc tgcagcagag cggccccgag ctggtgaaac ccggcaccag cgtgaagatc  60
ccctgcaaga cctctggcta catcttcacc gactacagca tcgactgggt gaagcagagc  120
cacggcaagt ctctggagtg gattggggac atcgacccca actacggcga ccccatctac  180
aaccacaagt tcaagggcaa ggccaccctg accgtggaca ggagcagcag caccgcctac  240
atggaactca ggagcctgac cagcgaggac accgccgtgt atttttgcgc caggagggcc  300
accggcactg attggttcgc cttctggggc cagggcacac tagtgaccgt gtccagcgcc  360
agcaccaagg gccccagcgt gttccccctg gcccccagca gcaagagcac cagcggcggc  420
acagccgccc tgggctgcct ggtgaaggac tacttccccg aaccggtgac cgtgtcctgg  480
aacagcggag ccctgaccag cggcgtgcac accttccccg ccgtgctgca gagcagcggc  540
ctgtacagcc tgagcagcgt ggtgaccgtg cccagcagca gcctgggcac ccagacctac  600
atctgtaacg tgaaccacaa gcccagcaac accaaggtgg acaagaaggt ggagcccaag  660
agctgtgaca agacccacac ctgccccccc tgccctgccc ccgagctgct gggaggcccc  720
agcgtgttcc tgttcccccc caagcctaag gacaccctga tgatcagcag aacccccgag  780
```

-continued

```
gtgacctgtg tggtggtgga tgtgagccac gaggaccctg aggtgaagtt caactggtac  840
gtggacggcg tggaggtgca caatgccaag accaagccca gggaggagca gtacaacagc  900
acctaccggg tggtgtccgt gctgaccgtg ctgcaccagg attggctgaa cggcaaggag  960
tacaagtgta aggtgtccaa caaggccctg cctgccccta tcgagaaaac catcagcaag  1020
gccaagggcc agcccagaga gccccaggtg tacaccctgc cccctagcag agatgagctg  1080
accaagaacc aggtgtccct gacctgcctg gtgaagggct tctaccccag cgacatcgcc  1140
gtggagtggg agagcaacgg ccagcccgag aacaactaca agaccacccc ccctgtgctg  1200
gacagcgatg gcagcttctt cctgtacagc aagctgaccg tggacaagag cagatggcag  1260
cagggcaacg tgttcagctg ctccgtgatg cacgaggccc tgcacaatca ctacacccag  1320
aagagcctga gcctgtcccc tggcaag                                      1347

SEQ ID NO: 128         moltype = AA  length = 108
FEATURE                Location/Qualifiers
source                 1..108
                       mol_type = protein
                       organism = Mus musculus
SEQUENCE: 128
DIQMTQSPAS LSVSVGETVT ITCRASENIY NNLAWYQQKQ GKSPQLLVYA ATILADGVPS  60
RFSGSGSGTQ YSLKINSLQS GDFGTYYCQH FWGTPLTFGA GTKLELKR               108

SEQ ID NO: 129         moltype = DNA  length = 324
FEATURE                Location/Qualifiers
source                 1..324
                       mol_type = genomic DNA
                       organism = Mus musculus
SEQUENCE: 129
gacatccaga tgacccagag ccccgctagc ctcagcgtgt ccgtcggcga gaccgtgacc  60
atcacctgca gggccagcga gaacatctac aacaacctgg cctggtatca gcagaagcag  120
ggcaaaagcc cccagctgct ggtgtacgcc gccaccattc tggccgacgg cgtgcccagc  180
aggttctctg gaagcggcag cggcacccag tacagcctga agatcaacag cctgcagagc  240
ggggacttcg gcacctacta ctgccagcac ttctggggca ctcccctgac cttcggagcc  300
ggcaccaagc tggagctgaa gcgt                                         324

SEQ ID NO: 130         moltype = AA  length = 214
FEATURE                Location/Qualifiers
REGION                 1..214
                       note = Chimeric antibody sequence
source                 1..214
                       mol_type = protein
                       organism = synthetic construct
SEQUENCE: 130
DIQMTQSPAS LSVSVGETVT ITCRASENIY NNLAWYQQKQ GKSPQLLVYA ATILADGVPS  60
RFSGSGSGTQ YSLKINSLQS GDFGTYYCQH FWGTPLTFGA GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 131         moltype = DNA  length = 642
FEATURE                Location/Qualifiers
misc_feature           1..642
                       note = Chimeric antibody sequence
source                 1..642
                       mol_type = other DNA
                       organism = synthetic construct
SEQUENCE: 131
gacatccaga tgacccagag ccccgctagc ctcagcgtgt ccgtcggcga gaccgtgacc  60
atcacctgca gggccagcga gaacatctac aacaacctgg cctggtatca gcagaagcag  120
ggcaaaagcc cccagctgct ggtgtacgcc gccaccattc tggccgacgg cgtgcccagc  180
aggttctctg gaagcggcag cggcacccag tacagcctga agatcaacag cctgcagagc  240
ggggacttcg gcacctacta ctgccagcac ttctggggca ctcccctgac cttcggagcc  300
ggcaccaagc tggagctgaa gcgtacggtg gccgcccca gcgtgttcat cttcccccc  360
agcgatgagc agctgaagag cggcaccgcc agcgtggtgt gtctgctgaa caacttctac  420
cccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                     642

SEQ ID NO: 132         moltype = AA  length = 118
FEATURE                Location/Qualifiers
source                 1..118
                       mol_type = protein
                       organism = Mus musculus
SEQUENCE: 132
QVQLQQPGAE LVKPGASVKL SCKASGYTFT NYWMHWVKQR PGQGLEWIGI IHPNSGSTNY  60
NEKFKSKATL TVDKSSSTAY MQLSSLTSED SAVYYCARGI YDYPFAYWGQ GTLVTVSS    118

SEQ ID NO: 133         moltype = DNA  length = 354
FEATURE                Location/Qualifiers
source                 1..354
                       mol_type = genomic DNA
```

```
                         organism = Mus musculus
SEQUENCE: 133
caggtgcagc tccagcagcc cggagccgaa ctggtgaagc ccggagccag cgtcaaactg  60
tcctgcaagg ccagcggcta caccttcacc aactactgga tgcactgggt gaagcagagg  120
cccggccagg gcctggagtg gatcggcatc atccacccca acagcgggag caccaactac  180
aacgagaagt tcaagagcaa ggccaccctg accgtggaca agagcagcag cactgcctac  240
atgcagctga gcagcctgac cagcgaggac agcgctgtgt actactgcgc caggggcatc  300
tacgactacc ccttcgccta ttggggccag ggcacactag tgaccgtgtc cagc        354

SEQ ID NO: 134           moltype = AA  length = 448
FEATURE                  Location/Qualifiers
REGION                   1..448
                         note = Chimeric antibody sequence
source                   1..448
                         mol_type = protein
                         organism = synthetic construct
SEQUENCE: 134
QVQLQQPGAE LVKPGASVKL SCKASGYTFT NYWMHWVKQR PGQGLEWIGI IHPNSGSTNY  60
NEKFKSKATL TVDKSSSTAY MQLSSLTSED SAVYYCARGI YDYPFAYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 135           moltype = DNA  length = 1344
FEATURE                  Location/Qualifiers
misc_feature             1..1344
                         note = Chimeric antibody sequence
source                   1..1344
                         mol_type = other DNA
                         organism = synthetic construct
SEQUENCE: 135
caggtgcagc tccagcagcc cggagccgaa ctggtgaagc ccggagccag cgtcaaactg  60
tcctgcaagg ccagcggcta caccttcacc aactactgga tgcactgggt gaagcagagg  120
cccggccagg gcctggagtg gatcggcatc atccacccca acagcgggag caccaactac  180
aacgagaagt tcaagagcaa ggccaccctg accgtggaca agagcagcag cactgcctac  240
atgcagctga gcagcctgac cagcgaggac agcgctgtgt actactgcgc caggggcatc  300
tacgactacc ccttcgccta ttggggccag ggcacactag tgaccgtgtc cagcgccagc  360
accaagggcc ccagcgtgtt ccccctggcc cccagcagca agagcaccag cggcggcaca  420
gccgccctgg gctgcctggt gaaggactac ttccccgaac cggtgaccgt gtcctggaac  480
agcggagccc tgaccagcgg cgtgcacacc ttccccgccg tgctgcagag cagcggcctg  540
tacagcctga gcagcgtggt gaccgtgccc agcagcagcc tgggcaccca gacctacatc  600
tgtaacgtga accacaagcc cagcaacacc aaggtggaca agaaggtgga gcccaagagc  660
tgtgacaaga cccacacctg ccccccctgc cctgcccccg agctgctggg aggccccagc  720
gtgttcctgt tcccccccaa gcctaaggac accctgatga tcagcagaac ccccgaggtg  780
acctgtgtgg tggtggatgt gagccacgag gaccctgagg tgaagttcaa ctggtacgtg  840
gacggcgtgg aggtgcacaa tgccaagacc aagcccaggg aggagcagta caacagcacc  900
taccgggtgg tgtccgtgct gaccgtgctg caccaggatt ggctgaacgg caaggagtac  960
aagtgtaagg tgtccaacaa ggccctgcct gcccctatcg agaaaaccat cagcaaggcc  1020
aagggccagc ccagagagcc ccaggtgtac accctgcccc ctagcagaga tgagctgacc  1080
aagaaccagg tgtccctgac ctgcctggtg aagggcttct accccagcga catcgccgtg  1140
gagtgggaga gcaacggcca gcccgagaac aactacaaga ccaccccccc tgtgctggac  1200
agcgatggca gcttcttcct gtacagcaag ctgaccgtgg acaagagcag atggcagcag  1260
ggcaacgtgt tcagctgctc cgtgatgcac gaggccctgc acaatcacta cacccagaag  1320
agcctgagcc tgtcccctgg caag                                         1344

SEQ ID NO: 136           moltype = AA  length = 112
FEATURE                  Location/Qualifiers
source                   1..112
                         mol_type = protein
                         organism = Mus musculus
SEQUENCE: 136
DIVLTQSPAS LAVSLGQRAT ISCRASESVS IHGTHLMHWY QQKPGQPPKL LIYAASNLES  60
GVPARFSGSG SETDFTLNIH PVEEEDAATY FCQQSIEDPY TFGGGTKLEI KR          112

SEQ ID NO: 137           moltype = DNA  length = 336
FEATURE                  Location/Qualifiers
source                   1..336
                         mol_type = genomic DNA
                         organism = Mus musculus
SEQUENCE: 137
gacatcgtgc tgacccagtc tcccgctagc ctggccgtgt ctctgggcca gagggccaca  60
atcagctgca gggccagcga gagcgtcagc attcacggca cccacctgat gcactggtac  120
cagcagaagc ccggccagcc tcccaagctc ctgatctacg ccgccagcaa cctggaaagc  180
ggagtgcccg ccaggttcag cggcagcggc tccgagaccg acttcaccct gaacatccac  240
cccgtggagg aggaggacgc cgccacctac ttctgccagc agagcatcga ggacccctac  300
accttcggcg gcggcaccaa gctggagatc aagcgt                            336
```

```
SEQ ID NO: 138          moltype = AA  length = 218
FEATURE                 Location/Qualifiers
REGION                  1..218
                        note = Chimeric antibody sequence
source                  1..218
                        mol_type = protein
                        organism = synthetic construct
SEQUENCE: 138
DIVLTQSPAS LAVSLGQRAT ISCRASESVS IHGTHLMHWY QQKPGQPPKL LIYAASNLES  60
GVPARFSGSG SETDFTLNIH PVEEEDAATY FCQQSIEDPY TFGGGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 139          moltype = DNA  length = 654
FEATURE                 Location/Qualifiers
misc_feature            1..654
                        note = Chimeric antibody sequence
source                  1..654
                        mol_type = other DNA
                        organism = synthetic construct
SEQUENCE: 139
gacatcgtgc tgacccagtc tcccgctagc ctggccgtgt ctctgggcca gagggccaca  60
atcagctgca gggccagcga gagcgtcagc attcacggca cccacctgat gcactggtac  120
cagcagaagc ccggccagcc tcccaagctc ctgatctacg ccgccagcaa cctggaaagc  180
ggagtgcccg ccaggttcag cggcagcggc tccgagaccg acttcaccct gaacatccac  240
cccgtggagg aggaggacgc cgccacctac ttctgccagc agagcatcga ggacccctac  300
accttcggcg gcggcaccaa gctggagatc aagcgtacgg tggccgcccc cagcgtgttc  360
atcttccccc ccagcgatga gcagctgaag agcggcaccg ccagcgtggt gtgtctgctg  420
aacaacttct acccccggga ggccaaggtg cagtggaagg tggacaatgc cctgcagagc  480
ggcaacagcc aggagagcgt gaccgagcag gacagcaagg actccaccta cagcctgagc  540
agcaccctga ccctgagcaa ggccgactac gagaagcaca aggtgtacgc ctgtgaggtg  600
acccaccagg gcctgtccag ccccgtgacc aagagcttca accggggcga gtgc        654

SEQ ID NO: 140          moltype = AA  length = 120
FEATURE                 Location/Qualifiers
source                  1..120
                        mol_type = protein
                        organism = Mus musculus
SEQUENCE: 140
EVKLLQSGGG LVQPGGSLKL SCAASGIDFS RYWMSWVRRA PGKGLEWIGE INPDRSTINY  60
APSLKDKFII SRDNAKNTLY LQMSKVRSED TALYYCAVFY YDYEGAMDYW GQGTSVTVSS  120

SEQ ID NO: 141          moltype = DNA  length = 360
FEATURE                 Location/Qualifiers
source                  1..360
                        mol_type = genomic DNA
                        organism = Mus musculus
SEQUENCE: 141
gaggtgaagc ttctccagtc tggaggtggc ctggtgcagc ctggaggatc cctgaaactc  60
tcctgtgcag cctcaggaat cgattttagt agatactgga tgagttgggt tcggcgggct  120
ccagggaaag gactagaatg gattggagaa attaatccag ataggagtac aatcaactat  180
gcaccatctc taaaggataa attcatcatc tccagagaca acgccaaaaa tacgctgtac  240
ctgcaaatga gcaaagtgag atctgaggac acagcccttt attactgtgc agttttctac  300
tatgattacg agggtgctat ggactactgg ggtcaaggaa cctcagtcac cgtctcctca  360

SEQ ID NO: 142          moltype = AA  length = 450
FEATURE                 Location/Qualifiers
REGION                  1..450
                        note = Chimeric antibody sequence
source                  1..450
                        mol_type = protein
                        organism = synthetic construct
SEQUENCE: 142
EVKLLQSGGG LVQPGGSLKL SCAASGIDFS RYWMSWVRRA PGKGLEWIGE INPDRSTINY  60
APSLKDKFII SRDNAKNTLY LQMSKVRSED TALYYCAVFY YDYEGAMDYW GQGTSVTVSS  120
AKTTAPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 143          moltype = DNA  length = 1350
FEATURE                 Location/Qualifiers
misc_feature            1..1350
                        note = Chimeric antibody sequence
source                  1..1350
                        mol_type = other DNA
```

```
                         organism = synthetic construct
SEQUENCE: 143
gaggtgaagc ttctccagtc tggaggtggc ctggtgcagc ctggaggatc cctgaaactc  60
tcctgtgcag cctcaggaat cgattttagt agatactgga tgagttgggt tcggcgggct  120
ccagggaaag gactagaatg gattggagaa attaatccag ataggagtac aatcaactat  180
gcaccatctc taaaggataa attcatcatc tccagagaca acgccaaaaa tacgctgtac  240
ctgcaaatga gcaaagtgag atctgaggac acagcccttt attactgtgc agttttctac  300
tatgattacg agggtgctat ggactactgg ggtcaaggaa cctcagtcac cgtctcctca  360
gccaaaacaa cagcccccag cgtgttcccc ctggccccca gcagcaagag caccagcggc  420
ggcacagccg ccctgggctg cctggtgaag gactacttcc ccgaaccggt gaccgtgtcc  480
tggaacagcg gagccctgac cagcggcgtg cacaccttcc ccgccgtgct gcagagcagc  540
ggcctgtaca gcctgagcag cgtggtgacc gtgcccagca gcagcctggg cacccagacc  600
tacatctgta acgtgaacca caagcccagc aacaccaagg tggacaagaa ggtggagccc  660
aagagctgtg acaagaccca cacctgcccc ccctgccctg cccccgagct gctgggaggc  720
cccagcgtgt tcctgttccc ccccaagcct aaggacaccc tgatgatcag cagaaccccc  780
gaggtgacct gtgtggtggt ggatgtgagc cacgaggacc ctgaggtgaa gttcaactgg  840
tacgtggacg gcgtggaggt gcacaatgcc aagaccaagc ccagggagga gcagtacaac  900
agcacctacc gggtggtgtc cgtgctgacc gtgctgcacc aggattggct gaacggcaag  960
gagtacaagt gtaaggtgtc caacaaggcc ctgcctgccc ctatcgagaa aaccatcagc  1020
aaggccaagg gccagcccag agagccccag gtgtacaccc tgccccctag cagagatgag  1080
ctgaccaaga accaggtgtc cctgacctgc ctggtgaagg gcttctaccc cagcgacatc  1140
gccgtggagt gggagagcaa cggccagccc gagaacaact acaagaccac cccccctgtg  1200
ctggacagcg atggcagctt cttcctgtac agcaagctga ccgtggacaa gagcagatgg  1260
cagcagggca acgtgttcag ctgctccgtg atgcacgagg ccctgcacaa tcactacacc  1320
cagaagagcc tgagcctgtc ccctggcaag                                  1350

SEQ ID NO: 144          moltype = AA  length = 108
FEATURE                 Location/Qualifiers
source                  1..108
                        mol_type = protein
                        organism = Mus musculus
SEQUENCE: 144
DIVMTQSQKF MSTSVGDRVS VTCKASQNVD TNVAWYQQKP GQSPKALIYS ASYRFSGVPD  60
RFTGSGSGTD FTLTISNVQS EDLAEYFCQQ YNSFPFTFGS GTKLEIKR               108

SEQ ID NO: 145          moltype = DNA  length = 324
FEATURE                 Location/Qualifiers
source                  1..324
                        mol_type = genomic DNA
                        organism = Mus musculus
SEQUENCE: 145
gacattgtga tgacccagtc tcaaaaattc atgtccacat cagtaggaga cagggtcagc  60
gtcacctgca aggccagtca gaatgtggat actaatgtag cctggtatca acaaaaacca  120
gggcaatctc ctaaagcact gatttactcg gcatcctacc ggttcagtgg agtccctgat  180
cgcttcacag gcagtggatc tgggacagat ttcactctca ccatcagcaa tgtgcagtct  240
gaagacttgg cagagtattt ctgtcagcaa tataacagct ttccattcac gttcggctcg  300
gggacaaagt tggaaataaa acgt                                        324

SEQ ID NO: 146          moltype = AA  length = 214
FEATURE                 Location/Qualifiers
REGION                  1..214
                        note = Chimeric antibody sequence
source                  1..214
                        mol_type = protein
                        organism = synthetic construct
SEQUENCE: 146
DIVMTQSQKF MSTSVGDRVS VTCKASQNVD TNVAWYQQKP GQSPKALIYS ASYRFSGVPD  60
RFTGSGSGTD FTLTISNVQS EDLAEYFCQQ YNSFPFTFGS GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 147          moltype = AA  length = 642
FEATURE                 Location/Qualifiers
REGION                  1..642
                        note = Chimeric antibody sequence
source                  1..642
                        mol_type = protein
                        organism = synthetic construct
SEQUENCE: 147
GACATTGTGA TGACCCAGTC TCAAAAATTC ATGTCCACAT CAGTAGGAGA CAGGGTCAGC  60
GTCACCTGCA AGGCCAGTCA GAATGTGGAT ACTAATGTAG CCTGGTATCA ACAAAAACCA  120
GGGCAATCTC CTAAAGCACT GATTTACTCG GCATCCTACC GGTTCAGTGG AGTCCCTGAT  180
CGCTTCACAG GCAGTGGATC TGGGACAGAT TTCACTCTCA CCATCAGCAA TGTGCAGTCT  240
GAAGACTTGG CAGAGTATTT CTGTCAGCAA TATAACAGCT TTCCATTCAC GTTCGGCTCG  300
GGGACAAAGT TGGAAATAAA ACGTACGGTG GCCGCCCCCA GCGTGTTCAT CTTCCCCCCC  360
AGCGATGAGC AGCTGAAGAG CGGCACCGCC AGCGTGGTGT GTCTGCTGAA CAACTTCTAC  420
CCCCGGGAGG CCAAGGTGCA GTGGAAGGTG GACAATGCCC TGCAGAGCGG CAACAGCCAG  480
GAGAGCGTGA CCGAGCAGGA CAGCAAGGAC TCCACCTACA GCCTGAGCAG CACCCTGACC  540
CTGAGCAAGG CCGACTACGA GAAGCACAAG GTGTACGCCT GTGAGGTGAC CCACCAGGGC  600
```

```
CTGTCCAGCC CCGTGACCAA GAGCTTCAAC CGGGGCGAGT GC                    642

SEQ ID NO: 148          moltype = AA  length = 118
FEATURE                 Location/Qualifiers
source                  1..118
                        mol_type = protein
                        organism = Mus musculus
SEQUENCE: 148
PVQLQQPGTE LVRPGTSVKL SCKASGYTFT SYWMHWVKQR PGQGLEWIGV IDPSDSYTNY  60
NQKFKGKATL TVDTSSSTAY MQLSSLTSED SAVYYCARQV FDYPMDYWGQ GTSVTVSS    118

SEQ ID NO: 149          moltype = DNA  length = 354
FEATURE                 Location/Qualifiers
source                  1..354
                        mol_type = genomic DNA
                        organism = Mus musculus
SEQUENCE: 149
ccggtccaac tgcagcagcc tgggactgag ctggtgaggc ctgggacttc agtgaagttg  60
tcctgcaagg cttctggcta caccttcacc agctactgga tgcactgggt aaagcagagg  120
cctggacaag gccttgagtg gatcggagtg attgatcctt ctgatagtta tactaactac  180
aatcaaaagt tcaagggcaa ggccacattg actgtagaca catcctccag cacagcctac  240
atgcagctca gcagcctgac atctgaggac tctgcggtct attactgtgc aagacaggtg  300
tttgactatc ctatggacta ctggggtcaa ggaacctcag tcaccgtctc ctca        354

SEQ ID NO: 150          moltype = AA  length = 448
FEATURE                 Location/Qualifiers
REGION                  1..448
                        note = Chimeric antibody sequence
source                  1..448
                        mol_type = protein
                        organism = synthetic construct
SEQUENCE: 150
PVQLQQPGTE LVRPGTSVKL SCKASGYTFT SHWMHWVKQR PGQGLEWIGV IDPSDSYTNY  60
NQKFKGKATL TVDTSSSTAY MQLSSLTSED SAVYYCARQV FDYPMDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 151          moltype = DNA  length = 1344
FEATURE                 Location/Qualifiers
misc_feature            1..1344
                        note = Chimeric antibody sequence
source                  1..1344
                        mol_type = other DNA
                        organism = synthetic construct
SEQUENCE: 151
ccggtccaac tgcagcagcc tgggactgag ctggtgaggc ctgggacttc agtgaagttg  60
tcctgcaagg cttctggcta caccttcacc agccactgga tgcactgggt aaagcagagg  120
cctggacaag gccttgagtg gatcggagtg attgatcctt ctgatagtta tactaactac  180
aatcaaaagt tcaagggcaa ggccacattg actgtagaca catcctccag cacagcctac  240
atgcagctca gcagcctgac atctgaggac tctgcggtct attactgtgc aagacaggtg  300
tttgactatc ctatggacta ctggggtcaa ggaacactag tgaccgtgtc cagcgccagc  360
accaagggcc ccagcgtgtt cccccctggcc cccagcagca agagcaccag cggcggcaca  420
gccgccctgg gctgcctggt gaaggactac ttccccgaac cggtgaccgt gtcctggaac  480
agcggagccc tgaccagcgg cgtgcacacc ttccccgccg tgctgcagag cagcggcctg  540
tacagcctga gcagcgtggt gaccgtgccc agcagcagcc tgggcaccca gacctacatc  600
tgtaacgtga accacaagcc cagcaacacc aaggtggaca agaaggtgga gcccaagagc  660
tgtgacaaga cccacacctg ccccccctgc cctgccccccg agctgctggg aggccccagc  720
gtgttcctgt tcccccccaa gcctaaggac accctgatga tcagcagaac cccgaggtg  780
acctgtgtgg tggtggatgt gagccacgag gaccctgagg tgaagttcaa ctggtacgtg  840
gacggcgtgg aggtgcacaa tgccaagacc aagcccaggg aggagcagta caacagcacc  900
taccgggtgg tgtccgtgct gaccgtgctg caccaggatt ggctgaacgg caaggagtac  960
aagtgtaagg tgtccaacaa ggccctgcct gcccctatcg agaaaaccat cagcaaggcc  1020
aagggccagc ccagagagcc ccaggtgtac accctgcccc ctagcagaga tgagctgacc  1080
aagaaccagg tgtccctgac ctgcctggtg aagggcttct accccagcga catcgccgtg  1140
gagtgggaga gcaacggcca gcccgagaac aactacaaga ccaccccccc tgtgctggac  1200
agcgatggca gcttcttcct gtacagcaag ctgaccgtgg acaagagcag atggcagcag  1260
ggcaacgtgt tcagctgctc cgtgatgcac gaggccctgc acaatcacta cacccagaag  1320
agcctgagcc tgtcccctgg caag                                        1344

SEQ ID NO: 152          moltype = AA  length = 112
FEATURE                 Location/Qualifiers
source                  1..112
                        mol_type = protein
                        organism = Mus musculus
SEQUENCE: 152
```

```
DIVLTQSPAS LAVSLGQRAT ISCRASESVS IHGTHLMHWY QQKPGQPPKL LIYAASNLES  60
GVPARFSGSG SETDFTLNIH PVEEEDAATY FCQQSIEDPW TFGGGTKLEI KR          112

SEQ ID NO: 153         moltype = DNA  length = 336
FEATURE                Location/Qualifiers
source                 1..336
                       mol_type = genomic DNA
                       organism = Mus musculus
SEQUENCE: 153
gacattgtgc tgacccaatc tccagcttct ttggctgtgt ctctagggca gagggccacc  60
atctcctgca gagccagtga aagtgtcagt attcatggta ctcatttaat gcactggtac  120
caacagaaac caggacagcc acccaaactc ctcatctatg ctgcatccaa cctagaatct  180
ggagtccctg ccaggttcag tggcagtggg tctgagacag acttcaccct caacatccat  240
cctgtggagg aggaggatgc tgcaacctat ttctgtcagc aaagtattga ggatccgtgg  300
acgttcggtg gaggcaccaa gctggaaatc aaacgt                            336

SEQ ID NO: 154         moltype = AA  length = 218
FEATURE                Location/Qualifiers
REGION                 1..218
                       note = Chimeric antibody sequence
source                 1..218
                       mol_type = protein
                       organism = synthetic construct
SEQUENCE: 154
DIVLTQSPAS LAVSLGQRAT ISCRASESVS IHGTHLMHWY QQKPGQPPKL LIYAASNLES  60
GVPARFSGSG SETDFTLNIH PVEEEDAATY FCQQSIEDPW TFGGGTKLEI NRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 155         moltype = DNA  length = 654
FEATURE                Location/Qualifiers
misc_feature           1..654
                       note = Chimeric antibody sequence
source                 1..654
                       mol_type = other DNA
                       organism = synthetic construct
SEQUENCE: 155
gacattgtgc tgacccaatc tccagcttct ttggctgtgt ctctagggca gagggccacc  60
atctcctgca gagccagtga aagtgtcagt attcatggta ctcatttaat gcactggtac  120
caacagaaac caggacagcc acccaaactc ctcatctatg ctgcatccaa cctagaatct  180
ggagtccctg ccaggttcag tggcagtggg tctgagacag acttcaccct caacatccat  240
cctgtggagg aggaggatgc tgcaacctat ttctgtcagc aaagtattga ggatccgtgg  300
acgttcggtg gaggcaccaa gctggaaatc aatcgtacgg tggccgcccc cagcgtgttc  360
atcttccccc ccagcgatga gcagctgaag agcggcaccg ccagcgtggt gtgtctgctg  420
aacaacttct acccccggga ggccaaggtg cagtggaagg tggacaatgc cctgcagagc  480
ggcaacagcc aggagagcgt gaccgagcag gacagcaagg actccaccta cagcctgagc  540
agcaccctga ccctgagcaa ggccgactac gagaagcaca aggtgtacgc ctgtgaggtg  600
acccaccagg gcctgtccag ccccgtgacc aagagcttca accggggcga gtgc        654

SEQ ID NO: 156         moltype = AA  length = 118
FEATURE                Location/Qualifiers
source                 1..118
                       mol_type = protein
                       organism = Mus musculus
SEQUENCE: 156
QVQLQQSGAE LVRPGASVTL SCKASGYTFT DYEMHWVKQT PVHGLEWIGA IDPETGGTAY  60
NQKFKGKAIL TADKSSSTAY MELRSLTSED SAVYYCTRSI YDYYFDYWGQ GTTLTVSS    118

SEQ ID NO: 157         moltype = DNA  length = 354
FEATURE                Location/Qualifiers
source                 1..354
                       mol_type = genomic DNA
                       organism = Mus musculus
SEQUENCE: 157
caggttcaac tgcagcagtc tggggctgag ctggtgaggc ctggggcttc agtgacgctg  60
tcctgcaagg cttcgggcta cacatttact gactatgaaa tgcactgggt gaagcagaca  120
cctgtgcatg gcctggaatg gattggagct attgatcctg aaactggtgg tactgcctac  180
aatcagaagt tcaagggcaa ggccatactg actgcagaca aatcctccag cacagcctac  240
atggagctcc gcagcctgac atctgaggac tctgccgtct attactgtac aagatcgatt  300
tatgattact actttgacta ctggggccaa ggcaccactc tcacagtctc ctca        354

SEQ ID NO: 158         moltype = AA  length = 448
FEATURE                Location/Qualifiers
REGION                 1..448
                       note = Chimeric antibody sequence
source                 1..448
                       mol_type = protein
                       organism = synthetic construct
SEQUENCE: 158
```

-continued

```
QVQLQQSGAE LVRPGASVTL SCKASGYTFT DYEMHWVKQT PVHGLEWIGA IDPETGGTAY  60
NQKFKGKAIL TADKSSSTAY MELRSLTSED SAVYYCTRSI YDYYFDYWGQ GTTLTVSSAK  120
TTPPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 159          moltype = DNA  length = 1344
FEATURE                 Location/Qualifiers
misc_feature            1..1344
                        note = Chimeric antibody sequence
source                  1..1344
                        mol_type = other DNA
                        organism = synthetic construct
SEQUENCE: 159
caggttcaac tgcagcagtc tggggctgag ctggtgaggc ctggggcttc agtgacgctg  60
tcctgcaagg cttcgggcta cacatttact gactatgaaa tgcactgggt gaagcagaca  120
cctgtgcatg gcctggaatg gattggagct attgatcctg aaactggtgg tactgcctac  180
aatcagaagt tcaagggcaa ggccatactg actgcagaca aatcctccag cacagcctac  240
atggagctcc gcagcctgac atctgaggac tctgccgtct attactgtac aagatcgatt  300
tatgattact actttgacta ctggggccaa ggcaccactc tcacagtctc ctcagccaaa  360
acgacacccc ccagcgtgtt cccctggcc cccagcagca agagcaccag cggcggcaca  420
gccgccctgg gctgcctggt gaaggactac ttccccgaac cggtgaccgt gtcctggaac  480
agcggagccc tgaccagcgg cgtgcacacc ttccccgccg tgctgcagag cagcggcctg  540
tacagcctga gcagcgtggt gaccgtgccc agcagcagcc tgggcaccca gacctacatc  600
tgtaacgtga accacaagcc cagcaacacc aaggtggaca agaaggtgga gcccaagagc  660
tgtgacaaga cccacacctg cccccctgc cctgccccg agctgctggg aggccccagc  720
gtgttcctgt tcccccccaa gcctaaggac accctgatga tcagcagaac ccccgaggtg  780
acctgtgtgg tggtggatgt gagccacgag gaccctgagg tgaagttcaa ctggtacgtg  840
gacggcgtgg aggtgcacaa tgccaagacc aagcccaggg aggagcagta caacagcacc  900
taccgggtgg tgtccgtgct gaccgtgctg caccaggatt ggctgaacgg caaggagtac  960
aagtgtaagg tgtccaacaa ggccctgcct gcccctatcg agaaaaccat cagcaaggcc  1020
aagggccagc ccagagagcc ccaggtgtac accctgcccc ctagcagaga tgagctgacc  1080
aagaaccagg tgtccctgac ctgcctggtg aagggcttct accccagcga catcgccgtg  1140
gagtgggaga gcaacggcca gcccgagaac aactacaaga ccaccccccc tgtgctggac  1200
agcgatggca gcttcttcct gtacagcaag ctgaccgtgg acaagagcag atggcagcag  1260
ggcaacgtgt tcagctgctc cgtgatgcac gaggccctgc acaatcacta cacccagaag  1320
agcctgagcc tgtcccctgg caag                                        1344

SEQ ID NO: 160          moltype = AA  length = 112
FEATURE                 Location/Qualifiers
source                  1..112
                        mol_type = protein
                        organism = Mus musculus
SEQUENCE: 160
DIVLTQSPAS LAVSLGQRAT ISCRASESVS IHGTHLMHWY QQKPGQPPKL LIYAASNLES  60
GVPARFSGGG SETDFTLNIH PVEEEDGATY FCQQSIEYPR TFGGGTKLEI NR          112

SEQ ID NO: 161          moltype = DNA  length = 336
FEATURE                 Location/Qualifiers
source                  1..336
                        mol_type = genomic DNA
                        organism = Mus musculus
SEQUENCE: 161
gacattgtgc tgacccaatc tccagcttct ttggctgtgt ctctagggca gagggccacc  60
atctcctgca gagccagtga aagtgtcagt attcatggta ctcatttaat gcactggtac  120
caacagaaac caggacagcc acccaaactc ctcatctatg ctgcatccaa cctagaatct  180
ggagtccctg ccaggttcag tggcggtggg tctgagacag acttcaccct caacatccat  240
cctgtggagg aggaggatgg tgcaacctat ttctgtcagc aaagtattga gtatcctcgg  300
acgttcggtg gaggcaccaa gctggaaatc aatcgt                            336

SEQ ID NO: 162          moltype = AA  length = 218
FEATURE                 Location/Qualifiers
REGION                  1..218
                        note = Chimeric antibody sequence
source                  1..218
                        mol_type = protein
                        organism = synthetic construct
SEQUENCE: 162
DIVLTQSPAS LAVSLGQRAT ISCRASESVS IHGTHLMHWY QQKPGQPPKL LIYAASNLES  60
GVPARFSGGG SETDFTLNIH PVEEEDGATY FCQQSIEYPR TFGGGTKLEI NRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 163          moltype = DNA  length = 654
FEATURE                 Location/Qualifiers
misc_feature            1..654
```

```
                         note = Chimeric antibody sequence
source                   1..654
                         mol_type = other DNA
                         organism = synthetic construct
SEQUENCE: 163
gacattgtgc tgacccaatc tccagcttct ttggctgtgt ctctagggca gagggccacc  60
atctcctgca gagccagtga aagtgtcagt attcatggta ctcatttaat gcactggtac  120
caacagaaac caggacagcc acccaaactc ctcatctatg ctgcatccaa cctagaatct  180
ggagtccctg ccaggttcag tggcggtggg tctgagacag acttcaccct caacatccat  240
cctgtggagg aggaggatgg tgcaacctat ttctgtcagc aaagtattga gtatcctcgg  300
acgttcggtg gaggcaccaa gctggaaatc aatcgtacgg tggccgcccc cagcgtgttc  360
atcttccccc ccagcgatga gcagctgaag agcggcaccg ccagcgtggt gtgtctgctg  420
aacaacttct acccccggga ggccaaggtg cagtggaagg tggacaatgc cctgcagagc  480
ggcaacagcc aggagagcgt gaccgagcag gacagcaagg actccaccta cagcctgagc  540
agcaccctga ccctgagcaa ggccgactac gagaagcaca aggtgtacgc ctgtgaggtg  600
acccaccagg gcctgtccag ccccgtgacc aagagcttca accggggcga gtgc        654

SEQ ID NO: 164           moltype = AA  length = 5
FEATURE                  Location/Qualifiers
source                   1..5
                         mol_type = protein
                         organism = Mus musculus
SEQUENCE: 164
DYYNM                                                              5

SEQ ID NO: 165           moltype = AA  length = 16
FEATURE                  Location/Qualifiers
source                   1..16
                         mol_type = protein
                         organism = Mus musculus
SEQUENCE: 165
VINPYNGGTD YNQKFG                                                  16

SEQ ID NO: 166           moltype = AA  length = 9
FEATURE                  Location/Qualifiers
source                   1..9
                         mol_type = protein
                         organism = Mus musculus
SEQUENCE: 166
SVYDYPFDY                                                          9

SEQ ID NO: 167           moltype = AA  length = 15
FEATURE                  Location/Qualifiers
source                   1..15
                         mol_type = protein
                         organism = Mus musculus
SEQUENCE: 167
RASESVSIHG THLMH                                                   15

SEQ ID NO: 168           moltype = AA  length = 7
FEATURE                  Location/Qualifiers
source                   1..7
                         mol_type = protein
                         organism = Mus musculus
SEQUENCE: 168
AASNLES                                                            7

SEQ ID NO: 169           moltype = AA  length = 9
FEATURE                  Location/Qualifiers
source                   1..9
                         mol_type = protein
                         organism = Mus musculus
SEQUENCE: 169
QQSIEDPRT                                                          9

SEQ ID NO: 170           moltype = AA  length = 5
FEATURE                  Location/Qualifiers
source                   1..5
                         mol_type = protein
                         organism = Mus musculus
SEQUENCE: 170
DYSID                                                              5

SEQ ID NO: 171           moltype = AA  length = 17
FEATURE                  Location/Qualifiers
source                   1..17
                         mol_type = protein
                         organism = Mus musculus
SEQUENCE: 171
```

```
DIDPNYGDPI YNHKFKG                                                17

SEQ ID NO: 172         moltype = AA  length = 10
FEATURE                Location/Qualifiers
source                 1..10
                       mol_type = protein
                       organism = Mus musculus
SEQUENCE: 172
RATGTDWFAF                                                        10

SEQ ID NO: 173         moltype = AA  length = 11
FEATURE                Location/Qualifiers
source                 1..11
                       mol_type = protein
                       organism = Mus musculus
SEQUENCE: 173
RASENIYNNL A                                                      11

SEQ ID NO: 174         moltype = AA  length = 7
FEATURE                Location/Qualifiers
source                 1..7
                       mol_type = protein
                       organism = Mus musculus
SEQUENCE: 174
AATILAD                                                           7

SEQ ID NO: 175         moltype = AA  length = 9
FEATURE                Location/Qualifiers
source                 1..9
                       mol_type = protein
                       organism = Mus musculus
SEQUENCE: 175
QHFWGTPLT                                                         9

SEQ ID NO: 176         moltype = AA  length = 5
FEATURE                Location/Qualifiers
source                 1..5
                       mol_type = protein
                       organism = Mus musculus
SEQUENCE: 176
NYWMH                                                             5

SEQ ID NO: 177         moltype = AA  length = 17
FEATURE                Location/Qualifiers
source                 1..17
                       mol_type = protein
                       organism = Mus musculus
SEQUENCE: 177
IIHPNSGSTN YNEKFKS                                                17

SEQ ID NO: 178         moltype = AA  length = 9
FEATURE                Location/Qualifiers
source                 1..9
                       mol_type = protein
                       organism = Mus musculus
SEQUENCE: 178
GIYDYPFAY                                                         9

SEQ ID NO: 179         moltype = AA  length = 15
FEATURE                Location/Qualifiers
source                 1..15
                       mol_type = protein
                       organism = Mus musculus
SEQUENCE: 179
RASESVSIHG THLMH                                                  15

SEQ ID NO: 180         moltype = AA  length = 7
FEATURE                Location/Qualifiers
source                 1..7
                       mol_type = protein
                       organism = Mus musculus
SEQUENCE: 180
AASNLES                                                           7

SEQ ID NO: 181         moltype = AA  length = 9
FEATURE                Location/Qualifiers
source                 1..9
                       mol_type = protein
                       organism = Mus musculus
```

```
SEQUENCE: 181
QQSIEDPYT                                                          9

SEQ ID NO: 182         moltype = AA  length = 5
FEATURE                Location/Qualifiers
source                 1..5
                       mol_type = protein
                       organism = Mus musculus
SEQUENCE: 182
RYWMS                                                              5

SEQ ID NO: 183         moltype = AA  length = 17
FEATURE                Location/Qualifiers
source                 1..17
                       mol_type = protein
                       organism = Mus musculus
SEQUENCE: 183
EINPDRSTIN YAPSLKD                                                 17

SEQ ID NO: 184         moltype = AA  length = 11
FEATURE                Location/Qualifiers
source                 1..11
                       mol_type = protein
                       organism = Mus musculus
SEQUENCE: 184
FYYDYEGAMD Y                                                       11

SEQ ID NO: 185         moltype = AA  length = 11
FEATURE                Location/Qualifiers
source                 1..11
                       mol_type = protein
                       organism = Mus musculus
SEQUENCE: 185
KASQNVDTNV A                                                       11

SEQ ID NO: 186         moltype = AA  length = 7
FEATURE                Location/Qualifiers
source                 1..7
                       mol_type = protein
                       organism = Mus musculus
SEQUENCE: 186
SASYRFS                                                            7

SEQ ID NO: 187         moltype = AA  length = 9
FEATURE                Location/Qualifiers
source                 1..9
                       mol_type = protein
                       organism = Mus musculus
SEQUENCE: 187
QQYNSFPFT                                                          9

SEQ ID NO: 188         moltype = AA  length = 5
FEATURE                Location/Qualifiers
source                 1..5
                       mol_type = protein
                       organism = Mus musculus
SEQUENCE: 188
SYWMH                                                              5

SEQ ID NO: 189         moltype = AA  length = 17
FEATURE                Location/Qualifiers
source                 1..17
                       mol_type = protein
                       organism = Mus musculus
SEQUENCE: 189
VIDPSDSYTN YNQKFKG                                                 17

SEQ ID NO: 190         moltype = AA  length = 9
FEATURE                Location/Qualifiers
source                 1..9
                       mol_type = protein
                       organism = Mus musculus
SEQUENCE: 190
QVFDYPMDY                                                          9

SEQ ID NO: 191         moltype = AA  length = 15
FEATURE                Location/Qualifiers
source                 1..15
                       mol_type = protein
```

-continued

```
                       organism = Mus musculus
SEQUENCE: 191
RASESVSIHG THLMH                                                    15

SEQ ID NO: 192         moltype = AA  length = 7
FEATURE                Location/Qualifiers
source                 1..7
                       mol_type = protein
                       organism = Mus musculus
SEQUENCE: 192
AASNLES                                                             7

SEQ ID NO: 193         moltype = AA  length = 9
FEATURE                Location/Qualifiers
source                 1..9
                       mol_type = protein
                       organism = Mus musculus
SEQUENCE: 193
QQSIEDPWT                                                           9

SEQ ID NO: 194         moltype = AA  length = 5
FEATURE                Location/Qualifiers
source                 1..5
                       mol_type = protein
                       organism = Mus musculus
SEQUENCE: 194
DYEMH                                                               5

SEQ ID NO: 195         moltype = AA  length = 17
FEATURE                Location/Qualifiers
source                 1..17
                       mol_type = protein
                       organism = Mus musculus
SEQUENCE: 195
AIDPETGGTA YNQKFKG                                                  17

SEQ ID NO: 196         moltype = AA  length = 9
FEATURE                Location/Qualifiers
source                 1..9
                       mol_type = protein
                       organism = Mus musculus
SEQUENCE: 196
SIYDYYFDY                                                           9

SEQ ID NO: 197         moltype = AA  length = 15
FEATURE                Location/Qualifiers
source                 1..15
                       mol_type = protein
                       organism = Mus musculus
SEQUENCE: 197
RASESVSIHG THLMH                                                    15

SEQ ID NO: 198         moltype = AA  length = 7
FEATURE                Location/Qualifiers
source                 1..7
                       mol_type = protein
                       organism = Mus musculus
SEQUENCE: 198
AASNLES                                                             7

SEQ ID NO: 199         moltype = AA  length = 9
FEATURE                Location/Qualifiers
source                 1..9
                       mol_type = protein
                       organism = Mus musculus
SEQUENCE: 199
QQSIEYPRT                                                           9
```

The invention claimed is:

1. A method of treating a human patient afflicted with a B-cell maturation antigen (BCMA)-expressing B-cell lymphoma comprising:
   administering to said human a dose of an immunoconjugate comprising an antibody and a cytotoxic agent,
   wherein said antibody comprises a heavy chain variable region set forth in SEQ ID NO: 23 and a light chain variable region set forth in SEQ ID NO: 31, and
   wherein said dose is in the range of about 1 mg/kg to about 5 mg/kg.

2. The method of claim 1, wherein the dose is administered once every 3 weeks.

3. The method of claim 1, wherein the cytotoxic agent is one selected from the group consisting of a calicheamicin, a maytansinoid, a dolastatin, an auristatin, a trichothecene, a DNA minor groove binding agent, a DNA minor groove alkylating agent, an enediyne, a lexitropsin, a duocarmycin, a taxane, a puromycin, a vinca alkaloid, an anti-tubulin agent, a podophyllotoxin, a baccatin derivative, a cryptophycin, and a combretastatin.

4. The method of claim 1, wherein the cytotoxic agent is an auristatin or a dolastatin.

5. The method of claim 1, wherein the cytotoxic agent is selected from monomethyl auristatin E (MMAE) and monomethyl auristatin F (MMAF).

6. The method of claim 1, wherein the cytotoxic agent is covalently bound to said antibody.

7. The method of claim 1, wherein the antibody is linked to the cytotoxic agent via a linker.

8. The method of claim 7, wherein said linker is a cleavable linker.

9. The method of claim 7, wherein said linker is a non-cleavable linker.

10. The method of claim 7, wherein the linker is selected from 6-maleimidocaproyl (MC), maleimidopropanoyl (MP), valine-citrulline (val-cit), alanine-phenylalanine (ala-phe), p-aminobenzyloxycarbonyl (PAB), N-succinimidyl 4-(2-pyridylthio)pentanoate (SPP), N-succinimidyl 4-(N-maleimidomethyl)cyclohexane-1 carboxylate (SMCC), and N-succinimidyl (4-iodo-acetyl) aminobenzoate (SIAB).

11. The method of claim 7, wherein the linker is 6-maleimidocaproyl (MC) and the cytotoxic agent is monomethyl auristatin F (MMAF).

12. The method of claim 11, wherein the antibody is afucosylated.

13. The method of claim 11, wherein the antibody comprises the heavy chain amino acid sequence of SEQ ID NO: 55 and the light chain amino acid sequence of SEQ ID NO: 63.

14. The method of claim 13, wherein the antibody is afucosylated.

15. The method of claim 1, wherein the BCMA-expressing B-cell lymphoma is selected from: multiple myeloma (MM) and chronic lymphocytic leukemia (CLL).

16. The method of claim 1, wherein the BCMA-expressing B-cell lymphoma is multiple myeloma (MM).

17. The method of claim 16, wherein the patient has newly diagnosed MM.

18. The method of claim 16, wherein the patient has relapsed MM.

19. The method of claim 16, wherein the patient has MM that is in remission.

20. The method of claim 16, wherein the patient is a MM patient that has progressive disease.

21. The method of claim 11, wherein the BCMA-expressing B-cell lymphoma is selected from: multiple myeloma (MM) and chronic lymphocytic leukemia (CLL).

22. The method of claim 12, wherein the BCMA-expressing B-cell lymphoma is multiple myeloma (MM).

23. The method of claim 22, wherein the patient has newly diagnosed MM.

24. The method of claim 22, wherein the patient has relapsed MM.

25. The method of claim 22, wherein the patient has MM that is in remission.

26. The method of claim 22, wherein the patient is a MM patient that has progressive disease.

27. The method of claim 14, wherein the BCMA-expressing B-cell lymphoma is multiple myeloma (MM).

28. The method of claim 27, wherein the patient has newly diagnosed MM.

29. The method of claim 27, wherein the patient has relapsed MM.

30. The method of claim 27, wherein the patient has MM that is in remission.

31. The method of claim 27, wherein the patient is a MM patient that has progressive disease.

* * * * *